US012358929B2

(12) United States Patent
Anderson et al.

(10) Patent No.: US 12,358,929 B2
(45) Date of Patent: Jul. 15, 2025

(54) NMDA RECEPTOR MODULATORS AND USES THEREOF

(71) Applicant: Novartis AG, Basel (CH)

(72) Inventors: David R. Anderson, Salem, CT (US); Robert A. Volkmann, Mystic, CT (US); Frank S. Menniti, Mystic, CT (US); Christopher Fanger, Bolton, MA (US); Yuelian Xu, East Haven, CT (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/368,244

(22) Filed: Sep. 14, 2023

(65) Prior Publication Data
US 2024/0294546 A1 Sep. 5, 2024

Related U.S. Application Data

(60) Continuation of application No. 17/585,849, filed on Jan. 27, 2022, now Pat. No. 11,807,650, which is a division of application No. 16/471,880, filed as application No. PCT/US2017/068135 on Dec. 22, 2017, now Pat. No. 11,274,107.

(60) Provisional application No. 62/438,080, filed on Dec. 22, 2016, provisional application No. 62/438,086, filed on Dec. 22, 2016, provisional application No. 62/438,070, filed on Dec. 22, 2016.

(51) Int. Cl.
C07D 513/04 (2006.01)
C07D 471/04 (2006.01)
C07D 487/04 (2006.01)
C07D 495/04 (2006.01)
C07D 498/04 (2006.01)
C07D 513/20 (2006.01)

(52) U.S. Cl.
CPC ......... C07D 513/04 (2013.01); C07D 471/04 (2013.01); C07D 487/04 (2013.01); C07D 495/04 (2013.01); C07D 498/04 (2013.01); C07D 513/20 (2013.01)

(58) Field of Classification Search
CPC ............................ C07D 513/04; C07D 471/04
USPC .................................................... 514/210.21
See application file for complete search history.

(56) References Cited

U.S. PATENT DOCUMENTS

| 4,581,358 | A | 4/1986 | Barthelemy et al. |
| 4,921,854 | A | 5/1990 | Bozsing et al. |
| 5,298,502 | A | 3/1994 | Halling et al. |
| 6,339,093 | B1 | 1/2002 | Alanine et al. |
| 6,852,731 | B2 | 2/2005 | Larsen et al. |
| 9,963,434 | B2 | 5/2018 | Anderson et al. |
| 10,500,205 | B2 | 12/2019 | Anderson et al. |
| 10,584,131 | B2 | 3/2020 | Anderson et al. |
| 10,626,122 | B2 | 4/2020 | Anderson et al. |
| 10,752,633 | B2 | 8/2020 | Anderson et al. |
| 10,973,825 | B2 | 4/2021 | Anderson et al. |
| 11,236,104 | B2 | 2/2022 | Anderson et al. |
| 11,274,107 | B2 | 3/2022 | Anderson et al. |
| 11,541,057 | B2 | 1/2023 | Anderson et al. |
| 11,542,264 | B2 | 1/2023 | Anderson et al. |
| 11,807,650 | B2 | 11/2023 | Anderson et al. |
| 2002/0013329 | A1 | 1/2002 | Claremon et al. |
| 2003/0114447 | A1 | 6/2003 | Choong et al. |
| 2006/0014945 | A1 | 1/2006 | Galley et al. |
| 2007/0093509 | A1 | 4/2007 | Washburn et al. |
| 2008/0064678 | A1 | 3/2008 | Letourneau et al. |
| 2008/0090802 | A1 | 4/2008 | Letourneau et al. |
| 2008/0214553 | A1 | 9/2008 | Letourneau et al. |
| 2008/0280900 | A1 | 11/2008 | Pajouhesh et al. |
| 2010/0249087 | A1 | 9/2010 | Wang et al. |
| 2012/0165330 | A1 | 6/2012 | Vu |
| 2012/0178742 | A1 | 7/2012 | Henrich et al. |
| 2013/0123231 | A1 | 5/2013 | Harriman et al. |
| 2016/0222033 | A1 | 8/2016 | Yu et al. |
| 2017/0305861 | A1 | 10/2017 | Kim et al. |
| 2017/0313719 | A1 | 11/2017 | Traynelis et al. |
| 2020/0038403 | A1 | 2/2020 | Poudel et al. |
| 2022/0047600 | A1 | 2/2022 | Anderson et al. |
| 2023/0023543 | A1 | 1/2023 | Anderson et al. |

FOREIGN PATENT DOCUMENTS

| AU | 20090243006 A1 | 11/2009 |
| AU | 2009266889 A1 | 1/2010 |
| CN | 102336768 A | 2/2012 |
| CN | 103664877 A | 3/2014 |
| GB | 1588166 A | 4/1981 |
| JP | 60-051190 A | 3/1985 |
| JP | 2004-501901 A | 1/2004 |
| JP | 2010-513463 A | 4/2010 |
| JP | 2011-525908 A | 9/2011 |

(Continued)

OTHER PUBLICATIONS

El-Sherief et al. Journal of Heterocyclic Chemistry (2010), 47(6), 1294-1302.*

(Continued)

Primary Examiner — Kahsay Habte
(74) Attorney, Agent, or Firm — McCarter & English, LLP; Michael J. DeGrazia

(57) ABSTRACT

Disclosed herein, in part, are heteroaromatic compounds and methods of use in treating neuropsychiatric disorders, e.g., schizophrenia and major depressive disorder. Pharmaceutical compositions and methods of making heteroaromatic compounds are provided. The compounds are contemplated to modulate the NMDA receptor.

14 Claims, No Drawings

(56) References Cited

FOREIGN PATENT DOCUMENTS

| | | |
|---|---|---|
| JP | 2011-528322 A | 11/2011 |
| JP | 2015-508075 A | 3/2015 |
| JP | 2016-532669 A | 10/2016 |
| RU | 2271361 C2 | 3/2006 |
| WO | WO-1994/027975 A1 | 12/1994 |
| WO | WO-1998/000401 A1 | 1/1998 |
| WO | WO-2002/000629 A1 | 1/2002 |
| WO | WO-2003/097637 A1 | 11/2003 |
| WO | WO-2006/095014 A1 | 9/2006 |
| WO | WO-2008/033757 A2 | 3/2008 |
| WO | WO-2008/033764 A2 | 3/2008 |
| WO | WO-2008/076883 A2 | 6/2008 |
| WO | WO-2008/078196 A2 | 7/2008 |
| WO | WO-2008/097538 A1 | 8/2008 |
| WO | WO-2008/128982 A1 | 10/2008 |
| WO | WO-2008/138126 A1 | 11/2008 |
| WO | WO-2009/025784 A1 | 2/2009 |
| WO | WO-2009/062930 A1 | 5/2009 |
| WO | WO-2009/134973 A1 | 11/2009 |
| WO | WO-2009/146358 A1 | 12/2009 |
| WO | WO-2009/156864 A2 | 12/2009 |
| WO | WO-2010/003048 A1 | 1/2010 |
| WO | WO-2010/006496 A1 | 1/2010 |
| WO | WO-2010/037127 A1 | 4/2010 |
| WO | WO-2010/037129 A1 | 4/2010 |
| WO | WO-2010/079443 A1 | 7/2010 |
| WO | WO-2010/111573 A1 | 9/2010 |
| WO | WO-2010/139483 A1 | 12/2010 |
| WO | WO-2011/045258 A1 | 4/2011 |
| WO | WO-2011/117381 A1 | 9/2011 |
| WO | WO-2011/117382 A1 | 9/2011 |
| WO | WO-2012/009688 A1 | 1/2012 |
| WO | WO-2012/052540 A1 | 4/2012 |
| WO | WO-2012/129562 A2 | 9/2012 |
| WO | WO-2012/154760 A1 | 11/2012 |
| WO | WO-2013/048928 A1 | 4/2013 |
| WO | WO-2013/048942 A1 | 4/2013 |
| WO | WO-2013/049104 A1 | 4/2013 |
| WO | WO-2013/119916 A2 | 8/2013 |
| WO | WO-2014/066743 A1 | 5/2014 |
| WO | WO-2014/139325 A1 | 9/2014 |
| WO | WO-2014/179144 A1 | 11/2014 |
| WO | WO-2014/206343 A1 | 12/2014 |
| WO | WO-2015/007453 A1 | 1/2015 |
| WO | WO-2015/052226 A1 | 4/2015 |
| WO | WO-2015/064714 A1 | 5/2015 |
| WO | WO-2015/096611 A1 | 7/2015 |
| WO | WO-2016/034703 A1 | 3/2016 |
| WO | WO-2016/081649 A1 | 5/2016 |
| WO | WO-2016/166078 A1 | 10/2016 |
| WO | WO-2017/066590 A1 | 4/2017 |
| WO | WO-2017/100591 A1 | 6/2017 |
| WO | WO-2017/100593 A1 | 6/2017 |
| WO | WO-2017/100599 A1 | 6/2017 |
| WO | WO-2017/188694 A1 | 11/2017 |
| WO | WO-2018/026371 A1 | 2/2018 |
| WO | WO-2018/119374 A1 | 6/2018 |
| WO | WO-2019/067594 A1 | 4/2019 |

OTHER PUBLICATIONS

Dotsenko et al. Russian Chemical Bulletin (2007), 56(7), 1437-1440.*
U.S. Appl. No. 15/024,870, filed Mar. 25, 2016, U.S. Pat. No. 9,963,434, Issued.
U.S. Appl. No. 16/471,880, filed Jun. 20, 2019, U.S. Pat. No. 11,274,107, Issued.
U.S. Appl. No. 17/585,849, filed Jan. 27, 2022, U.S. Pat. No. 11,807,650, Issued.
U.S. Appl. No. 16/060,056, filed Jun. 7, 2018, U.S. Pat. No. 10/626,122, Issued.
U.S. Appl. No. 16/779,517, filed Jan. 31, 2020, U.S. Pat. No. 11,236,104, Issued.
U.S. Appl. No. 17/550,435, filed Dec. 14, 2021, 2023-0023543, Published.
U.S. Appl. No. 16/060,267, filed Jun. 7, 2018, U.S. Pat. No. 10,973,825, Issued.
U.S. Appl. No. 16/929,602, filed Jul. 15, 2020, Abandoned.
U.S. Appl. No. 17/186,137, filed Feb. 26, 2021, U.S. Pat. No. 11,541,057, Issued.
U.S. Appl. No. 18/077,996, filed Dec. 8, 2022, Abandoned.
U.S. Appl. No. 16/060,294, filed Jun. 7, 2018, U.S. Pat. No. 10,500,205, Issued.
U.S. Appl. No. 16/658,686, filed Oct. 21, 2019, Abandoned.
U.S. Appl. No. 16/893,659, filed Jun. 5, 2020, Abandoned.
U.S. Appl. No. 17/150,222, filed Jan. 15, 2021, Abandoned.
U.S. Appl. No. 17/458,797, filed Aug. 27, 2021, U.S. Pat. No. 11,648,253, Issued.
U.S. Appl. No. 16/530,274, filed Aug. 2, 2019, U.S. Pat. No. 10,584,131, Issued.
U.S. Appl. No. 16/678,806, filed Nov. 8, 2019, U.S. Pat. No. 10,752,633, Issued.
U.S. Appl. No. 16/919,136, filed Jul. 2, 2020, Abandoned.
U.S. Appl. No. 17/174,826, filed Feb. 12, 2021, U.S. Pat. No. 11,542,264, Issued.
U.S. Appl. No. 18/071,254, filed Nov. 29, 2022, Abandoned.
U.S. Appl. No. 18/221,694, filed Jul. 13, 2023, Abandoned.
U.S. Appl. No. 18/591,531, filed Feb. 29, 2024, Pending.
Almasi et al., Characterization of potential NMDA and cholecystokinin antagonists II. Lipophilicity studies on 2-methyl-4-oxo-3H-quinazoline-3-alkyl-carboxylic acid derivatives. International Journal of Pharmaceutics. 1999;180:13-22.
Beutler et al., Diastereoselective Dimerisation of Alkenylthiazolines: A Combined Synthetic and Computational Study. European Journal of Organic Chemistry. 2005;2005(17):3791-3800.
Bonacorso et al., Beta-Alkoxyvinyl trichloromethyl ketones as N-heterocyclic acylating agent. A new access to 5H-thiazolo[3-2-alpha]pyrimidin-5-ones. Tetrahedron Letters. 2002;43:9315-9318.
Broddefalk et al., Use of acid-labile protective groups for carbohydrate moieties in synthesis of glycopeptides related to type II collagen. Tetrahedron. Sep. 24, 1998;54(39):12047-12070.
Ciapetti et al., Molecular Variations Based on Isosteric Replacements. The Practice of Medicinal Chemistry, Third Edition. Camille Georges Wermuth (Ed.), Academic Press, Amsterdam. Chapter 15, pp. 290-342, (2008).
Ding et al., Parallel synthesis of 5-cyano-6-aryl-2-thiouracil derivatives as inhibitors for hepatitis C viral NS5B RNA-dependent RNA polymerase. Bioorg Chem. 2006;34(1):26-38.
Dotsenko et al., The Mannich reaction in the synthesis of N,S-containing heterocycles 5. Synthesis and structures of new pyrimido[2,1-b][1,3,5]thiadiazine derivatives. Russian Chemical Bulletin, International Edition. Jul. 2007;56(7):1437-1440.
El-Sherief et al., Intramolecular Cyclization of Mannich Reaction for Synthesis of Pyrimido[2, 1-b]-1,3,5-tiadiazines. J Heterocyclic Chem. 2010;47:1294-1302.
Hamouda, Snythesis of novel pyrimidines thiazolopyrimidines, triazolopyrimidines and pyrimidotriazines as potent antimicrobial agent. Der Pharma Chemica. 2014;6(6):346-357.
Hanefeld et al., Iminium carbonic acid derivative salts. XI †. Synthesis of N,S-containing heterobicycles from N-protected 2-methylthio-1,3-thiazinium and 2-methylthiothiazoüum salts. Part 3. Reaction of N-protected 2-methylthio-1,3-thiazinium and 2-methylthiothiazolium salts with 3-amino-2-cyano-3-arylacrylonitriles. Journal of Heterocyclic Chemistry. Nov. 1, 1996;33(6):1903-1907.
Jeanneau-Nicolle et al., New thiazolo[3,2-alpha]pyrimidine derivatives, synthesis and structure-activity relationships. European Journal of Medicinal Chemistry. Mar. 1992;27(2):115-120.
Jia et al., Identification, design and bio-evaluation of novel Hsp90 inhibitors by ligand-based virtual screening. PLoS One. 2013;8(4):e59315, 15 pages.
Kubo et al., Studies on the syntheses of 2(1H)-pyridone derivatives. IV. Synthesis of condensed heterocyclic 2(1H)-pyridones. Yakugaku Zasshi. Sep. 1979;99(9):880-8.
Kümmerer et al., Pharmaceuticals in the Environment. Annu. Rev. Environ. Resour. Aug. 18, 2010;35:57-75.

(56) References Cited

OTHER PUBLICATIONS

Lensen et al., Hexakis (pyridyl-functionalised porphyrinato)benzene as a building block for the construction of multi-chromophoric arrays. Tetrahedron Letters. Dec. 16, 2002;43(51)9351-9355.

Mahran et al., Synthesis and biological evaluation of novel pyrimidines derived from 6-aryl-5-cyano-2-thiouracil. Zeitschrift fur Naturforschung. 2016;71(5-6):133-140.

Napier et al., Synthesis and SAR studies of novel 2-(6-aminomethylaryl-2-aryl-4-oxo-quinazolin-3(4H)-yl)acetamide vasopressin V1b receptor antagonists. Bioorg Med Chem Lett. Jun. 15, 2011;21(12):3813-7.

Nerkar et al., In Silico Design, Synthesis and Pharmacological Screening of Novel Mono and Di-Bromo Quinazolinone Derivatives as NMDA Receptor Antagonists for Anticonvulsant Activity. International Journal of Pharmacy and Pharmaceutical Sciences. 2013;5(1):331-335.

Noueiry et al., Identification of Novel Small-Molecule Inhibitors of West Nile Virus Infection. J Virol. Nov. 2007; 81(21):11992-12004.

PUBCHEM-CID 10587973, Create Date: Oct. 25, 2006, 9 pages.

PUBCHEM-CID 16957685, 8-(4-tert-butylphenyl)-6-oxo-3,4-dihydro-2H,6H-pyrimido[2,1-b][1,3]thiazine-7-carbonitrile. Create Date: Nov. 13, 2007, 7 pages.

PUBCHEM-CID 6612590, 7-phenyl-8H-[1,2,4]triazolo[4,3-a]pyrimidin-5-one. Create Date: Jun. 5, 2006, 8 pages.

Ram et al., 5-Cyano-2-thiouracils and their derivatives: a new class of leishmanicides. Bioorganic & Medicinal Chemistry Letters. Nov. 1994;4(22):2653-2656.

Ram et al., 5-Cyano-6-aryluracil and 2-Thiouracil Derivatives as Potential Chemotherapeutic Agents. IV. J Heterocyclic Chem. Sep.-Oct. 1984;21:1307-1312.

Ram et al., Chemotherapeutic agents, Part XVIII: Synthesis of pi-deficient pyrimidines and fused pyrimidines as leishmanicidal agents. Arch Pharm (Weinheim). Nov. 1990;323(11):895-9.

Ram et al., Chemotherapeutic agents: Part XIV. Synthesis of pi-deficient pyrimidines linked with pi-rich heterocycles as antimicrobial agents. Indian Journal of Chemistry—Section B Organic and Medicinal Chemistry. 1989;28(2):159-162.

Ram et al., Chemotherapeutic agents: Part XX. Antileishmanial and immunoadjuvant activities of rationally designed thiopyrimidines. Indian Journal of Chemistry—Section B Organic and Medicinal Chemistry. 1990;29(12):1129-1133.

Ram et al., Chemotherapeutical Agents, V. Syntheses and Activities of Novel Pyrimidines Derived from 5-Cyano-6-aryl-2-thiouracil. Liebigs Ann Chem. 1987 Sep. 14;1987(9):797-801.

Ram, Chemotherapeutic agents, XXI: Synthesis of Pi-deficient pyrimidines as leishmanicides. Arch Pharm (Weinheim). 1991;324(11):837-839.

Ram, Chemotherapeutic agents. XII [1]. Synthesis of Pyrimidines and Fused Pyrimidines as leishmanicides and herbicides. Journal fur Praktische Chemie. 1989;331(6):893-905.

Registry (STN) online search of compounds available as of Nov. 23, 2007, 29 pages.

Salem et al., Antioxidant Activity of Novel Fused Heterocyclic Compounds Derived from Tetrahydropyrimidine Derivative. Chem Pharm Bull (Tokyo). 2015;63(11):866-872.

Salem et al., Pyrimidinthiones (Part I): Utility of 2-Thioxopyrimidin-6-(1H)ones as Ring Transformer in the Synthesis of Fused Bi- and Tri-Cyclic Heterocyclic Compounds and Their Potential Biological Activities. Phosphorus, Sulfur, and Silicon. 2008;183:2596-2614.

Santangelo et al., Novel NMDA receptor modulators: an update. Expert Opin Ther Pat. Nov. 2012;22(11):1337-52.

Singh et al., Synthesis and Antiviral Activity of Some Novel N-Substituted Benzimidazolyl Annulated Pyrimidines. Journal of Indian Council of Chemists. 2008;25(1):19-22.

STN Registry No. 309740-20-3, 5H-Thiazolo[3,2-a]pyrimidine-6-carbonitrile, 7-[4-1(1, 1-dimethylethyl)phenyl]-2,3-dihydro-5-oxo. 1 page, Dec. 19, 2000.

STN Registry No. 896665-59-1, 5H-Thiazolo[3,2-a]pyrimidine-6-carbonitrile, 7-(2,4-dimethoxyphenyl)-2,3-dihydro-5-oxo. 1 page, Jul. 28, 2006.

STN Registry No. 903460-76-4, 5H-Thiazolo[3,2-a]pyrimidine-6-carbonitrile, 2,3-dihydro-7-[4-(methylthio)phenyl]-5-oxo. 1 page, Aug. 22, 2006.

STN Registry No. 924249-59-2, Thieno[2,3-d]pyrimidin-4(3H)-one, 3-[3-(1-azetidinyl)-3-oxopropyl]-5-(4-methylphenyl)-, dated Mar. 2, 2007, 3 pages.

STN Registry No. 927964-07-6, 2H, 6H-Pyrimido[2,1-b][1,3]thiazine-7-carbonitrile, 8-[4-(1,1-dimethylethyl)phenyl]-3,4-dihydro-6-oxo. 1 page, Mar. 23, 2007.

Troisi et al., Synthesis and isomerization of N-alpha-aza-heteroaryl-beta-lactams. Tetrahedron. Dec. 18, 2006;62(51):12064-12070.

Upadhyay et al., Synthesis of pyrimidine and azolopyrimidines as biodynamic agents. Indian Journal of Chemistry. Feb. 1999;38B:173-177.

* cited by examiner

NMDA RECEPTOR MODULATORS AND USES THEREOF

RELATED APPLICATIONS

This application is a Continuation of U.S. patent application Ser. No. 17/585,849, filed Jan. 27, 2022, which is a Divisional of U.S. patent application Ser. No. 16/471,880, filed Jun. 20, 2019, now U.S. Pat. No. 11,274,107, issued Mar. 15, 2022 which is a U.S. national stage filing under 35 U.S.C. § 371 of international application No. PCT/US2017/068135, filed Dec. 22, 2017, which claims the benefit of priority to U.S. provisional application No. 62/438,086, filed Dec. 22, 2016, U.S. provisional application No. 62/438,080, filed Dec. 22, 2016, and U.S. provisional application No. 62/438,070, filed Dec. 22, 2016. The entire contents of each of the aforementioned application are incorporated herein by reference.

BACKGROUND

Neurons that utilize glutamate as neurotransmitter comprise the vast majority of the neurons in the mammalian brain and form the core brain architecture. Glutamate synaptic transmission is mediated by 3 types of ionotropic glutamate receptors, AMPA, KA, and NMDA, and a family of metabotropic receptors (mGluRs). AMPA receptors mediate fast excitatory transmission, whereas KA and mGluRs are primarily involved in pre- and post-synaptic modulatory functions. NMDA receptors mediate slow excitatory synaptic transmission and play a role in integrating synaptic inputs. NMDA receptors also regulate the strength of glutamate synapses by signaling the insertion or removal of AMPA receptors in response to the strength and timing of pre- and post-synaptic activity. The plasticity of glutamate synapses is a principal molecular mechanism for modifying the informational content and flow in brain neuronal networks and so is critical to the adaptive functions of the brain including learning and memory. Given these functions of NMDA receptors, in mediation of excitatory glutamatergic synaptic transmission, in the integration of synaptic inputs, and in regulation of synaptic plasticity, there are broad therapeutic utilities for agents that modulate the activity of these receptors to treat neurological and neuropsychiatric disease.

The NMDA receptor is a tetramer consisting of 2 GluN1 subunits and 2 GluN2 subunits, arranged as a dimer of GluN1/GluN2 dimers. Each subunit is comprised of 4 modules: a ligand binding domain for the neurotransmitter glutamate (GluN2) or co-transmitter glycine/D-serine (GluN1), a transmembrane domain that forms the ion channel pore, an amino terminal domain that serves a modulatory function, and an intracellular c-terminal domain involved in anchoring the receptors to intracellular scaffolds and signaling complexes.

There are 4 GluN2 subunits, GluN2A-D, coded by individual genes. The single GluN1 subunit is expressed as 8 variants resulting from alternative RNA splicing. NMDA receptors may be di-heteromeric, consisting of a single type of GluN2 subunit and GluN1 (e.g., GluN2D/GluN1), or tri-heteromeric consisting of 2 different GluN2 subunits and GluN1 (e.g., GluN2B/GluN2D/GluN1). The GluN2 composition of NMDA receptors confers specific physiological characteristics including differences in glutamate and glycine affinities, channel kinetics, and interaction with allosteric modulators and intracellular complexes. NADA receptors with different GluN2 subunit compositions are deployed by different populations of neurons to fine-tune NMDA receptor activity. In the adult mammalian brain, forebrain principal neurons and striatal projection neurons express primarily GluN2A and GluN2B di-heteromers and GluN2A/GluN2B tri-heteromers. GluN2C is co-expressed primarily with GluN2A by forebrain interneurons, thalamic neurons, and cerebellar neurons. GluN2D is co-expressed primarily with GluN2B in forebrain interneurons as well as pallidal, dopaminergic, and subthalamic nucleus neurons of the basal ganglia circuit. The subunit composition of NMDA receptors also changes over the course of brain development, with GluN2B and GluN2D subunits predominating early in development.

There is a rich pharmacology of NMDA receptor antagonists that act as channel blockers or as glutamate- or glycine-binding site competitive inhibitors. These agents have similar potencies and efficacies across NMDA receptors with different GluN2 subunits and so have the potential to affect activity across essentially all neuronal circuits. Such broad activity can result in unwanted side effects, which have in some cases limited therapeutic utility. Thus, there has been a long interest in the discovery of agents that selectively modulate the activity of NMDA receptors comprised of distinct GluN2 subunits, since such agents may have more circuit and neuron specific activities. However, to date there is only one well-developed class of subunit-selective antagonist, the GluN2B negative allosteric modulators (NAMs). More recently disclosed are very limited classes of GluN2A NAMs and GluN2C or GluN2C/D NAMs.

There are significantly fewer pharmacological agents that can increase NMDA receptor activity. The majority of these are agents that act as ligands at the glutamate or glycine binding sites and so, again, have the potential to broadly affect brain neuronal circuits. Recently, very limited classes of subunit-selective positive allosteric modulators (PAMs) of NMDA receptors have been disclosed. This includes GluN2A PAMs, GluN2C PAMs and GluN2C/D PAMs.

The study of the molecular basis of NMDA receptor function continues to be an area of importance. As glutamate is the major excitatory neurotransmitter, dysfunction of glutamate neurotransmission and NMDA receptor-dependent mechanisms of synaptic transmission, plasticity, and neuronal network connectivity are broadly implicated in diseases of the nervous system. Accordingly, compounds that are capable of modulating NMDA receptors may be useful for the treatment of nervous system disorders and diseases, for example, schizophrenia, Alzheimer's disease, attention deficit and hyperactivity disorder, and autism.

SUMMARY

The present disclosure provides, for example, compounds which are modulators of NMDA receptors (e.g., positive allosteric modulators of NMDA receptors, e.g., GluN2C and GluN2D PAMs) and their use as medicinal agents, processes for their preparation, and pharmaceutical compositions containing them as an active ingredient. The disclosure provides for the use of disclosed compounds as medicaments and/or in the manufacture of medicaments for the modulation of NMDA receptors in warm-blooded animals such as humans. In particular this disclosure relates to compounds useful for the treatment of psychiatric, neurological and/or neurodevelopmental disorders and/or diseases of the nervous system, for example, schizophrenia, Alzheimer's disease, attention deficit and hyperactivity, autism, and other nervous system-associated conditions. Also provided are pharmaceutical compositions comprising at least one disclosed compound and a pharmaceutically acceptable carrier.

In an embodiment, provided herein are compounds represented by Formula I:

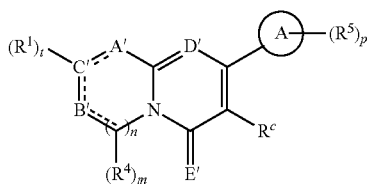

I wherein the dashed lines indicate optional double bonds;
n is 0, 1 or 2;
A' is $C(R^2)_w$, $N(R^6)_s$, O or S; w is 1 or 2, and s is 0 or 1;
B' is $C(R^3)_q$ or $N(R^6)_s$; q is 1 or 2, and s is 0 or 1;
C' is Carbon or Nitrogen;
D' is $CR^7$ or N;
E' is O or $NR^8$;
when n is zero, B' is $O(R^3)_q$, C' is carbon, and A' is S; or
when n is zero, the dashed line is a double bond between C' and B', each of C' and B' is carbon and t and q are each one, or
when n is zero, A' is $NR^6$ or S; B' is $C(R^3)_q$ or $N(R^6)_s$; and C' is carbon or N;
when n is 1 or 2, A' is S or $C(R^2)_w$, B' is $C(R^3)_q$ or $N(R^6)_s$ and C' is carbon; or
when n is 1, A' is O, B' is $C(R^3)_q$ and C' is carbon;
Ring A is optionally substituted phenyl or 5-7 membered heteroaryl having one, two or three heteroatoms each independently selected from the group consisting of N, S, and O, and p is 0, 1, 2 or 3;
$R^C$ is selected from the group consisting of cyano, hydrogen, halogen, $S(C_{1-6})$alkyl, $S(O)(C_{1-6})$alkyl, $SO_2(C_{1-6})$alkyl, $C(O)NR^aR^b$, —C(O)OH, —C(O)O($C_{1-6}$)alkyl, ($C_{1-6}$)alkyl, ($C_{2-6}$)alkenyl, ($C_{2-6}$)alkynyl and heteroaryl (optionally substituted by $C_{1-4}$alkyl or halogen);
$R^1$ is selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, —C(O)OH, —C(O)O$C_{1-6}$alkyl, ($C_{3-6}$)cycloalkyl and phenyl (optionally substituted by one, two or three substituents each selected from halogen, $C_{1-6}$alkyl, $C_{1-6}$alkoxy, C(O)OH, —C(O)O$C_{1-6}$alkyl and $NR^aR^b$); t is 0, 1 or 2;
$R^2$, $R^3$ and $R^4$ are each independently selected from the group consisting of hydrogen, halogen, hydroxyl, $C_{1-6}$alkyl, $C_{2-6}$alkenyl, $C_{2-6}$alkynyl, $C_{1-6}$alkoxy, —CO$_2$H, —CO$_2$C$_{1-6}$alkyl, —CO$_2$NR$^a$R$^b$, NR$^a$R$^b$, $C_{3-6}$cycloalkyl and phenyl (optionally substituted by one or two substituents each selected from halogen or methyl); or when w, q or m is two, each of said $R^3$ or $R^4$ may be taken together with the carbon to which they are attached to form a 3-5 membered carbocyclic ring, methylene group or a 4-5 membered heterocyclic ring having at least one heteroatom, wherein one or more carbon atoms of said $C_{3-6}$cycloalkyl may be optionally replaced by N or O; m is one or two;
$R^5$ independently for each occurrence is selected from the group consisting of hydrogen, $C_{1-6}$alkyl, $C_{1-6}$alkoxy, halogen, cyano, OH, $C_{2-6}$alkenyl, $C_{2-6}$alkynyl, $C_{3-6}$cycloalkyl, heteroaryl, phenyl, —NR$^a$R$^b$, —C(O)OH, $C_{1-6}$alkylcarbonyl, $C_{1-6}$alkoxycarbonyl, (NR$^a$R$^b$)carbonyl-, $C_{1-6}$alkyl-S(O)$_w$— (where w is 0, 1 or 2), and R$^a$R$^b$N—SO$_w$— (where w is 0, 1 or 2); wherein heteroaryl and phenyl may optionally be substituted by one, two or three substituents each selected from the group consisting of halogen, cyano, $C_{1-6}$alkyl, $C_{1-6}$alkoxy, and —NR$^a$R$^b$; wherein one or more carbon atoms of said $C_{3-6}$cycloalkyl may be optionally replaced by N or O;
or two $R^5$, together with two adjacent carbons on ring A to which they are attached, form a 5-7 membered unsaturated, partially unsaturated or saturated carbocyclic or heterocyclic ring;
$R^6$ for each occurrence is independently selected from the group consisting of hydrogen, $C_{1-6}$alkyl, $C_{3-6}$cycloalkyl, —C(O)—$C_{1-6}$alkyl, and phenyl (optionally substituted by one or two substituents each selected from halogen or methyl);
$R^7$ is selected from the group consisting of hydrogen or $(C_{1-6})$alkyl;
$R^8$ is selected from the group consisting of hydrogen, $(C_{1-6})$alkyl, $C_{1-6}$alkoxycarbonyl, or (NR$^a$R$^b$)carbonyl-;
wherein each of said $C_{1-6}$alkyl, $C_{2-6}$alkenyl, $C_{2-6}$alkynyl, and $C_{3-6}$cycloalkyl wherever they occur may be optionally independently substituted by one or more substituents each independently selected from the group consisting of halogen, hydroxyl, cyano, $C_{3-6}$cycloalkyl (wherein one or more ring carbon atoms is replaced by N, O or S), heteroaryl, phenyl, CF$_3$, NR$^a$R$^b$, $C_{1-6}$alkyl, $C_{1-6}$alkoxy, $C_{1-6}$alkyl-S—, $C_{1-6}$alkoxyC$_{1-6}$alkoxy, $C_{1-6}$alkoxyC$_{1-6}$alkyl-S—, $C_{1-6}$alkoxycarbonyl, $C_{1-6}$alkylcarbonyl, (NR$^a$R$^b$)carbonyl-, and $C_{1-6}$alkylcarbonyl-(NR$^a$R$^b$)—;
$R^a$ and $R^b$ are independently selected, for each occurrence, from the group consisting of: hydrogen, $C_{1-4}$alkylcarbonyl, $C_{1-6}$alkoxycarbonyl, cyclopropyl, and $C_{1-3}$alkyl; wherein $C_{1-3}$alkyl may optionally be substituted on a carbon not bound to the nitrogen by one or more substituents each selected from the group consisting of fluorine, cyano, oxo and hydroxyl; or
$R^a$ and $R^b$, together with the nitrogen to which they are attached, form a 4-6 membered heterocyclic ring which may have an additional heteroatom selected from O, S, or N (optionally substituted by one or two methyl groups); and wherein the 4-6 membered heterocyclic ring may optionally be substituted on a carbon not bound to the nitrogen by one or more substituents each selected from the group consisting of fluorine, methyl, cyano, oxo and hydroxyl;
or a pharmaceutically acceptable salt thereof.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

As used herein, each of said $C_{1-6}$alkyl, $C_{2-6}$alkenyl, $C_{2-6}$alkynyl, and $C_{3-6}$cycloalkyl wherever they occur, including particularly when referring to $R^5$ and $R^3$, may be optionally independently substituted by one or more substituents each independently selected from the group consisting of halogen, hydroxyl, cyano, CF3, $NR^aR^b$, $C_{1-6}$alkyl, $C_{1-6}$alkoxy, $C_{1-6}$alkyl-S—, $C_{1-6}$alkoxy$C_{1-6}$alkoxy, $C_{1-6}$alkoxy$C_{1-6}$alkyl-S—, $C_{1-6}$alkoxycarbonyl, and $(NR^aR^b)$carbonyl- The term "carbonyl" as used herein refers to the radical —C(O)—.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively, may optionally contain one, two or more non cumulative non aromatic double or triple bonds. Exemplary cycloalkyl groups include, but are not limited to, cyclohexyl, cyclopentyl, cyclopentenyl, cyclobutyl or cyclopropyl. Such cycloalkyl may include replacement of one or more ring carbon atoms with Nitrogen or Oxygen heteroatoms. As used herein, cycloalkyl includes "bicycloalkyl" which is defined to include a cycloalkyl as defined above which is bridged to a second carbocyclic ring (e.g., bicyclo[2.2.1] heptanyl, bicyclo[3.2.1]octanyl and bicyclo[5.2.0]nonanyl, etc.). Preferably, the bicycloalkyl group has 6 to 20 carbon atoms. More preferably, the bicycloalkyl group has 6 to 15 carbon atoms. Most preferably, the bicycloalkyl group has 6 to 12 carbon atoms. The bicycloalkyl is optionally substituted by 1 to 5 suitable substituents. In one embodiment the bicycloalkyl may optionally contain one, two or more non cumulative non aromatic double or triple bonds.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The terms "halo" or "halogen" as used herein refer to F, Cl, Br, or I.

As used herein, the term "aryl" is defined to include all-carbon monocyclic or fused-ring polycyclic (i.e., rings which share adjacent pairs of carbon atoms) groups having a completely conjugated pi-electron system. The aryl group has 6, 8, 9, 10 or 12 carbon atoms in the ring(s). In one embodiment the aryl group has 6 or 10 carbon atoms in the ring(s). One aryl group of particular interest is the 6 carbon atom phenyl ring. For example, as used herein, the term aryl means aromatic radicals containing from 6 to 10 carbon atoms such as phenyl, naphthyl, tetrahydronaphthyl, anthracenyl, indanyl and the like. The aryl group is optionally substituted by 1 to 5 suitable substituents. Substituents of particular interest include alkyl, alkoxymethyl, hydroxymethyl, aminomethyl, amidomethyl, carbamoylmethyl, and fluoromethyl.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furanyl, thiophenyl, pyrrolyl, thiazolyl, oxazolyl, isothiazolyl, isoxazolyl, imidazolyl, pyrazolyl, triazolyl, pyridinyl, pyrimidinyl, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like.

The terms "heterocyclyl" or "heterocyclic group" are art-recognized and refer to saturated or partially unsaturated, 4-10 membered ring structures, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran. Other examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Further examples of said heterocycloalkyl rings are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2 pyrazolidin-2-yl, 1,3-pyrazolidin-1-yl, 1,2-tetrahydrothiazin-2-yl, 1,3 tetrahydrothiazin-3-yl, 1,2-tetrahydrodiazin-2-yl, 1,3 tetrahydrodiazin-1-yl, 1,4-oxazin-2-yl, 1,2,5-oxathiazin-4-yl and the like. The heterocycloalkyl ring is optionally substituted by 1 to 5 suitable substituents.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to an OH functionality.

The term "oxo" as used herein refers to a carbonyl functionality (e.g., C=O).

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The compounds of Formula I (and Formulae Ia io) may exist in the form of pharmaceutically acceptable salts such as, e.g., acid addition salts and base addition salts of the compounds of Formula I. The phrase "pharmaceutically acceptable salt(s)", as used herein, unless otherwise indicated, includes salts of acidic or basic groups which may be present in the compounds of Formula I.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

As used herein the terms ""Formula I" and "Formula I or pharmaceutically acceptable salts thereof" (including all subgeneric Formulae Ia io)) are defined to include all forms of the compound of Formula I, including hydrates, solvates, isomers, crystalline and non-crystalline forms, isomorphs, polymorphs, metabolites, and prodrugs thereof.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Treating" includes any effect, e.g., lessening, reducing, modulating, or eliminating, that results in the improvement of the condition, disease, disorder and the like.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of e.g., schizophrenia desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in substantially relief of symptoms associated with schizophrenia.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesultonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may be chiral or exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a stereogenic center implicitly. The present invention encompasses various stereoisomers of these compounds and mixtures thereof. Mixtures of enantiomers or diastereomers may be designated "(±)" in nomenclature, but the skilled artisan will recognize that a structure may denote a stereogenic center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO-Na+, —COO—K+, or —SO$_3$—Na+) or non-ionic (such as —N—N+(CH$_3$)$_3$) polar head group. For more information, see Crystals and the Polarizing Microscope by N. H. Hartshorne and A. Stuart, 4th Edition (Edward Arnold, 1970).

Hereinafter all references to compounds of formula I include references to salts, solvates, multi-component complexes and liquid crystals thereof and to solvates, multi-component complexes and liquid crystals of salts thereof.

The compounds of the invention include compounds of formula I as hereinbefore defined, including all polymorphs and crystal habits thereof, prodrugs and isomers thereof (including optical, geometric and tautomeric isomers) as hereinafter defined and isotopically-labeled compounds of formula I.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^2$H, $^{13}$C, $^{14}$C, $^{15}$N, $^{18}$O, $^{17}$O, $^{31}$P, $^{32}$P, $^{35}$S, $^{18}$F, and $^{31}$Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-6}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of the invention contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, (α-amino($C_{1-4}$)alkylcarbonyl, arylalkylcarbonyl and α-aminoalkylcarbonyl, or α-aminoalkylcarbonyl-α-aminoalkylcarbonyl, where each aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al, Molecules 2008, 13, 519 and references therein.

An embodiment of the invention relates to compounds of Formula I wherein $R^C$ is selected from the group consisting of cyano, hydrogen, halogen, C(O)NR$^a$R$^b$, —C(O)OH, —C(O)O($C_{1-6}$)alkyl, ($C_{2-6}$)alkenyl, ($C_{2-6}$)alkynyl and heteroaryl (optionally substituted by $C_{1-4}$alkyl or halogen).

An embodiment of the invention relates to compounds of Formula I, wherein $R^1$ is selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, —C(O)OH, —C(O)OC$_{1-6}$alkyl, ($C_{3-6}$)cycloalkyl and phenyl (optionally substituted by one, two or three substituents each selected from halogen, $C_{1-6}$alkyl, $C_{1-6}$alkoxy, C(O)OH, —C(O)OC$_{1-6}$alkyl and NR$^a$R$^b$); t is 0, 1 or 2.

An embodiment of the invention relates to compounds of Formula I, wherein $R^2$, $R^3$ and $R^4$ are each independently selected from the group consisting of hydrogen, halogen, hydroxyl, $C_{1-6}$alkyl, $C_{2-6}$alkenyl, $C_{2-6}$alkynyl, $C_{1-6}$alkoxy, $C_{3-6}$cycloalkyl and phenyl (optionally substituted by one or two substituents each selected from halogen or methyl); or when q or m is two, each of said $R^3$ or $R^4$ may be taken together with the carbon to which they are attached to form a 3-5 membered carbocyclic ring or a 4-5 membered heterocyclic ring having at least one heteroatom;

An embodiment of the invention relates to compounds of Formula I, wherein $R^4$ for each occurrence is independently selected from the group consisting of hydrogen, halogen, hydroxyl, ($C_{1-6}$)alkyl, ($C_{2-6}$)alkenyl, ($C_{2-6}$)alkynyl, ($C_{1-6}$)alkoxy, ($C_{1-6}$)cycloalkyl and phenyl (optionally substituted by one or two substituents each selected from halogen or methyl);

An embodiment of the invention relates to compounds of Formula I, wherein when $R^2$, $R^3$ or $R^4$ is bound to a carbon adjacent to a ring nitrogen, $R^2$, $R^3$ or $R^4$ must be other than halogen, hydroxyl or $C_{1-6}$alkoxy.

An embodiment of the invention relates to compounds of Formula I, wherein $R^5$ independently for each occurrence is selected from the group consisting of hydrogen, C1-6alkyl, C1-6alkoxy, halogen, cyano, $C_{2-6}$alkenyl, $C_{2-6}$alkynyl, $C_{3-6}$cycloalkyl, heteroaryl, phenyl, —NR$^a$R$^b$, —C(O)OH, $C_{1-6}$alkylcarbonyl, $C_{1-6}$alkoxycarbonyl, (NR$^a$R$^b$)carbonyl-, $C_{1-6}$alkyl-S(O)$_w$— (where w is 0, 1 or 2), and $R^aR^bN$—SO$_w$— (where w is 0, 1 or 2); wherein heteroaryl and phenyl may optionally be substituted by one, two or three substituents each selected from the group consisting of halogen, cyano, $C_{1-6}$ alkyl, $C_{1-6}$alkoxy, and —NR$^a$R$^b$;

or two R$^5$, together with two adjacent carbons on ring A to which they are attached, form a 5-7 membered unsaturated, partially unsaturated or saturated carbocyclic or heterocyclic ring;

An embodiment of the invention relates to compounds of Formula I, wherein R$^6$ for each occurrence is independently selected from the group consisting of hydrogen, $C_{1-6}$alkyl, $C_{3-6}$cycloalkyl, —C(O)—$C_{1-6}$alkyl, and phenyl (optionally substituted by one or two substituents each selected from halogen or methyl);

R$^7$ is selected from the group consisting of hydrogen or $(C_{1-6})$alkyl;

R$^3$ is selected from the group consisting of hydrogen or $(C_{1-6})$alkyl;

wherein each of said $C_{1-6}$alkyl, $C_{2-6}$alkenyl, $C_{2-6}$alkynyl, and $C_{3-6}$cycloalkyl wherever they occur may be optionally independently substituted by one or more substituents each independently selected from the group consisting of halogen, hydroxyl, cyano, and NR$^a$R$^b$;

R$^a$ and R$^b$ are independently selected, for each occurrence, from the group consisting of: hydrogen, $C_{1-4}$alkylcarbonyl, cyclopropyl, and $C_{1-3}$alkyl; wherein $C_{1-3}$alkyl may optionally be substituted on a carbon not bound to the nitrogen by one or more substituents each selected from the group consisting of fluorine, cyano, oxo and hydroxyl; or R$^a$ and R$^b$, together with the nitrogen to which they are attached, form a 4-6 membered heterocyclic ring which may have an additional heteroatom selected from O, S, or N (optionally substituted by one or two methyl groups); and wherein the 4-6 membered heterocyclic ring may optionally be substituted on a carbon not bound to the nitrogen by one or more substituents each selected from the group consisting of fluorine, methyl, cyano, oxo and hydroxyl.

An embodiment of the invention relates to compounds of Formula I wherein R$^3$ is selected from the group consisting of hydrogen, halogen, hydroxyl, $C_{1-6}$alkyl, $C_{2-6}$alkenyl, $C_{2-6}$alkynyl, $C_{1-6}$ alkoxy, —CO$_2$H, —CO$_2$C$_{1-6}$alkyl, —CO$_2$NR$^a$R$^b$, NR$^a$R$^b$, $C_{3-6}$cycloalkyl and phenyl; wherein each of said $C_{1-6}$alkyl, $C_{2-6}$alkenyl, $C_{2-6}$alkynyl, and $C_{3-6}$cycloalkyl wherever they occur may be optionally independently substituted by one or more substituents each independently selected from the group consisting of halogen, hydroxyl, cyano, $C_{3-6}$cycloalkyl (wherein one or more ring carbon atoms is replaced by N, O or S), CF$_3$, NR$^a$R$^b$, $C_{1-6}$alkyl, $C_{1-6}$alkoxy, $C_{1-6}$alkyl-S—, $C_{1-6}$alkoxyC$_{1-6}$alkoxy, $C_{1-6}$alkoxyC$_{1-6}$alkyl-S—, $C_{1-6}$alkoxycarbonyl, and (NR$^a$R$^b$)carbonyl-.

An embodiment of the invention relates to compounds of Formula I, wherein R$^3$ are each independently selected from the group consisting of hydrogen, fluoro, methoxy, methyl, hydroxyl, $C_{1-6}$alkoxymethyl, hydroxymethyl, aminomethyl, amidomethyl, carbamoylmethyl, fluoromethyl.

In certain embodiments, a disclosed compound may be represented by Formula I which has the formula

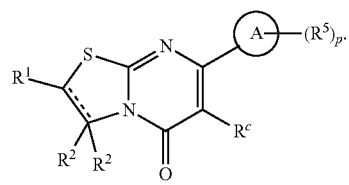

Ia

In certain embodiments, a disclosed compound may be represented by Formula I which has the formula

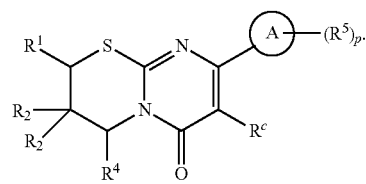

Ib

In certain embodiments, a disclosed compound may be represented by Formula I which has the formula

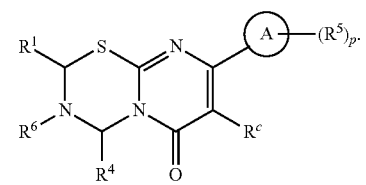

Ic

In certain embodiments, a disclosed compound may be represented by Formula I which has the formula

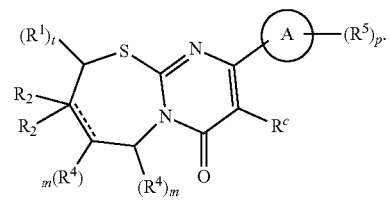

Id

In certain embodiments, a disclosed compound may be represented by Formula I which has the formula

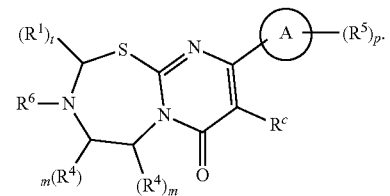

Ie

In certain embodiments, a disclosed compound may be represented by Formula I which has the formula If

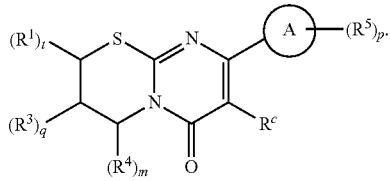

In certain embodiments, a disclosed compound may be represented by Formula I which has the formula Ig

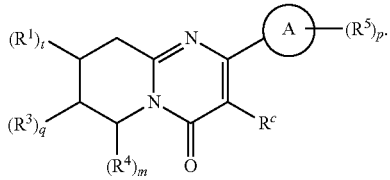

In certain embodiments, a disclosed compound may be represented by Formula I which has the formula Ih

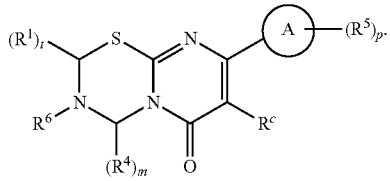

In certain embodiments, a disclosed compound may be represented by Formula I which has the formula Ii

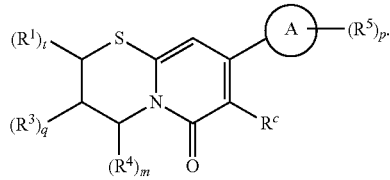

In certain embodiments, a disclosed compound may be represented by Formula I which has the formula Ij

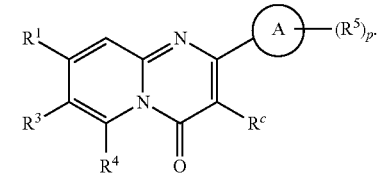

In certain embodiments, a disclosed compound may be represented by Formula I which has the formula Ik

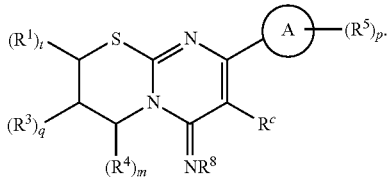

In certain embodiments, a disclosed compound may be represented by Formula I which has the formula Il

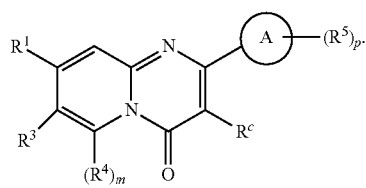

In certain embodiments, a disclosed compound may be represented by Formula I which has the formula Im

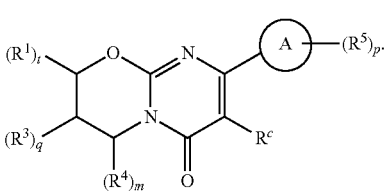

In certain embodiments, a disclosed compound may be represented by Formula I which has the formula In

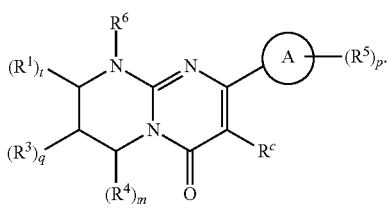

In certain embodiments, a disclosed compound may be represented by Formula I which has the formula Io

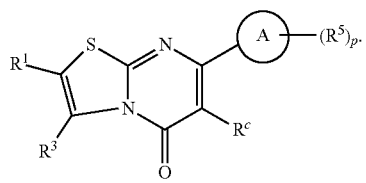

In certain embodiments, a disclosed compound may be represented by Formula I which has the formula

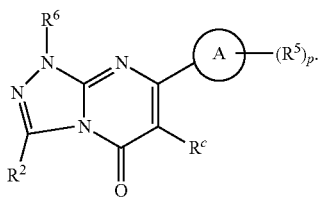
Ip

In certain embodiments, a disclosed compound may be represented by Formula I which has the formula

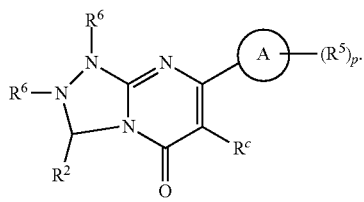
Iq

In certain embodiments, a disclosed compound may be represented by Formula I which has the formula

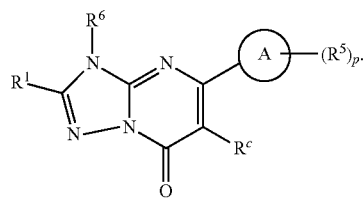
Ir

In certain embodiments, a disclosed compound may be represented by Formula I which has the formula

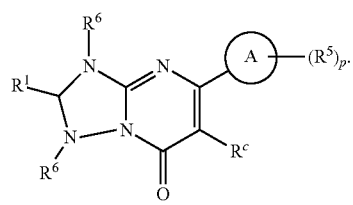
Is

Another embodiment of the invention wherein the compound is represented by:

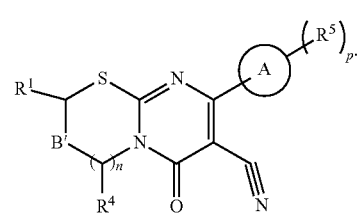

Another embodiment of the invention, includes compounds of Formulae If-Im, wherein ring A is phenyl.

Another embodiment of the invention, includes compounds of Formulae If-Im, wherein ring A is 5-7 membered heteroaryl having one, two or three heteroatoms each independently selected from the group consisting of N, S, and O. More particularly wherein said ring A is pyridinyl, pyrimidinyl or pyridazinyl.

Another embodiment of the invention, includes compounds wherein $R^5$ is independently for each occurrence selected from the group consisting of hydrogen, halogen, methoxy, methyl, ethyl, propyl, isopropyl, cyclopropyl, t-butyl, t-butyloxy, t-butylthio, pyridinyl (optionally substituted by halogen), and phenyl (optionally substituted by halogen). Another embodiment relates to compounds wherein $R^5$ is t-butyl.

Another embodiment of the invention includes compounds wherein $R^c$ is —CN.

Another embodiment of the invention includes compounds wherein p is 0, 1 or 2.

Another embodiment of the invention, includes compounds wherein p is 1.

Another embodiment of the invention includes compounds wherein p is 2.

Another embodiment of the invention includes compounds wherein n is 1. Another embodiment of the invention includes compounds wherein n is 0.

Another embodiment of the invention includes compounds, wherein $R^4$ is selected from the group consisting of hydrogen, $C_{1-4}$alkyl, and phenyl. Another embodiment of the invention, includes compounds, wherein $R^4$ is hydrogen.

Another embodiment of the invention, includes compounds wherein $R^1$ is selected from the group consisting of hydrogen, $(C_{1-6})$alkyl, $(C_{2-6})$alkenyl, $(C_{2-6})$alkynyl, $(C_{3-6})$ cycloalkyl and phenyl (optionally substituted by one or two substituents each selected from halogen or methyl), t is 0, 1 or 2. Another embodiment of the invention, includes compounds wherein $R^1$ is hydrogen.

Another embodiment of the invention, includes compounds wherein one of said $R^3$ is selected from the group consisting of hydrogen, methoxy, methyl and hydroxyl; and the other of said $R^3$ is selected from the group consisting of hydrogen or methyl; wherein when $R^3$ is bound to a carbon adjacent to a ring nitrogen, $R^3$ cannot be methoxy or hydroxyl.

Another embodiment of the invention includes compounds wherein $R^3$ are each independently selected from the group consisting of hydrogen, fluoro, methoxy, methyl, and hydroxyl.

Another embodiment of the invention includes compounds wherein each $R^3$ is hydrogen.

Another embodiment of the invention, includes compounds wherein the compound is represented by:

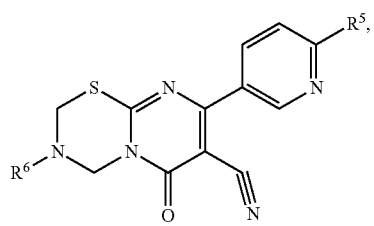

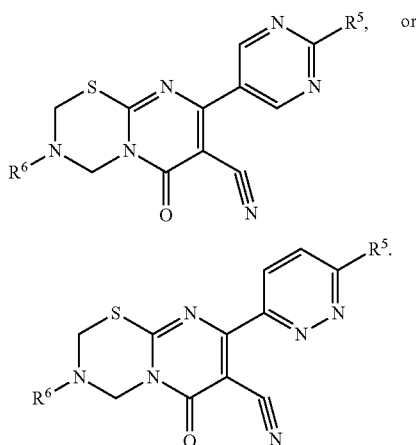

Another embodiment of the invention, includes compounds wherein the compound is represented by:

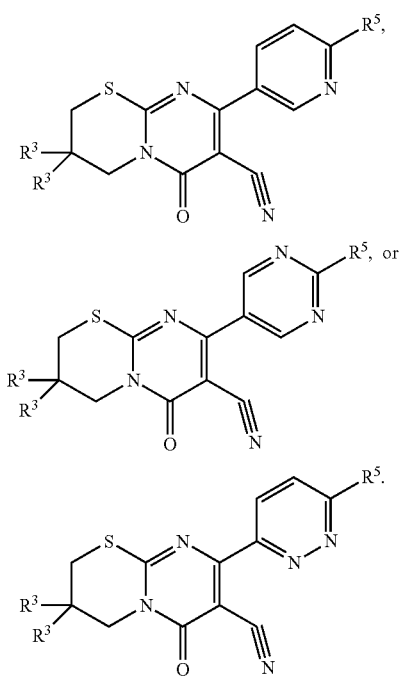

Another embodiment of the invention, includes compounds wherein the compound is represented by:

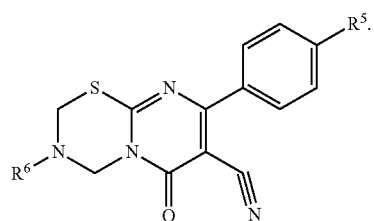

Another embodiment of the invention includes compounds wherein the compound is represented by:

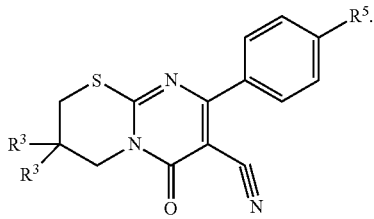

Another embodiment of the invention includes compounds wherein $R^5$ is t-butyl.

In certain embodiments a compound of Formula I may be represented by:

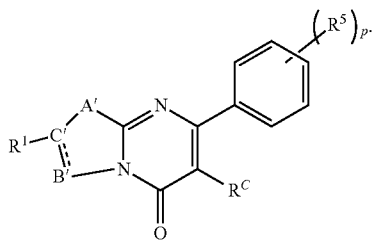

In certain embodiments, ring A may be pyridinyl, pyrimidinyl or pyridazinyl. In certain other embodiments, wherein $R^1$ may be cyano.

In an embodiment, A' may be S, C' may be Carbon and B' may be $CNR^aR^b$.

In another embodiment, A' may be $NR^6$, C' may be N and B' may be $CR^3$. In a further embodiment, A' may be $NR^6$, C' may be N and B' may be C=O. In yet a further embodiment, A' may be $NR^6$, C' may be Carbon and B' may be N.

In another embodiment the compound may have the Formula

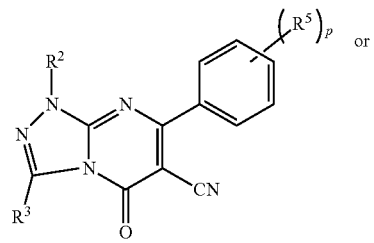

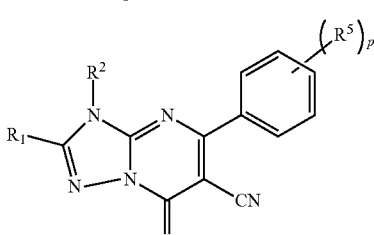

For example, a disclosed compound may be selected from the group consisting of:

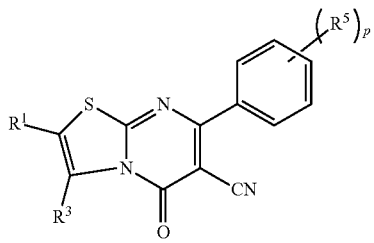

In an embodiment, a disclosed compound may be represented by:

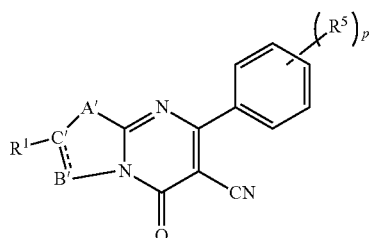

Also provided herein are compounds represented by:

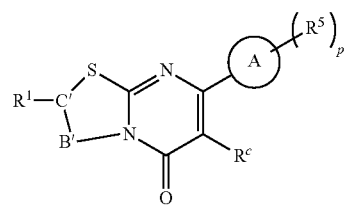

and pharmaceutically acceptable salts, stereoisomers and prodrugs thereof, wherein:
ring A is phenyl or a 5-6 membered heteroaryl;
$R^c$ is selected from the group consisting of cyano, hydrogen, halogen, $C(O)NR^aR^b$, —C(O)OH, —C(O)OC$_{1-6}$ alkyl, $C_{2-6}$alkenyl, $C_{2-6}$alkynyl and heteroaryl (optionally substituted by $C_{1-4}$ alkyl or halogen);
p is 0, 1, 2 or 3;
C' is $C_{1-2}$alkylene;
B' is selected from the group consisting of C(O)OH, and —C(O)OC$_{1-6}$alkyl;
Each $R^5$ is independently selected from the group consisting of hydrogen, $C_{1-6}$alkyl, $C_{1-6}$alkoxy, halogen, cyano, $C_{2-6}$alkenyl, $C_{2-6}$alkynyl, $C_{3-6}$cycloalkyl, heteroaryl, phenyl, —NR$^a$R$^b$, —C(O)OH, $C_{1-6}$alkylcarbonyl, $C_{1-6}$alkoxycarbonyl, NR$^a$R$^b$carbonyl-, $C_{1-6}$alkyl-S(O)$_w$— (where w is 0, 1 or 2), and R$^a$R$^b$N—SO$_w$— (where w is 0, 1 or 2); wherein heteroaryl and phenyl are optionally substituted by one, two or three substituents each selected from the group consisting of halogen, cyano, $C_{1-6}$alkyl, $C_{1-6}$alkoxy, and —NR$^a$R$^b$;
wherein $C_{1-6}$alkyl, $C_{2-6}$alkenyl, $C_{2-6}$alkynyl, and $C_{3-6}$cycloalkyl, for each occurrence, may be optionally substituted by one or more substituents each independently selected from the group consisting of halogen, hydroxyl, cyano, and NR$^a$R$^b$;

$R^a$ and $R^b$ are independently selected, for each occurrence, from the group consisting of hydrogen, $C_{1-4}$alkylcarbonyl, cyclopropyl, and $C_{1-3}$alkyl; wherein $C_{1-6}$alkyl may optionally be substituted on a carbon not bound to the nitrogen by one or more substituents each selected from the group consisting of fluorine, cyano, oxo and hydroxyl; or
$R^a$ and $R^b$, together with the nitrogen to which they are attached, form a 4-6 membered heterocyclic ring which may have an additional heteroatom selected from O, S, or N (optionally substituted by one or two methyl groups); and wherein the 4-6 membered heterocyclic ring may optionally be substituted on a carbon not bound to the nitrogen by one or more substituents each selected from the group consisting of fluorine, methyl, cyano, oxo and hydroxyl.

Another embodiment relates to a compound represented by:

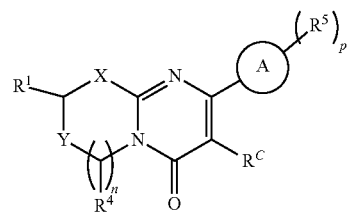

and pharmaceutically acceptable salts, stereoisomers and prodrugs thereof, wherein:
Ring A is a 5-7 membered heteroaryl having one, two or three heteroatoms each selected from N, S, and O, and X is either S or CR$^6$R$^7$; or
Ring A is phenyl, or a 5-7 membered heteroaryl having one, two or three heteroatoms each selected from N, S, and O; and X is either O or CR$^6$R$^7$;
$R^C$ is selected from the group consisting of cyano, hydrogen, halogen, C(O)NR$^a$R$^b$, —C(O)OH, —C(O)OC$_{1-6}$ alkyl, $C_{2-6}$alkenyl, $C_{2-6}$alkynyl and heteroaryl (optionally substituted by $C_{1-4}$alkyl or halogen);
n is 0 and Y is CR$^2$R$^3$; or
n is 1 or 2 and Y is CR$^2$R$^3$ or NR$^{22}$;
p is 0, 1, 2 or 3;
$R^1$ is selected from the group consisting of hydrogen, $C_{1-6}$alkyl, $C_{2-6}$alkenyl, $C_{2-6}$alkynyl, $C_{3-6}$cycloalkyl and phenyl (optionally substituted by one or two substituents each selected from halogen or methyl);
$R^4$ for each occurrence is selected from the group consisting of hydrogen, halogen, hydroxyl, $C_{1-6}$alkyl, $C_{2-6}$alkenyl, $C_{2-6}$alkynyl, $C_{1-6}$alkoxy, $C_{3-6}$cycloalkyl and phenyl (optionally substituted by one or two substituents each selected from halogen or methyl);
$R^2$ and $R^3$ are each independently selected from the group consisting of hydrogen, halogen, hydroxyl, $C_{1-6}$alkyl, $C_{2-6}$alkenyl, $C_{2-6}$alkynyl, $C_{1-6}$alkoxy, $C_{3-6}$cycloalkyl and phenyl (optionally substituted by one or two substituents each selected from halogen or methyl); or $R^2$ and $R^3$ taken together with the carbon to which they are attached form a 3-5 membered carbocyclic ring or a 4-5 membered heterocyclic ring having at least one heteroatom;
wherein when $R^2$, $R^3$ or $R^4$ is bound to a carbon adjacent to a ring nitrogen, $R^2$, $R^3$ or $R^4$ cannot be halogen, hydroxyl or $C_{1-6}$alkoxy;
$R^{22}$ is selected from the group consisting of hydrogen, $C_{1-4}$alkyl, C cycloalkyl, —C(O)—$C_{1-6}$alkyl, and phenyl (optionally substituted by one or two substituents each selected from halogen or methyl);

R⁵ independently for each occurrence is selected from the group consisting of hydrogen, $C_{1-6}$alkyl, $C_{1-6}$alkoxy, halogen, cyano, $C_{2-6}$alkenyl, $C_{2-6}$alkynyl, $C_{3-6}$cycloalkyl, heteroaryl, phenyl, —NR$^a$R$^b$, —C(O)OH, $C_{1-6}$alkylcarbonyl, $C_{1-6}$alkoxycarbonyl, NR$^a$R$^b$carbonyl-, $C_{1-6}$alkyl-S(O)$_w$— (where w is 0, 1 or 2), and R$^a$R$^b$N—SO$_w$— (where w is 0, 1 or 2); wherein heteroaryl and phenyl may optionally be substituted by one, two or three substituents each selected from the group consisting of halogen, cyano, $C_{1-6}$alkyl, $C_{1-6}$alkoxy, and —NR$^a$R$^b$;

or two R⁵, together with two adjacent carbons on ring A to which they are attached, form a 5-7 membered unsaturated, partially unsaturated or saturated carbocyclic or heterocyclic ring;

wherein $C_{1-6}$ alkyl, $C_{2-6}$alkenyl, $C_{2-6}$alkynyl, and $C_{3-5}$cycloalkyl may be optionally substituted by one or more substituents each independently selected from the group consisting of halogen, hydroxyl, cyano, and NR$^a$R$^b$;

R⁶ and R⁷ are independently selected from the group consisting of hydrogen, $C_{1-6}$alkyl, $C_{2-6}$alkenyl, $C_{2-6}$alkynyl, $C_{3-6}$cycloalkyl and phenyl (optionally substituted by one or two substituents each selected from halogen or methyl);

R$^a$ and R$^b$ are independently selected, for each occurrence, from the group consisting of hydrogen, $C_{1-4}$ alkylcarbonyl, cyclopropyl, and $C_{1-3}$alkyl; wherein $C_{1-3}$alkyl may optionally be substituted on a carbon not bound to the nitrogen by one or more substituents each selected from the group consisting of fluorine, cyano, oxo and hydroxyl; or R$^a$ and R$^b$, together with the nitrogen to which they are attached, form a 4-6 membered heterocyclic ring which may have an additional heteroatom selected from O, S, or N (optionally substituted by one or two methyl groups); and wherein the 4-6 membered heterocyclic ring may optionally be substituted on a carbon not bound to the nitrogen by one or more substituents each selected from the group consisting of fluorine, methyl, cyano, oxo and hydroxyl.

Other compounds of interest include

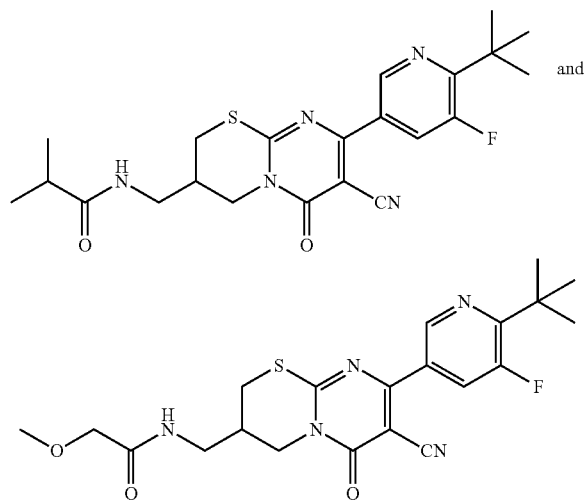

Procedures for making compounds disclosed herein are provided below. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of any of Formula I, as depicted above, or any of the intermediates described below, can be further derivatised by using one or more standard synthetic methods known to those skilled in the art. Such methods can involve substitution, oxidation or reduction reactions. These methods can also be used to obtain or modify compounds of Formula I or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide: or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride) followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl suphonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid group by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyllithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (I) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of Formula I can be prepared by the reaction of a compound of Formula I with an appropriate acid or base in a suitable solvent, or mixture of solvents (such as an ether, for example, diethyl ether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diastereomeric derivatives (such as salts) can be produced by reaction of a mixture of enantiomers of a compound of Formula I (such a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the disclosure provides methods of modulating the activity of the NMDA receptor. Such methods may for example, comprise exposing said receptor to a compound described herein. In some embodiments, the compound utilized by one or more of the foregoing methods is one of the generic, subgeneric, or specific compounds described herein, such as a compound of Formula I. The ability of compounds described herein to modulate the NMDA receptor can be evaluated by procedures known in the art and/or described herein.

In certain embodiments, the present disclosure provides a method of treating and or ameliorating a disease and/or disorder of the nervous system in a patient in need thereof by administering an effective amount of a disclosed compound. Exemplary diseases and disorders of the nervous system include psychiatric diseases, neurological diseases, and neurodevelopmental disorders, further described below.

In one embodiment, an exemplary psychiatric disease is schizophrenia. Schizophrenia is a debilitating mental disorder encompassing three symptom domains: positive (psychosis, hallucination, delusions), negative (withdrawal), and cognitive (global reduction in cognitive ability). Positive symptoms of Schizophrenia typically emerge early in adulthood and are treated with antipsychotic medications. However, cognitive deficits are severe, emerge in the adolescent prodromal stage, are resistant to antipsychotic therapy, and are the leading cause of lifetime disability as measured by impaired global function (inability to live independently, unemployment, etc). NMDA receptor hypofunction is the leading hypothesis for the cause of schizophrenia. This hypothesis is supported by substantial clinical evidence including clinical pharmacology, electrophysiology, imaging, cognition, computational neuroscience, neuroanatomical studies, and genetics.

The present disclosure provides herein a method of treating schizophrenia, including positive, negative, and cognitive symptoms, in a patient in need thereof, comprising administering an effective amount of a disclosed compound. For example, provided herein are methods of ameliorating positive, negative, and cognitive symptoms of a patient not adequately treated by approved antipsychotic medications, for example the treatment of cognitive impairments in schizophrenia, by administering an effective amount of a disclosed compound to such a patient.

Also provided herein are methods to improve cognitive and global function, and/or substantially preventing the onset of schizophrenia in people at risk of developing schizophrenia, by administering an effective amount of a disclosed compound to such a patient.

Contemplated herein are methods of treating and/or ameliorating cognitive and emotional deficits and other symptoms associated with exemplary psychiatric disorders including major depressive disorder, and including but not limited to those suffering from bipolar disorder, obsessive-compulsive disorder, dysphobic disorder, dysthymic disorder, psychotic depression, post-traumatic stress disorder, and other anxiety disorders. For example, provided herein are methods of treating attention deficit disorder, ADHD (attention deficit hyperactivity disorder), schizophrenia, anxiety, amelioration of opiate, nicotine and/or ethanol addiction (e.g., method of treating such addiction or ameliorating the side effects of withdrawing from such addiction), spinal cord injury, diabetic retinopathy, traumatic brain injury, and/or post-traumatic stress syndrome in a patient in need thereof, that includes administering a disclosed compound.

In other embodiments, provided herein is a method of treating and/or ameliorating cognitive and emotional deficits and other symptoms resulting from neurological diseases, including but not limited to a patient suffering from Alzheimer's disease, Parkinson's disease, Huntington's disease, amyotrophic lateral sclerosis, multiple sclerosis, and seizure disorders comprising administering to the patient an effective amount of a disclosed compound.

The present disclosure contemplates a method of treating and/or ameliorating dysfunction caused by neurodevelopmental disorders, e.g., abnormal brain development, including but not limited to Rett Syndrome, Attention Deficit and Hyperactivity Disorder, autism and autism spectrum disorders such as Phelan-McDermid Syndrome, and other forms of intellectual disability such as Fragile X syndrome, tuberous sclerosis, Smith-Lemli-Opitz Syndrome, and Down's syndrome. A method is also provided to treat patients suffering from abnormal brain function resulting from infections of the central nervous system, exposure to toxic agents or other xenobiotics or naturally occurring toxins, and/or autoimmune disorders including, but not limited to anti-NMDA receptor encephalitis comprising administering an effective amount of a disclosed compound.

In particular, in certain embodiments, the disclosure provides a method of treating, preventing, and/or preventing the development of the above medical indications comprising administering to a subject in need thereof a therapeutically effective amount of a compound described herein, such as a compound of Formula I.

In certain embodiments, the compound utilized by one or more of the foregoing methods is one of the generic, subgeneric, or specific compounds described herein, such as a compound of Formula I.

Disclosed compounds may be administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment regimen can include a corrective phase, during which dose sufficient to maintain cognitive and/or emotional function is administered, and can be followed by a maintenance phase, during which, e.g., a lower dose sufficient to prevent a deficit in cognitive and/or emotional function is administered. A suitable maintenance dose is likely to be found in the lower parts of the dose ranges provided herein, but corrective and maintenance doses can readily be established for individual subjects by those of skill in the art without undue experimentation, based on the disclosure herein.

The compound of Formula I or a pharmaceutically acceptable salt thereof is optionally used in combination with another active agent. Such an active agent may be, for example, neurological diseases, including but not limited to a patient suffering from Alzheimer's disease, Parkinson's disease, Huntington's disease, amyotrophic lateral sclerosis, multiple sclerosis, and seizure disorders. Accordingly, another embodiment of the invention provides methods of treating neurological and psychiatric disorders associated with NR2D, comprising administering to a mammal an effective amount of a compound of Formula I or a pharmaceutically acceptable salt thereof and further comprising administering another active agent.

As used herein, the term "another active agent" refers to any therapeutic agent, other than the compound of Formula I (or Formulae Ia-Io), or salt thereof, that is useful for the treatment of a subject disorder. Examples of additional therapeutic agents include antidepressants, antipsychotics, anti-pain, anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, 5-HT1A partial agonists, and corticotropin releasing factor (CRF) antagonists. Suitable benzodiazepines include aiprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Pharmaceutical compositions of the present disclosure may also be administered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, Disclosed compounds are not covalently bound to a polymer, e.g., a polycarboxylic acid polymer, or a polyacrylate.

Advantageously, the invention also provides kits for use by, e.g., a consumer in need of a disclosed NMDA modulator. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

In the following Examples, LC-MS conditions for the characterization of the compounds herein are:
1. Analytical HPLC/MS instrumentation: Analysis are performed using a Waters 2545 Binary Gradient Module (Waters Corporation, Milford, MA), a Waters SFO System Fluidics Organizer, a Waters 2996 Diode Array Detector and a Waters 2767 auto-sampler, 3100 mass detector. Data are acquired using MassLynx™ 4.0 software, with OpenLynx™ and AutoLynx™ processing.
2. Analytical HPLC conditions: 4.6×50 mm column; UV 10 spectra/sec, 220-340 nm summed; flow rate 2.0 mL/min; injection volume 5 µL; Gradient condition: mobile phase A is Water with 0.1% formic acid; mobile phase B is acetonitrile with 0.1% formic acid, and the gradient is 1.50 minutes 99.0% A to 95.0% B; 0.5 minutes hold; then recycle to 99.0% A over 0.5 minutes.

$^1$H NMR spectral chemical shifts are expressed in ppm relative to tetramethylsilane. The following abbreviations have been used: br=broad signal, s=singlet, d=doublet, dd=double doublet, ddd=double double doublet, dt=double triplet, t=triplet, td=triple doublet, q=quartet, m=multiplet.

Example 1: Preparation of 7-(6-(tert-butyl) pyridin-3-yl)-5-oxo-2,3-dihydro-5H-thiazolo[3,2-a]pyrimidine-6-carbonitrile 4

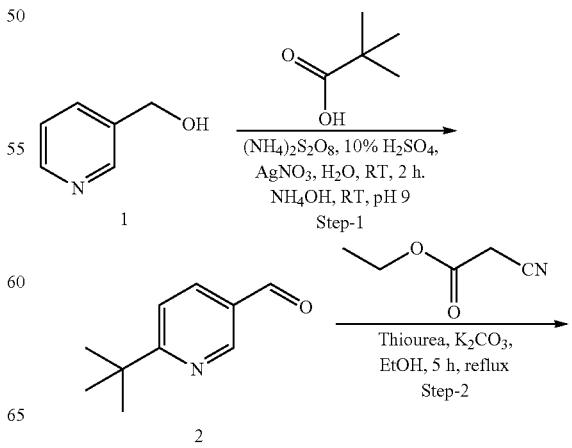

35
-continued

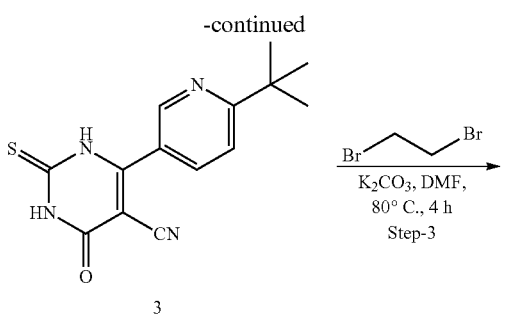

3

Step-1:

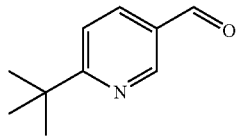

Preparation of 6-(tert-butyl)nicotinaldehyde 2

To a stirred solution of pyridin-3-yl-methanol (1, 0.5 g, 4.58 mmol), pivalic acid (2.34 g, 22.9 mmol) and silver nitrate (0.155 g, 0.91 mmol) in 10% aqueous sulfuric acid solution (4.5 mL) was added a solution of ammonium persulfate (2.09 g, 9.16 mmol) in water (10 mL). The resulting mixture was stirred at room temperature for 2 h. The reaction mixture was basified to pH 9 with aqueous ammonia and extracted with ethyl acetate (2×50 mL). The combined organic layer was dried over anhydrous sodium sulphate, filtered and concentrated. The crude product was purified by silica gel column chromatography using 20% ethyl acetate in hexane to afford the title compound 6-(tert-butyl)nicotinaldehyde (2, 0.26 g, 35%) as a pale yellow liquid. Calculated (M+H): 164.1; Found (M+H): 164.1.

Step-2:

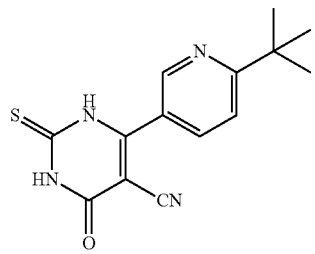 [SMILES: CC(C)(C)c1ccc(-c2[nH]c(=S)[nH]c(=O)c2C#N)cn1]

36

Preparation of 6-(6-(tert-butyl)pyridin-3-yl)-4-oxo-2-thioxo-1,2,3,4 tetrahydropyrimidine-5-carbonitrile 3

A mixture of 6-(tert-butyl)nicotinaldehyde (2, 0.25 g, 1.53 mmol), thiourea (0.12 g, 1.53 mmol), ethyl 2-cyanoacetate (0.16 mL, 1.53 mmol) and potassium carbonate (0.63 g, 4.59 mmol) in ethanol (5 mL) was heated at reflux for 5 h. The reaction mixture was concentrated, the residue was diluted with water (5 mL), neutralized with acetic acid and extracted with ethyl acetate (2×50 mL). The combined organic layer was dried over anhydrous sodium sulphate, filtered and concentrated. The crude product was purified by silica gel column chromatography using 65% ethyl acetate in hexane to afford the title compound 6-(6-(tert-butyl)pyridin-3-yl)-4-oxo-2-thioxo-1,2,3,4-tetrahydropyrimidine-5-carbonitrile (3, 0.14 g, 32%) as pale yellow solid. Calculated (M+H): 287.1; Found (M+H): 287.1.

Step-3:

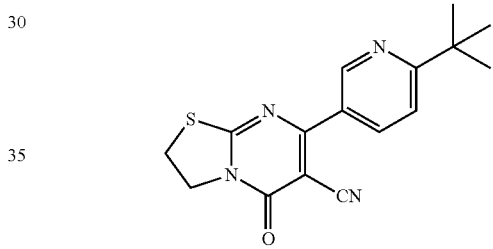

Preparation of 7-(6-(tert-butyl)pyridin-3-yl)-5-oxo-2,3-dihydro-5H-thiazolo[3,2-a]pyrimidine-6-carbonitrile 4

A mixture of 6-(6-(tert-butyl)pyridin-3-yl)-4-oxo-2-thioxo-1,2,3,4-tetrahydropyrimidine-5-carbonitrile (3, 0.11 g, 0.38 mmol), 1,2-dibromoethane (0.072 mL, 0.38 mmol) and potassium carbonate (0.16 g, 1.15 mmol) in N,N-dimethylformamide (2 mL) was heated at 80° C. for 4 h in a sealed tube. The reaction mixture was cooled to room temperature, diluted with water (5 mL) and extracted with ethyl acetate (3×25 mL). The combined organic layer was dried over anhydrous sodium sulphate, filtered and concentrated. The crude product was purified by silica gel column chromatography using 45% ethyl acetate in hexane to afford the title compound 7-(6-(tert-butyl)pyridin-3-yl)-5-oxo-2,3-dihydro-5H-thiazolo[3,2-a]pyrimidine-6-carbonitrile (4 (Example 1), 0.04 g, 36% yield) as white solid. $^1$H NMR (DMSO-$d_6$, 400 MHz) δ (ppm): 8.95 (d, J=1.2 Hz, 1H), 8.16 (dd, $J_1$=2.0 Hz, $J_2$=8.0 Hz, 1H), 7.62 (d, J=8.0 Hz, 1H), 4.46 (t, J=8.0 Hz, 2H), 3.63 (t, J=8.0 Hz, 2H), 1.33 (s, 9H). Calculated (M+H): 313.11; Found (M+H): 313.1, HPLC purity: 99.17%

TABLE 1

The following compounds were prepared by the method described above:

| Ex. # | Structure | IUPAC Name | Analytical Data |
|---|---|---|---|
| 2 | 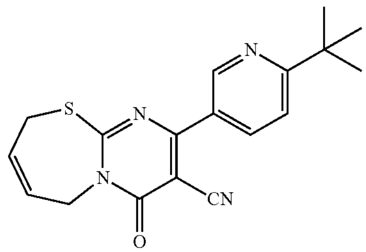 [SMILES: CC(C)(C)c1ccc(-c2nc3n(c(=O)c2C#N)CC=CCS3)cn1] | 2-(6-(tert-butyl)pyridin-3-yl)-4-oxo-6,9-dihydro-4H-pyrimido[2,1-b][1,3]thiazepine-3-carbonitrile | $^1$H-NMR (DMSO-$d_6$, 400 MHz) δ (ppm): 8.97 (s, 1H), 8.19 (dd, $J_1$ = 1.6 Hz, $J_2$ = 8.0 Hz, 1H), 7.62 (d, J = 8.4 Hz, 1H), 6.05-5.97 (m, 1H), 5.62-5.59 (m, 1H), 5.32-5.22 (m, 2H), 3.99-3.94 (m, 1H), 3.42 (d, J = 11.6 Hz, 1H), 1.33 (s, 9H). Calculated (M + H): 339.12, found (M + H): 339.1, HPLC purity: 99.92% |
| 3 | 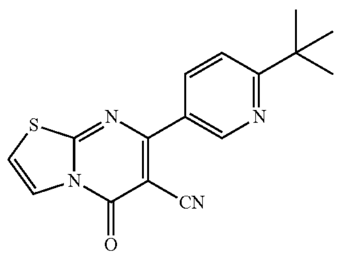 [SMILES: CC(C)(C)c1ccc(-c2nc3sccn3c(=O)c2C#N)cn1] | 7-(6-(tert-butyl)pyridin-3-yl)-5-oxo-5H-thiazolo[3,2-a]pyrimidine-6-carbonitrile | $^1$H-NMR (DMSO-$d_6$, 400 MHz) δ (ppm): 9.00 (d, J = 2.0 Hz, 1H), 8.23-8.21 (m, 2H), 7.78 (d, J = 4.8 Hz, 1H), 7.64 (d, J = 8.4 Hz, 1H), 1.35 (s, 9H); Calculated (M + H): 311.09, found (M + H): 311.1, HPLC purity: 99.72% |

Example 4: Preparation of 7-(2-(tert-butyl)pyrimidin-5-yl)-5-oxo-2,3-dihydro-5H-thiazolo[3,2-a]pyrimidine-6-carbonitrile 6

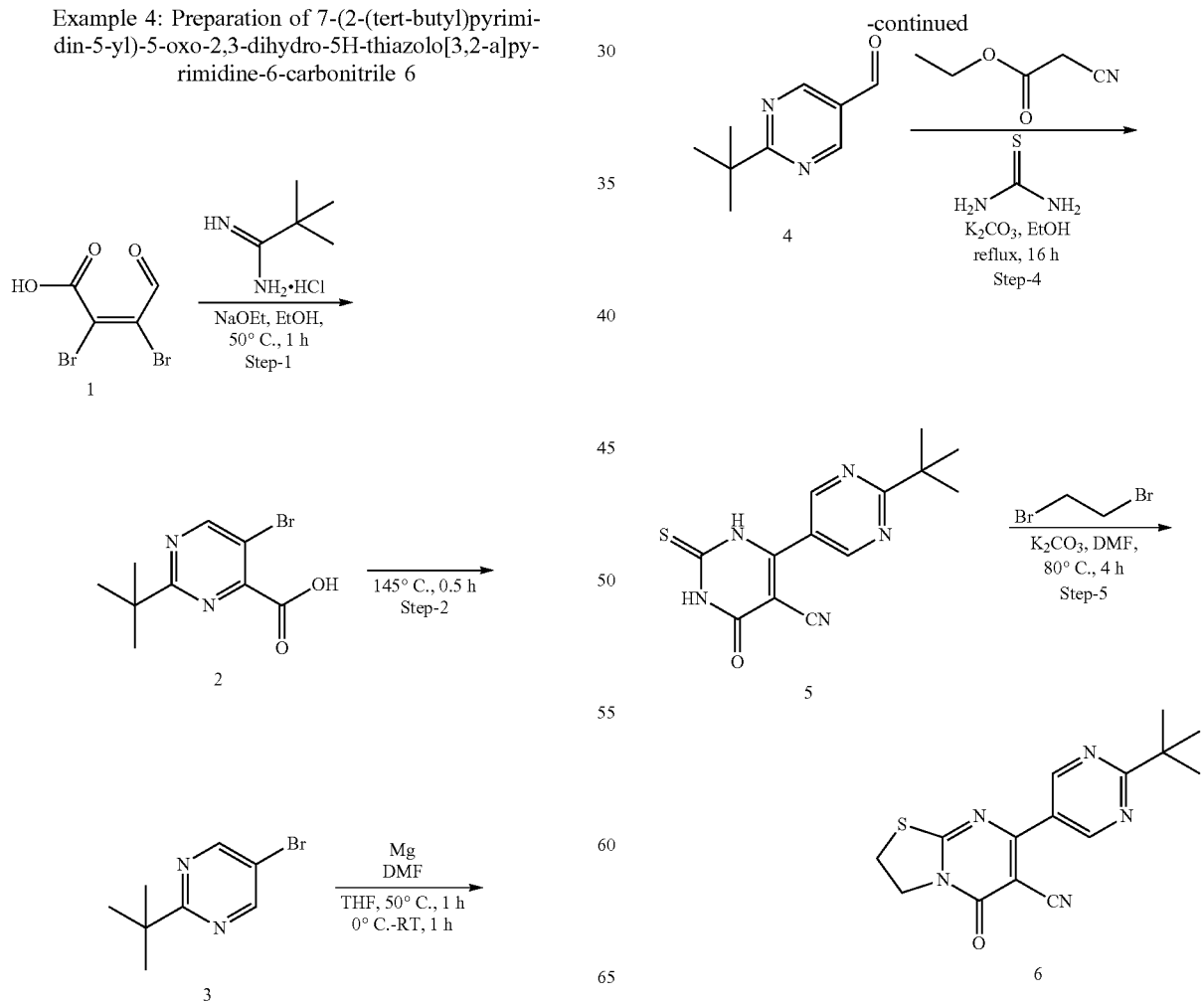

Step-1:

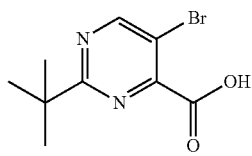

Preparation of
5-bromo-2-(tert-butyl)pyrimidine-4-carboxylic acid
2

A solution of sodium ethoxide in ethanol [14.5 mL of the solution obtained by dissolving sodium (1.38 g, 60.03 mmol) in dry ethanol (24 mL)] was added carefully to a stirred mixture of pivalamidine hydrochloride (5.19 g, 38.01 mmol) and dry ethanol (5 mL) at 40° C. After stirring the mixture for a further 10 min, a solution of mucobromic acid [5.4 mL of the solution obtained by dissolving mucobromic acid (1, 5.16 g, 20.01 mmol) in ethanol (8 mL)] was added to the mixture drop wise resulting in an exothermic reaction during which the temperature raise to 65° C. After the temperature reduced to 50° C., the remainder of the sodium ethoxide solution and mucobromic acid solution were added slowly. The reaction mixture was stirred at 50° C. for 1 h. The reaction mixture was filtered hot and the solid was washed with ethanol. The combined filtrate was concentrated, the residue was washed with 2M hydrochloric acid solution (10 mL), filtered, washed with ice water and dried under suction to afford the title compound 5-bromo-2-(tert-butyl)pyrimidine-4-carboxylic acid (2, 3.9 g, 75% yield) as a brownish solid. Calculated (M+H): 259; Found (M+H): 259.

Step-2:

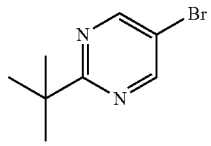

Preparation of 5-bromo-2-(tert-butyl)pyrimidine 3

5-bromo-2-(tert-butyl)pyrimidine-4-carboxylic acid (2, 4.1 g) was heated at 145° C. until it melts into brownish liquid (0.5 h). The reaction mixture was diluted with dichloromethane, slurried with silica gel and purified by silica gel column chromatography using 20% ethyl acetate in hexane to afford the title compound 5-bromo-2-(tert-butyl)pyrimidine (3, 2.7 g, 79% yield) as a colorless liquid. Calculated (M+H): 215.01; Found (M+H): 215

Step-3:

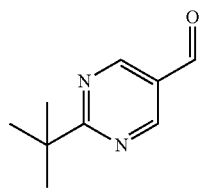

Preparation of
2-(tert-butyl)pyrimidine-5-carbaldehyde 4

To magnesium metal (0.062 g, 2.55 mmol) and few crystals of iodine was added a solution of 5-bromo-2-(tert-butyl)pyrimidine (3, 0.5 g, 2.32 mmol) in tetrahydrofuran (5 mL) drop wise (heated with heat gun occasionally to initiate the reaction). After the complete addition, the reaction mixture was heated at 50° C. for 1 h for completion of the reaction. The reaction mixture was cooled to 0° C. and a solution of N,N-dimethyl formamide (0.18 mL, 2.32 mmol) in tetrahydrofuran (1.5 mL) was added drop wise. The reaction mixture was allowed to attain room temperature (45 min). The reaction mixture was quenched with saturated ammonium chloride solution (20 mL) and extracted with diethyl ether (2×40 mL). The combined organic layer was dried over anhydrous sodium sulphate, filtered and concentrated under mild vacuum (volatile). The crude product was purified by silica gel column chromatography using 2% ethyl acetate in dichloromethane to afford the title compound 2-(tert-butyl)pyrimidine-5-carbaldehyde (4, 0.19 g, 50% yield) as a colorless solid. Calculated (M+H): 165.09; Found (M+H): 165.1.

Step-4:

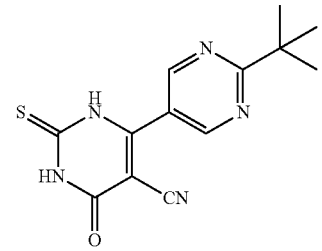

Preparation of 2'-(tert-butyl)-6-oxo-2-thioxo-1,2,3,6-tetrahydro-[4,5'-bipyrimidine]-5-carbonitrile 5

To a solution of 2-(tert-butyl)pyrimidine-5-carbaldehyde (4, 0.2 g, 1.21 mmol), ethyl cyano acetate (0.13 mL, 1.21 mmol) and thiourea (0.092 g, 1.21 mmol) in ethanol (8 mL), potassium carbonate (1 g, 7.30 mmol) was added and the reaction mixture was refluxed at 80° C. for 16 h. The reaction mixture was concentrated, the residue was diluted with ice water (4 mL) and neutralized with acetic acid. The precipitated solid was filtered and dried under suction to afford the title compound 2'-(tert-butyl)-6-oxo-2-thioxo-1,2,3,6-tetrahydro-[4,5'-bipyrimidine]-5-carbonitrile (5, 0.11 g, 31% yield) as a yellow solid. Calculated (M+H): 288.08; Found (M+H): 288.1

Step-5:

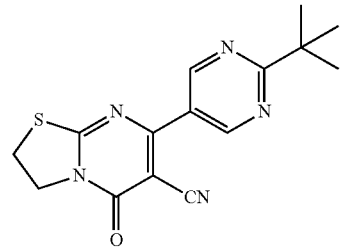 [SMILES: CC(C)(C)c1ncc(-c2nc3n(c(=O)c2C#N)CCS3)cn1]

Preparation of 7-(2-(tert-butyl)pyrimidin-5-yl)-5-oxo-2,3-dihydro-5H-thiazolo[3,2-a]pyrimidine-6-carbonitrile 6

To a solution of 2'-(tert-butyl)-6-oxo-2-thioxo-1,2,3,6-tetrahydro-[4,5'-bipyrimidine]-5-carbonitrile (5, 0.12 g, 0.41 mmol) and 1,2-dibromoethane (0.078 g, 0.41 mmol) in N,N-dimethyl formamide (7 mL), potassium carbonate (0.173 g, 1.25 mmol) was added and the reaction mixture was heated at 80° C. for 1 h. The reaction mixture was diluted with water (20 mL) and extracted with ethyl acetate (2×40 mL). The combined organic layer was dried over anhydrous sodium sulphate, filtered and concentrated. The crude product was purified by silica gel column chromatography using 40% ethyl acetate in hexane to afford the title compound 7-(2-(tert-butyl)pyrimidin-5-yl)-5-oxo-2,3-dihydro-5H-thiazolo[3,2-a]pyrimidine-6-carbonitrile 6 (example 4), 0.014 g, 11% yield) as an off-white solid. $^1$H NMR (400 MHz, DMSO-de) δ (ppm): 9.16 (s, 2H), 4.47 (t, J=8 Hz, 2H), 3.64 (t. J=8.4 Hz, 2H), 1.38 (s, 9H). Calculated (M+H): 314.10; Found (M+H): 314.1. HPLC purity: 99.96%

Example 5: Preparation of 8-(4-(tert-butyl)phenyl)-6-oxo-3-phenyl-3,4-dihydro-2H,6H-pyrimido[2,1-b][1,3,5]thiadiazine-7-carbonitrile 3

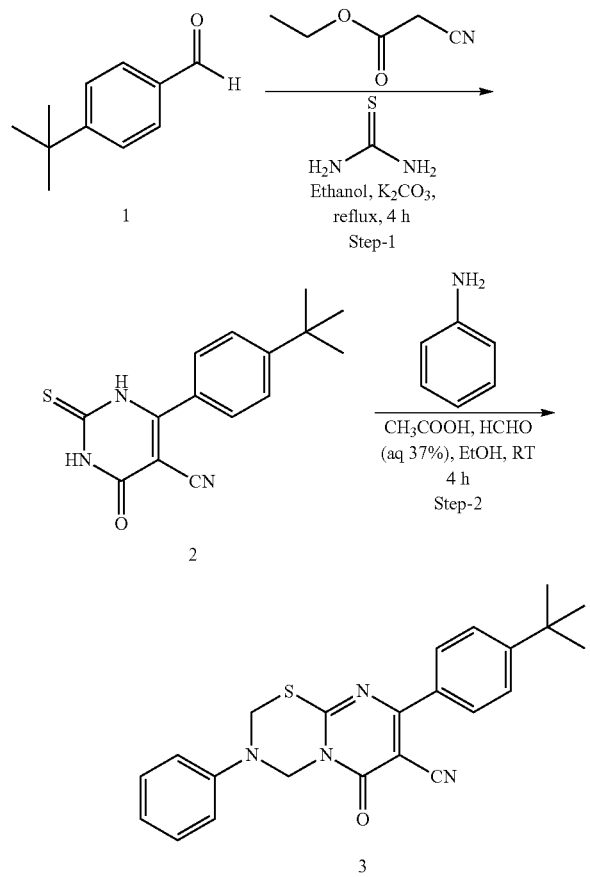

Step-1:

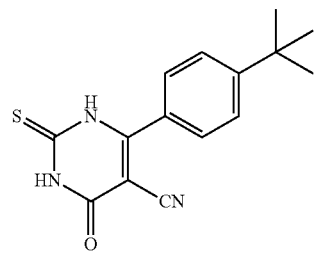 [SMILES: CC(C)(C)c1ccc(-c2[nH]c(=S)[nH]c(=O)c2C#N)cc1]

Preparation of 6-(4-(tert-butyl)phenyl)-4-oxo-2-thioxo-1,2,3,4-tetrahydropyrimidine-5-carbonitrile 2

To a solution of 4-(tert-butyl)benzaldehyde (1, 10 g, 61.64 mmol) in ethanol (300 mL), ethyl cyanoacetate (6.9 g, 61.64 mmol), thiourea (4.68 g, 61.64 mmol), potassium carbonate (25.53 g, 184.93 mmol) were added at room temperature and the reaction mixture was stirred at reflux for 4 h. The reaction mixture was concentrated to remove ethanol. The residue was diluted with ice water (100 mL) and neutralized with acetic acid. The precipitated solid was filtered and dried under suction to afford the title compound 6-(4-(tert-butyl)phenyl)-4-oxo-2-thioxo-1,2,3,4-tetrahydropyrimidine-5-carbonitrile (2, 5.5 g, 31% yield) as a pale yellow solid. Calculated (M+H): 286.09; Found (M+H): 286.1.

Step-2:

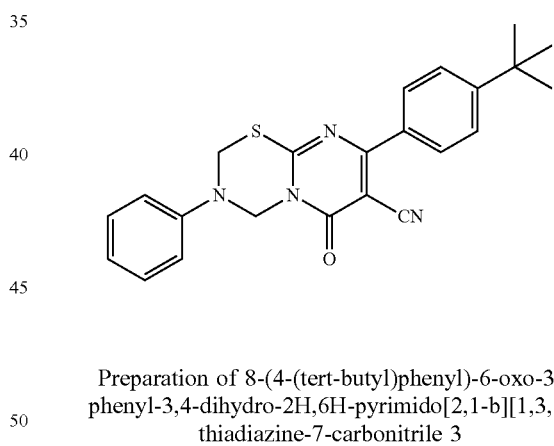

Preparation of 8-(4-(tert-butyl)phenyl)-6-oxo-3-phenyl-3,4-dihydro-2H,6H-pyrimido[2,1-b][1,3,5]thiadiazine-7-carbonitrile 3

To a solution of 6-(4-(tert-butyl)phenyl)-4-oxo-2-thioxo-1,2,3,4-tetrahydropyrimidine-5-carbonitrile (2, 0.1 g, 0.35 mmol) in ethanol (5 mL) taken in a sealed tube, aniline (0.063 mL, 0.70 mmol), acetic acid (0.5 mL), formaline solution (1.98 mL, 24.5 mmol) were added and the reaction mixture was stirred at room temperature for 4 h. The reaction mixture was filtered, solid was washed with water, diethyl ether and dried under suction to afford the title compound 8-(4-(tert-butyl)phenyl)-6-oxo-3-phenyl-3,4-dihydro-2H,6H-pyrimido[2,1-b][1,3,5]thiadiazine-7-carbonitrile (3 (example 5), 0.015 g, 11% yield) as an off white solid. $^1$H NMR (400 MHz, DMSO-d$_6$) δ (ppm): 7.78 (d, J=8.4 Hz, 2H), 7.53 (d, J=7.6 Hz, 2H), 7.33 (t. J=7.6 Hz, 2H), 7.15 (d, J=8.0 Hz, 2H), 7.00 (t, J=7.6 Hz, 1H), 5.74 (s, 2H), 5.52 (s, 2H), 1.28 (s, 9H). HPLC purity: 99.03%

TABLE 2

The following compounds were prepared by the method described above:

| Ex. # | Structure | IUPAC Name | Analytical Data |
|---|---|---|---|
| 6 | 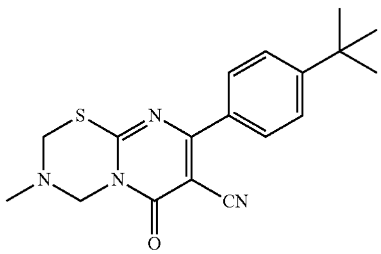 [SMILES: CN1CSc2nc(-c3ccc(C(C)(C)C)cc3)c(C#N)c(=O)n2C1] | 8-(4-(tert-butyl)phenyl)-3-methyl-6-oxo-3,4-dihydro-2H,6H-pyrimido[2,1-b][1,3,5]thiadiazine-7-carbonitrile | $^1$H NMR (400 MHz, DMSO-$d_6$) δ (ppm): 7.83 (d, J = 8.4 Hz, 2H), 7.56 (d, J = 8.0 Hz, 2H) 5.03 (s, 2H), 4.86 (s, 2H), 2.50 (d, J = 20.0 Hz, 3H), 1.30 (s, 9H). HPLC purity: 98.62% |
| 7 | 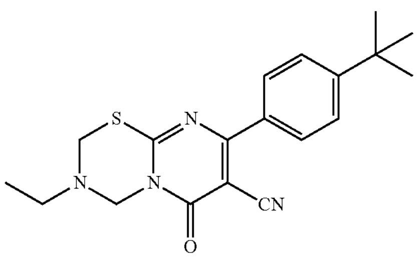 | 8-(4-(tert-butyl)phenyl)-3-ethyl-6-oxo-3,4-dihydro-2H,6H-pyrimido[2,1-b][1,3,5]thiadiazine-7-carbonitrile | $^1$H-NMR (DMSO-$d_6$, 400 MHz) δ (ppm): 7.82 (d, J = 8.4 Hz, 2H), 7.56 (d, J = 8.4 Hz, 2H), 5.09 (s, 2H), 4.91 (s, 2H), 2.75-2.70 (q, 2H), 1.30 (s, 9H), 1.08 (t, J = 7.2 Hz, 3H). HPLC purity: 99.20% |
| 8 | 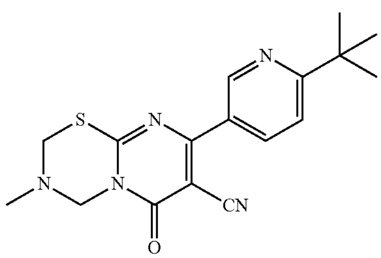 [SMILES: CN1CSc2nc(-c3ccc(C(C)(C)C)nc3)c(C#N)c(=O)n2C1] | 8-(6-(tert-butyl)pyridin-3-yl)-3-methyl-6-oxo-3,4-dihydro-2H,6H-pyrimido[2,1-b][1,3,5]thiadiazine-7-carbonitrile | $^1$H-NMR (DMSO-$d_6$, 400 MHz) δ (ppm): 8.95 (d, J = 2.0 Hz, 1H), 8.17 (dd, $J_1$ = 2.0 Hz, $J_2$ = 8.4 Hz, 1H), 7.62 (d, J = 8.0 Hz, 1H), 5.05 (s, 2H), 4.87 (s, 2H), 2.53 (s, 3H), 1.33 (s, 9H). HPLC purity: 99.42% |
| 9 | 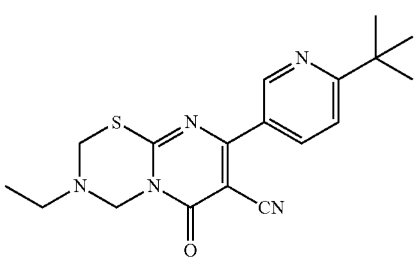 [SMILES: CCN1CSc2nc(-c3ccc(C(C)(C)C)nc3)c(C#N)c(=O)n2C1] | 8-(6-(tert-butyl)pyridin-3-yl)-3-ethyl-6-oxo-3,4-dihydro-2H,6H-pyrimido[2,1-b][1,3,5]thiadiazine-7-carbonitrile | $^1$H-NMR (DMSO-$d_6$, 400 MHz) δ (ppm): 8.95 (s, 1H), 8.16 (d, J = 8.4 Hz, 1H), 7.62 (d, J = 8.4 Hz, 1H), 5.11 (s, 2H), 4.92 (s, 2H), 2.76-2.70 (q, 2H), 1.33 (s, 9H), 1.08 (t, J = 7.2 Hz, 3H). HPLC purity: 99.91% |
| 10 | 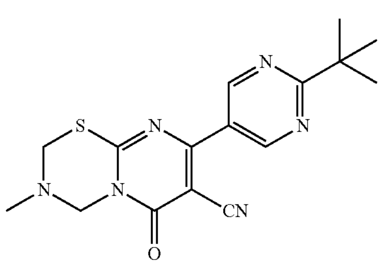 [SMILES: CN1CSc2nc(-c3cnc(C(C)(C)C)nc3)c(C#N)c(=O)n2C1] | 8-(2-(tert-butyl)pyrimidin-5-yl)-3-methyl-6-oxo-3,4-dihydro-2H,6H-pyrimido[2,1-b][1,3,5]thiadiazine-7-carbonitrile | $^1$H-NMR (DMSO-$d_6$, 400 MHz) δ (ppm): 9.16 (s, 2H), 5.07 (s, 2H), 4.89 (s, 2H), 2.53 (s, 3H), 1.38 (s, 9H). HPLC purity: 98.65% |

TABLE 2-continued

The following compounds were prepared by the method described above:

| Ex. # | Structure | IUPAC Name | Analytical Data |
|---|---|---|---|
| 11 | 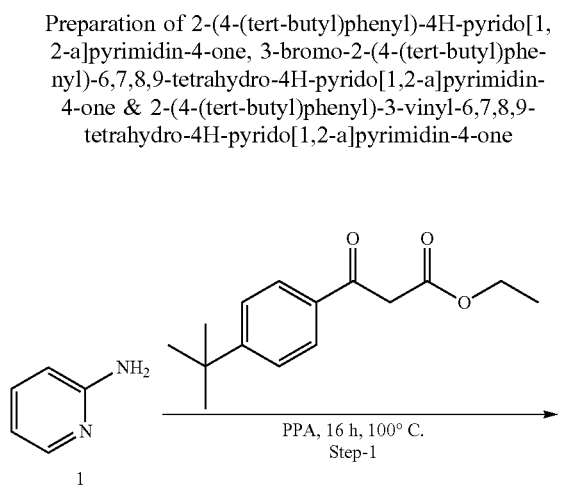 | 8-(2-(tert-butyl)pyrimidin-5-yl)-3-ethyl-6-oxo-3,4-dihydro-2H,6H-pyrimido[2,1-b][1,3,5]thiadiazine-7-carbonitrile | $^1$H-NMR (DMSO-$d_6$, 400 MHz) δ (ppm): 9.15 (s, 2H), 5.12 (s, 2H), 4.94 (s, 2H), 2.75-2.70 (q, 2H), 1.38 (s, 9H), 1.08 (t, J = 7.2 Hz, 3H). HPLC purity: 99.84% |

Examples 12-14

Preparation of 2-(4-(tert-butyl)phenyl)-4H-pyrido[1,2-a]pyrimidin-4-one, 3-bromo-2-(4-(tert-butyl)phenyl)-6,7,8,9-tetrahydro-4H-pyrido[1,2-a]pyrimidin-4-one & 2-(4-(tert-butyl)phenyl)-3-vinyl-6,7,8,9-tetrahydro-4H-pyrido[1,2-a]pyrimidin-4-one

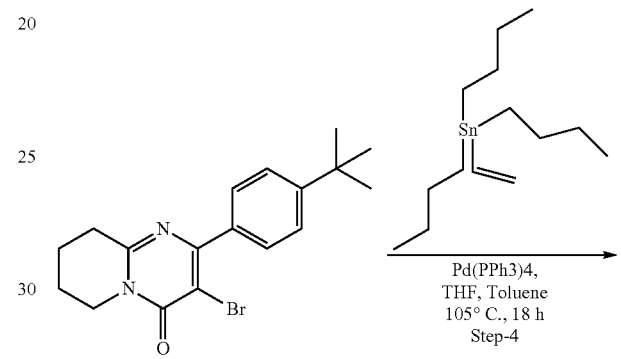

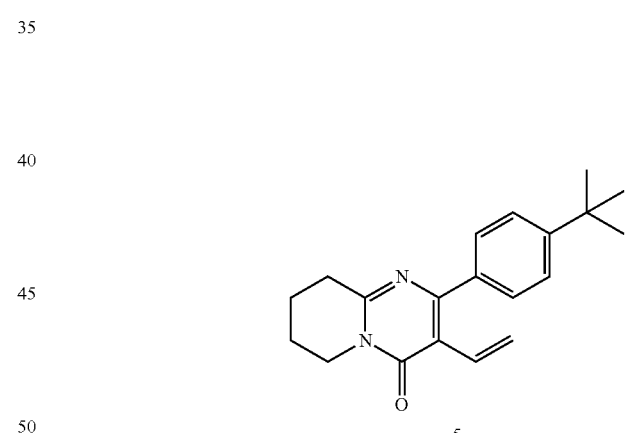

Step-1:

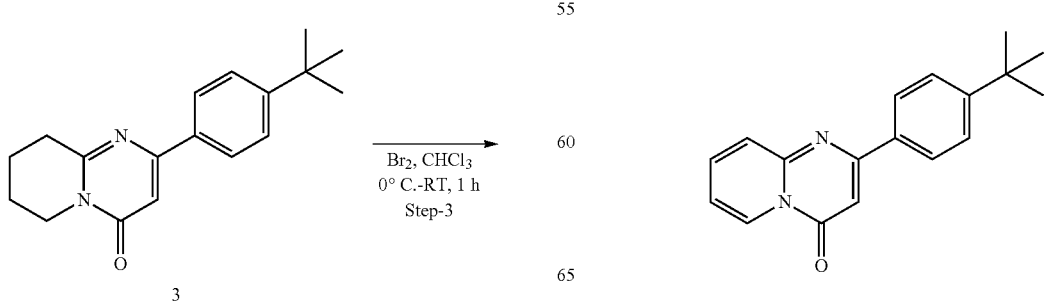

Preparation of 2-(4-(tert-butyl)phenyl)-4H-pyrido[1,2-a]pyrimidin-4-one 2

To a solution of pyridin-2-amine (1, 3.6 g, 38.2 mmol) in polyphosphoric acid (100 g) was added ethyl 3-(4-(tert-butyl)phenyl)-3-oxopropanoate (9.49 g, 38.2 mmol) and the reaction mixture was stirred at 100° C. for 16 h. The reaction mixture was quenched with saturated sodium bicarbonate solution slowly (100 mL) and extracted with ethyl acetate (2×200 mL). The combined organic layer was dried over anhydrous sodium sulphate, filtered and concentrated. The crude product was purified by silica gel column chromatography using 30% ethyl acetate in hexane to afford the title compound 2-(4-(tert-butyl)phenyl)-4H-pyrido[1,2-a]pyrimidin-4-one (2 (example 12), 4 g, 40% yield) as an off white solid. $^1$H NMR (400 MHz, DMSO-de) δ (ppm): 8.94 (d, J=6.8 Hz, 1H), 8.11 (d, J=8 Hz, 2H), 7.97-7.93 (m, 1H), 7.74 (d, J=9.2 Hz, 1H), 7.52 (d, J=9.2 Hz, 2H), 7.34-7.31 (m, 1H), 6.94 (s, 1H), 1.31 (s, 9H). Calculated (M+H): 279.14; Found (M+H): 279.1. HPLC purity: 99.66%

Step-2:

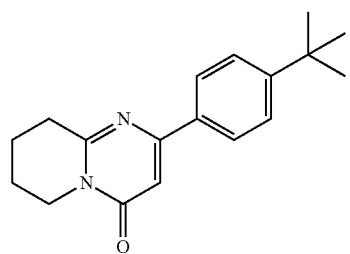 [SMILES: CC(C)(C)c1ccc(-c2cc(=O)n3c(n2)CCCC3)cc1]

Preparation of 2-(4-(tert-butyl)phenyl)-6,7,8,9-tetrahydro-4H-pyrido[1,2-a]pyrimidin-4-one 3

To a solution of 2-(4-(tert-butyl)phenyl)-4H-pyrido[1,2-a]pyrimidin-4-one (2, 4.3 g) in 6N hydrochloric acid solution (50 mL) was added palladium on carbon (0.8 g) and the reaction mixture was stirred at room temperature for 16 h under hydrogen atmosphere (100 psi). The reaction mixture was filtered through celite bed and the filtrate was concentrated. The crude product was purified by silica gel column chromatography using 1% methanol in dichloromethane to afford the title compound 2 2-(4-(tert-butyl)phenyl)-6,7,8,9-tetrahydro-4H-pyrido[1,2-a]pyrimidin-4-one (3, 1.7 g, crude) as an off white solid. Calculated (M+H): 283.17; Found (M+H): 283.2.

Step-3:

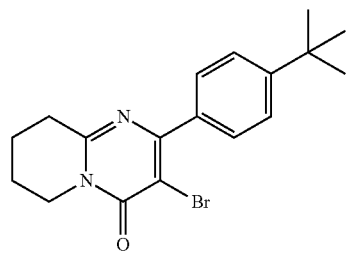 [SMILES: CC(C)(C)c1ccc(-c2nc3n(c(=O)c2Br)CCCC3)cc1]

Preparation of 3-bromo-2-(4-(tert-butyl)phenyl)-6,7,8,9-tetrahydro-4H-pyrido[1,2-a]pyrimidin-4-one 4

To a solution of 2 2-(4-(tert-butyl)phenyl)-6,7,8,9-tetrahydro-4H-pyrido[1,2-a]pyrimidin-4-one (3, 1.7 g, 6 mmol) in chloroform (30 mL) was added bromine (0.37 mL, 7.2 mmol) at 0° C. and the reaction mixture was then stirred at room temperature for 1 h. The reaction mixture was quenched with saturated sodium bicarbonate solution (100 mL) and extracted with ethyl acetate (2×150 mL). The combined organic layer was dried over anhydrous sodium sulphate, filtered and concentrated. The crude product was purified by silica gel column chromatography using 1% methanol in dichloromethane to afford the title compound 3-bromo-2-(4-(tert-butyl)phenyl)-6,7,8,9-tetrahydro-4H-pyrido[1,2-a]pyrimidin-4-one (4 (example 13), 1.9 g, 87.5% yield) as an off white solid. $^1$H NMR (400 MHz, DMSO-$d_6$) δ (ppm): 7.59 (d, J=8.4 Hz, 2H), 7.47 (d, J=8 Hz, 2H), 3.89-3.86 (m, 2H), 2.85-2.82 (m, 2H), 1.92-1.87 (m, 2H), 1.82-1.76 (m, 2H), 1.29 (s, 9H). Calculated (M+H): 363.28; Found (M+H): 363.1. HPLC purity: 99.66%

Step-4:

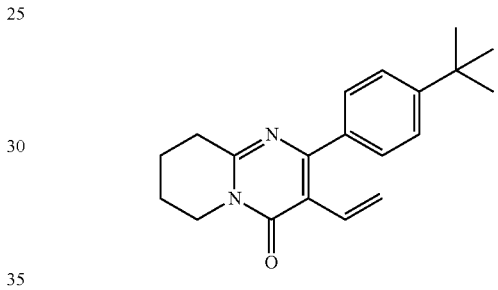

Preparation of 2-(4-(tert-butyl)phenyl)-3-vinyl-6,7,8,9-tetrahydro-4H-pyrido[1,2-a]pyrimidin-4-one 5

A stirred solution of 3-bromo-2-(4-(tert-butyl)phenyl)-6,7,8,9-tetrahydro-4H-pyrido[1,2-a]pyrimidin-4-one (4, 0.15 g, 0.41 mmol) and tributyl(vinyl)stannane (0.199, 0.62 mmol) in toluene:tetrahydofuran mixture (6 mL, 1:1) was purged with nitrogen was for 5 min. Then tetrakis(triphenylphosphine)palladium (0) (0.024 g, 0.02 mmol) was added and the reaction mixture was heated at 105° C. for 18 h. The reaction mixture was cooled to room temperature, diluted with water (20 mL) and extracted with ethyl acetate (2×50 mL). The combined organic layer was washed with brine (50 mL), dried over sodium sulfate, filtered and concentrated. The crude product was purified by preparative HPLC (column: Inertsil ODS 3V (250 mm×4.6 mm×5 mic), mobile phase (A): 0.1% ammonia in water, mobile phase (B): acetonitrile, flow rate: 1.0 mL/min, T/% B: 0/20, 10/80, 25/90, 27/20, 30/20) to afford the title compound 2-(4-(tert-butyl)phenyl)-3-vinyl-6,7,8,9-tetrahydro-4H-pyrido[1,2-a]pyrimidin-4-one (5 (example 14), 0.03 g, 23.6% yield) as an off white solid. $^1$H NMR (400 MHz, DMSO-$d_6$) δ (ppm): 7.47 (d, J=8 Hz, 2H), 7.38 (d, J=8 Hz, 2H), 6.45-6.34 (m, 2H), 5.28-5.25 (m, 1H), 3.88-3.85 (m, 2H), 2.85-2.82 (m, 2H), 1.93-1.87 (m, 2H), 1.82-1.77 (m, 2H), 1.34 (s, 9H). Calculated (M+H): 309.19; Found (M+H): 309.7. HPLC purity: 99.88%

TABLE 3

The following compounds were prepared by the method described above:

| Ex. # | Structure | IUPAC Name | Analytical Data |
|---|---|---|---|
| 15 | 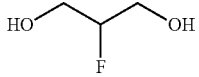 | 3-bromo-2-(6-(tert-butyl)pyridin-3-yl)-6,7,8,9-tetrahydro-4H-pyrido[1,2-a]pyrimidin-4-one | $^1$H NMR (400 MHz, DMSO-$d_6$) δ (ppm): 8.77 (d, J = 2 Hz, 1H), 7.97 (dd, $J_1$ = 2.4 Hz, 4.12 = 8.4 Hz, 1H), 7.52 (d, J = 8.4 Hz, 1H), 3.90-3.87 (m, 2H), 2.86-2.83 (m, 2H), 1.92-1.86 (m, 2H), 1.82-1.76 (m, 2H), 1.33 (s, 9H). Calculated (M + H): 362.08; Found (M + H): 362.1, HPLC purity: 99.16% |

Example 16

Preparation of 8-(6-(tert-butyl)pyridin-3-yl)-3-fluoro-6-oxo-3,4-dihydro-2H,6H-pyrimido[2,1-b][1,3]thiazine-7-carbonitrile 4

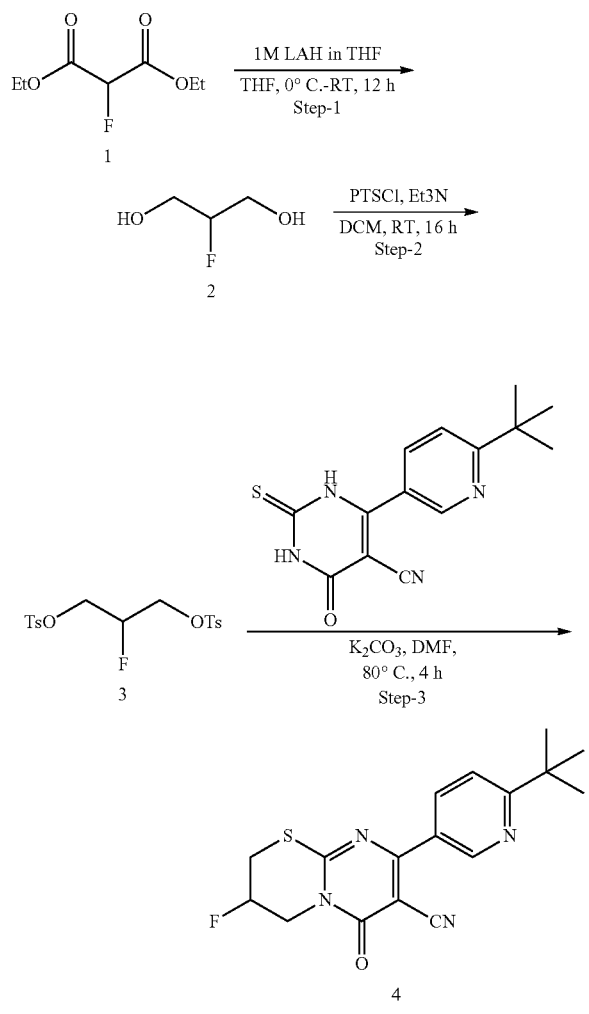

Step-1:

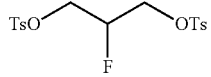

Preparation of 2-fluoropropane-1,3-diol 2

To a solution of diethyl 2-fluoromalonate (1, 5.0 g, 28.06 mmol) in tetrahydrofuran (150 mL) cooled to 0° C. was added lithium aluminium hydride (45 mL, 44.9 mmol, 1M in tetrahydrofuran) drop wise. The reaction mixture was warmed to room temperature and stirred for 12 h. Water (300 mL) was added carefully and the pH was adjusted to 3 by adding 1M hydrochloric acid solution. Then concentrated to half the volume under vacuum and the residue was extracted with ethyl acetate (3×300 mL). The combined organic layer was dried over anhydrous sodium sulphate, filtered and concentrated to afford the title compound 2-fluoropropane-1,3-diol (2, 0.26 g, 10% yield) as a brownish liquid. $^1$H NMR (DMSO-$d_6$, 400 MHz) δ (ppm): 4.79 (t, J=4.0 Hz, 2H), 3.58-3.38 (m, 5H).

Step-2:

Preparation of 2-fluoropropane-1,3-diyl bis(4-methylbenzenesulfonate 3

To a stirred solution of 2-fluoropropane-1,3-diol (2, 0.26 g, 2.76 mmol) and triethylamine (1.93 mL, 13.81 mmol) in dichloromethane (10 mL), p-toluenesulfonyl chloride (1.58 g, 8.28 mmol) was added at 0° C. The resulting mixture was stirred at room temperature for 16 h. The reaction mixture was concentrated under reduced pressure and the residue was purified by silica gel column chromatography using 10% ethyl acetate in hexane to afford the title compound 2-fluoropropane-1,3-diyl bis(4-methylbenzenesulfonate) (3, 0.29 g, 26% yield) as a white solid. Calculated (M+H): 403.06; Found (M+H): 403.1.

Step-3:

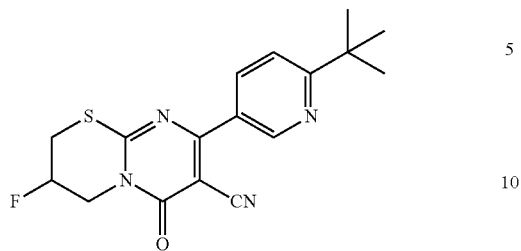

Preparation of 8-(6-(tert-butyl)pyridin-3-yl)-3-fluoro-6-oxo-3,4-dihydro-2H,6H-pyrimido[2,1-b][1,3]thiazine-7-carbonitrile 4

A mixture of 6-(6-(tert-butyl)pyridin-3-yl)-4-oxo-2-thioxo-1,2,3,4-tetrahydropyrimidine-5-carbonitrile (3, 0.15 g, 0.52 mmol), 2-fluoropropane-1,3-diyl bis(4-methylbenzenesulfonate) (0.15 mL, 0.36 mmol) and triethylamine (0.9 mL, 62.85 mmol) in N,N-dimethylformamide (12 mL) was heated at 80° C. for 4 h. The reaction mixture was cooled to room temperature, diluted with water (20 mL) and extracted with ethyl acetate (3×50 mL). The combined organic layer was dried over anhydrous sodium sulphate, filtered and concentrated. The crude product was purified by silica gel column chromatography using 40% ethyl acetate in hexane to afford the title compound 8-(6-(tert-butyl)pyridin-3-yl)-3-fluoro-6-oxo-3,4-dihydro-2H,6H-pyrimido[2,1-b][1,3]thiazine-7-carbonitrile (4 (example 16), 0.045 g, 25% yield) as pale yellow solid. $^1$H NMR (DMSO-$d_6$, 400 MHz) δ (ppm): 8.96 (d, J=2.4 Hz, 1H), 8.18 (dd, $J_1$=2.4 Hz, $J_2$=8.4 Hz, 1H), 7.63 (d, J=8.4 Hz, 1H), 5.67 (d, J=44.8 Hz, 1H), 4.74 (t, J=12.8 Hz, 1H), 3.85-3.57 (m, 3H), 1.34 (s, 9H). Calculated (M+H): 345.11; Found (M+H): 345.1. HPLC purity: 99.68%

TABLE 4

The following compound was prepared by the method described above:

| Ex. # | Structure | IUPAC Name | Analytical Data |
|---|---|---|---|
| 17 | 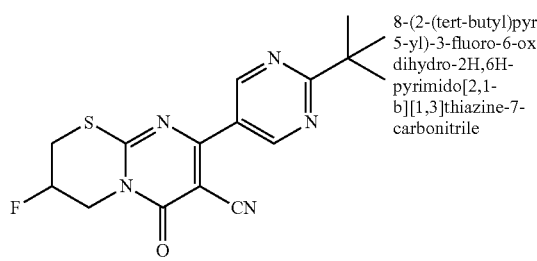 | 8-(2-(tert-butyl)pyrimidin-5-yl)-3-fluoro-6-oxo-3,4-dihydro-2H,6H-pyrimido[2,1-b][1,3]thiazine-7-carbonitrile | $^1$H-NMR (DMSO-$d_6$, 400 MHz) δ (ppm): 9.17 (s, 2H), 5.68 (d, J = 44.8 Hz, 1H), 4.77 (t, J = 12.8 Hz, 1H), 3.86-3.58 (m, 3H), 1.38 (s, 9H); Calculated (M + H): 346.11, found (M + H): 346.1, HPLC purity: 99.66% |

Example 18

Preparation of 2-(4-(tert-butyl)phenyl)-4-oxo-4H-pyrido[1,2-a]pyrimidine-3-carbonitrile 4

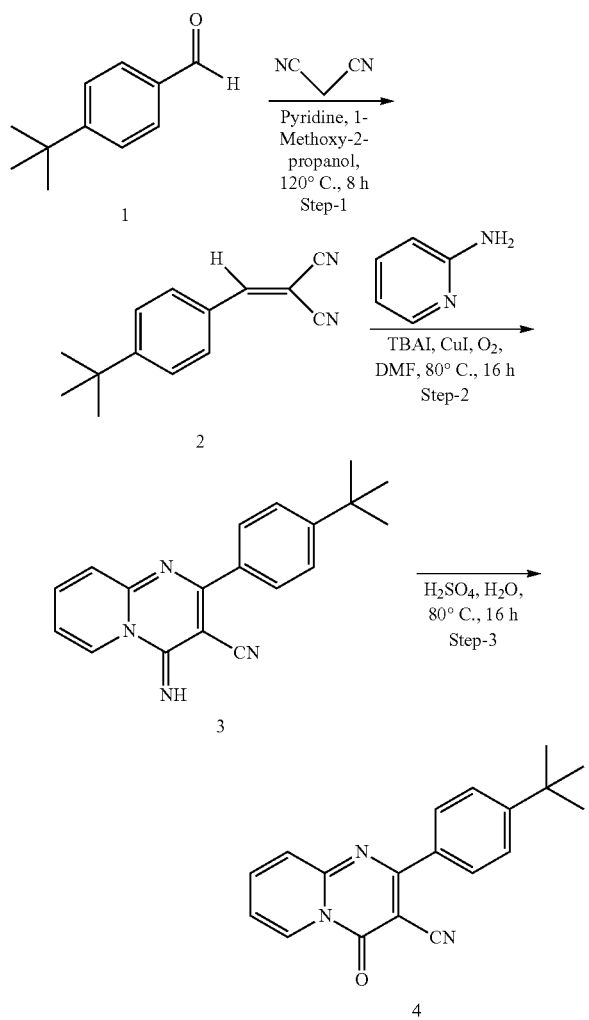

Step-1:

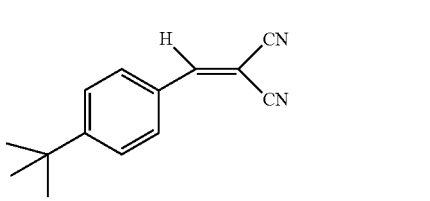 [SMILES: CC(C)(C)c1ccc(C=C(C#N)C#N)cc1]

Preparation of 2-(4-(tert-butyl)benzylidene)malononitrile 2

To a solution of 4-(tert-butyl)benzaldehyde (1, 1 g, 6.16 mmol) in 1-methoxy-2-propanol (7 mL), malononitrile (0.40 g, 6.16 mmol), pyridine (0.97 mL, 12.32 mmol) were added at room temperature and the reaction mixture was stirred at 120° C. for 8 h. The reaction mixture was concentrated to remove 1-methoxy-2-propanol. The crude product was purified by silica gel chromatography using 5% ethyl acetate in hexane to afford the title compound 2-(4-(tert-buty)benzylidene)malononitrile (2, 1.29 g, 85% yield) as a white solid. $^1$H NMR (400 MHz, DMSO-$d_6$) δ (ppm): 8.47 (s, 1H), 7.89 (d, J=8.4 Hz, 2H), 7.64 (d, J=8.4 Hz, 2H), 1.29 (s, 9H).

Step-2:

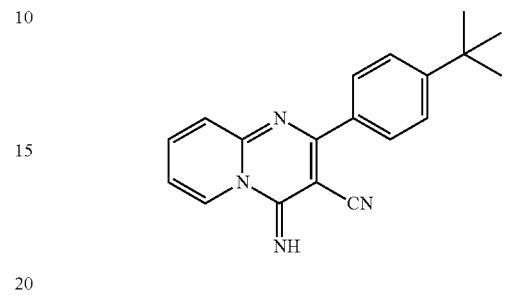

Preparation of 2-(4-(tert-butyl)phenyl)-4-imino-4H-pyrido[1,2-a]pyrimidine-3-carbonitrile 3

To a solution of 2-(4-(tert-butyl)benzylidene)malononitrile (2, 0.1 g, 0.47 mmol) in N,N-dimethylformamide (4 mL), 2-amino pyridine (0.04 g, 0.47 mmol), tetrabutylammonium iodide (0.17 g, 0.47 mmol), copper iodide (0.009 g, 0.047 mmol) were added at room temperature and the reaction mixture was purged with oxygen. The reaction mixture was stirred at 80° C. for 16 h under oxygen atmosphere. The reaction mixture was quenched with water (30 mL) and extracted with ethyl acetate (2×40 mL). The combined organic layer was dried over anhydrous sodium sulfate, filtered and concentrated. The crude product was purified by silica gel chromatography using 60% ethyl acetate in hexane to afford the title compound 2-(4-(tert-butyl)phenyl)-4-imino-4H-pyrido[1,2-a]pyrimidine-3-carbonitrile (3, 0.02 g, 13% yield) as a yellow solid. $^1$H NMR (400 MHz, DMSO-$d_6$) δ (ppm): 9.26 (d, J=6.8 Hz, 1H), 8.08 (t, J=7.6 Hz, 1H), 7.84 (d, J=8.4 Hz, 2H), 7.75 (s, 1H), 7.62 (d, J=8.8 Hz, 1H), 7.56 (d, J=8.4 Hz, 2H), 7.40 (t, J=7.2 Hz, 1H), 1.32 (s, 9H). Calculated (M+H): 303.15; Found (M+H): 303.2, HPLC Purity: 99.74%

Step-3:

Preparation of 2-(4-(tert-butyl)phenyl)-4-oxo-4H-pyrido[1,2-a]pyrimidine-3-carbonitrile 4

To a solution of 2-(4-(tert-butyl)phenyl)-4-oxo-4H-pyrido[1,2-a]pyrimidine-3-carbonitrile (3, 0.1 g, 0.32 mmol) in water (10 mL), sulphuric acid (1 mL) was added and the reaction mixture was stirred at 80° C. for 16 h. The reaction mixture was extracted with ethyl acetate (2×40 mL), the combined organic layer was dried over anhydrous sodium sulfate, filtered and concentrated. The crude product was purified by silica gel chromatography using 40% ethyl acetate in hexane to afford the title compound 2-(4-(tert-butyl)phenyl)-4-oxo-4H-pyrido[1,2-a]pyrimidine-3-carbonitrile (4 (example 18), 0.012 g, 12% yield) as an off white solid. $^1$H NMR (400 MHz, DMSO-d$_6$) δ (ppm): 9.05 (d, J=7.2 Hz, 1H), 8.22 (t, J=7.6 Hz, 1H), 7.93-7.87 (m, 3H), 7.61-7.55 (m, 3H), 1.33 (s, 9H). Calculated (M+H): 304.14; Found (M+H): 304.0, HPLC Purity: 99.91%

TABLE 5

The following compounds were prepared by the method described above:

| Ex. # | Structure | IUPAC Name | Analytical Data |
|---|---|---|---|
| 19 | 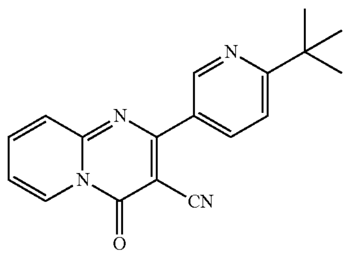 [SMILES: CC(C)(C)c1ccc(-c2nc3ccccn3c(=O)c2C#N)cn1] | 2-(6-(tert-butyl)pyridin-3-yl)-4-oxo-4H-pyrido[1,2-a]pyrimidine-3-carbonitrile | $^1$H-NMR (DMSO-d$_6$, 400 MHz) δ (ppm): 9.08 (d, J = 7.2 Hz, 1H), 9.04 (d, J = 6.8 Hz, 1H), 8.28-8.25 (m, 2H), 7.92 (d, J = 8.8 Hz, 1H), 7.66 (d, J = 8.4 Hz, 1H), 7.61 (t, J = 6.8 Hz, 1H), 1.36 (s, 9H). Calculated (M + H): 305.13, found (M + H): 305.1, HPLC purity: 99.20% |
| 20 | 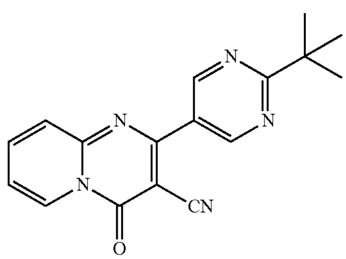 [SMILES: CC(C)(C)c1ncc(-c2nc3ccccn3c(=O)c2C#N)cn1] | 2-(2-(tert-butyl)pyrimidin-5-yl)-4-oxo-4H-pyrido[1,2-a]pyrimidine-3-carbonitrile | $^1$H-NMR (DMSO-d$_6$, 400 MHz) δ (ppm): 9.26 (s, 2H), 9.12 (d, J = 7.2 Hz, 1H), 8.30 (t, J = 6.8 Hz, 1H) 7.96 (d, J = 8.8 Hz, 1H), 7.65 (t, J = 7.2 Hz, 1H), 1.41 (s, 9H). Calculated (M + H): 306.13, found (M + H): 306.1, HPLC purity: 99.65% |
| 21 | 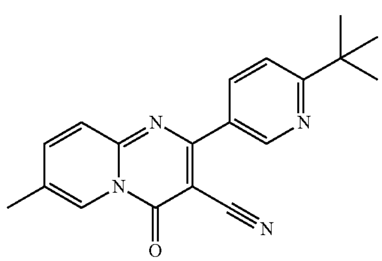 | 2-(6-(tert-butyl)pyridin-3-yl)-7-methyl-4-oxo-4H-pyrido[1,2-a]pyrimidine-3-carbonitrile | $^1$H NMR (400 MHz, CDCl$_3$) δ (ppm): 9.22 (s, 1H), 8.97 (s, 1H), 8.34 (d, J = 6.4 Hz, 1H), 7.87 (d, J = 8.8 Hz, 1H), 7.78 (d, J = 9.2 Hz, 1H), 7.51 (d, J = 8.4 Hz, 1H), 2.53 (s, 3H), 1.38 (s, 9H). Calculated (M + H): 319.15, found (M + H): 319.1, HPLC purity: 99.33% |
| 22 | 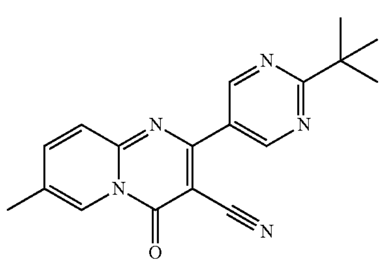 [SMILES: Cc1ccc2nc(-c3cnc(C(C)(C)C)nc3)c(C#N)c(=O)n2c1] | 2-(2-(tert-butyl)pyrimidin-5-yl)-7-methyl-4-oxo-4H-pyrido[1,2-a]pyrimidine-3-carbonitrile | $^1$H-NMR (DMSO-d$_6$, 400 MHz) δ (ppm): 9.34 (s, 2H), 8.99 (s, 1H), 7.91 (d, J = 9.2 Hz, 1H), 7.79 (d, J = 9.2 Hz, 1H), 2.55 (s, 3H), 1.47 (s, 9H). Calculated (M + H): 320.14, found (M + H): 320.1, HPLC purity: 99.13% |

Example 23

Preparation of 2-(4-(tert-butyl)phenyl)-4-oxo-6,7,8, 9-tetrahydro-4H-pyrido[1,2-a]pyrimidine-3-carbonitrile 2

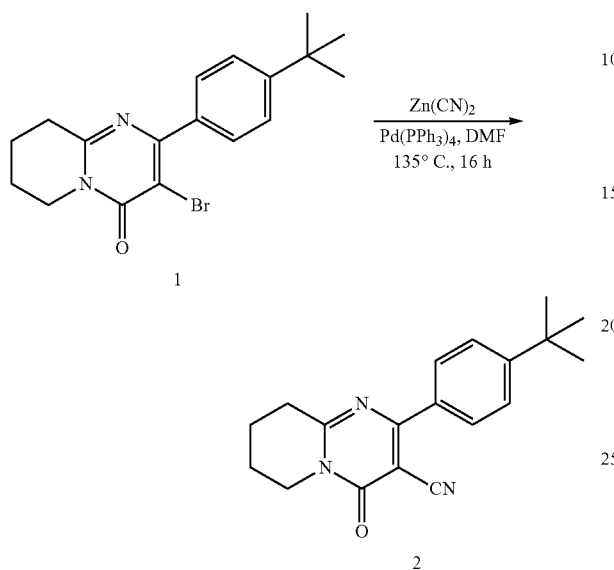

To a solution of 3-bromo-2-(4-(tert-butyl)phenyl)-6,7,8, 9-tetrahydro-4H-pyrido[1,2-a]pyrimidin-4-one (1, 0.15 g, 0.41 mmol) in N,N-dimethylformamide (10 mL), zinc cyanide (0.048 g, 0.41 mmol), tetrakis(triphenylphosphine) palladium(0) (0.047 g, 0.04 mmol) were added and the reaction mixture was stirred at 130° C. for 16 h. The reaction mixture was quenched with water (50 mL) and extracted with ethyl acetate (2×40 mL). The combined organic layer was dried over anhydrous sodium sulfate, filtered and concentrated. The crude product was purified by silica gel column chromatography followed by preparative HPLC (analytical conditions: column: inertsil ODS 3V (250 mm×4.6 mm×5 mic), mobile phase (A): 0.1% ammonia in water, mobile phase (B): acetonitrile, flow rate: 1.0 mL/min. T/% B: 0/20, 10/80, 25/90, 27/20, 30/20) to afford the title compound 2-(4-(tert-butyl)phenyl)-4-oxo-6,7,8,9-tetrahydro-4H-pyrido[1,2-a]pyrimidine-3-carbonitrile (2 (example 23), 0.015 g, 12% yield) as a white solid. $^1$H NMR (400 MHz, DMSO-$d_6$) δ (ppm): 7.86 (d, J=8.0 Hz, 2H), 7.57 (d, J=8.0 Hz, 2H), 3.85 (t, J=5.6 Hz, 2H), 2.96 (t, J=6.8 Hz, 2H), 1.90 (d, J=5.2 Hz, 2H), 1.81 (d, J=6.4 Hz, 2H), 1.31 (s, 9H). Calculated (M+H): 308.17; Found (M+H): 308.2, HPLC Purity: 99.89%

Example 24

Preparation of 8-(6-(tert-butyl)pyridin-3-yl)-3,3-difluoro-6-oxo-3,4-dihydro-2H,6H-pyrimido[2,1-b][1,3]thiazine-7-carbonitrile 4

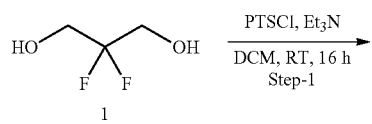

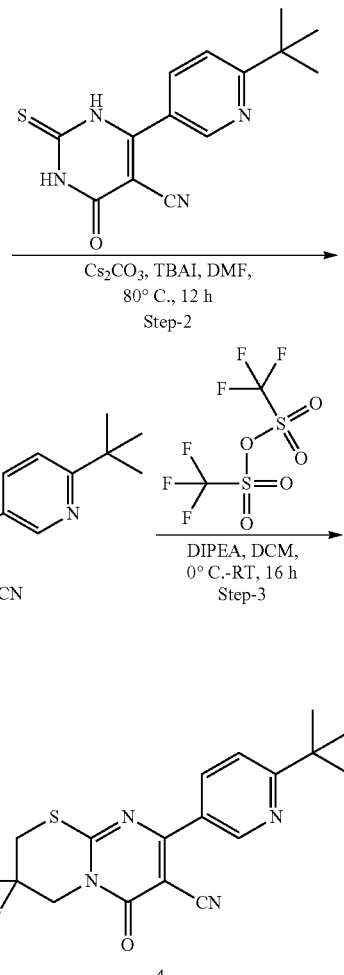

Step-1:

HO⌒⌒OTs
    F F

Preparation of 2,2-difluoro-3-hydroxypropyl 4-methylbenzenesulfonate 2

To a stirred solution of 2,2-difluoropropane-1,3-diol (1, 2 g, 17.84 mmol) and triethylamine (12.4 mL, 89.22 mmol) in dichloromethane (80 mL), was added p-toluenesulfonyl chloride (2 g, 10.7 mmol) at room temperature. The resulting mixture was stirred at room temperature for 16 h. After completion of the reaction, the reaction mixture was concentrated under reduced pressure and the residue was purified by silica gel column chromatography using 15% ethyl acetate in hexane to afford the title compound 2,2-difluoro-3-hydroxypropyl 4-methylbenzenesulfonate (2, 1.4 g, 29% yield) as colorless oil. $^1$H NMR (DMSO-$d_6$, 400 MHz) δ (ppm): 7.80 (d, J=8.4 Hz, 2H), 7.49 (d, J=8.0 Hz, 2H), 5.61 (t, J=6.0 Hz, 1H), 4.33 (t, J=14.0 Hz, 2H), 3.63-3.55 (m, 2H), 2.41 (s, 3H).

Step-2:

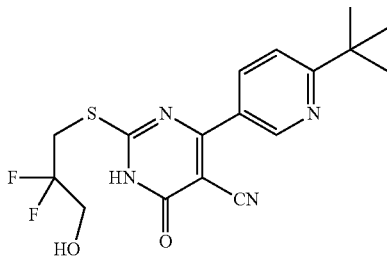 [SMILES: CC(C)(C)c1ccc(-c2nc(SCC(F)(F)CO)[nH]c(=O)c2C#N)cn1]

Preparation of 4-(6-(tert-butyl)pyridin-3-yl)-2-((2,2-difluoro-3-hydroxypropyl)thio)-6-oxo-1,6-dihydro-pyrimidine-5-carbonitrile 3

To a mixture of 2,2-difluoro-3-hydroxypropyl 4-methylbenzenesulfonate (2, 1.37 g, 5.16 mmol), 6-(6-(tert-butyl)pyridin-3-yl)-4-oxo-2-thioxo-1,2,3,4-tetrahydropyrimidine-5-carbonitrile (1.85 g, 6.46 mmol) and tetrabutylammonium iodide (1.19 g, 3.23 mmol) in N,N-dimethylformamide (60 mL), was added cesium carbonate (4.2 g, 12.92 mmol) at room temperature. The resulting mixture was stirred at 80° C. for 12 h in a sealed tube. The reaction mixture was cooled to room temperature, diluted with water (100 mL) and extracted with ethyl acetate (3×150 mL). The combined organic layer was dried over anhydrous sodium sulphate, filtered and concentrated. The crude product was purified by silica gel column chromatography using 5% methanol in dichloromethane to afford the title compound 4-(6-(tert-butyl)pyridin-3-yl)-2-((2,2-difluoro-3-hydroxypropyl)thio)-6-oxo-1,6-dihydropyrimidine-5-carbonitrile (3, 0.61 g, 25% yield) as brownish solid. Calculated (M+H): 381.11; Found (M+H): 381.1.

Step-3:

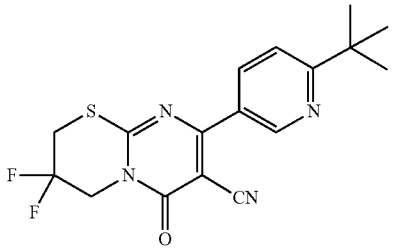 [SMILES: CC(C)(C)c1ccc(-c2nc3n(c(=O)c2C#N)CC(F)(F)CS3)cn1]

Preparation of 8-(6-(tert-butyl)pyridin-3-yl)-3,3-difluoro-6-oxo-3,4-dihydro-2H,6H-pyrimido[2,1-b][1,3]thiazine-7-carbonitrile 4

To a stirred solution of 4-(6-(tert-butyl)pyridin-3-yl)-2-((2,2-difluoro-3-hydroxypropyl)thio)-6-oxo-1,6-dihydropyrimidine-5-carbonitrile (3, 0.35 g, 0.92 mmol) and N,N-diisopropylethylamine (0.8 mL, 4.6 mmol) in dichloromethane (10 mL), triflic anhydride (0.39 mL, 2.3 mmol) was added at 0° C. The reaction mixture was allowed to stir at room temperature for 16 h. The reaction mixture was diluted with water (10 mL) and extracted with dichloromethane (3×50 mL). The combined organic layer was dried over anhydrous sodium sulphate, filtered and concentrated. The crude product was purified by silica gel column chromatography using 35% ethyl acetate in hexane followed by preparative HPLC [column: Inertsil ODS 3V (250 mm×4.6 mm×5 mic); mobile phase (A): 0.1% ammonia in water, mobile phase (B): acetonitrile; flow rate: 1.0 mL/min; T/% B: 0/20, 10/70, 25/80, 27/20, 30/20] to afford the title compound 8-(6-(tert-butyl)pyridin-3-yl)-3,3-difluoro-6-oxo-3,4-dihydro-2H,6H-pyrimido[2,1-b][1,3]thiazine-7-carbonitrile (4 (example 24), 0.03 g, 9% yield) as a white solid. $^1$H NMR (DMSO-$d_6$, 400 MHz) δ (ppm): 8.98 (d, J=1.6 Hz, 1H), 8.19 (dd, J$_1$=2.0 Hz, J$_2$=8.4 Hz, 1H), 7.64 (d, J=8.4 Hz, 1H), 4.47 (t, J=12.4 Hz, 2H), 3.92 (t, J=12.4 Hz, 2H), 1.34 (s, 9H). Calculated (M+H): 363.1; Found (M+H): 363.1, HPLC purity: 98.21%

Examples 25 and 26

Preparation of 2-(4-(tert-butyl)phenyl)-3-(methylthio)-6,7,8,9-tetrahydro-4H-pyrido[1,2-a]pyrimidin-4-one & 2-(4-(tert-butyl)phenyl)-3-(methylsulfinyl)-6,7,8,9-tetrahydro-4H-pyrido[1,2-a]pyrimidin-4-one

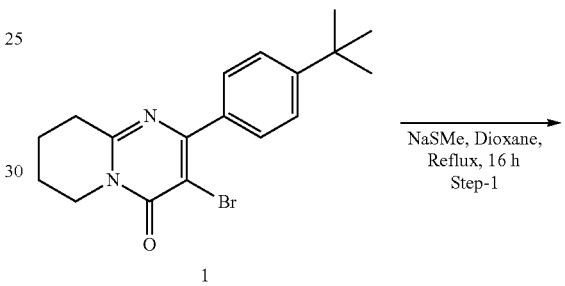

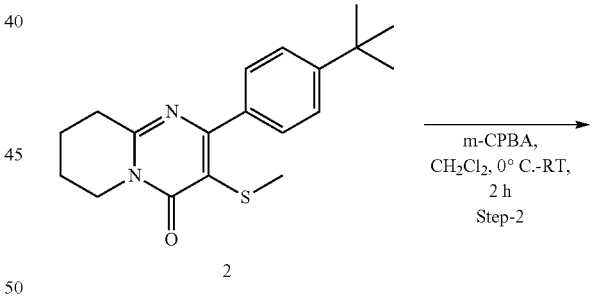

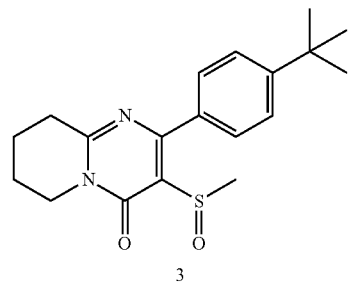

Step-1:

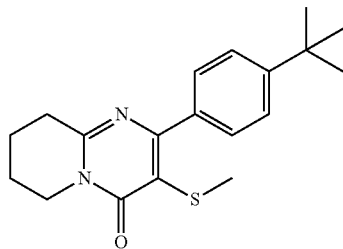 [SMILES: CSc1c(-c2ccc(C(C)(C)C)cc2)nc2n(c1=O)CCCC2]

Preparation of 2-(4-(tert-butyl)phenyl)-3-(methyl-thio)-6,7,8,9-tetrahydro-4H-pyrido[1,2-a]pyrimidin-4-one 2

To a stirred solution of 3-bromo-2-(4-(tert-butyl)phenyl)-6,7,8,9-tetrahydro-4H-pyrido[1,2-a]pyrimidin-4-one (1, 0.48 g, 1.3 mmol) in 1,4 dioxane (50 mL) was added sodium thio methoxide (0.28 g, 3.9 mmol). The reaction mixture was refluxed for 16 h. After completion of reaction, the reaction mixture was diluted with ethyl acetate (50 mL), washed with water (2×30 mL), brine (30 mL), dried over anhydrous sodium sulfate, filtered and concentrated. The crude product was purified by silica gel column chromatography using 30% ethyl acetate in hexane to afford the title compound 2-(4-(tert-butyl)phenyl)-3-(methylthio)-6,7,8,9-tetrahydro-4H-pyrido[1,2-a]pyrimidin-4-one (2 (example 25), 0.400 g, 93% yield) as an off-white solid. $^1$H NMR (400 MHz, DMSO-$d_6$) δ (ppm): 7.48 (d, J=8.4 Hz, 2H), 7.43 (d, J=8.4 Hz, 2H), 3.85 (t, J=6 Hz, 2H), 2.83 (t, J=6.8 Hz, 2H), 2.20 (s, 3H), 1.88 (d, J=6 Hz, 2H), 1.79 (d, J=6.4 Hz, 2H), 1.29 (s, 9H). Calculated (M+H): 329.16, Found (M+H): 329.2. HPLC purity: 99.58%

Step-2:

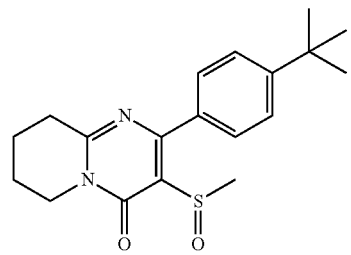 [SMILES: CS(=O)c1c(-c2ccc(C(C)(C)C)cc2)nc2n(c1=O)CCCC2]

Preparation of 2-(4-(tert-butyl)phenyl)-3-(methyl-sulfinyl)-6,7,8,9-tetrahydro-4H-pyrido[1,2-a]pyrimi-din-4-one To a stirred solution of 2-(4-(tert-butyl)phenyl)-3-(methylthio)-6,7,8,9-tetrahydro-4H-pyrido[1,2-a]pyrimidin-4-one (2, 0.07 g, 0.21 mmol) in dichloromethane (5 mL) cooled to 0° C. was added meta chloro perbenzoic acid (0.028 g, 0.16 mmol) portion wise and the reaction mixture was stirred at room temperature for 16 h. After completion of the reaction, the reaction mixture was quenched with saturated sodium bicarbonate solution (20 mL) and extracted with ethyl acetate (2×40 mL). The combined organic layer was washed with water (30 mL), brine (30 mL), dried over sodium sulfate, filtered and concentrated. The crude product was purified by silica gel column chromatography using 60% ethyl acetate in hexane to afford the title compound 2-(4-(tert-butyl)phenyl)-3-(methylsulfinyl)-6,7,8,9-tetrahydro-4H-pyrido[1,2-a]pyrimidin-4-one (3 (example 26), 0.032 g, 43% yield) as a white solid. $^1$H NMR (400 MHz, DMSO-$d_6$) δ (ppm): 7.48 (d, J=8.4 Hz, 2H), 7.41 (d, J=8.4 Hz, 2H), 3.86 (t, J=5.6 Hz, 2H), 3.11 (s, 3H), 2.92-2.85 (m, 2H), 1.93-1.91 (m, 2H), 1.82-1.78 (m, 2H), 1.30 (s, 9H). Calculated (M+H): 345.16; Found (M+H): 345.1. HPLC purity: 98.00%

TABLE 6

The following compounds were prepared by the method described above:

| Example Number | Structure | IUPAC Name | Analytical data |
|---|---|---|---|
| 27 | 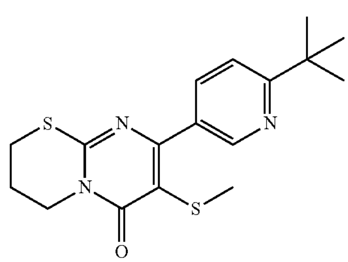 [SMILES: CSc1c(-c2ccc(C(C)(C)C)nc2)nc2n(c1=O)CCCS2] | 8-(6-(tert-butyl)pyridin-3-yl)-7-(methylthio)-3,4-dihydro-2H,6H-pyrimido[2,1-b][1,3]thiazin-6-one | $^1$H NMR (400 MHz, DMSO-$d_6$) δ (ppm): 8.88 (s, 1H), 7.90 (s, 1H), 7.40 (d, J = 9.2 Hz, 1H), 4.16 (t, J = 6 Hz, 2H), 3.21 (t, J = 6 Hz, 2H), 2.27-2.20 (m, 5H), 1.39 (s, 9H). Calculated (M + H): 348.11, Found (M + H): 348.1. HPLC purity: 99.23% |

Example 28

Preparation of 7-bromo-8-(4-(tert-butyl)phenyl)-3,4-dihydro-2H,6H-pyrimido[2,1-b][1,3]thiazin-6-one 5

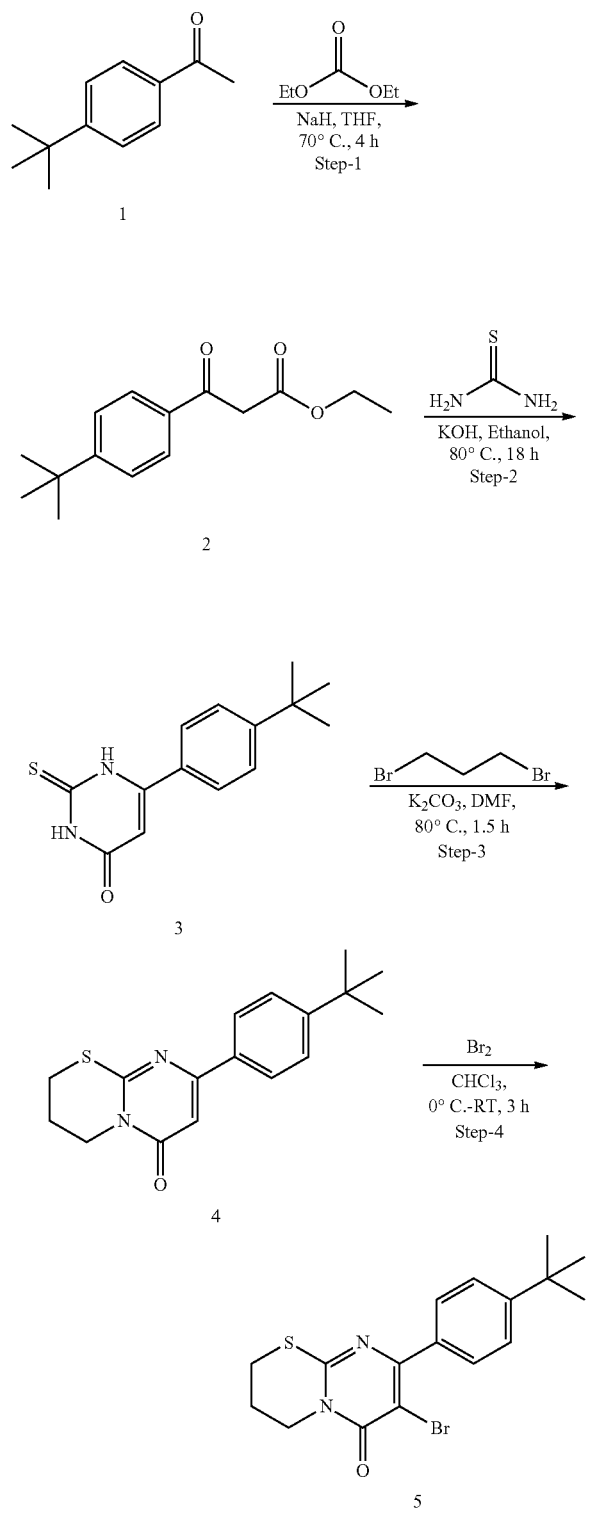

Step-1:

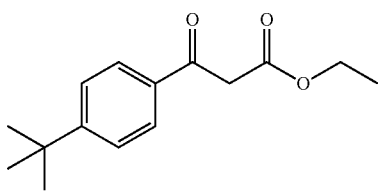 [SMILES: CCOC(=O)CC(=O)c1ccc(C(C)(C)C)cc1]

Preparation of ethyl 3-(4-(tert-butyl)phenyl)-3-oxopropanoate 2

To a stirred suspension of sodium hydride (2.4 g, 59.61 mmol) in tetrahydrofuran (100 mL), diethyl carbonate (9.63 mL, 79.49 mmol) was added at room temperature. Then 1-(4-(tert-butyl)phenyl)ethan-1-one (1, 3.63 mL, 19.87 mmol) was added to the reaction mixture drop wise over a period of 30 minutes and heated to 70° C. for 4 h. The reaction mixture was cooled to room temperature, quenched with crushed ice and extracted with ethyl acetate (3×150 mL). The combined organic layer was dried over anhydrous sodium sulphate, filtered and concentrated. The crude product was purified by silica gel column chromatography using 10% ethyl acetate in hexane to afford the title compound ethyl 3-(4-(tert-butyl)phenyl)-3-oxopropanoate (2, 4.8 g, 97% yield) as brown oil. Calculated (M+H): 249.1; Found (M+H): 249.1.

Step-2:

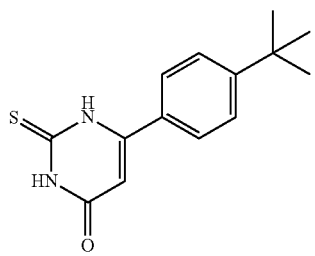 [SMILES: CC(C)(C)c1ccc(-c2cc(=O)[nH]c(=S)[nH]2)cc1]

Preparation of 6-(4-(tert-butyl)phenyl)-2-thioxo-2,3-dihydropyrimidin-4(1H)-one 3

To a stirred mixture of ethyl 3-(4-(tert-butyl)phenyl)-3-oxopropanoate (2, 2.9 g, 11.67 mmol) and thiourea (0.89 g, 11.67 mmol) in ethanol (40 mL), potassium hydroxide (0.65 g, 11.67 mmol) was added at room temperature. The resulting mixture was stirred at 80° C. for 18 h. The reaction mixture was cooled to room temperature and the solvent was evaporated. The obtained residue was dissolved in water (20 mL) and extracted with ethyl acetate (3×100 mL). The combined organic layer was dried over anhydrous sodium sulphate, filtered and concentrated to afford the title compound 6-(4-(tert-butyl)phenyl)-2-thioxo-2,3-dihydropyrimidin-4(1H)-one (3, 3 g, crude). Calculated (M+H): 261.1: Found (M+H): 261.1.

Step-3:

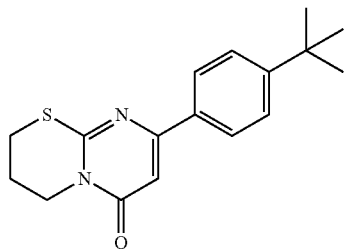 [SMILES: CC(C)(C)c1ccc(-c2cc(=O)n3c(n2)SCCC3)cc1]

Preparation of 8-(4-(tert-butyl)phenyl)-3,4-dihydro-2H,6H-pyrimido[2,1-b][1,3]thiazin-6-one 4

A mixture of 6-(4-(tert-butyl)phenyl)-2-thioxo-2,3-dihydropyrimidin-4(1H)-one (3, 3 g, 11.52 mmol), 1,3-dibromopropane (1.2 mL, 11.52 mmol) and potassium carbonate (4.78 g, 34.56 mmol) in N,N-dimethylformamide (30 mL) was heated at 80° C. for 1.5 h. The reaction mixture was cooled to room temperature, diluted with water (50 mL) and extracted with ethyl acetate (3×150 mL). The combined organic layer was dried over anhydrous sodium sulphate, filtered and concentrated. The crude product was purified by silica gel column chromatography using 35% ethyl acetate in hexane to afford the title compound 8-(4-(tert-butyl)phenyl)-3,4-dihydro-2H,6H-pyrimido[2,1-b][1,3]thiazin-6-one (4, 1.92 g, 55% yield) as off white solid. Calculated (M+H): 301.1; Found (M+H): 301.1.

Step-4:

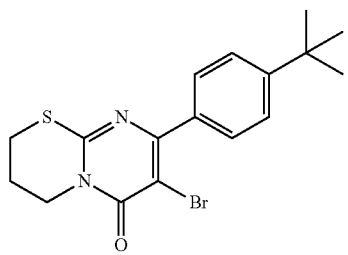 [SMILES: CC(C)(C)c1ccc(-c2nc3n(c(=O)c2Br)CCCS3)cc1]

Preparation of 7-bromo-8-(4-(tert-butyl)phenyl)-3,4-dihydro-2H,6H-pyrimido[2,1-b][1.3]thiazin-6-one 5

To a stirred solution of 8-(4-(tert-butyl)phenyl)-3,4-dihydro-2H,6H-pyrimido[2,1-b][1,3]thiazin-6-one (4, 1.92 g, 6.39 mmol) in chloroform (20 mL), bromine (0.36 mL, 7.03 mmol) was added drop wise at 0° C. and the reaction mixture was allowed to stir at room temperature for 3 h. The reaction mixture was diluted with dichloromethane (250 mL) and washed with saturated sodium bicarbonate solution (50 mL). The organic layer was dried over anhydrous sodium sulphate, filtered and concentrated. The crude product was washed with diethyl ether and n-pentane to afford the title compound 7-bromo-8-(4-(tert-butyl)phenyl)-3,4-dihydro-2H,6H-pyrimido[2,1-b][1,3]thiazin-6-one (5 (example 28), 2.3 g, 95% yield) as an off white solid. $^1$H NMR (DMSO-d$_6$, 400 MHz) δ (ppm): 7.56 (d, J=8.4 Hz, 2H), 7.47 (d, J=8.0 Hz, 2H), 4.02 (t, J=5.2 Hz, 2H), 3.2 (t, J=5.6 Hz, 2H), 2.2 (bs, 2H), 1.29 (s, 9H). Calculated (M+H): 381.1; Found (M+H): 381.1, HPLC purity: 99.96%

Example 29

Preparation of 8-(4-(tert-butyl)phenyl)-7-methyl-3,4-dihydro-2H,6H-pyrimido[2,1-b][1,3]thiazin-6-one 2

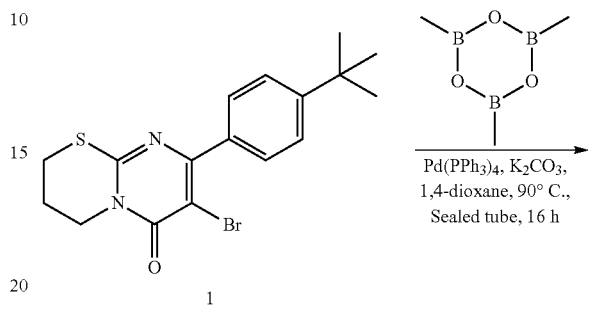

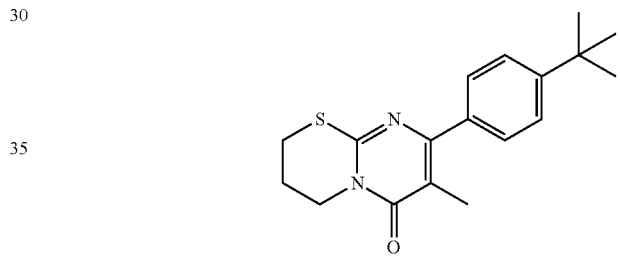

To a stirred solution of 7-bromo-8-(4-(tert-butyl)phenyl)-3,4-dihydro-2H,6H-pyrimido[2,1-b][1,3]thiazin-6-one (1, 0.15 g, 0.39 mmol) in 1,4-dioxane (3 mL), tetrakis(triphenylphosphine)palladium (0.045 g, 0.039 mmol) and potassium carbonate (0.16 g, 1.18 mmol) were added in a sealed tube under nitrogen atmosphere. The reaction mixture was purged with nitrogen for 10 min. Then 2,4,6-trimethyl-1,3,5,2,4,6-trioxatriborinane (0.083 mL, 0.59 mmol) was added and the reaction mixture was heated at 90° C. for 16 h. The reaction mixture was cooled to room temperature, diluted with water (5 mL) and extracted with ethyl acetate (3×50 mL). The combined organic layer was dried over anhydrous sodium sulphate, filtered and concentrated. The crude product was purified by silica gel column chromatography using 30% ethyl acetate in hexane to afford the title compound 8-(4-(tert-butyl)phenyl)-7-methyl-3,4-dihydro-2H,6H-pyrimido[2,1-b][1,3]thiazin-6-one (2 (example 29), 0.058 g, 46% yield) as a white solid. $^1$H NMR (DMSO-d$_6$, 400 MHz) δ (ppm): 7.46-7.4 (m, 4H), 3.98 (t, J=5.2 Hz, 2H), 3.18 (t, J=5.6 Hz, 2H), 2.18 (bs, 2H), 1.96 (s, 3H), 1.29 (s, 9H). Calculated (M+H): 315.1; Found (M+H): 315.1. HPLC purity: 99.94%

Example 30

Preparation of 7-bromo-8-(6-(tert-butyl)pyridin-3-yl)-3,4-dihydro-2H,6H-pyrimido[2,1-b][1,3]thiazin-6-one 6

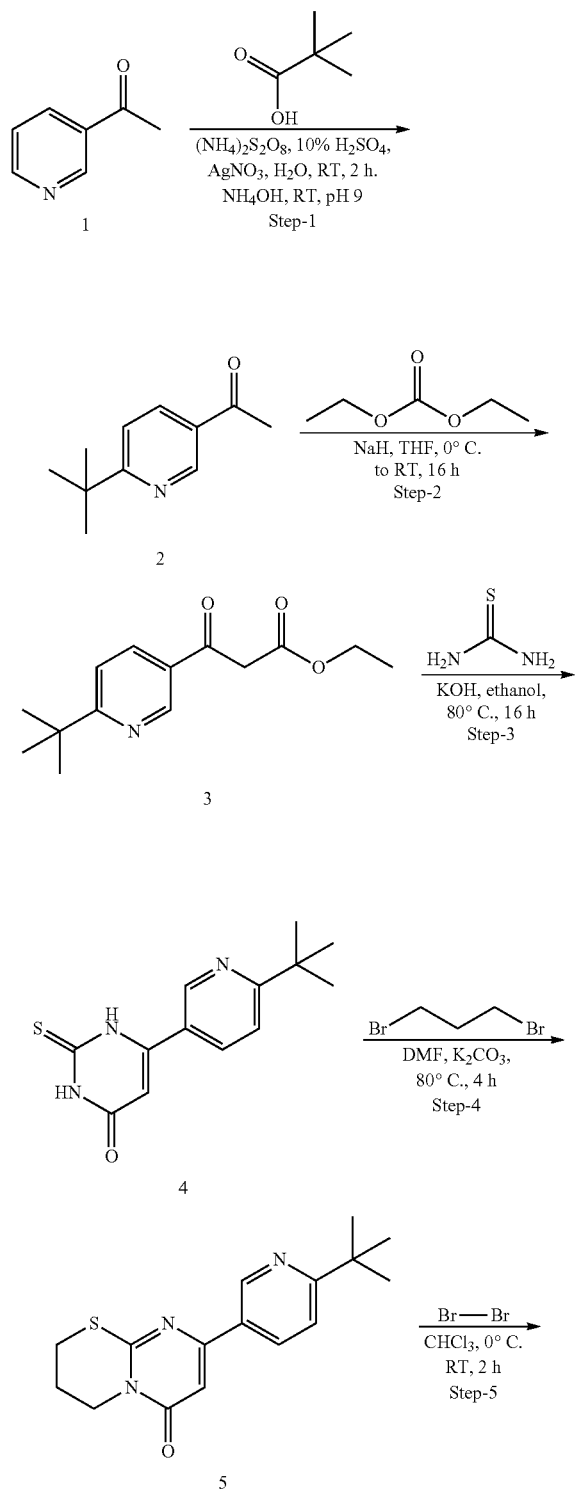

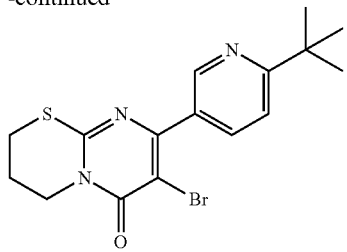

Step-1:

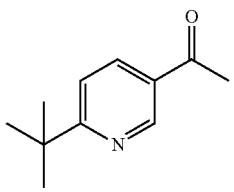

Preparation of 1-(6-(tert-butyl)pyridin-3-yl)ethan-1-one 2

To a solution of 1-(pyridin-3-yl)ethan-1-one (1, 10 g, 82.54 mmol), pivalic acid (42 g, 412.71 mmol), silver nitrate (2.8 g, 16.52 mmol) in 10% aqueous sulphuric acid (90 mL), ammonium persulphate (37.64 g, 165.31 mmol) dissolved in water (200 mL) was added at room temperature and the reaction mixture was stirred at room temperature for 2 h. The reaction mixture was basified with aqueous ammonia solution to pH 9 and extracted with ethyl acetate (3×150 mL). The combined organic layer was dried over anhydrous sodium sulfate, filtered and concentrated. The crude product was purified by silica gel chromatography using 10% ethyl acetate in hexane to afford the title compound 1-(6-(tert-butyl)pyridin-3-yl)ethan-1-one (2, 13.0 g, 89% yield) as a yellow liquid. Calculated (M+H): 118.12; Found (M+H): 118.2.

Step-2:

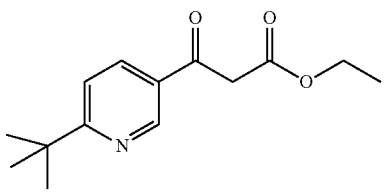 [SMILES: CCOC(=O)CC(=O)c1ccc(C(C)(C)C)nc1]

Preparation of ethyl 3-(6-(tert-butyl)pyridin-3-yl)-3-oxopropanoate 3

To a solution of 1-(6-(tert-butyl)pyridin-3-yl)ethan-1-one (2, 13 g, 73.34 mmol) in tetrahydrofuran (150 mL), sodium hydride (7.5 g, 220 mmol) was added at 0° C. After 15 min, diethyl carbonate (37.32 g, 293 mmol) was added drop wise at the same temperature. The reaction mixture was stirred at room temperature for 16 h. The reaction mixture was quenched with ice cold water (100 mL) and extracted with ethyl acetate (3×150 mL). The combined organic layer was dried over anhydrous sodium sulfate, filtered and concentrated. The crude product was purified by silica gel chromatography using 20% ethyl acetate in hexane to afford the title compound ethyl 3-(6-(tert-butyl)pyridin-3-yl)-3-oxopropanoate (3, 10.0 g, 50% yield) as a yellow liquid. Calculated (M+H): 250.14; Found (M+H): 250.2.

Step-3:

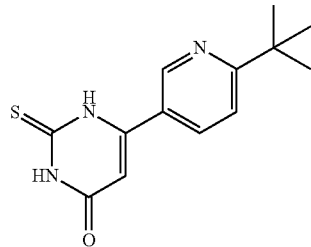 [SMILES: CC(C)(C)c1ccc(-c2cc(=O)[nH]c(=S)[nH]2)cn1]

Preparation of 6-(6-(tert-butyl)pyridin-3-yl)-2-thioxo-2,3-dihydropyrimidin-4(1H)-one 4

To a solution of ethyl 3-(6-(tert-butyl)pyridin-3-yl)-3-oxopropanoate (3, 5.0 g, 20 mmol) in ethanol (100 mL), thiourea (1.5 g, 20 mmol) and potassium hydroxide (1.12 g, 20 mmol) were added. The reaction mixture was stirred at 80 TC for 16 h. The reaction mixture was concentrated to remove ethanol and the obtained crude product was washed with diethyl ether to afford the title compound 6-(6-(tert-butyl)pyridin-3-yl)-2-thioxo-2,3-dihydropyrimidin-4(1H)-one (4, 1.4 g, 26% yield) as a yellow solid. Calculated (M+H): 262.09; Found (M+H): 262.2.

Step-4:

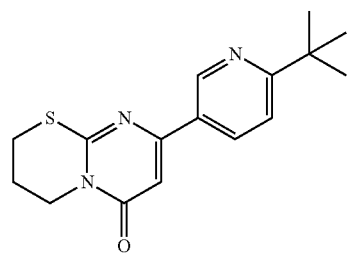 [SMILES: CC(C)(C)c1ccc(-c2cc(=O)n3c(n2)SCCC3)cn1]

Preparation of 8-(6-(tert-butyl)pyridin-3-yl)-3,4-dihydro-2H,6H-pyrimido[2,1-b][1,3]thiazin-6-one 5

To a solution of 6-(6-(ter-butyl)pyridin-3-yl)-2-thioxo-2,3-dihydropyrimidin-4(1H)-one (4, 0.15 g, 0.51 mmol) in N,N-dimethylformamide (10 mL), 1,3-dibromopropane (0.07 mL, 0.63 mmol) and potassium carbonate (0.21 g, 1.5 mmol) were added. The reaction mixture was stirred at 80 °C for 4 h. The reaction mixture was quenched with water (20 mL) and extracted with ethyl acetate (3×30 mL). The combined organic layer was dried over anhydrous sodium sulfate, filtered and concentrated. The crude product was purified by silica gel chromatography using 35% ethyl acetate in hexane to afford the title compound 8-(6-(tert-butyl)pyridin-3-yl)-3,4-dihydro-2H,6H-pyrimido[2,1-b][1,3]thiazin-6-one (5, 0.15 g, crude) as a yellow solid. Calculated (M+H): 302.12; Found (M+H): 302.1.

Step-5:

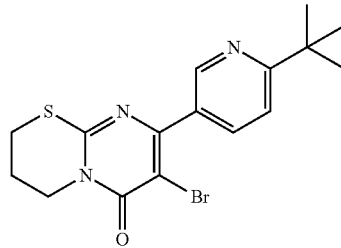

Preparation of 7-bromo-8-(6-(tert-butyl)pyridin-3-yl)-3,4-dihydro-2H,6H-pyrimido[2,1-b][1,3]thiazin-6-one 6

To a solution of 8-(6-(tert-butyl)pyridin-3-yl)-3,4-dihydro-2H,6H-pyrimido[2,1-b][1,3]thiazin-6-one (5, 0.15 g, 0.49 mmol) in chloroform (10 mL), bromine (0.04 mL, 0.74 mmol) was added drop wise at 0° C. and the reaction mixture was stirred at room temperature for 2 h. The reaction mixture was quenched with water (15 mL) and extracted with dichloromethane (2×30 mL). The combined organic layer was dried over anhydrous sodium sulfate, filtered and concentrated. The crude product was purified by silica gel chromatography using 30% ethyl acetate in hexane to afford the title compound 7-bromo-8-(6-(tert-butyl)pyridin-3-yl)-3,4-dihydro-2H,6H-pyrimido[2,1-b][1,3]thiazin-6-one (6, (example 30) 0.027 g, 14% yield) as a white solid. $^1$H NMR (400 MHz, DMSO-$d_6$) δ (ppm): 8.74 (s, 1H), 7.94 (t, J=6.4 Hz, 1H), 7.52 (d, J=8.4 Hz, 1H), 4.03 (t, J=5.2 Hz, 2H), 3.21 (t, J=6.0 Hz, 2H), 2.21 (s, 2H), 1.32 (s, 9H). Calculated (M+H): 380.04; Found (M+H): 380.0, HPLC Purity: 99.91%

Example 31

Preparation of 8-(6-(tert-butyl)pyridin-3-yl)-7-methyl-3,4-dihydro-2H,6H-pyrimido[2,1-b][1,3]thiazin-6-one 2

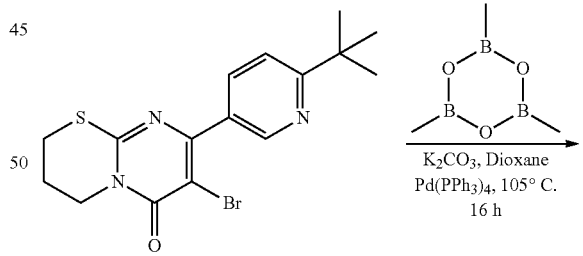

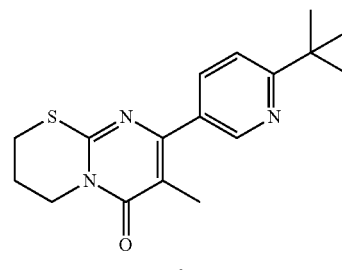

To a solution of 7-bromo-8-(6-(tert-butyl)pyridin-3-yl)-3,4-dihydro-2H,6H-pyrimido[2,1-b][1,3]thiazin-6-one (1, 0.17 g, 0.44 mmol) in 1,4-dioxane (20 mL), potassium carbonate (0.18 g, 1.32 mmol) and tetrakis(triphenylphosphine)palladium(0) (0.046 g, 0.04 mmol) were added. The reaction mixture was purged with argon for 10 min and then 2,4,6-trimethyl-1,3,5,2,4,6-trioxatriborinane (0.084 g, 0.67 mmol) was added. The reaction mixture was stirred at 105° C. for 16 h. The reaction mixture was quenched with water (50 mL) and extracted with ethyl acetate (2×40 mL). The combined organic layer was dried over anhydrous sodium sulfate, filtered and concentrated. The crude product was purified by silica gel chromatography using 30% ethyl acetate in hexane to afford the title compound 8-(6-(tert-butyl)pyridin-3-yl)-7-methyl-3,4-dihydro-2H,6H-pyrimido[2,1-b][1,3]thiazin-6-one (2 (example 31), 0.035 g, 25% yield) as a white solid. $^1$H NMR (400 MHz, DMSO-$d_6$) δ (ppm): 8.61 (d, J=2.0 Hz, 1H), 7.83-7.81 (dd, $J_1$=2.4 Hz, $J_2$=8.4 Hz, 1H), 7.50 (d, J=8.4 Hz, 1H), 3.99 (t, J=5.2 Hz, 2H), 3.27-3.17 (m, 2H), 2.21-2.16 (m, 2H), 1.91 (s, 3H), 1.32 (s, 9H). Calculated (M+H): 316.14; Found (M+H): 316.3, HPLC Purity: 99.86%

Table 9: The following compound was prepared by the method described above:

Example 32

Preparation of 8-(4-(tert-butyl)phenyl)-7-vinyl-3,4-dihydro-2H,6H-pyrimido[2,1-b][1,3]thiazin-6-one 2

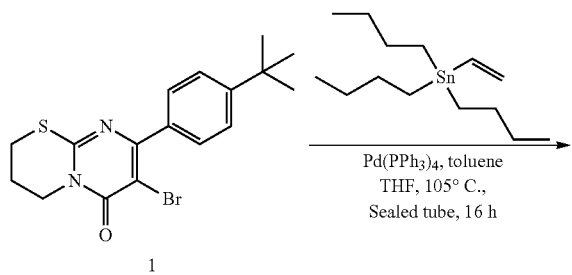

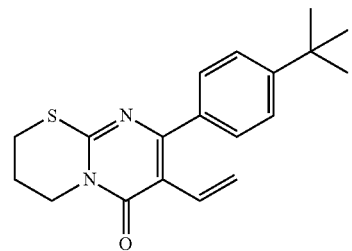

To a stirred solution of 8-(4-(tart-butyl)phenyl)-7-methyl-3,4-dihydro-2H,6H-pyrimido[2,1-b][1,3]thiazin-6-one (1, 0.2 g, 0.52 mmol) in toluene:tetrahydrofuran mixture (5 mL, 1:1), tributyl(vinyl)stannane (0.23 mL, 0.79 mmol) and tetrakis(triphenylphosphine)palladium (0.061 g, 0.052 mmol) were added in a sealed tube under nitrogen atmosphere. The reaction mixture was purged with nitrogen for 10 min and then heated to 105° C. for 16 h. The reaction mixture was cooled to room temperature, diluted with water (10 mL) and extracted with ethyl acetate (3×50 mL). The combined organic layer was dried over anhydrous sodium sulphate, filtered and concentrated. The crude product was purified by silica gel column chromatography using 35% ethyl acetate in hexane to afford the title compound 8-(4-(tert-butyl)phenyl)-7-vinyl-3,4-dihydro-2H,6H-pyrimido[2,1-b][1,3]thiazin-6-one (2 (example 32) 0.085 g, 49% yield) as pale yellow solid. $^1$H NMR (DMSO-$d_6$, 400 MHz) δ (ppm): 7.46 (d, J=7.2 Hz, 2H), 7.36 (d, J=8.0 Hz, 2H), 6.35 (d, J=7.6 Hz, 2H), 5.23 (t, J=8.0 Hz, 1H), 4.01 (bs, 2H), 3.19 (bs, 2H), 2.2 (bs, 2H), 1.29 (s, 9H). Calculated (M+H): 327.1; Found (M+H): 327.1. HPLC purity: 99.14%

TABLE 7

The following compounds were prepared by the method described above:

| Example Number | Structure | IUPAC Name | Analytical data |
|---|---|---|---|
| 33 | 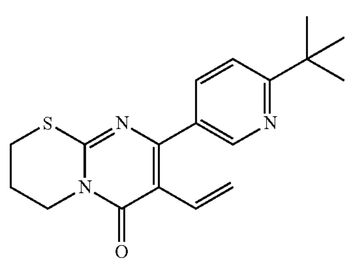 [SMILES: C=Cc1c(-c2ccc(C(C)(C)C)nc2)nc2n(c1=O)CCCS2] | 8-(6-(tert-butyl)pyridin-3-yl)-7-vinyl-3,4-dihydro-2H,6H-pyrimido[2,1-b][1,3]thiazin-6-one | $^1$H NMR (400 MHz, DMSO-$d_6$) δ (ppm): 8.53 (s, 1H), 7.77 (t, J = 5.6 Hz, 1H), 7.51 (d, J = 7.6 Hz, 1H), 6.32 (t, J = 4.0 Hz, 2H), 5.30-5.27 (m, 1H), 4.02 (t, J = 5.2 Hz, 2H), 3.21 (t, J = 5.2 Hz, 2H), 2.21 (bs, 2H), 1.32 (s, 9H). Calculated (M + H): 328.14; Found (M + H): 328.1, HPLC Purity: 99.12% |

Example 34

Preparation of 2-(6-(tert-butyl)pyridin-3-yl)-7-methyl-4-oxo-6,7,8,9-tetrahydro-4H-pyrido[1,2-a]pyrimidine-3-carbonitrile 2

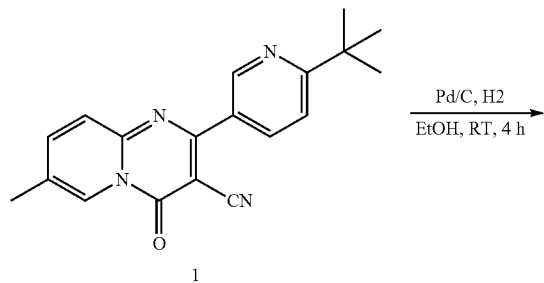

Example 35

Preparation of 7-(6-(tert-butyl)pyridin-3-yl)-3-methyl-5-oxo-5H-thiazolo[3,2-a]pyrimidine-6-carbonitrile 2

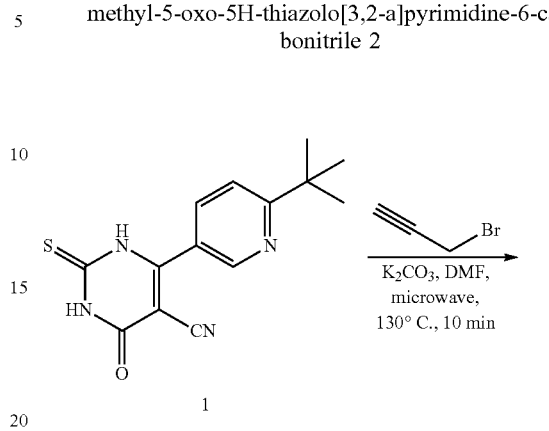

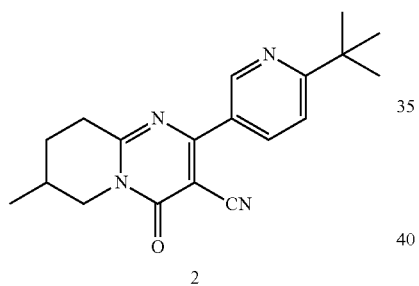

To a stirred solution of 2-(6-(tert-butyl)pyridin-3-yl)-7-methyl-4-oxo-4H-pyrido[1,2-a]pyrimidine-3-carbonitrile (1, 0.11 g) in ethanol (6 mL), palladium on carbon (0.025 g) was added carefully and the reaction mixture was stirred at room temperature for 4 h under hydrogen atmosphere using a balloon. The reaction mixture was filtered through celite bed and the filtrate was concentrated. The crude was purified by column chromatography followed by preparative HPLC (analytical conditions: column: inertsil ODS 3V (250 mm×4.6 mm×5 mic) mobile phase (A): 0.1% ammonia in water, mobile phase (B): acetonitrile, flow rate: 1.0 mL/min, T/% B: 0/10, 10/80, 25/90, 27/10, 30/10) to afford the title compound 2-(6-(tert-butyl)pyridin-3-yl)-7-methyl-4-oxo-6,7,8,9-tetrahydro-4H-pyrido[1,2-a]pyrimidine-3-carbonitrile (2 (example 34), 0.025 g, 22% yield) as a white solid. $^1$H NMR (400 MHz, DMSO-$d_6$) δ (ppm): 8.99 (d, J=1.6 Hz, 1H), 8.20 (dd, $J_1$=2 Hz, $J_2$=8.4 Hz, 1H), 7.63 (d, J=8.4 Hz, 1H), 4.20-4.15 (m, 1H), 3.27-3.18 (m, 1H), 3.04-3.01 (m, 2H), 2.05-2.02 (m, 1H), 1.90-1.86 (m, 1H), 1.54-1.44 (m, 1H), 1.33 (s, 9H), 1.05 (d, J=6.4 Hz, 3H). Calculated (M+H): 323.18; Found (M+H): 323.2, HPLC purity: 99.82%

To a stirred mixture of 6-(6-(tert-butyl)pyridin-3-yl)-4-oxo-2-thioxo-1,2,3,4-tetrahydropyrimidine-5-carbonitrile (1, 0.1 g, 0.349 mmol) and potassium carbonate (0.048 g, 0.349 mmol) in N,N-dimethylformamide (1 mL), 3-bromoprop-1-yne (0.032 mL, 0.349 mmol) was added and the reaction mixture was heated to 130° C. for 10 min under microwave irradiation condition. Then the reaction mixture was cooled to room temperature, diluted with water (5 mL) and extracted with ethyl acetate (3×25 mL). The combined organic layer was dried over anhydrous sodium sulphate, filtered and concentrated. The crude product was purified by silica gel column chromatography using 35% ethyl acetate in hexane to afford the title compound 7-(6-(tert-butyl)pyridin-3-yl)-3-methyl-5-oxo-5H-thiazolo[3,2-a]pyrimidine-6-carbonitrile (2 (example 35), 0.01 g, 5% yield) as a white solid. $^1$H NMR (DMSO-$d_6$, 400 MHz) δ (ppm): 8.99 (d, J=1.6 Hz, 1H), 8.21 (dd, $J_1$=1.6 Hz, $J_2$=8.0 Hz, 1H), 8.09 (s, 1H), 7.63 (d, J=8.4 Hz, 1H), 2.48 (s, 3H), 1.35 (s, 9H). Calculated (M+H): 325.1; Found (M+H): 325.2, HPLC purity: 99.76%

Examples 36 and 37

Preparation of 8-(4-(tert-butyl)phenyl)-6-imino-3,4-dihydro-2H,6H-pyrimido[2,1-b][1.3]thiazine-7-carbonitrile 4 & (Z)-8-(4-(tert-butyl)phenyl)-6-(methylimino)-3,4-dihydro-2H,6H-pyrimido[2,1-b][1,3]thiazine-7-carbonitrile 5

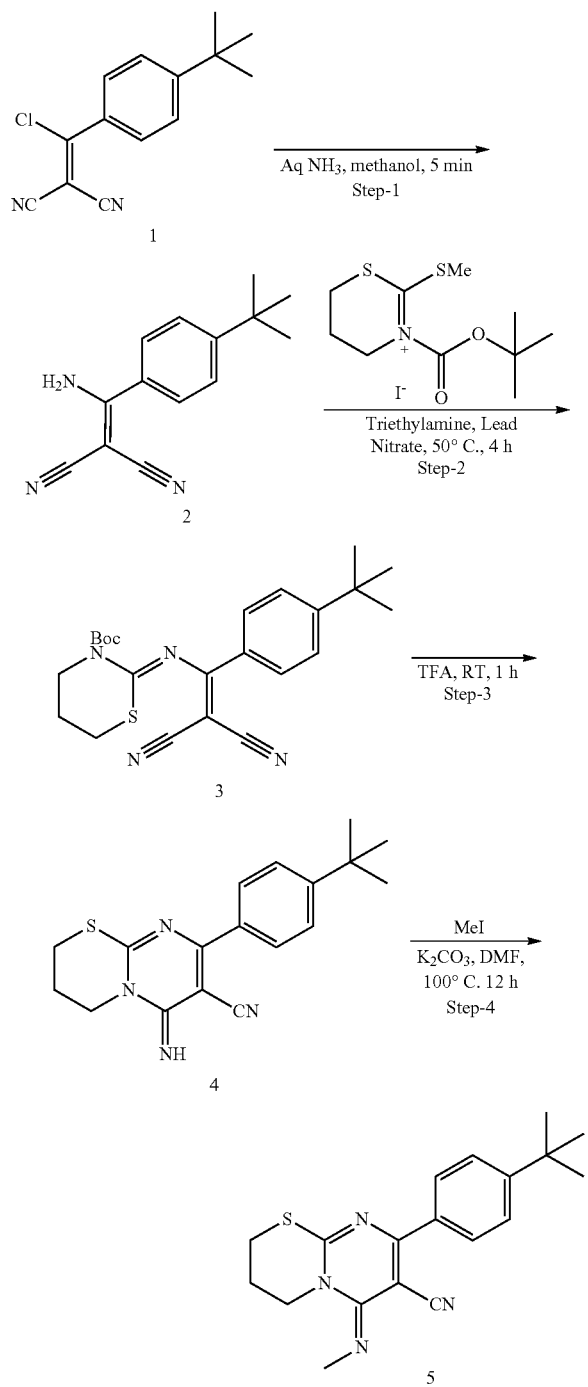

Step-1:

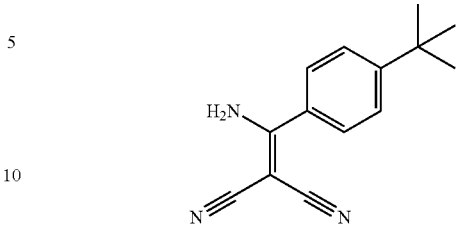

Preparation of 2-(amino(4-(tert-butyl)phenyl)methylene)malononitrile 2

To a solution of 2-((4-(tert-butyl)phenyl)chloromethylene)malononitrile (1, 0.9 g) in methanol (16 mL), 25% aqueous ammonia (8 mL) was added at 0° C. and the reaction mixture was stirred at room temperature for 5 min. The reaction mixture was evaporated completely and the crude product was purified by silica gel column chromatography using 30% ethyl acetate in hexane to afford the title compound 2-(amino(4-(tert-butyl)phenyl)methylene)malononitrile (2, 1 g, 91% yield) as an off white solid. Calculated (M−H): 224.1; Found (M−H): 224.1

Step-2:

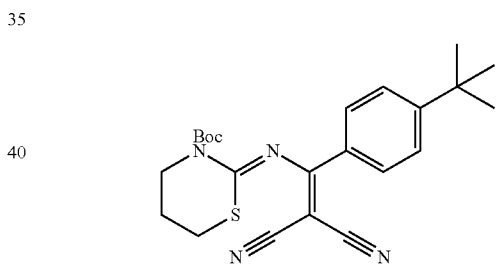

Preparation of 2tert-butyl (Z)-2-((1-(4-(tert-butyl)phenyl)-2,2-dicyanovinyl)imino)-1,3-thiazinane-3-carboxylate 3

To a solution of 2-(amino(4-(tert-butyl)phenyl)methylene)malononitrile (2, 0.9 g, 4 mmol) and 3-(tert-butoxycarbonyl)-2-(methylthio)-5,6-dihydro-4H-1,3-thiazin-3-ium iodide (0.99 g, 4 mmol) in dichloromethane (15 mL), triethylamine (2.78 mL, 20 mmol) and lead nitrate (1.98 g, 6 mmol) were added. The reaction mixture was stirred at 50° C. for 4 h. The reaction mixture was quenched with water (25 mL) and extracted with dichloromethane (2×100 mL). The combined organic layer was dried over anhydrous sodium sulphate, filtered and concentrated. The crude product was purified by silica gel column chromatography using 30% ethyl acetate in hexane to afford the title 2 tert-butyl (Z)-2-((1-(4-(tert-butyl)phenyl)-2,2-dicyanovinyl)imino)-1,3-thiazinane-3-carboxylate (3,075 g, crude) as a pale yellow gum. Calculated (M+H): 325.19; Found (M+H): 325.1.

Step-3:

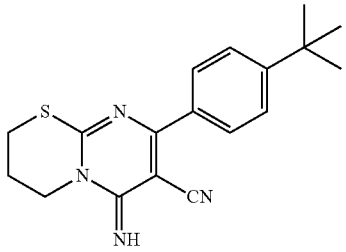 [SMILES: CC(C)(C)c1ccc(-c2nc3n(c(=N)c2C#N)CCCS3)cc1]

Preparation of 8-(4-(tert-butyl)phenyl)-6-imino-3,4-dihydro-2H,6H-pyrimido[2,1-b][1,3]thiazine-7-carbonitrile 4

To a solution of 2 tart-butyl (Z)-2-((1-(4-(tert-butyl)phenyl)-2,2-dicyanovinyl)imino)-1,3-thiazinane-3-carboxylate (3, 0.1 g) in dichloromethane (2 mL), was added trifluoro acetic acid (2 mL) and the reaction mixture was stirred at room temperature for 1 h. The reaction mixture was quenched with water (20 mL) and extracted with dichloromethane (2×50 mL). The combined organic layer was dried over anhydrous sodium sulphate, filtered and concentrated. The crude product was purified by silica gel column chromatography using 5% methanol in dichloromethane to afford the title 8-(4-(tert-butyl)phenyl)-6-imino-3,4-dihydro-2H,6H-pyrimido[2,1-b][1,3]thiazine-7-carbonitrile (4 (example 36), 0.014 g, 14% yield) as a pale yellow solid. $^1$H NMR (400 MHz, DMSO-$d_6$) δ (ppm): 7.74 (d, J=8.4 Hz, 2H), 7.53 (d, J=8.4 Hz, 2H), 7.23 (bs, 1H), 4.02 (bs, 2H), 3.23-3.21 (m, 2H), 2.23 (bs, 2H), 1.29 (s, 9H). Calculated (M+H): 325.14; Found (M+H): 325.1. HPLC purity: 99.72%

Step-4:

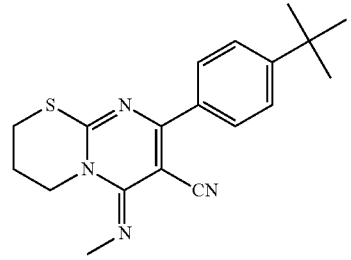 [SMILES: C/N=c1/c(C#N)c(-c2ccc(C(C)(C)C)cc2)nc2n1CCCS2]

Preparation of (Z)-8-(4-(tert-butyl)phenyl)-6-(methylimino)-3,4-dihydro-2H,6H-pyrimido[2,1-b][1,3]thiazine-7-carbonitrile 5

To a solution of 8-(4-(tert-butyl)phenyl)-6-imino-3,4-dihydro-2H,6H-pyrimido[2,1-b][1,3]thiazine-7-carbonitrile (4, 0.15 g, 0.46 mmol) in N,N-dimethyl formamide (5 mL), were added potassium carbonate (0.19 g, 1.38 mmol) and methyl iodide (0.28 mL, 4.62 mmol). The reaction mixture was stirred at 100° C. for 12 h. The reaction mixture was quenched with water (25 mL) and extracted with ethyl acetate (2×50 mL). The combined organic layer was dried over anhydrous sodium sulphate, filtered and concentrated. The crude product was purified by preparative HPLC (column: Inertsil ODS 3V (250 mm×4.6 mm×5 mic), mobile phase (A): 0.1% ammonia in water, mobile phase (B): acetonitrile, flow rate: 1.0 mL/min, T/% B: 0/10,10/70, 25/80, 27/10, 30/10) to afford the title compound (Z)-8-(4-(tert-butyl)phenyl)-6-(methylimino)-3,4-dihydro-2H,6H-pyrimido[2,1-b][1,3]thiazine-7-carbonitrile (5 (example 37), 0.013 g, 8.3% yield) as an off white solid. $^1$H NMR (400 MHz, DMSO-$d_6$) δ (ppm): 7.67 (d, J=8.4 Hz, 2H), 7.49 (d, J=7.6 Hz, 2H), 3.91-3.89 (m, 2H), 3.37 (s, 3H), 3.27-3.15 (m, 2H), 2.17 (bs, 2H), 1.29 (s, 9H). Calculated (M+H): 339.16; Found (M+H): 339.2. HPLC purity: 99.21%

TABLE 8

The following compounds were prepared by the method described above:

| Ex. # | Structure | IUPAC Name | Analytical Data |
|---|---|---|---|
| 38 | 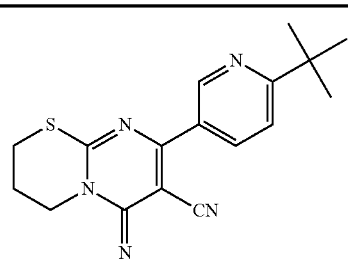 | 8-(6-(tert-butyl)pyridin-3-yl)-6-imino-3,4-dihydro-2H,6H-pyrimido[2,1-b][1,3]thiazine-7-carbonitrile | $^1$H NMR (400 MHz, DMSO-$d_6$) δ (ppm): 8.88 (s, 1H), 8.08 (d, J = 7.2 Hz, 1H), 7.58 (d, J = 8.4 Hz, 1H), 7.33 (s, 1H), 4.04 (bs, 2H), 3.27-3.23 (m, 2H), 2.23 (bs, 2H), 1.32 (s, 9H). Calculated (M + H): 326.14; Found (M + H): 326.1, HPLC purity: 98.90% |
| 39 | 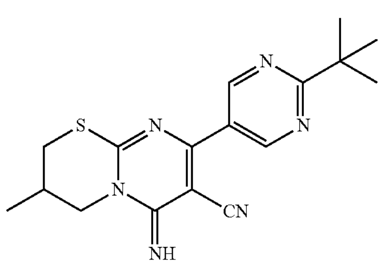 [SMILES: CC1CSc2nc(-c3cnc(C(C)(C)C)nc3)c(C#N)c(=N)n2C1] | 8-(2-(tert-butyl)pyrimidin-5-yl)-6-imino-3-methyl-3,4-dihydro-2H,6H-pyrimido[2,1-b][1,3]thiazine-7-carbonitrile | $^1$H NMR (400 MHz, DMSO-$d_6$) δ (ppm): 10.21-9.25 (bs, 1H), 9.20 (s, 2H), 4.19 (d, J = 11.6 Hz, 1H), 3.64-3.58 (m, 1H), 3.28 (d, J = 6.0 Hz, 1H), 3.16 (t, J = 10.8 Hz, 1H), 1.34 (s, 9H), 1.16 (d, J = 6.8 Hz, 3H). 1H was merged with DMSO residual peak. Calculated (M + H): 341.15; Found (M + H): 341.2, HPLC purity: 99.16% |

TABLE 8-continued

The following compounds were prepared by the method described above:

| Ex. # | Structure | IUPAC Name | Analytical Data |
|---|---|---|---|
| 40 | 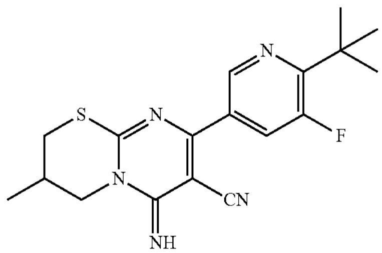 | 8-(6-(tert-butyl)-5-fluoropyridin-3-yl)-6-imino-3,4-dihydro-2H,6H-pyrimido[2,1-b][1,3]thiazine-7-carbonitrile | $^1$H NMR (400 MHz, DMSO-$d_6$) (ppm): 8.74 (s, 1H), 7.93 (dd, $J_1$ = 1.6 Hz, $J_2$ = 12.8 Hz, 1H), 7.58 (bs, 1H), 4.00 (bs, 2H), 3.24 (t, J = 6.0 Hz, 2H), 2.23 (s, 2H), 1.38 (s, 9H). Calculated (M + H): 344.13; Found (M + H): 344.3, HPLC purity: 98.29% |
| 41 | 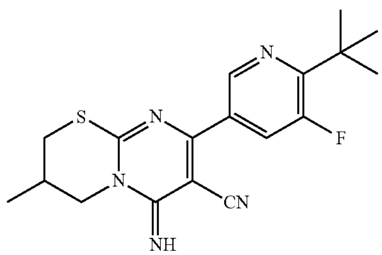 [SMILES: CC1CSc2nc(-c3cnc(C(C)(C)C)c(F)c3)c(C#N)c(=N)n2C1] | 8-(6-(tert-butyl)-5-fluoropyridin-3-yl)-6-imino-3-methyl-3,4-dihydro-2H,6H-pyrimido[2,1-b][1,3]thiazine-7-carbonitrile | $^1$H NMR (400 MHz, DMSO-$d_6$) δ (ppm): 8.74 (s, 1H), 7.92 (dd, $J_1$ = 1.2 Hz, $J_2$ = 12.8 Hz, 1H), 7.44 (bs, 1H), 4.35 (d, J = 14.8 Hz, 1H), 3.48-3.42 (m, 1H), 3.19 (d, J = 11.2 Hz, 1H), 3.05 (t, J = 9.6 Hz, 1H), 2.36-2.31 (m, 1H), 1.37 (s, 9H), 1.13 (d, J = 6.4 Hz, 3H). Calculated (M + H): 358.14; Found (M + H): 358.1, HPLC purity: 99.45% |

Example 42

Preparation of (Z)-3-(8-(4-(tart-butyl)phenyl)-7-cyano-3,4-dihydro-2H,6H-pyrimido[2,1-b][1,3]thiazin-6-ylidene)-1,1-dimethylurea 2

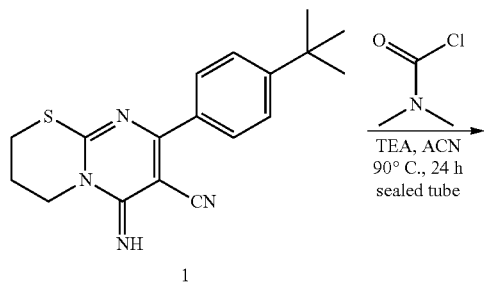

To a solution of 8-(4-(tert-butyl)phenyl)-6-imino-3,4-dihydro-2H,6H-pyrimido[2,1-b][1,3]thiazine-7-carbonitrile (1, 0.15 g, 0.46 mmol) in acetonitrile (10 mL) was added triethylamine (1.2 mL, 9.25 mmol) under inert atmosphere followed by dimethyl carbamic chloride (0.42 mL, 4.62 mmol). The resulting reaction mixture was stirred at 90° C. in a sealed tube for 24 h. The reaction mixture was concentrated, obtained residue was diluted with ethyl acetate (40 mL), washed with water (20 mL) and brine (20 mL). The organic layer was dried over anhydrous sodium sulphate, filtered and concentrated. The crude product was purified by silica gel column chromatography using 100% ethyl acetate to afford the title compound (Z)-3-(8-(4-(tert-butyl)phenyl)-7-cyano-3,4-dihydro-2H,6H-pyrimido[2,1-b][1,3]thiazin-6-ylidene)-1,1-dimethylurea (2 (example 42), 0.05 g, 27% yield) as a yellow solid. $^1$H NMR (DMSO-$d_6$, 400 MHz) δ (ppm): 7.69 (d, J=8.4 Hz, 2H), 7.53 (d, J=8.4 Hz, 2H), 4.01 (t, J=5.2 Hz, 2H) 3.22-3.27 (m, 2H), 2.79 (s, 3H), 2.83 (s, 3H), 2.25-2.30 (m, 2H), 1.29 (s, 9H). Calculated (M+H): 396.18; Found (M+H): 396.2. HPLC purity: 98.67%

Example 43

Preparation of (Z)—N-(8-(4-(tert-butyl)phenyl)-7-cyano-3,4-dihydro-2H,6H-pyrimido[2,1-b][1,3]thiazin-6-ylidene)-2,2,2-trifluoroacetamide 2

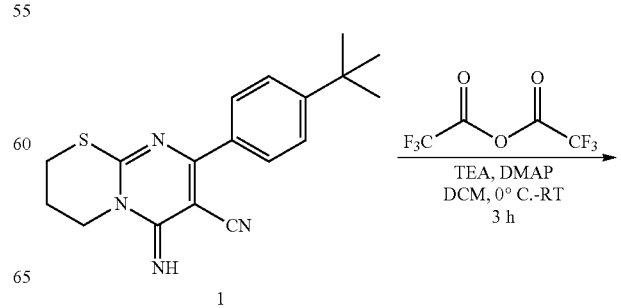

81
-continued

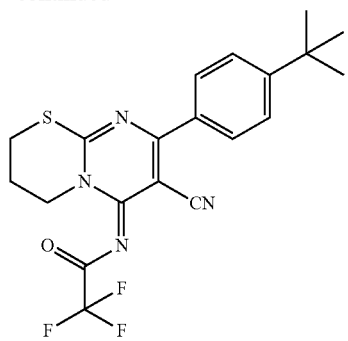

2

To a solution of 8-(4-(tert-butyl)phenyl)-6-imino-3,4-dihydro-2H,6H-pyrimido[2,1-b][1,3]thiazine-7-carbonitrile (1, 0.1 g, 0.308 mmol) in dichloromethane (20 mL), were added triethylamine (0.92 g, 0.925 mmol), 4-dimethylaminopyridine (0.02 g, 0.024 mmol) and 2,2,2-trifluoroacetic anhydride (0.97 g, 0.426 mmol) at 0° C. The reaction mixture was stirred at room temperature for 3 h. The reaction mixture was diluted with water (20 mL) and extracted with dichloromethane (20 mL). The combined organic layer was dried over anhydrous sodium sulfate, filtered and concentrated. The crude product was purified by silica gel column chromatography using 70% ethyl acetate in hexane to afford the title compound (Z)—N-(8-(4-(tert-butyl)phenyl)-7-cyano-3,4-dihydro-2H,6H-pyrimido[2,1-b][1,3]thiazin-6-ylidene)-2,2,2-trifluoroacetamide (2 (example 43), 0.056 g, 43.2% yield) as a yellow solid. $^1$H NMR (DMSO-$d_6$, 400 MHz) δ (ppm): 7.85 (d, J=8.4 Hz, 2H), 7.62 (d, J=8.0 Hz, 2H), 4.24 (bs, 2H), 3.32 (t, J=5.2 Hz, 2H), 2.31 (bs, 2H), 1.31 (s, 9H). Calculated (M+H): 421.12; Found (M+H): 421.1, HPLC purity: 99.49%

82

Examples 44 and 45

Preparation of (R)-8-(6-(tart-butyl)pyridin-3-yl)-3-methyl-6-oxo-3,4-dihydro-2H,6H-pyrimido[2,1-b][1,3]thiazine-7-carbonitrile 2 and (S)-8-(6-(tert-butyl)pyridin-3-yl)-3-methyl-6-oxo-3,4-dihydro-2H,6H-pyrimido[2,1-b][1,3]thiazine-7-carbonitrile 3

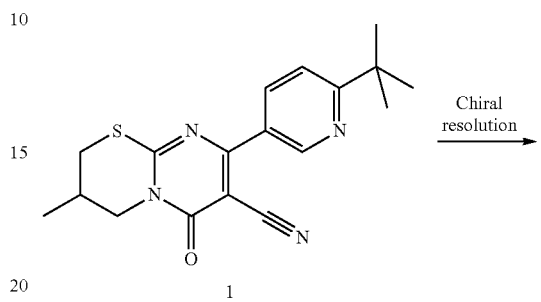

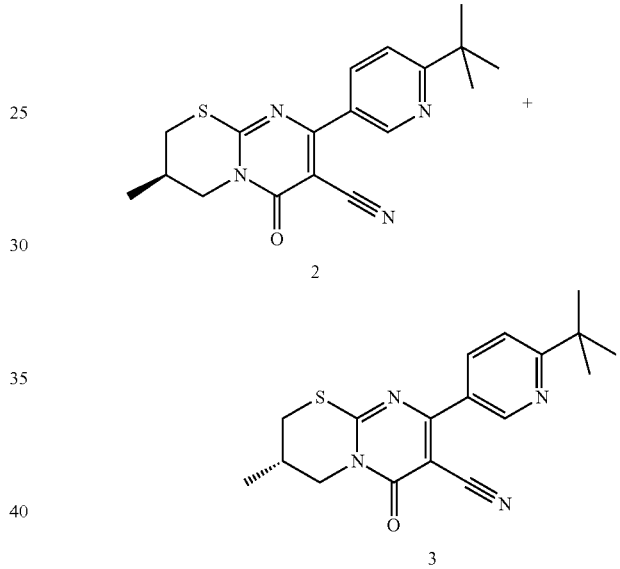

The chiral resolution was performed using the analytical condition: column: CHIRALPAK IC (250 mm×4.6 mm×5 mic), mobile phase: methyl tert-butyl ether:ethanol with 0.1% diethyl amine (50:50), flow rate: 1.0 mL/min. The analytical data for the enantiomers are given below.

TABLE 9

The following compounds were separated by the method described above

| Ex. # | Structure | IUPAC Name | Analytical Data |
|---|---|---|---|
| 44 | 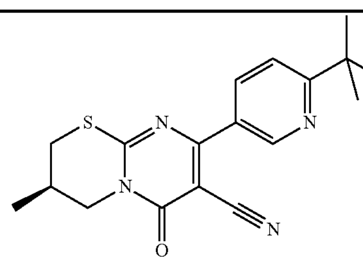 | (R)-8-(6-(tert-butyl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.94 (d, J =2.4 Hz, 1H), 8.16 (dd, $J_1$ = 1.6 Hz, $J_2$ = 8.4 Hz, 1H), 7.62 (d, J = 8.4 Hz, 1H), 4.27 (d, J = 14 Hz, 1H), 3.50-3.44 (m, 1H), 3.23 (bs, 1H), 3.07 (t, J = 10.4 Hz, 1H), 2.37-2.30 (m, 1H), 1.33 (s, 9H), 1.13 (d, J = 6.4 Hz, 3H). Calculated (M + H): 341.14; Found (M + H): 341.1, chiral HPLC purity: 99.99% |

TABLE 9-continued

The following compounds were separated by the method described above

| Ex. # | Structure | IUPAC Name | Analytical Data |
|---|---|---|---|
| 45 | 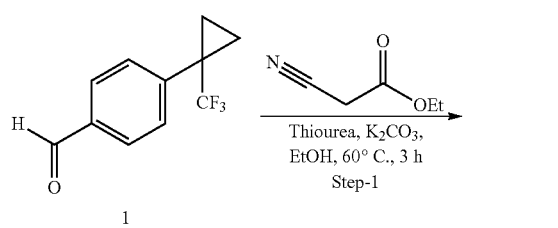 | (S)-8-(6-(tert-butyl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.94 (s, 1H), 8.16 (dd, $J_1$ = 2.4 Hz, $J_2$ = 8.4 Hz, 1H), 7.62 (d, J = 8.4 Hz, 1H), 4.27 (d, J = 14.4 Hz, 1H), 3.50-3.44 (m, 1H), 3.23 (bs, 1H), 3.07 (t, J = 10.4 Hz, 1H), 2.35-2.31 (m, 1H), 1.33 (s, 9H), 1.13 (d, J = 6.4 Hz, 3H). Calculated (M + H): 341.14; Found (M + H): 341.1, chiral HPLC purity: 99.39% |

Example 46

Preparation of 3-methyl-6-oxo-8-(4-(1-(trifluoromethyl)cyclopropyl)phenyl)-3,4-dihydro-2H,6H-pyrimido[2,1-b][1,3]thiazine-7-carbonitrile 3

Step-1:

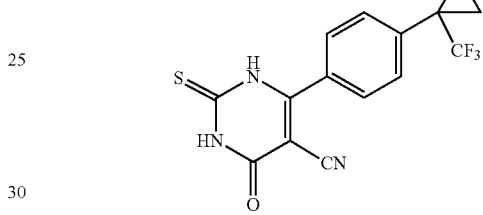

Preparation of 4-oxo-2-thioxo-6-(4-(1-(trifluoromethyl)cyclopropyl)phenyl)-1,2,3,4-tetrahydropyrimidine-5-carbonitrile 2

A mixture of 4-(1-(trifluoromethyl)cyclopropyl)benzaldehyde (1, 0.75 g, 3.5 mmol), thiourea (0.27 g, 3.5 mmol), ethyl 2-cyanoacetate (0.39 mL, 3.5 mmol) and potassium carbonate (1.45 g, 10.5 mmol) in ethanol (50 mL) was heated at 60° C. for 3 h. The reaction mixture was concentrated, the residue was diluted with water (20 mL), neutralized with acetic acid and extracted with ethyl acetate (2×150 mL). The combined organic layer was dried over anhydrous sodium sulphate, filtered and concentrated. The crude product was purified by silica gel column chromatography using 40% ethyl acetate in hexane to afford the title compound 4-oxo-2-thioxo-6-(4-(1-(trifluoromethyl)cyclopropyl)phenyl)-1,2,3,4-tetrahydropyrimidine-5-carbonitrile (2, 0.28 g, 23% yield) as pale brown solid. The material was as such taken to next step.

Step-2:

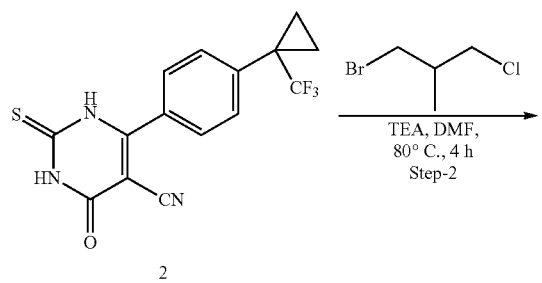

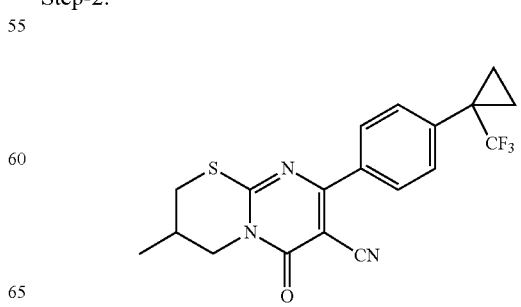

Preparation of 3-methyl-6-oxo-8-(4-(1-(trifluoromethyl)cyclopropyl)phenyl)-3,4-dihydro-2H,6H-pyrimido[2,1-b][1,3]thiazine-7-carbonitrile 3

A mixture of 4-oxo-2-thioxo-6-(4-(1-(trifluoromethyl)cyclopropyl)phenyl)-1,2,3,4-tetrahydropyrimidine-5-carbonitrile (2, 0.15 g, 0.44 mmol), 1-bromo-3-chloro-2-methylpropane (0.076 mL, 0.44 mmol) and triethylamine (0.25 mL, 1.76 mmol) in N,N-dimethylformamide (3 mL) was heated at 80° C. for 4 h in a sealed tube. The reaction mixture was cooled room temperature, diluted with water (5 mL) and extracted with ethyl acetate (3×25 mL). The combined organic layer was dried over anhydrous sodium sulphate, filtered and concentrated. The crude product was purified by silica gel column chromatography using 40% ethyl acetate in hexane to afford the title compound 3-methyl-6-oxo-8-(4-(1-(trifluoromethyl)cyclopropyl)phenyl)-3,4-dihydro-2H,6H-pyrimido[2,1-b][1,3]thiazine-7-carbonitrile (3 (example 46), 0.03 g, 17% yield) as an off white solid. $^1$H NMR (DMSO-$d_6$, 400 MHz) δ (ppm): 7.86 (d, J=8.0 Hz, 2H), 7.63 (d, J=8.0 Hz, 2H), 4.27 (d, J=13.6 Hz, 1H), 3.46 (t, J=10.0 Hz, 1H), 3.22 (bs, 1H), 3.06 (t, J=10.4 Hz, 1H), 2.31 (bs, 1H), 1.38 (bs, 2H), 1.19 (bs, 2H), 1.12 (d, J=6.8 Hz, 3H). Calculated (M+H): 392.1: Found (M+H): 392.1. HPLC purity: 99.74%

TABLE 10

The following compounds were prepared by the method described above:

| Ex. # | Structure | IUPAC Name | Analytical Data |
|---|---|---|---|
| 47 | 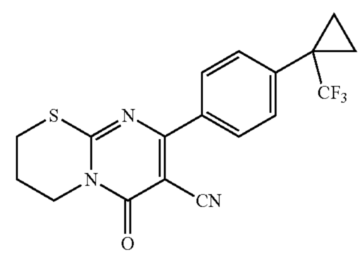 [SMILES: N#Cc1c(-c2ccc(C3(C(F)(F)F)CC3)cc2)nc2n(c1=O)CCCS2] | 6-oxo-8-(4-(1-(trifluoromethyl)cyclopropyl)phenyl)-3,4-dihydro-2H,6H-pyrimido[2,1-b][1,3]thiazine-7-carbonitrile | $^1$H-NMR (DMSO-$d_6$, 400 MHz) δ (ppm): 7.85 (d, J = 8.0 Hz, 2H), 7.63 (d, J = 8.4 Hz, 2H), 4.01 (t, J = 5.6 Hz, 2H), 3.25 (bs, 2H), 2.21 (bs, 2H), 1.38 (t, J = 6.4 Hz, 2H), 1.19 (bs, 2H). Calculated (M + H): 378.08, Found (M + H), 378.1, HPLC purity: 99.66% |
| 48 | 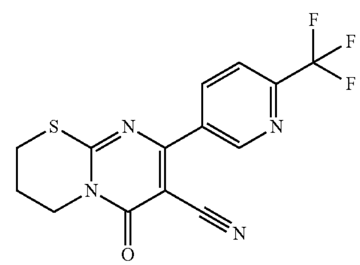 [SMILES: N#Cc1c(-c2ccc(C(F)(F)F)nc2)nc2n(c1=O)CCCS2] | 6-oxo-8-(6-(trifluoromethyl)pyridin-3-yl)-3,4-dihydro-2H,6H-pyrimido[2,1-b][1,3]thiazine-7-carbonitrile | $^1$H NMR (400 MHz, DMSO-$d_6$) δ (ppm): 9.14 (s, 1H), 8.48 (d, J = 8 Hz, 1H), 8.12 (d, J = 8 Hz, 1H), 4.03 (d, J = 4.8 Hz, 2H), 3.31-3.30 (m, 2H), 2.23 (bs, 2H). Calculated (M + H): 339.04; Found (M + H): 339, HPLC purity: 99.75% |
| 49 | 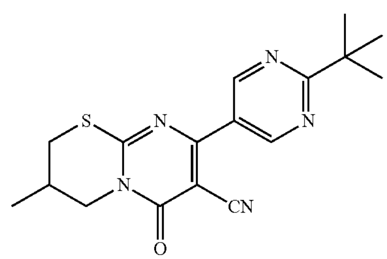 | 8-(2-(tert-butyl)pyrimidin-5-yl)-3-methyl-6-oxo-3,4-dihydro-2H,6H-pyrimido[2,1-b][1,3]thiazine-7-carbonitrile | $^1$H NMR (400 MHz, CDCl3) δ (ppm): 9.27 (s, 2H), 4.57-4.52 (m, 1H), 3.49-3.43 (m, 1H), 3.19-3.15 (m, 1H), 3.04-2.98 (m, 1H), 2.43-2.38 (m, 1H), 1.44 (s, 9H), 1.29 (d, J = 6.4 Hz, 3H). Calculated (M + H): 342.13; Found (M + H): 342.3, HPLC purity: 99.92% |
| 50 | 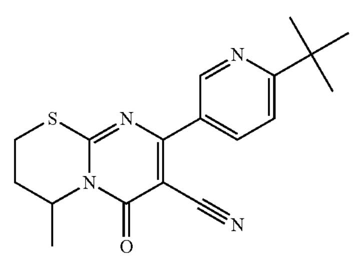 [SMILES: CC1CCSc2nc(-c3ccc(C(C)(C)C)nc3)c(C#N)c(=O)n21] | 8-(6-(tert-butyl)pyridin-3-yl)-4-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.93 (s, 1H), 8.14 (dd, $J_1$ = 2 Hz, $J_2$ = 8.4 Hz, 1H), 7.61 (d, J = 8.4 Hz, 1H), 5.08 (t, J = 3.2 Hz, 1H), 3.44-3.37 (m, 1H), 3.24 (s, 1H), 2.38-2.30 (m, 1H), 2.00 (t, J = 13.6 Hz, 1H), 1.33 (s, 9H), 1.25 (d, J = 6.8 Hz, 3H). Calculated (M + H): 341.14; Found (M + H): 341.2, HPLC purity: 97.3% |

TABLE 10-continued

The following compounds were prepared by the method described above:

| Ex. # | Structure | IUPAC Name | Analytical Data |
| --- | --- | --- | --- |
| 51 | 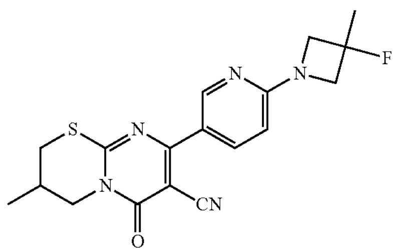 [SMILES: CC1CSc2nc(-c3ccc(N4CC(C)(F)C4)nc3)c(C#N)c(=O)n2C1] | 8-(6-(3-fluoro-3-methylazetidin-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.71 (d, J = 2 Hz, 1H), 8.05 (dd, $J_1$ = 2 Hz, $J_2$ = 8.8 Hz, 1H), 6.54 (d, J = 8.8 Hz, 1H), 4.25-4.10 (m, 5H), 3.46-3.40 (m, 1H), 3.27-3.20 (m, 1H), 3.07-3.01 (m, 1H), 2.34-2.30 (m, 1H), 1.63 (d, J = 22 Hz, 3H), 1.11 (d, J = 6.8 Hz, 3H). Calculated (M + H): 372.12; Found (M + H): 372.2, HPLC purity: 98.70% |
| 52 | 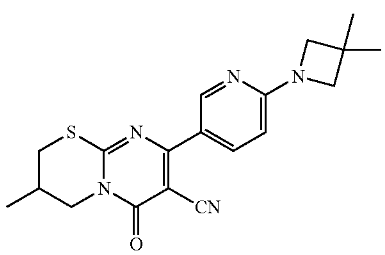 | 8-(6-(3,3-dimethylazetidin-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.70 (d, J = 2 Hz, 1H), 8.01 (dd, $J_1$ = 2.4 Hz, $J_2$ = 8.8 Hz, 1H), 6.42 (d, J = 8.8 Hz, 1H), 4.23 (d, J = 14 Hz, 1H), 3.75 (s, 4H), 3.45-3.39 (m, 1H), 3.22-3.19 (m, 1H), 3.06-3.01 (m, 1H), 2.30 (bs, 1H), 1.28 (s, 6H), 1.11 (d, J = 6.4 Hz, 3H). Calculated (M + H): 368.15; Found (M + H): 368.2, HPLC purity: 99.61% |
| 53 | 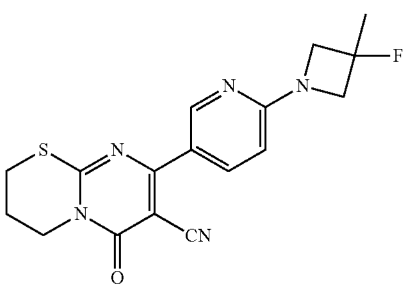 [SMILES: CC1(F)CN(c2ccc(-c3nc4n(c(=O)c3C#N)CCCS4)cn2)C1] | 8-(6-(3-fluoro-3-methylazetidin-1-yl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.71 (d, J = 2 Hz, 1H), 8.05 (dd, $J_1$ = 2 Hz, $J_2$ = 8.8 Hz, 1H), 6.54 (d, J = 8.8 Hz, 1H), 4.21-4.10 (m, 4H), 3.99-3.96 (m, 2H), 3.15-3.14 (m, 2H), 2.19 (bs, 2H), 1.63 (d, J = 22 Hz, 3H). Calculated (M + H): 358.11; Found (M + H): 358.1, HPLC purity: 98.52% |
| 54 | 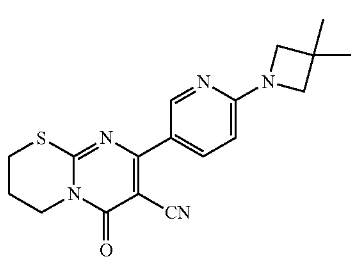 [SMILES: CC1(C)CN(c2ccc(-c3nc4n(c(=O)c3C#N)CCCS4)cn2)C1] | 8-(6-(3,3-dimethylazetidin-1-yl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.70 (d, J = 2.4 Hz, 1H), 8.01 (dd, $J_1$ = 2.8 Hz, $J_2$ = 9.2 Hz, 1H), 6.42 (d, J = 8.8 Hz, 1H), 3.98-3.95 (m, 2H), 3.75 (m, 4H), 3.24-3.23 (m, 2H), 2.19 (bs, 2H), 1.28 (s, 6H). Calculated (M + H): 354.13; Found (M + H): 354.3, HPLC purity: 99.79% |
| 55 | 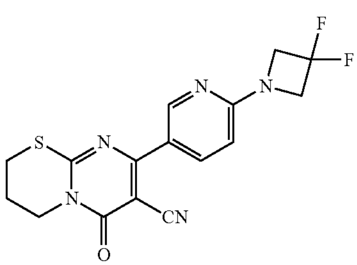 [SMILES: N#Cc1c(-c2ccc(N3CC(F)(F)C3)nc2)nc2n(c1=O)CCCS2] | 8-(6-(3,3-difluoroazetidin-1-yl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.72 (d, J = 1.6 Hz, 1H), 8.09 (dd, $J_1$ = 2 Hz, $J_2$ = 8.8 Hz, 1H), 6.66 (d, J = 8.8 Hz, 1H), 4.53-4.47 (m, 4H), 3.99-3.97 (m, 2H), 3.27-3.24 (m, 2H), 2.30-2.05 (m, 2H). Calculated (M + H): 362.08; Found (M + H): 362.1, HPLC purity: 99.61% |

TABLE 10-continued

The following compounds were prepared by the method described above:

| Ex. # | Structure | IUPAC Name | Analytical Data |
|---|---|---|---|
| 56 | 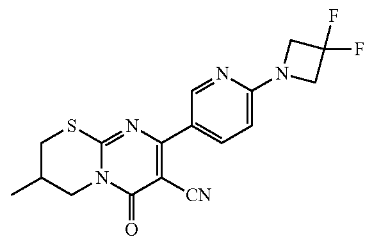 [SMILES: CC1CSc2nc(-c3ccc(N4CC(F)(F)C4)nc3)c(C#N)c(=O)n2C1] | 8-(6-(3,3-difluoroazetidin-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.72 (s, 1H), 8.10 (d, J = 8.4 Hz, 1H), 6.66 (d, J = 8.8 Hz, 1H), 4.50 (t, J = 12.4 Hz, 4H), 4.24 (d, J = 14 Hz, 1H), 3.47-3.41 (m, 1H), 3.27-3.21 (m, 1H), 3.07-3.02 (m, 1H), 2.31 (bs, 1H), 1.12 (d, J = 6.4 Hz, 3H). Calculated (M + H): 376.1; Found (M + H): 376.1, HPLC purity: 99.83% |
| 57 | 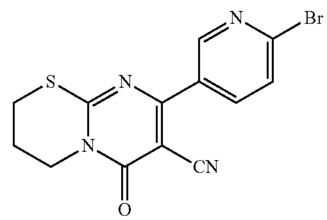 [SMILES: N#Cc1c(-c2ccc(Br)nc2)nc2n(c1=O)CCCS2] | 8-(6-bromopyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.80 (d, J = 2.4 Hz, 1H), 8.14 (dd, $J_1$ = 2.8 Hz, $J_2$ = 8.4 Hz, 1H), 7.87 (d, J = 8.4 Hz, 1H), 4.02 (t, J = 5.6 Hz, 2H), 3.30-3.27 (m, 2H), 2.21 (bs, 2H). Calculated (M + H): 348.97; Found (M + H): 349.0, HPLC purity 99.99% |
| 58 | 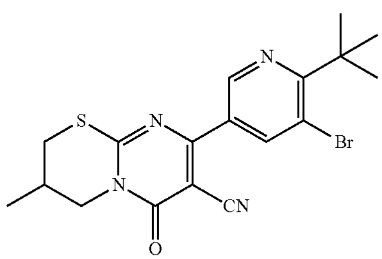 [SMILES: CC1CSc2nc(-c3cnc(C(C)(C)C)c(Br)c3)c(C#N)c(=O)n2C1] | 8-(5-bromo-6-(tert-butyl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.94 (d, J = 1.6 Hz, 1H), 8.37 (d, J = 8.4 Hz, 1H ), 4.27 (d, J = 14.0 Hz, 1H), 3.52-3.46 (m, 1H), 3.25 (bs, 1H), 3.08 (t, J = 10.4 Hz, 1H), 2.32 (bs, 1H), 1.51 (s, 9H), 1.13 (d, J = 6.4 Hz, 3H). Calculated (M + H): 419.05; Found (M + H): 419.1, HPLC purity: 99.79% |
| 59 | 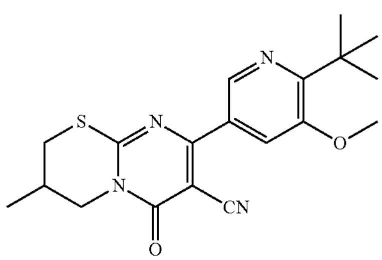 | 8-(6-(tert-butyl)-5-methoxypyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.49 (bs, 1H), 7.70 (bs, 1H), 4.26 (d, J = 13.6 Hz, 1H), 3.87 (s, 3H), 3.44-350 (m, 1H), 3.23 (d, J = 10.8 Hz, 1H), 3.06 (d, J = 9.6 Hz, 1H), 2.31-2.34 (m, 1H), 1.35 (s, 9H), 1.12 (d, J = 6.4 Hz, 3H). Calculated (M + H): 371.1, Found (M + H): 371.2, HPLC purity: 99.43% |
| 60 | 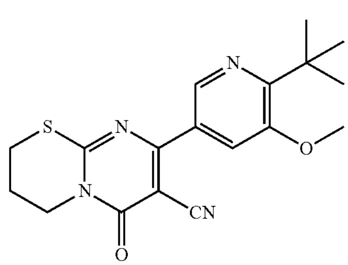 | 8-(6-(tert-butyl)-5-methoxypyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.51 (d, J = 1.6 Hz, 1H), 7.71 (bs, 1H), 4.02 (t, J = 5.2 Hz, 2H), 3.89 (s, 3H), 3.28 (d, J = 8.4 Hz, 2H), 2.22 (bs, 2H), 1.36 (s, 9H). Calculated (M + H): 357.1, Found (M + H): 357.1, HPLC purity: 99.88% |
| 61 | 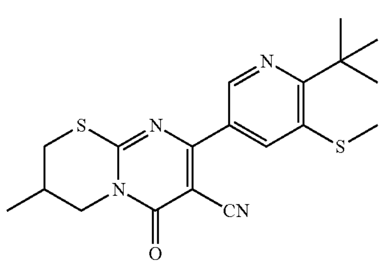 | 8-(6-(tert-butyl)-5-(methylthio)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.66 (d, J = 1.6 Hz, 1H), 8.08 (d, J = 1.2 Hz, 1H), 4.28 (d, J = 14 Hz, 1H), 3.45-351 (m, 1H), 3.24 (bs, 1H), 3.08 (t, J = 10.0 Hz, 1H), 2.55 (s, 3H), 2.31-2.36 (m, 1H), 1.47 (s, 9H), 1.13 (d, J = 6.8 Hz, 3H). Calculated (M + H): 387.1, Found (M + H): 387.3, HPLC purity: 99.60% |

TABLE 10-continued

The following compounds were prepared by the method described above:

| Ex. # | Structure | IUPAC Name | Analytical Data |
|---|---|---|---|
| 62 | 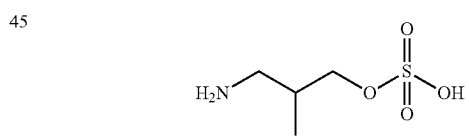 | 8-(6-(tert-butyl)-5-(methylthio)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.56 (d, J = 1.2 Hz, 1H), 8.07 (bs, 1H), 4.02 (t, J = 5.2 Hz, 2H), 3.28 (bs, 2H), 2.55 (s, 3H) 2.22 (bs, 2H), 1.47 (s, 9H). Calculated (M + H): 373.1, Found (M + H): 373.1, HPLC purity: 99.55% |

Example 63

Preparation of 8-(6-(tert-butyl)pyridin-3-yl)-6-imino-3-methyl-3,4-dihydro-2H,6H-pyrimido[2,1-b][1,3]thiazine-7-carbonitrile 7

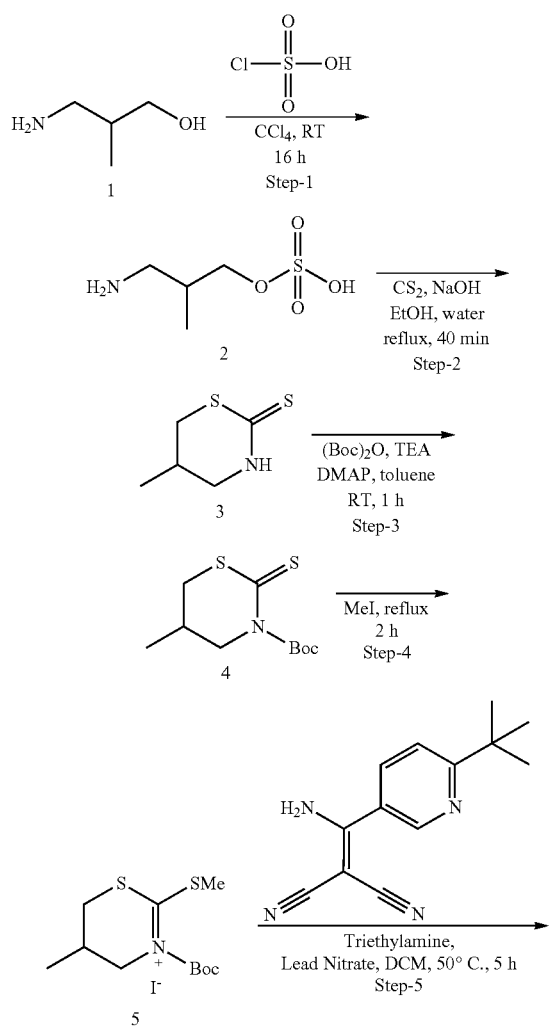

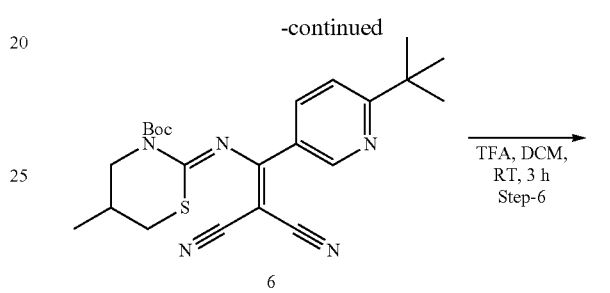

Step-1:

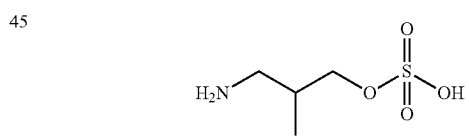

Preparation of 3-amino-2-methylpropyl hydrogen sulfate 2

To a solution of 3-amino-2-methylpropan-1-ol (1, 4.4 g, 49.36 mmol) in carbon tetrachloride (18 mL) cooled to 0° C. was added chloro sulphonic acid (3.31 mL, 49.85 mmol) drop wise using an addition funnel (highly exothermic) and the reaction mixture was stirred at room temperature for 16 h. The reaction mixture was concentrated, the residue was suspended in methanol, triturated, filtered and dried to afford the title compound 3-amino-2-methylpropyl hydrogen sulfate (2, 5.6 g, 67% yield) as an off-white solid. $^1$H NMR (400 MHz, DMSO-$d_6$) δ (ppm): 7.63 (bs, 3H), 3.74-3.70 (m, 1H), 3.65-3.61 (m, 1H), 2.87-2.80 (m, 1H), 2.70-2.64 (m, 1H), 2.05-1.97 (m, 1H), 0.88 (d, J=7.2 Hz, 3H).

Step-2:

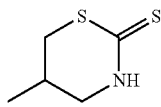

Preparation of 5-methyl-1,3-thiazinane-2-thione 3

To a suspension of 3-amino-2-methylpropyl hydrogen sulfate (2, 5.6 g, 33.09 mmol) and carbon disulphide (2.53 mL, 42.03 mmol) in 50% aqueous ethanol (15.4 mL) cooled to 0 IC was slowly added a solution of sodium hydroxide (2.91 g, 72.81 mmol) in 50% aqueous ethanol (7 mL). The reaction mixture was heated at reflux for 40 min and cooled to room temperature resulting in formation of off-white crystals. The crystals were filtered, washed with ice water and dried under high vacuum to afford the title compound 5-methyl-1,3-thiazinane-2-thione (3, 4.58 g, 94% yield) as an off-white crystalline solid. Calculated (M+H): 148.02; Found (M+H): 148

Step-3:

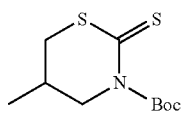

Preparation of tert-butyl 5-methyl-2-thioxo-1,3-thiazinane-3-carboxylate 4

To a solution of 5-methyl-1,3-thiazinane-2-thione (3, 4.57 g, 31.03 mmol) in toluene (45 mL), triethylamine (4.32 mL, 31.03 mL), di-tert-butyl dicarbonate (7.13 mL, 31.03 mmol) and 4-dimethylaminopyridine were added and the reaction mixture was stirred at room temperature for 1 h. The reaction mixture was concentrated and crude was purified by silica gel column chromatography using 0.5% methanol in dichloromethane to afford the title compound tert-butyl 5-methyl-2-thioxo-1,3-thiazinane-3-carboxylate (4, 6.7 g, 87% yield) as a pale yellow solid. Calculated (M+H): 248.07; Found (M+H): 148 (de-Boc mass was observed).

Step-4:

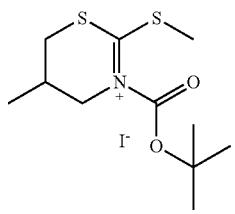

Preparation of 3-(tart-butoxycarbonyl)-5-methyl-2-(methylthio)-5,6-dihydro-4H-1,3-thiazin-3-ium iodide 5

A mixture of tert-butyl 5-methyl-2-thioxo-1,3-thiazinane-3-carboxylate (4, 6.7 g) and methyl iodide (40 mL) was heated at 45° C. for 2 h. The reaction mixture was cooled to room temperature and diluted with diethyl ether (80 mL). The crystallized solid was filtered, washed with diethyl ether and dried to afford the title compound 3-(tert-butoxycarbonyl)-5-methyl-2-(methylthio)-5,6-dihydro-4H-1,3-thiazin-3-ium iodide (5, 8.9 g, crude) as an off-white solid. Calculated (M+H): 390; Found (M+H): 162 (de-Boc and free base mass was observed).

Step-5:

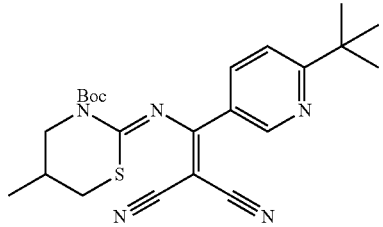 [SMILES: CC1CS/C(=N\C(=C(C#N)C#N)c2ccc(C(C)(C)C)nc2)N(C(=O)OC(C)(C)C)C1]

Preparation of tert-butyl (Z)-2-((1-(6-(tert-butyl)pyridin-3-yl)-2,2-dicyanovinyl)imino)-5-methyl-1,3-thiazinane-3-carboxylate 6

To a stirred solution of 2-(amino(6-(tert-butyl)pyridin-3-yl)methylene)malononitrile (0.25 g, 1.10 mmol) and 3-(tert-butoxycarbonyl)-5-methyl-2-(methylthio)-5,6-dihydro-4H-1,3-thiazin-3-ium iodide (5, 0.57 g, 2.21 mmol) in dichloromethane (5 mL), triethylamine (1.54 mL, 11.06 mmol) was added followed by lead nitrate (1.09 g, 3.31 mmol). The reaction mixture was heated at 50° C. for 5 h. The reaction mixture was filtered and the filtrate was concentrated. The crude was purified by silica gel column chromatography using 35% ethyl acetate in hexane to afford the title compound tert-butyl (Z)-2-((1-(6-(tert-butyl)pyridin-3-yl)-2,2-dicyanovinyl)imino)-5-methyl-1,3-thiazinane-3-carboxylate (6, 0.45 g, 93% yield) as a brownish gum. Calculated (M+H): 440.20; Found (M+H): 440.2.

Step-6:

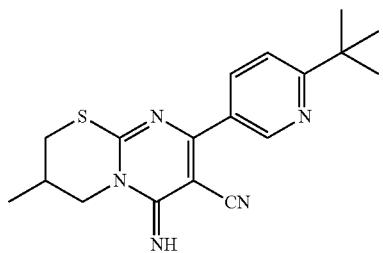

Preparation of 8-(6-(tert-butyl)pyridin-3-yl)-6-imino-3-methyl-3,4-dihydro-2H,6H-pyrimido[2,1-b][1,3]thiazine-7-carbonitrile 7

To a stirred solution of tert-butyl (Z)-2-((1-(6-(tert-butyl)pyridin-3-yl)-2,2-dicyanovinyl)imino)-5-methyl-1,3-thiazinane-3-carboxylate (6, 0.45 g) in dichloromethane (6 mL) cooled to 0° C., was added trifluoro acetic acid (3 mL) drop wise and the reaction mixture was stirred at room temperature for 3 h. The reaction mixture was concentrated, the residue was diluted with ice water (20 mL), basified with saturated sodium bicarbonate solution and extracted with dichloromethane (2×40 mL). The combined organic layer was dried over anhydrous sodium sulphate, filtered and concentrated. The crude was purified by silica gel column chromatography using 65% ethyl acetate in hexane to afford the title compound 8-(6-(tert-butyl)pyridin-3-yl)-6-imino-3-methyl-3,4-dihydro-2H,6H-pyrimido[2,1-b][1,3]thiazine-7-carbonitrile (7 (example 63), 0.13 g, 37% yield) as a yellow solid. $^1$H NMR (400 MHz, DMSO-$d_6$) δ (ppm): 8.88 (s, 1H), 8.09 (d, J=8 Hz, 1H), 7.58 (d, J=8.4 Hz, 1H), 7.35 (bs, 1H), 4.36 (d, J=14 Hz, 1H), 3.47-3.41 (m, 1H), 3.22-3.17 (m, 1H), 3.04 (t, J=10.8 Hz, 1H), 2.35 (bs, 1H), 1.32 (s, 9H), 1.13 (d, J=6.4 Hz, 3H). Calculated (M+H): 340.15: Found (M+H): 340.1. HPLC purity: 99.45%

Examples 64 and 65

Preparation of (R)-8-(6-(tert-butyl)pyridin-3-yl)-6-imino-3-methyl-3,4-dihydro-2H,6H-pyrimido[2,1-b][1,3]thiazine-7-carbonitrile 2 and (S)-8-(6-(tert-butyl)pyridin-3-yl)-6-imino-3-methyl-3,4-dihydro-2H,6H-pyrimido[2,1-b][1,3]thiazine-7-carbonitrile 3

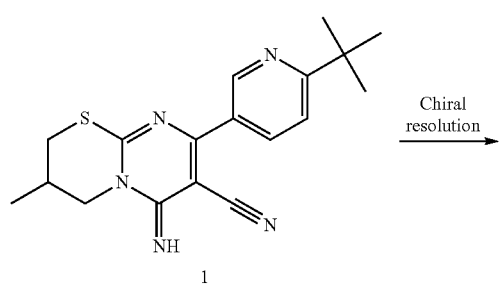

1

Chiral resolution →

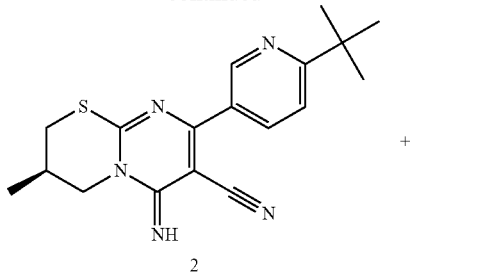

2

+

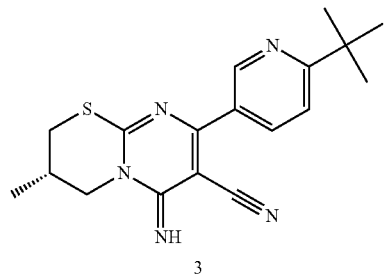

3

The chiral resolution was performed using the analytical condition: column: CHIRALPAK IC (250 mm×4.6 mm×5 mic), mobile phase: methyl tert-butyl ether:ethanol with 0.1% diethyl amine (50:50), flow rate: 1.0 mL/min. The analytical data for the enantiomers are given below.

TABLE 11

The following compounds were separated by the method described above

| Ex. # | Structure | IUPAC Name | Analytical Data |
|---|---|---|---|
| 64 | 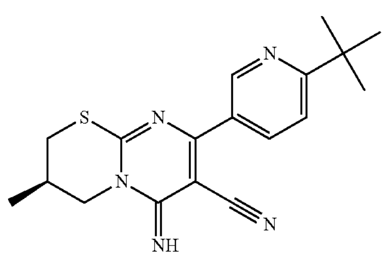 [SMILES: C[C@H]1CSc2nc(-c3ccc(C(C)(C)C)nc3)c(C#N)c(=N)n2C1] | (R)-8-(6-(tert-butyl)pyridin-3-yl)-6-imino-3-methyl-3,4-dihydro-2H,6H-pyrimido[2,1-b][1,3]thiazine-7-carbonitrile | $^1$H NMR (400 MHz, DMSO-$d_6$) δ (ppm): 8.88 (s, 1H), 8.08 (d, J = 8.4 Hz, 1H), 7.58 (d, J = 8.4 Hz, 1H), 7.35 (s, 1H), 4.36 (d, J = 14 Hz, 1H), 3.47-3.41 (m, 1H), 3.22-3.17 (m, 1H), 3.05 (t, J = 10 Hz, 1H), 2.30 (bs, 1H), 1.32 (s, 9H), 1.13 (d, J = 6.4 Hz, 3H). Calculated (M + H): 340.15; Found (M + H): 340.3, chiral HPLC purity: 99.91% |
| 65 | 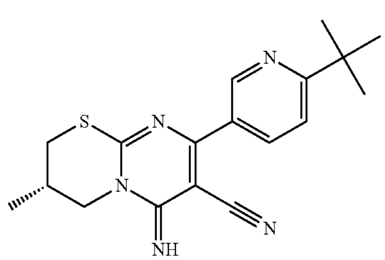 [SMILES: C[C@@H]1CSc2nc(-c3ccc(C(C)(C)C)nc3)c(C#N)c(=N)n2C1] | (S)-8-(6-(tert-butyl)pyridin-3-yl)-6-imino-3-methyl-3,4-dihydro-2H,6H-pyrimido[2,1-b][1,3]thiazine-7-carbonitrile | $^1$H NMR (400 MHz, DMSO-$d_6$) δ (ppm): 8.88 (d, J = 1.6 Hz, 1H), 8.09 (dd, $J_1$ = 2.4 Hz, $J_2$ = 8.4 Hz, 1H), 7.58 (d, J = 8.4 Hz, 1H), 7.35 (s, 1H), 4.36 (d, J = 14 Hz, 1H), 3.47-3.41 (m, 1H), 3.22-3.17 (m, 1H), 3.05 (t, J = 10 Hz, 1H), 2.36-2.30 (m, 1H), 1.32 (s, 9H), 1.13 (d, J = 6.4 Hz, 3H). Calculated (M + H): 340.14; Found (M + H): 340.3, chiral HPLC purity: 98.28% |

Example 66

Preparation of 8-(6-(dimethylamino)pyridin-3-yl)-6-oxo-3,4-dihydro-2H,6H-pyrimido[2,1-b][1,3]thiazine-7-carbonitrile 5

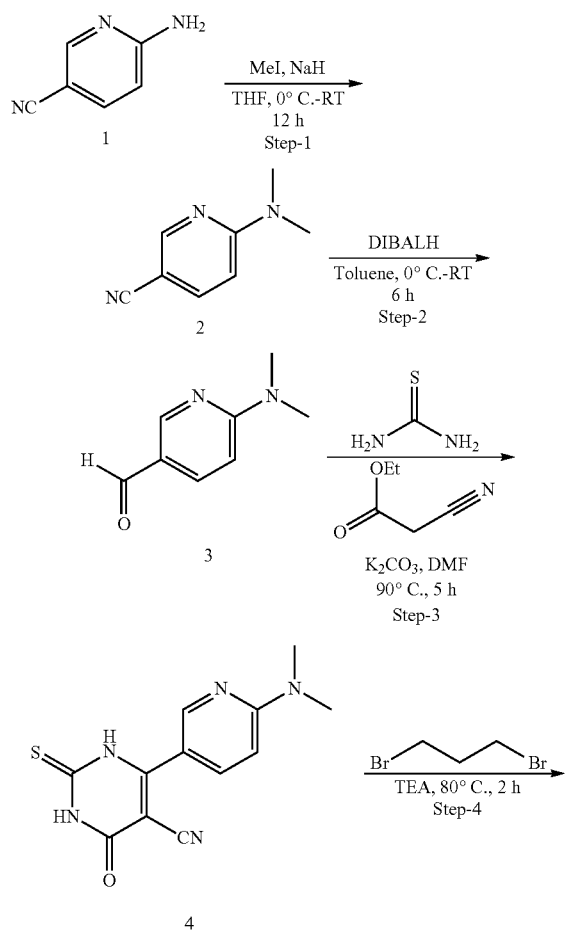

Step-1:

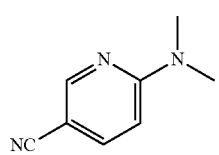

Preparation of 6-(dimethylamino)nicotinonitrile 2

To a solution of 6-aminonicotinonitrile (1, 8 g, 67.2 mmol) in tetrahydrofuran (100 mL) was added sodium hydride (8 g, 20 mmol, 60% in mineral oil) at 0° C. and the reaction mixture was stirred at 0° C. for 15 min. Then methyl iodide (20.9 mL, 33.6 mmol) was added to the reaction mixture and stirred at room temperature for 12 h. The reaction mixture was quenched with cold water (200 mL) and extracted with ethyl acetate (2×400 mL). The combined organic layer was dried over anhydrous sodium sulphate, filtered and concentrated. The crude product was purified by silica gel column chromatography using 30% ethyl acetate in hexane to afford the title compound 6-(dimethylamino)nicotinonitrile (2, 8.8 g, 89% yield) as an off white solid. Calculated (M+H): 148.08; Found (M+H): 148.2.

Step-2:

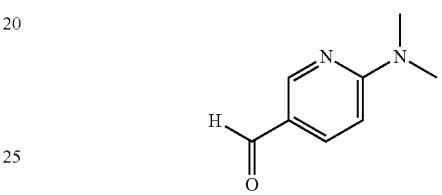

Preparation of 6-(dimethylamino)nicotinaldehyde 3

To a solution of 6-(dimethylamino)nicotinonitrile (2, 4 g, 27.2 mmol) in toluene (50 mL) was added diisobutylaluminium hydride (54 mL, 54.4 mmol) at 0° C. and the reaction mixture was then stirred at room temperature for 6 h. The reaction mixture was quenched with saturated ammonium chloride solution (50 mL) and extracted with ethyl acetate (2×200 mL). The combined organic layer was dried over anhydrous sodium sulphate, filtered and concentrated. The crude product was purified by silica gel column chromatography using 30% ethyl acetate in hexane to afford the title compound 6-(dimethylamino)nicotinaldehyde (3, 2.2 g, 55% yield) as a pale yellow solid. Calculated (M+H): 151.08; Found (M+H): 151.1.

Step-3:

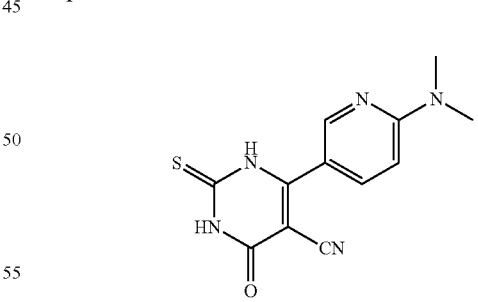

Preparation of 6-(6-(dimethylamino)pyridin-3-yl)-4-oxo-2-thioxo-1,2,3,4-tetrahydropyrimidine-5-carbonitrile 4

To a solution of 6-(dimethylamino)nicotinaldehyde (3, 0.5 g, 3.33 mmol) in ethanol (50 mL), thiourea (0.25 g, 3.3 mmol), ethyl cyano acetate (0.37 g, 3.3 mmol), potassium carbonate (2.76 g, 19.9 mmol) were added and the reaction mixture was stirred at 90° C. for 5 h. The reaction mixture was concentrated, the residue was diluted with water (10 mL) and neutralized with acetic acid. The precipitated solid was filtered, washed with hexane and dried under suction to afford the title compound 6-(6-(dimethylamino)pyridin-3-yl)-4-oxo-2-thioxo-1,2,3,4-tetrahydropyrimidine-5-carbonitrile (4, 0.33 g, 33% yield) as a pale yellow solid. Calculated (M+H): 274.07; Found (M+H): 274.0.

Step-4:

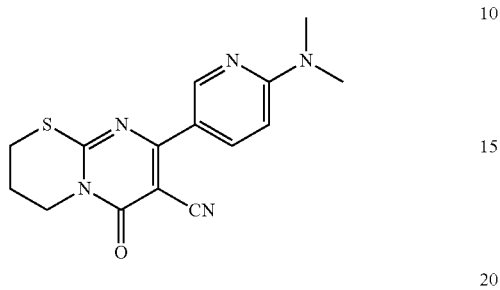

Preparation of 8-(6-(dimethylamino)pyridin-3-yl)-6-oxo-3,4-dihydro-2H,6H-pyrimido[2,1-b][1,3]thiazine-7-carbonitrile 5

To a solution of 6-(6-(dimethylamino)pyridin-3-yl)-4-oxo-2-thioxo-1,2,3,4-tetrahydropyrimidine-5-carbonitrile (4, 0.1 g, 0.36 mmol) in N,N-dimethyl formamide (3 mL), triethylamine (0.37 mL, 2.65 mmol), 1.3 dibromo propane (0.04 mL, 0.43 mmol) were added and the reaction mixture was stirred at 80 Or, for 2 h. The reaction mixture was quenched with water (20 mL) and extracted with ethyl acetate (2×40 mL). The combined organic layer was dried over anhydrous sodium sulphate, filtered and concentrated. The crude product was washed with pentane to afford the title compound 8-(6-(dimethylamino)pyridin-3-yl)-6-oxo-3,4-dihydro-2H,6H-pyrimido[2,1-b][1,3]thiazine-7-carbonitrile (5 (example 66), 0.07 g, 42% yield) as a pale yellow solid. $^1$H NMR (400 MHz, DMSO-$d_6$) δ (ppm): 8.76 (d, J=2.4 Hz, 1H), 8.05 (dd, $J_1$=2 Hz, $J_2$=8.8 Hz, 1H), 6.75 (d, J=9.2 Hz, 1H), 3.98-3.95 (m, 2H), 3.27-3.23 (m, 2H), 3.16 (s, 6H), 2.19 (m, 2H). Calculated (M+H): 314.10; Found (M+H): 314.1. HPLC purity: 99.20%

TABLE 12

The following compound was prepared by the method described above:

| Ex. # | Structure | IUPAC Name | Analytical Data |
|---|---|---|---|
| 67 | 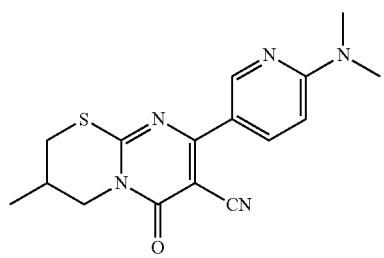 | 8-(6-(dimethylamino)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.76 (s, 1H), 8.059 (d, J = 8.4 Hz, 1H), 6.75 (d, J = 8.8 Hz, 1H), 4.23 (d, J = 13.6 Hz, 1H), 3.45-3.39 (m, 1H), 3.27-3.19 (m, 1H), 3.11 (s, 6H), 3.06-3.01 (m, 1H), 2.30 (s, 1H), 1.11 (d, J = 6 Hz, 3H). Calculated (M + H): 328.12; Found (M + H): 328.1. HPLC purity: 99.58% |

Example 68

Preparation of 8-(4-(tert-butyl)phenyl)-6-oxo-3,4-dihydro-2H,6H-pyrido[2,1-b][1,3]thiazine-7-carbonitrile 4

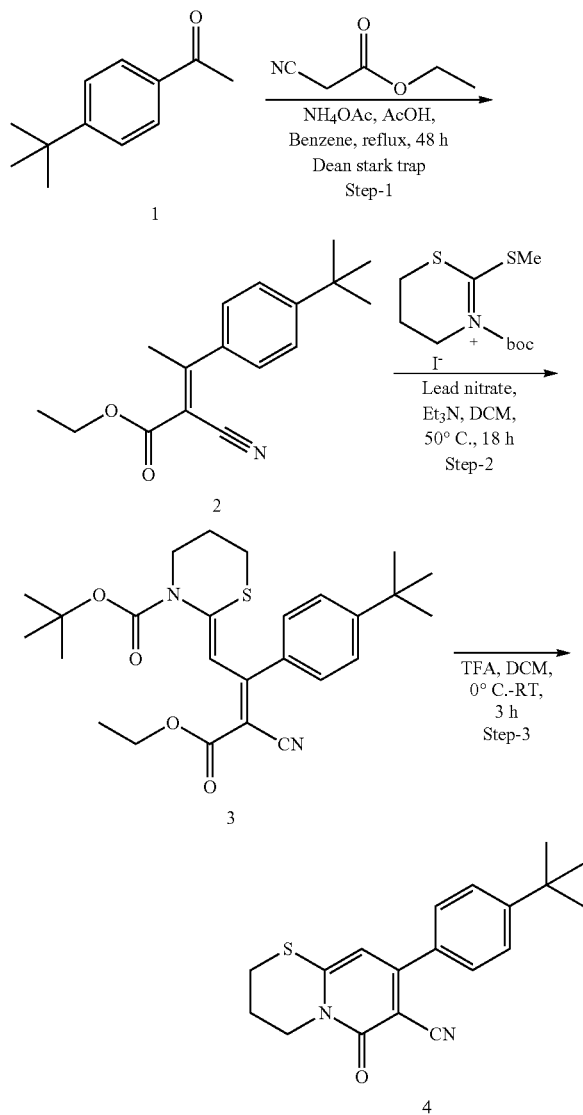

Step-1:

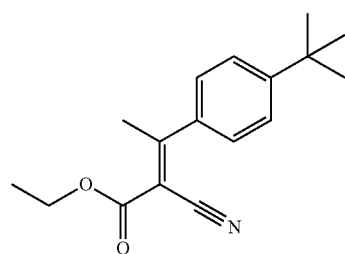 [SMILES: CCOC(=O)/C(C#N)=C(\C)c1ccc(C(C)(C)C)cc1]

Preparation of ethyl (E)-3-(4-(tert-butyl)phenyl)-2-cyanobut-2-enoate 2

To a solution of 1-(4-(tart-butyl)phenyl)ethan-1-one (1, 1 g, 5.67 mmol) in benzene (10 mL), were added ethyl cyanoacetate (0.65 mL, 6.12 mmol), acetic acid (0.18 mL, 2.94 mmol) and ammonium acetate (0.09 g, 1.13 mmol). The reaction mixture was stirred at 120° C. using Dean-stark trap for 48 h. The reaction mixture was concentrated to remove benzene, the residue was quenched with water (30 mL) and extracted with ethyl acetate (2×100 mL). The combined organic layer was dried over anhydrous sodium sulfate, filtered and concentrated. The crude product was purified by silica gel chromatography using 4% ethyl acetate in hexane to afford the title compound ethyl (E)-3-(4-(tert-butyl)phenyl)-2-cyanobut-2-enoate (2, 0.4 g, 26% yield) as colorless oil. Calculated (M+H): 272.16; Found (M+H): 272.2.

Step-2:

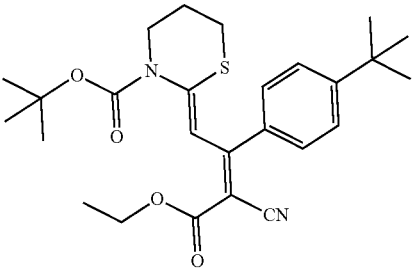 [SMILES: CCOC(=O)/C(C#N)=C(\C=C1/SCCCN1C(=O)OC(C)(C)C)c1ccc(C(C)(C)C)cc1]

Preparation of tert-butyl (Z)-2-((E)-2-(4-(tert-butyl)phenyl)-3-cyano-4-ethoxy-4-oxobut-2-en-1-ylidene)-1,3-thiazinane-3-carboxylate 3

To a stirred suspension of ethyl (E)-3-(4-(tert-butyl)phenyl)-2-cyanobut-2-enoate (2, 0.3 g, 1.1 mmol), 3-(tert-butoxycarbonyl)-2-(methylthio)-5,6-dihydro-4H-1,3-thiazin-3-ium iodide (0.55 g, 2.21 mmol) and triethylamine (1.54 mL, 11.0 mmol) in dichloromethane (15 mL), was added lead nitrate (1.09 g, 3.31 mmol) at room temperature and the reaction mixture was stirred at 50° C. for 18 h. The reaction mixture was cooled to room temperature, filtered through celite bed and washed with ethyl acetate (3×25 mL). The filtrate was concentrated and the residue was purified by silica gel column chromatography using 30% ethyl acetate in hexane to afford the title compound tert-butyl (Z)-2-((E)-2-(4-(tert-butyl)phenyl)-3-cyano-4-ethoxy-4-oxobut-2-en-1-ylidene)-1,3-thiazinane-3-carboxylate (3, 0.32 g, 60% yield) as brown solid. Calculated (M+H): 471.23; Found (M+H): 371.2. (Boc deprotected mass was observed).

Step-3:

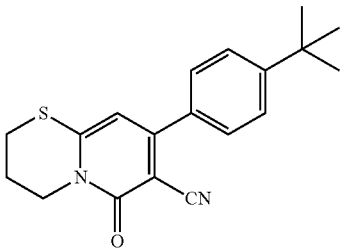 [SMILES: CC(C)(C)c1ccc(-c2cc3n(c(=O)c2C#N)CCCS3)cc1]

Preparation of 8-(4-(tert-butyl)phenyl)-6-oxo-3,4-dihydro-2H,6H-pyrido[2,1-b][1.3]thiazine-7-carbonitrile 4

To a stirred solution of tert-butyl (Z)-2-((E)-2-(4-(tert-butyl)phenyl)-3-cyano-4-ethoxy-4-oxobut-2-en-1-ylidene)-1,3-thiazinane-3-carboxylate (3, 0.05 g, 0.106 mmol) in dichloromethane (2 mL), was added trifluoro acetic acid (1 mL) at 0° C. and the reaction mixture was allowed to stir at room temperature for 3 h. The reaction mixture was concentrated under reduced pressure, the residue was diluted with saturated sodium bicarbonate solution (10 mL) and extracted with ethyl acetate (3×25 mL). The combined organic layer was dried over anhydrous sodium sulphate, filtered and concentrated. The crude product was purified by silica gel column chromatography using 50% ethyl acetate in hexane to afford the title compound 8-(4-(tert-butyl)phenyl)-6-oxo-3,4-dihydro-2H,6H-pyrido[2,1-b][1,3]thiazine-7-carbonitrile (4 (example 68), 0.015 g, 44% yield) as pale yellow solid. $^1$H NMR (400 MHz, DMSO-$d_6$) δ (ppm): 7.53 (s, 4H), 6.45 (s, 1H), 4.02 (d, J=4.8 Hz, 2H), 3.2 (t, J=5.6 Hz, 2H), 2.2 (bs, 2H), 1.3 (s, 9H). Calculated (M+H): 325.13; Found (M+H): 325.1. HPLC purity: 99.49%

TABLE 13

The following compounds were prepared by the method described above:

| Ex. # | Structure | IUPAC Name | Analytical Data |
|---|---|---|---|
| 69 | 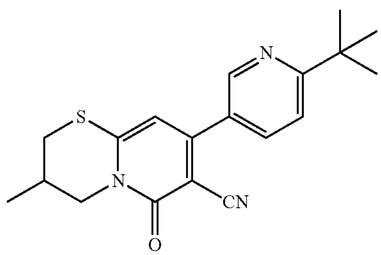 [SMILES: CC1CSc2cc(-c3ccc(C(C)(C)C)nc3)c(C#N)c(=O)n2C1] | 8-(6-(tert-butyl)pyridin-3-yl)-3-methyl-6-oxo-3,4-dihydro-2H,6H-pyrido[2,1-b][1,3]thiazine-7-carbonitrile | $^1$H-NMR (DMSO-$d_6$, 400 MHz) δ (ppm): 8.71 (d, J = 2.0 Hz, 1H), 7.96 (dd, $J_1$ = 2.0 Hz, $J_2$ = 8.4 Hz, 1H), 7.58 (d, J = 8.4 Hz, 1H), 6.58 (s, 1H), 4.34 (d, J = 14.4 Hz, 1H), 3.46-3.4 (m, 1H), 3.21 (dd, $J_1$ = 3.6 Hz, $J_2$ = 12.0 Hz, 1H), 2.98-2.93 (m, 1H), 2.3-2.26 (m, 1H), 1.33 (s, 9H), 1.11 (d, J = 6.4 Hz, 3H). Calculated (M + H): 340.14, Found (M + H): 340.1, HPLC purity: 99.34% |
| 70 | 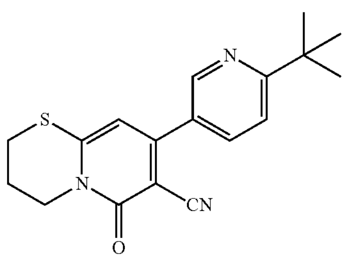 [SMILES: CC(C)(C)c1ccc(-c2cc3n(c(=O)c2C#N)CCCS3)cn1] | 8-(6-(tert-butyl)pyridin-3-yl)-6-oxo-3,4-dihydro-2H,6H-pyrido[2,1-b][1,3]thiazine-7-carbonitrile | $^1$H-NMR (DMSO-$d_6$, 400 MHz) δ (ppm): 8.71 (d, J = 2.4 Hz, 1H), 7.96 (dd, $J_1$ = 2.0 Hz, $J_2$ = 8.4 Hz, 1H), 7.58 (d, J = 8.4 Hz, 1H), 6.56 (s, 1H), 4.03 (t, J = 5.2 Hz, 2H), 3.21 (t, J = 6.0 Hz, 2H), 2.2 (bs, 2H), 1.33 (s, 9H). Calculated (M + H): 326.12, Found (M + H): 326.1, HPLC purity: 99.81% |
| 71 | 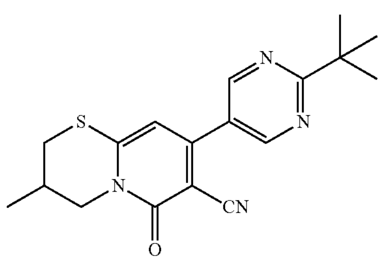 [SMILES: CC1CSc2cc(-c3cnc(C(C)(C)C)nc3)c(C#N)c(=O)n2C1] | 8-(2-(tert-butyl)pyrimidin-5-yl)-3-methyl-6-oxo-3,4-dihydro-2H,6H-pyrido[2,1-b][1,3]thiazine-7-carbonitrile | $^1$H-NMR (DMSO-$d_6$, 400 MHz) δ (ppm): 8.98 (s, 2H), 6.69 (s, 1H), 4.34 (d, J = 14.4 Hz, 1H), 3.48-3.42 (m, 1H), 3.25-3.21 (m, 1H), 2.99-2.94 (m, 1H), 2.3-2.27 (m, 1H), 1.38 (s, 9H), 1.11 (d, J = 6.4 Hz, 3H). Calculated (M + H): 341.14, Found (M + H): 341.2, HPLC purity: 99.67% |
| 72 | 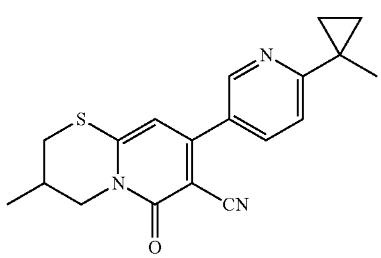 | 3-methyl-8-(6-(1-methylcyclopropyl)pyridin-3-yl)-6-oxo-3,4-dihydro-2H,6H-pyrido[2,1-b][1,3]thiazine-7-carbonitrile | $^1$H NMR (400 MHz, DMSO-$d_6$) δ (ppm): 8.63 (d, J = 1.6 Hz, 1H), 7.92 (dd, $J_1$ = 2.4 Hz, $J_2$ = 8.4 Hz, 1H), 7.45 (d, J = 8.4 Hz, 1H), 6.55 (s, 1H), 4.33 (d, J = 13.6 Hz, 1H), 3.45-3.39 (m, 1H), 3.27-3.19 (m, 1H), 2.98-2.92 (m, 1H), 2.29-2.26 (m, 1H), 1.49 (s, 3H), 1.21-1.16 (m, 2H), 1.15-1.09 (m, 3H), 0.88-0.85 (m, 2H). Calculated (M + H): 338.12; Found (M + H): 338.1, HPLC purity: 99.96% |

Examples 73 and 74

Preparation of (R)-8-(2-(tert-butyl)pyrimidin-5-yl)-3-methyl-6-oxo-3,4-dihydro-2H,6H-pyrimido[2,1-b][1.3]thiazine-7-carbonitrile 2 and (S)-8-(2-(tert-butyl)pyrimidin-5-yl)-3-methyl-6-oxo-3,4-dihydro-2H,6H-pyrimido[2,1-b][1.3]thiazine-7-carbonitrile 3

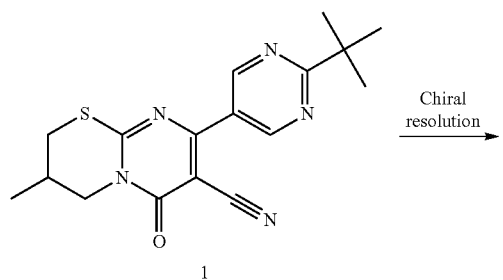

1

Chiral resolution →

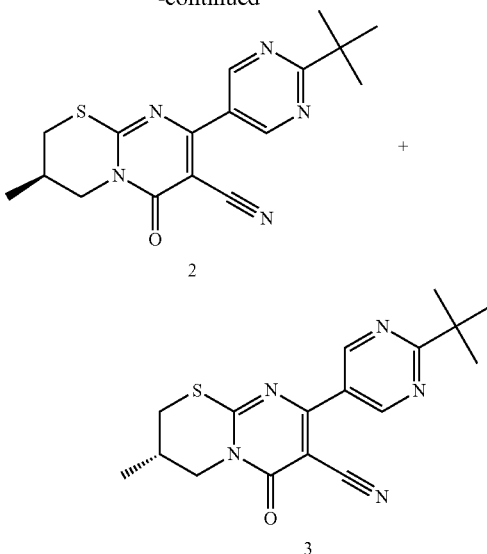

The chiral resolution was performed using the analytical condition: Column: CHIRALPAK IA (250 mm×4.6 mm×5 mic), mobile phase A: n-hexane, mobile phase B: 0.1% diethyl amine in isopropyl alcohol, composition: 70:30, flow rate: 1.0 mL/min. The analytical data for the enantiomers are given below.

TABLE 14

The following compounds were separated by the method described above

| Ex. # | Structure | IUPAC Name | Analytical Data |
|---|---|---|---|
| 73 | 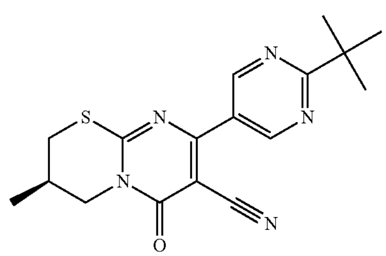 | (R)-8-(2-(tert-butyl)pyrimidin-5-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 4.28 (d, J = 14.8 Hz, 1H), 3.52-3.47 (m, 1H), 3.26-3.25 (m, 1H), 3.08 (t, J = 9.6 Hz, 1H), 2.35-2.30 (m, 1H), 1.38 (s, 9H), 1.13 (d, J = 6.4 Hz, 3H). Calculated (M + H): 342.13; Found (M + H): 342.1, chiral HPLC purity: 99.81% |
| 74 | 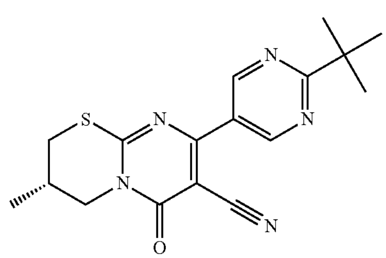 [SMILES: C[C@@H]1CSc2nc(-c3cnc(C(C)(C)C)nc3)c(C#N)c(=O)n2C1] | (S)-8-(2-(tert-butyl)pyrimidin-5-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 4.28 (d, J = 12.8 Hz, 1H), 3.52-3.47 (m, 1H), 3.27-3.24 (m, 1H), 3.10-3.05 (m, 1H), 2.37-2.30 (m, 1H), 1.38 (s, 9H), 1.13 (d, J = 6.4 Hz, 3H). Calculated (M + H): 342.13; Found (M + H): 342.1, chiral HPLC purity: 99.55% |

Example 75

Preparation of 8-(6-(tert-butyl)-5-fluoropyridin-3-yl)-6-oxo-3,4-dihydro-2H,6H-pyrimido[2,1-b][1,3]thiazine-7-carbonitrile 4

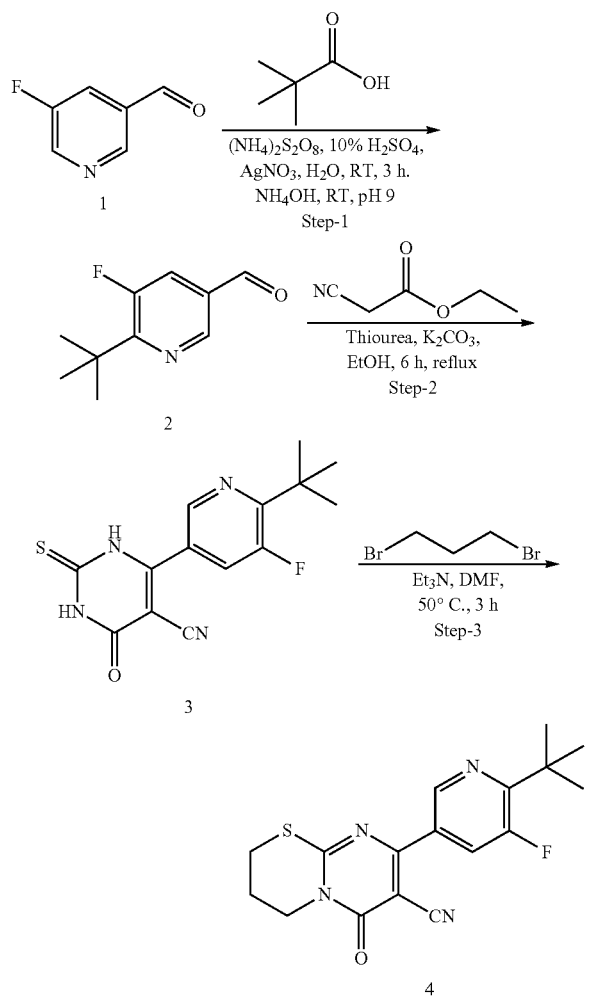

Step-1:

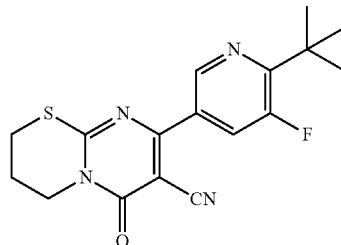

Preparation of 6-(tert-butyl)-5-fluoronicotinaldehyde 2

To a stirred solution of 5-fluoronicotinaldehyde (1, 0.6 g, 4.79 mmol), pivalic acid (2.44 g, 23.9 mmol) and silver nitrate (0.169, 0.959 mmol) in 10% aqueous sulfuric acid (5.5 mL), was added a solution of ammonium persulfate (2.18 g, 9.59 mmol) in water (10 mL). The resulting mixture was stirred at room temperature for 3 h. The reaction mixture was basified to pH 9 with aqueous ammonia and extracted with ethyl acetate (2×50 mL). The combined organic layer was dried over anhydrous sodium sulphate, filtered and concentrated. The crude product was purified by silica gel column chromatography using 10% ethyl acetate in hexane to afford the title compound 6-(tert-butyl)-5-fluoronicotinaldehyde (2, 0.6 g, 70%) as pale brown liquid. Calculated (M+H): 182.09; Found (M+H): 182.3.

Step-2:

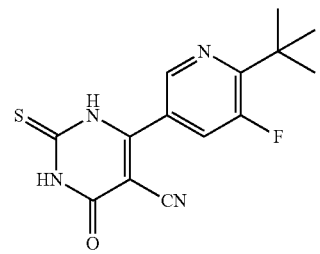 [SMILES: CC(C)(C)c1ncc(-c2[nH]c(=S)[nH]c(=O)c2C#N)cc1F]

Preparation of 6-(6-(tert-butyl)-5-fluoropyridin-3-yl)-4-oxo-2-thioxo-1,2,3,4-tetrahydropyrimidine-5-carbonitrile 3

A mixture of 6-(tert-butyl)-5-fluoronicotinaldehyde (2, 0.3 g, 1.65 mmol), thiourea (0.13 g, 1.65 mmol), ethyl 2-cyanoacetate (0.19 mL, 1.65 mmol) and potassium carbonate (1.14 g, 8.28 mmol) in ethanol (10 mL) was heated to reflux for 6 h. The reaction mixture was concentrated, the residue was diluted with water (10 mL), neutralized with acetic acid and extracted with ethyl acetate (2×50 mL). The combined organic layer was dried over anhydrous sodium sulphate, filtered and concentrated. The crude product was purified by silica gel column chromatography using 55% ethyl acetate in hexane to afford the title compound 6-(6-(tert-butyl)-5-fluoropyridin-3-yl)-4-oxo-2-thioxo-1,2,3,4-tetrahydropyrimidine-5-carbonitrile (3, 0.2 g, 40%) as pale brown solid. Calculated (M+H): 305.08; Found (M+H): 305.1.

Step-3:

Preparation of 8-(6-(tert-butyl)-5-fluoropyridin-3-yl)-6-oxo-3,4-dihydro-2H,6H-pyrimido[2,1-b][1,3]thiazine-7-carbonitrile 4

A mixture of 6-(6-(tert-butyl)-5-fluoropyridin-3-yl)-4-oxo-2-thioxo-1,2,3,4-tetrahydropyrimidine-5-carbonitrile (3, 0.15 g, 0.49 mmol), 1,3-dibromopropane (0.1 g, 0.49 mmol) and triethylamine (0.28 mL, 1.97 mmol) in N,N-dimethylformamide (4 mL) was heated at 80° C. for 3 h in a sealed tube. The reaction mixture was cooled to room temperature, diluted with water (5 mL) and extracted with ethyl acetate (3×25 mL). The combined organic layer was dried over anhydrous sodium sulphate, filtered and concentrated. The crude product was purified by silica gel column chromatography using 45% ethyl acetate in hexane to afford the title compound 8-(6-(tert-butyl)-5-fluoropyridin-3-yl)-6-oxo-3,4-dihydro-2H,6H-pyrimido[2,1-b][1,3]thiazine-7-carbonitrile (4 (example 75), 0.02 g, 12.5% yield) as an off white solid. $^1$H NMR (DMSO-$d_6$, 400 MHz) δ (ppm): 8.80 (s, 1H), 7.99 (dd, $J_1$=1.6 Hz, $J_2$=12.8 Hz, 1H), 4.02 (t, J=5.2 Hz, 2H), 3.29 (bs, 2H), 2.22 (bs, 2H), 1.38 (s, 9H). Calculated (M+H): 345.11; Found (M+H): 345.1. HPLC purity: 99.99%

TABLE 15

The following compound was prepared by the method described above:

| Ex. # | Structure | IUPAC Name | Analytical Data |
|---|---|---|---|
| 76 | 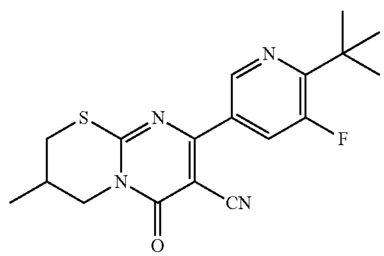 [SMILES: CC1CSc2nc(-c3cnc(C(C)(C)C)c(F)c3)c(C#N)c(=O)n2C1] | 8-(6-(tert-butyl)-5-fluoropyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.80 (s, 1H), 8.0 (d, J = 12.0 Hz, 1H), 4.27 (d, J = 14.0 Hz, 1H), 3.51-3.45 (m, 1H), 3.27-3.24 (m, 1H), 3.07 (t, J = 9.6 Hz, 1H), 2.34-2.3 (m, 1H), 1.38 (s, 9H), 1.13 (d, J = 6.4 Hz, 3H). Calculated (M + H): 359.13, found (M + H): 359.1, HPLC purity: 99.66% |

Example 77

Preparation of 8-(6-(tert-butyl)pyridin-3-yl)-6-oxo-3,4-dihydro-2H,6H-pyrimido[2,1-b][1,3]oxazine-7-carbonitrile 7

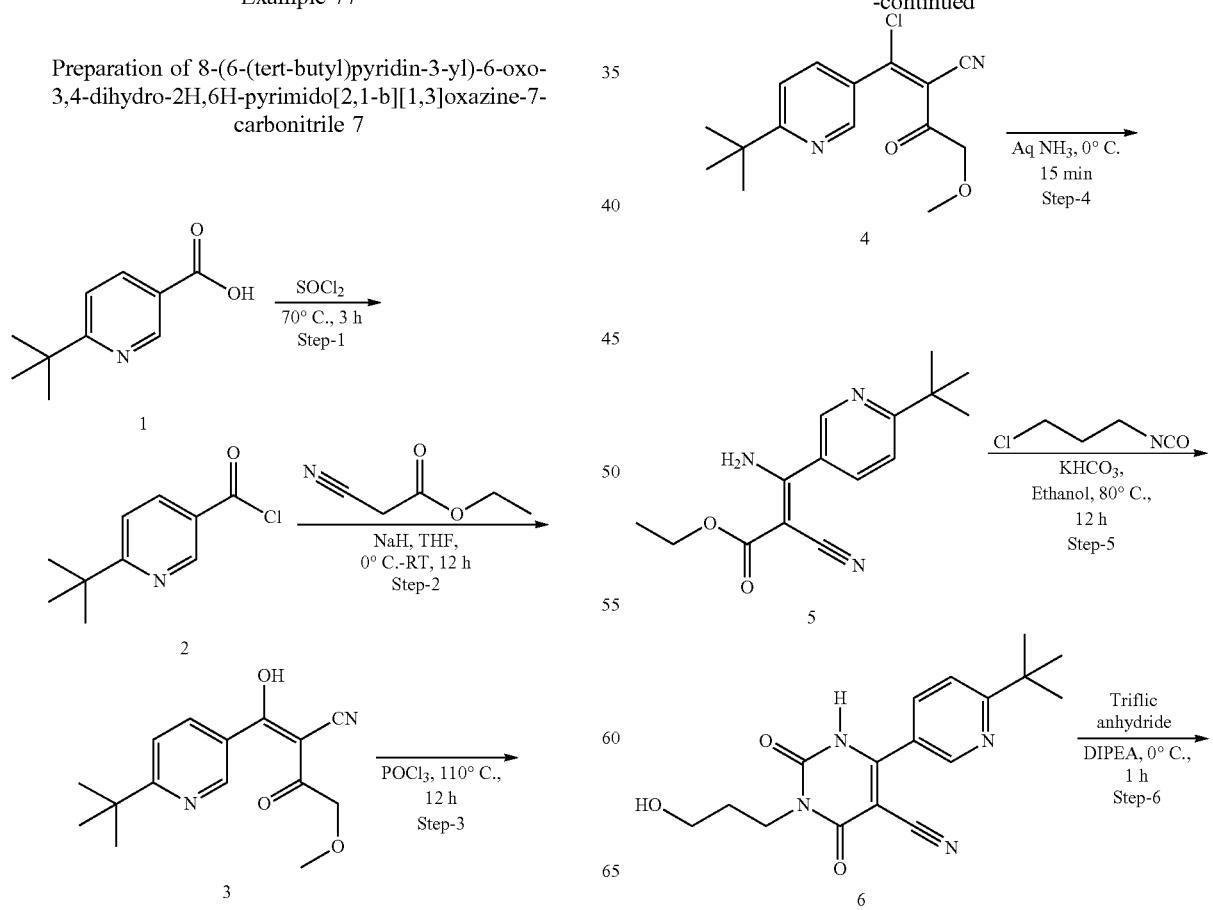

-continued

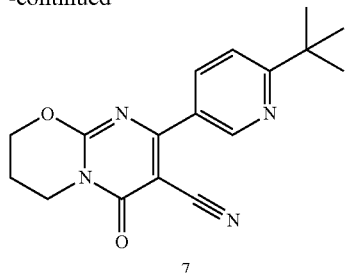

7

Step-1:

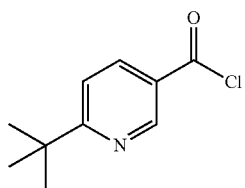

Preparation of 6-(tert-butyl)nicotinoyl chloride 2

A solution of 6-(tert-butyl)nicotinic acid (1, 1.8 g, 10.05 mmol) in thionyl chloride (20 mL) was heated at 70° C. for 3 h. The reaction mixture evaporated completely and dried to afford the title compound 6-(tert-butyl)nicotinoyl chloride (2, 1.8 g, crude) as a brownish liquid. The crude product was as such taken to next step without any purification.

Step-2:

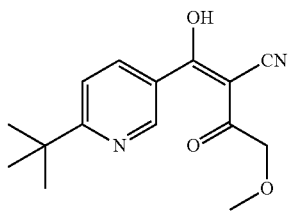 [SMILES: COCC(=O)/C(C#N)=C(/O)c1ccc(C(C)(C)C)nc1]

Preparation of (E)-2-((6-(tert-butyl)pyridin-3-yl)(hydroxy)methylene)-4-methoxy-3-oxobutanenitrile 3

To a solution of ethyl 2-cyanoacetate (2.05 g, 18 mmol) in tetrahydrofuran (30 mL) was added sodium hydride (3.6 g, 90 mmol, 60% in mineral oil) at 0° C. and the reaction mixture was stirred at 0° C. for 15 min. Then a solution of 6-(tert-butyl)nicotinoyl chloride (2, 1.8 g, 9 mmol) in tetrahydrofuran (20 mL) was added and the reaction mixture was stirred at room temperature for 12 h. The reaction mixture was quenched with cold water (50 mL) and extracted with ethyl acetate (2×100 mL). The combined organic layer was dried over anhydrous sodium sulphate, filtered and concentrated. The crude product was purified by silica gel column chromatography using 5% methanol in dichloromethane to afford the title compound (E)-2-((6-(tert-butyl)pyridin-3-yl)(hydroxy)methylene)-4-methoxy-3-oxobutanenitrile (3, 2.7 g, crude) as a brownish solid. Calculated (M+H): 275.13; Found (M+H): 275.1.

Step-3:

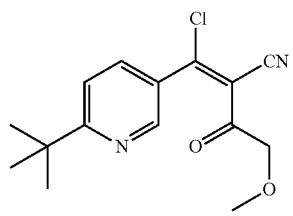 [SMILES: COCC(=O)/C(C#N)=C(/Cl)c1ccc(C(C)(C)C)nc1]

Preparation of (E)-2-((6-(tert-butyl)pyridin-3-yl)chloromethylene)-4-methoxy-3-oxobutanenitrile 4

A solution of E)-2-((6-(tert-butyl)pyridin-3-yl)(hydroxy)methylene)-4-methoxy-3-oxobutanenitrile (3, 2.8 g, 10.21 mmol) in phosphoryl chloride (30 mL) was heated at 110° C. for 12 h. The reaction mixture was evaporated completely and dried to afford the title compound (E)-2-((6-(tert-butyl)pyridin-3-yl)chloromethylene)-4-methoxy-3-oxobutanenitrile (4, 2.7 g, crude) as brownish liquid. The crude product was as such taken to next step without any purification.

Step-4:

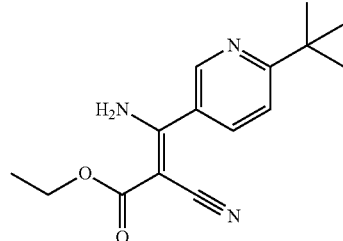

Preparation of ethyl (Z)-3-amino-3-(6-(tert-butyl)pyridin-3-yl)-2-cyanoacrylate 5

(E)-2-((6-(tert-butyl)pyridin-3-yl)chloromethylene)-4-methoxy-3-oxobutanenitrile (4, 2.7 g) was treated with aqueous ammonia (30 mL) at 0° C. and the reaction mixture was stirred at room temperature for 15 min. The reaction mixture was evaporated completely and the crude product was purified by silica gel column chromatography using 30% ethyl acetate in hexane to afford the title compound ethyl (Z)-3-amino-3-(6-(tert-butyl)pyridin-3-yl)-2-cyanoacrylate (5, 2 g, 72% yield) as a brown solid. Calculated (M−H): 274.15; Found (M−H): 274.2

Step-5:

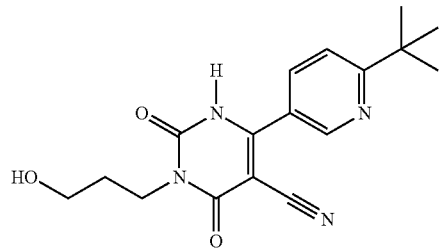 [SMILES: CC(C)(C)c1ccc(-c2[nH]c(=O)n(CCCO)c(=O)c2C#N)cn1]

Preparation of 6-(6-(tert-butyl)pyridin-3-yl)-3-(3-hydroxypropyl)-2,4-dioxo-1,2,3,4-tetrahydropyrimidine-5-carbonitrile 6

To a solution of ethyl (Z)-3-amino-3-(6-(tert-butyl)pyridin-3-yl)-2-cyanoacrylate (5, 0.2 g, 0.73 mmol) in ethanol (5 mL) was added 1-chloro-3-isocyanatopropane (0.08 g, 0.73 mmol) followed by potassium bicarbonate (0.036 g, 3.66 mmol) and the reaction mixture was stirred at 80 °C for 12 h. The reaction mixture was quenched with saturated ammonium chloride solution (20 mL) and extracted with ethyl acetate (2×50 mL). The combined organic layer was dried over anhydrous sodium sulphate, filtered and concentrated. The crude product was purified by silica gel column chromatography using 5% methanol in dichloromethane to afford the title compound 6-(6-(tert-butyl)pyridin-3-yl)-3-(3-hydroxypropyl)-2,4-dioxo-1,2,3,4-tetrahydropyrimidine-5-carbonitrile (6, 0.03 g, 12.4% yield) as an off white solid. $^1$H NMR (400 MHz, DMSO-$d_6$) δ (ppm): 12.41 (s, 1H), 8.78 (d, J=2 Hz, 1H), 8.03 (dd, $J_1$=2 Hz, $J_2$=8.4 Hz, 1H), 7.65 (d, J=8.4 Hz, 1H), 4.47 (bs, 1H), 3.87-3.83 (m, 2H), 3.44 (d, J=4.4 Hz, 2H), 1.73-1.68 (m, 2H), 1.38 (s, 9H). Calculated (M+H): 329.15; Found (M+H): 329.2. HPLC purity: 99.30%

Step-6:

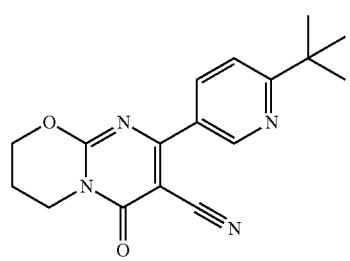 [SMILES: CC(C)(C)c1ccc(-c2nc3n(c(=O)c2C#N)CCCO3)cn1]

Preparation of 8-(6-(tert-butyl)pyridin-3-yl)-6-oxo-3,4-dihydro-2H,6H-pyrimido[2,1-b][1,3]oxazine-7-carbonitrile 7

To a stirred solution of 6-(6-(tert-butyl)pyridin-3-yl)-3-(3-hydroxypropyl)-2,4-dioxo-1,2,3,4-tetrahydropyrimidine-5-carbonitrile (6, 0.12 g, 0.36 mmol) in dichloromethane (5 mL) were added diisopropyl ethylamine (0.33 mL, 1.8 mmol), triflic anhydride (0.19 mL, 1 mmol) at 0° C. and the reaction mixture was stirred at 0° C. for 1 h. The reaction mixture was concentrated, the residue was diluted with saturated sodium bicarbonate solution (20 mL) and extracted with ethyl acetate (2×30 mL). The combined organic layer was washed with brine (20 mL), dried over sodium sulfate, filtered and concentrated. The crude product was purified by silica gel column chromatography using 80% ethyl acetate in hexane to afford the title compound 8-(6-(tert-butyl)pyridin-3-yl)-6-oxo-3,4-dihydro-2H,6H-pyrimido[2,1-b][1,3]oxazine-7-carbonitrile (7 (example 77), 0.035 g, 31% yield) as a pale yellow solid. $^1$H NMR (400 MHz, DMSO-$d_6$) δ (ppm): 8.95 (d, J=2 Hz, 1H), 8.17 (dd, $J_1$=2 Hz, 0.4=8 Hz, 1H), 7.62 (d, J=8 Hz, 1H), 4.56-4.54 (m, 2H), 3.89-3.86 (m, 2H), 2.21-2.18 (m, 2H), 1.33 (s, 9H). Calculated (M+H): 311.14; Found (M+H): 311.3. HPLC purity: 99.50%

Example 78

Preparation of 8-(6-(2-cyanopropan-2-yl)pyridin-3-yl)-6-oxo-3,4-dihydro-2H,6H-pyrimido[2,1-b][1,3]thiazine-7-carbonitrile 4

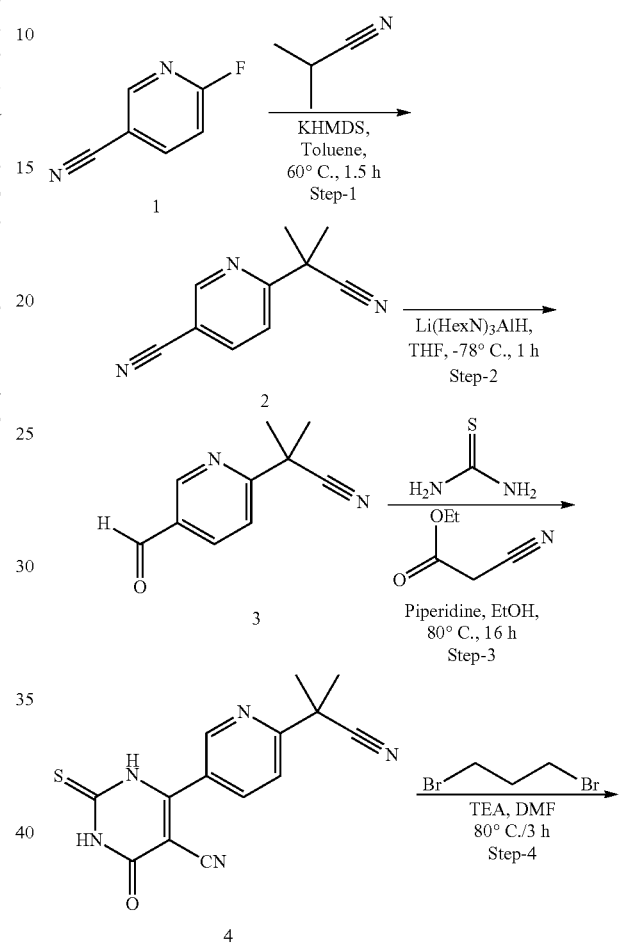

Step-1:

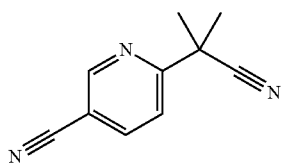

Preparation of 6-(2-cyanopropan-2-yl)nicotinonitrile 2

To a solution of 6-fluoronicotinonitrile (1, 4.0 g, 32.76 mmol) and isobutyronitrile (1.7 mL, 131 mmol) in toluene (100 mL) was added potassium bis(trimethylsilyl)amide (100 mL, 48 mmol) drop wise at room temperature and the reaction mixture was stirred at 60° C. for 1.5 h. The reaction mixture was cooled to room temperature, diluted with brine solution (200 mL) and extracted with ethyl acetate (200 mL). The combined organic layer was dried over anhydrous sodium sulfate, filtered and concentrated. The crude product was purified by silica gel column chromatography using 7% ethyl acetate in hexane to afford the title compound 6-(2-cyanopropan-2-yl)nicotinonitrile (2, 1.5 g, 27.3% yield) as a yellow solid. Calculated (M+H): 172.08; Found (M+H): 172.1.

Step-2:

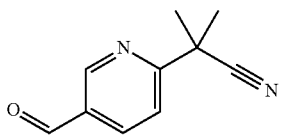

Preparation of 2-(5-formylpyridin-2-yl)-2-methylpropanenitrile 3

To a solution of 6-(2-cyanopropan-2-yl)nicotinonitrile (2, 1.20 g, 7.00 mmol) in tetrahydrofuran (200 mL), was added Li(HexN)$_3$AlH solution (70 mL, 35.04 mmol, 0.5 M in tetrahydrofuran) drop wise over 15 min at −78 $^4$C and the reaction mixture was stirred at the same temperature for 1 h. Then the reaction mixture was quenched with saturated ammonium chloride solution (150 mL) and extracted with ethyl acetate (2×150 mL). The combined organic layer was dried over anhydrous sodium sulfate, filtered and concentrated. The crude product was purified by silica gel column chromatography using 10% ethyl acetate in hexane to afford the title compound 2-(5-formylpyridin-2-yl)-2-methylpropanenitrile (3, 0.25 g, 20% yield) as pale yellow solid. Calculated (M+H): 175.08; Found (M+H): 175.1.

Step-3:

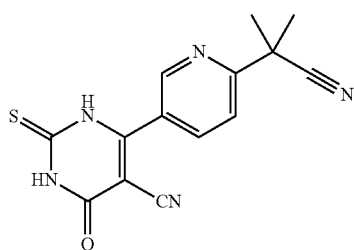 [SMILES: CC(C)(C#N)c1ccc(-c2[nH]c(=S)[nH]c(=O)c2C#N)cn1]

Preparation of 6-(6-(2-cyanopropan-2-yl)pyridin-3-yl)-4-oxo-2-thioxo-1,2,3,4-tetrahydropyrimidine-5-carbonitrile 4

To a solution of 2-(5-formylpyridin-2-yl)-2-methylpropanenitrile (3, 0.1 g, 0.574 mmol) in ethanol (10 mL), were added ethyl cyanoacetate (0.064 g, 0.574 mmol), thiourea (0.043 g, 0.574 mmol) and piperidine (0.1 mL, 1.148 mmol). Then the reaction mixture was stirred at 80° C. for 16 h. The reaction mixture was concentrated to afford the title compound 6-(6-(2-cyanopropan-2-yl)pyridin-3-yl)-4-oxo-2-thioxo-1,2,3,4-tetrahydropyrimidine-5-carbonitrile (4, 0.19 g, crude) as brown gum. Calculated (M−H): 296.07; Found (M−H): 296.1

Step-4:

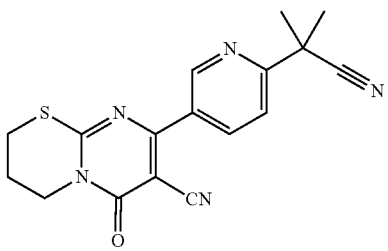 [SMILES: CC(C)(C#N)c1ccc(-c2nc3n(c(=O)c2C#N)CCCS3)cn1]

Preparation of 8-(6-(2-cyanopropan-2-yl)pyridin-3-yl)-6-oxo-3,4-dihydro-2H,6H-pyrimido[2,1-b][1,3]thiazine-7-carbonitrile 5

A mixture of 6-(6-(2-cyanopropan-2-yl)pyridin-3-yl)-4-oxo-2-thioxo-1,2,3,4-tetrahydropyrimidine-5-carbonitrile (4, 0.25 g, 0.84 mmol), 1,3-dibromopropane (0.34 mL, 3.36 mmol) and triethylamine (0.70 mL, 5.04 mmol) in N,N-dimethylformamide (10 mL) was heated at 80° C. for 3 h in a sealed tube. The reaction mixture was cooled to room temperature, diluted with water (30 mL) and extracted with ethyl acetate (2×25 mL). The combined organic layer was washed with brine (30 mL), dried over anhydrous sodium sulphate, filtered and concentrated. The crude product was purified by silica gel column chromatography using 50% ethyl acetate in hexane to afford the title compound 8-(6-(2-cyanopropan-2-yl)pyridin-3-yl)-6-oxo-3,4-dihydro-2H,6H-pyrimido[2,1-b][1,3]thiazine-7-carbonitrile (5 (example 78), 0.04 g, 14% yield) as yellow solid. $^1$H NMR (DMSO-d$_6$. 400 MHz) δ (ppm): 9.00 (d, J=1.6 Hz, 1H), 8.30 (dd, J$_1$=8.4 Hz, J$_2$=2.0 Hz, 1H), 7.79 (d, J=8.4 Hz, 1H), 4.04 (t, J=5.2 Hz, 2H), 3.30-3.27 (m, 2H), 2.27 (bs, 2H), 1.73 (s, 6H). Calculated (M+H): 338.1; Found (M+H): 338.1, HPLC purity: 96.85%

TABLE 16

The following compound was prepared by the method described above:

| Example Number | Structure | Name | Analytical data |
|---|---|---|---|
| 79 | 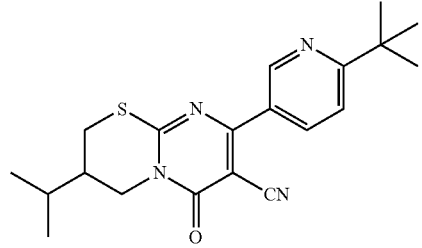 | 8-(6-(2-cyanopropan-2-yl)pyridin-3-yl)-3-methyl-6-oxo-3,4-dihydro-2H,6H-pyrimido[2,1-b][1,3]thiazine-7-carbonitrile | $^1$H NMR DMSO-$d_6$, 400 MHz) δ (ppm): 9.00 (bs, 1H), 8.30 (dd, $J_1$ = 2.0 Hz, $J_2$ = 8.4 Hz, 1H), 7.79 (d, J = 8.4 Hz, 1H), 4.28 (d, J = 14.4 Hz, 1H), 3.51-3.46 (m, 1H), 3.24 (bs, 1H), 3.08 (t, J = 10.4 Hz, 1H), 2.36-2.30 (m, 1H), 1.73 (s, 6H), 1.13 (d, J = 6.8 Hz, 3H). Calculated (M + H): 352.12; Found (M + H): 352.2, HPLC purity 99.67% |

Example 80

Preparation of 8-(6-(tert-butyl)pyridin-3-yl)-3-isopropyl-6-oxo-3,4-dihydro-2H,6H-pyrimido[2,1-b][1,3]thiazine-7-carbonitrile 5

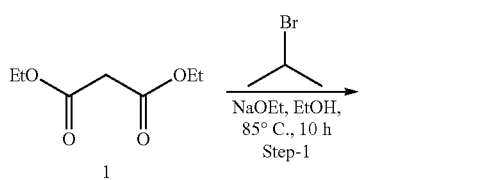

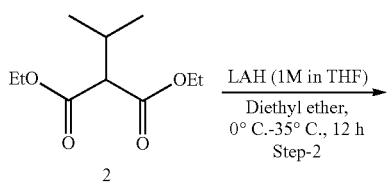

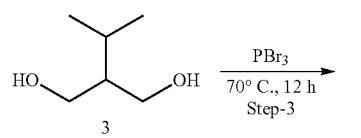

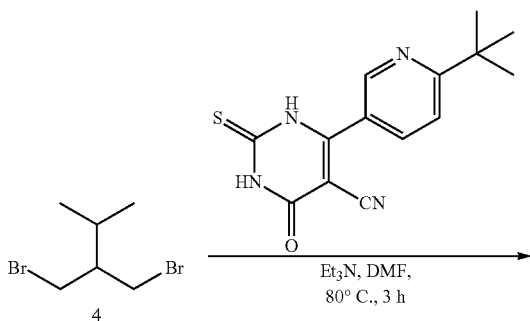

Step-1:

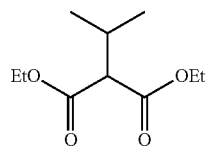

Preparation of diethyl 2-isopropylmalonate 2

To a stirred solution of diethyl malonate (1, 4 g, 24.97 mmol) in ethanol (5 mL), was added 21% sodium ethoxide in ethanol (12.25 mL, 29.96 mmol) and allowed to stir at room temperature for 30 min. Then 2-bromopropane (3.5 mL, 37.46 mmol) was added to the reaction mixture and allowed to stir at 85° C. for 9.5 h. The reaction mixture was concentrated, the residue was diluted with water (20 mL) and extracted with ethyl acetate (3×100 mL). The combined organic layer was dried over anhydrous sodium sulphate, filtered and concentrated. The crude product was purified by silica gel column chromatography using 5% ethyl acetate in hexane to afford the title compound diethyl 2-isopropylmalonate (2, 4.4 g, 87%) as colorless liquid. Calculated (M+H): 203.12; Found (M+H): 203.1.

Step-2:

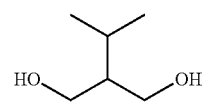

Preparation of 2-isopropylpropane-1,3-diol 3

To a stirred solution of diethyl 2-isopropylmalonate (2, 4.4 g, 21.76 mmol) in diethyl ether (50 mL), was added lithium aluminium hydride solution (45 mL, 43.53 mmol, 1M in tetrahydrofuran) drop wise at 0° C. and the reaction mixture was allowed to stir at same temperature for 4 h, then heated to 35° C. for 8 h. The reaction mixture was cooled to 0° C., quenched with saturated ammonium chloride solution and extracted with ethyl acetate (3×100 mL). The combined organic layer was dried over anhydrous sodium sulphate, filtered and concentrated. The crude product was purified by silica gel column chromatography using 40% ethyl acetate in hexane to afford the title compound 2-isopropylpropane-1,3-diol (3.1.6 g, 62% yield) as a colorless liquid. $^1$H NMR (DMSO-$d_6$, 400 MHz) δ (ppm): 4.19 (t, J=4.8 Hz, 2H), 3.45-3.34 (m, 4H), 1.78-1.70 (m, 1H), 1.28-1.22 (m, 1H), 0.84 (d, J=7.2 Hz, 6H).

Step-3:

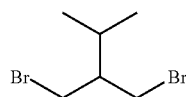

Preparation of 1-bromo-2-(bromomethyl)-3-methylbutane 4

2-isopropylpropane-1,3-diol (3, 0.6 g, 5.07 mmol) was placed in a 10 mL 2 necked round bottomed flask fitted with a reflux condenser holding a calcium chloride guard tube. The diol was warmed to 70° C. and phosphorus tribromide (0.35 mL, 3.75 mmol) was added, with stirring, at such a rate as to maintain the temperature at 65-75° C. Stirring and heating at 70° C. were continued for 12 h. The reaction mixture was cooled to room temperature, poured into ice-water (20 mL) and extracted with ether (2×50 mL). The combined organic layer was washed successively 10% sodium bicarbonate and water until neutral to litmus and then dried over anhydrous sodium sulphate, filtered and concentrated to afford the title compound 1-bromo-2-(bromomethyl)-3-methylbutane (4, 0.8 g, 65% yield) as colorless liquid. $^1$H NMR (CDCl$_3$, 400 MHz) δ (ppm): 3.73 (dd, J$_1$=4.0 Hz, J$_2$=10.4 Hz, 2H), 3.53 (dd, J$_1$=6.4 Hz, J$_2$=10.0 Hz, 2H), 1.86-1.79 (m, 1H), 1.72-1.65 (m, 1H), 0.99 (d, J=7.2 Hz, 6H).

Step-4:

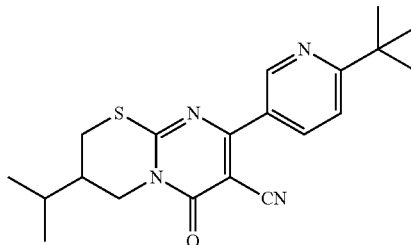

Preparation of 8-(6-(tert-butyl)pyridin-3-yl)-3-isopropyl-6-oxo-3,4-dihydro-2H,6H-pyrimido[2,1-b][1,3]thiazine-7-carbonitrile 5

A mixture of 6-(6-(tert-butyl)pyridin-3-yl)-4-oxo-2-thioxo-1,2,3,4-tetrahydropyrimidine-5-carbonitrile (0.1 g, 0.35 mmol), 1-bromo-2-(bromomethyl)-3-methylbutane (4, 0.09 g, 0.35 mmol) and triethylamine (0.28 mL, 1.39 mmol) in N,N-dimethylformamide (3 mL) was heated at 80° C. for 3 h in a sealed tube. The reaction mixture was diluted with water (5 mL) and extracted with ethyl acetate (3×50 mL). The combined organic layer was dried over anhydrous sodium sulphate, filtered and concentrated. The crude product was purified by silica gel column chromatography using 40% ethyl acetate in hexane to afford the title compound 8-(6-(tert-butyl)pyridin-3-yl)-3-isopropyl-6-oxo-3,4-dihydro-2H,6H-pyrimido[2,1-b][1,3]thiazine-7-carbonitrile (5 (example 80), 0.065 g, 50% yield) as a white solid. $^1$H NMR (DMSO-$d_6$, 400 MHz) δ (ppm): 8.94 (d, J=2.0 Hz, 1H), 8.16 (dd, J$_1$=2.4 Hz, J$_2$=8.4 Hz, 1H), 7.62 (d, J=8.4 Hz, 1H), 4.33 (d, J=14.0 Hz, 1H), 3.63 (dd, J$_1$=9.2 Hz, J$_2$=14.0 Hz, 1H), 3.30 (bs, 1H), 3.18 (t, J=9.6 Hz, 1H), 2.0-1.97 (m, 1H), 1.79-1.74 (m, 1H), 1.33 (s, 9H), 0.96 (d, J=6.4 Hz, 6H). Calculated (M+H): 369.17, Found (M+H): 369.2. HPLC purity: 99.54%

TABLE 17

The following compound was prepared by the method described above:

| Ex. # | Structure | IUPAC Name | Analytical Data |
|---|---|---|---|
| 81 | 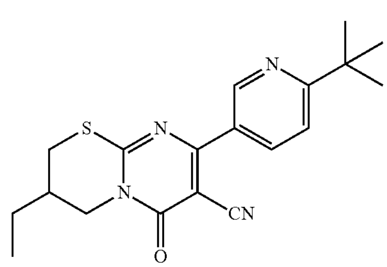 [SMILES: CCC1CSc2nc(-c3ccc(C(C)(C)C)nc3)c(C#N)c(=O)n2C1] | 8-(6-(tert-butyl)pyridin-3-yl)-3-ethyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.94 (s, 1H), 8.15 (d, J = 6.8 Hz, 1H), 7.62 (d, J = 8.4 Hz, 1H), 4.27 (d, J = 14.4 Hz, 1H), 3.58 (dd, J$_1$ = 9.6 Hz, J$_2$ = 14.0 Hz, 1H), 3.32 (bs, 1H), 3.07 (t, J = 9.6 Hz, 1H), 2.13 (bs, 1H), 1.54-1.4 (m, 2H), 1.33 (s, 9H), 0.95 (t, J = 7.6 Hz, 3H). Calculated (M + H): 355.15, Found (M + H): 355.3, HPLC purity: 99.27% |

Examples 82 and 83

Preparation ethyl 5-(7-cyano-6-oxo-3,4-dihydro-2H, 6H-pyrimido[2,1-b][1,3]thiazin-8-yl)picolinate 4 and 8-(6-(2-hydroxypropan-2-yl)pyridin-3-yl)-6-oxo-3,4-dihydro-2H,6H-pyrimido[2,1-b][1.3]thiazine-7-carbonitrile 5

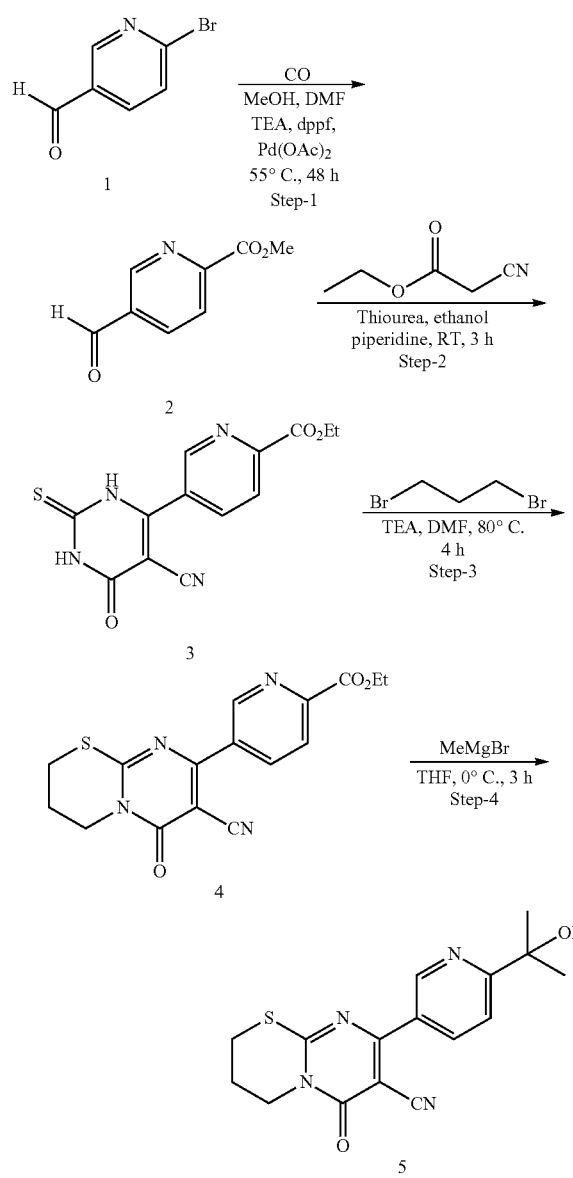

Preparation of methyl 5-formylpicolinate 2

To a solution of 6-bromonicotinaldehyde (1, 5.0 g, 26.88 mmol) in methanol (40 mL) and N,N-dimethylformamide (40 mL) mixture, triethylamine (7.45 mL, 53.76 mmol), palladium acetate (0.15 g, 0.67 mmol), 1,1'-bis(diphenylphosphino)ferrocene (0.07 g, 0.01 mmol) were added and the reaction mixture was degassed by bubbling carbon monoxide gas. The reaction mixture was stirred at 55° C. for 48 h under carbon monoxide atmosphere. The reaction mixture was quenched with water (100 mL) and extracted with ethyl acetate (3×100 mL). The combined organic layer was dried over anhydrous sodium sulfate, filtered and concentrated. The crude product was purified by silica gel chromatography using 45% ethyl acetate in hexane to afford the title compound methyl 5-formylpicolinate (2, 3.5 g, 39% yield) as a brown solid. Calculated (M+H): 166.15; Found (M+H): 166.1.

Step-2:

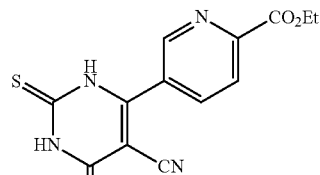

Preparation of ethyl 5-(5-cyano-6-oxo-2-thioxo-1,2,3,6-tetrahydropyrimidin-4-yl)picolinate 3

To a solution of methyl 5-formylpicolinate (2, 1.2 g, 72.66 mmol) in ethanol (40 mL), thiourea (0.54 g, 72.66 mmol), ethyl cyanoacetate (0.76 mL, 72.66 mmol) and piperidine (1.48 mL, 145.22 mmol) were added. The reaction mixture was stirred at room temperature for 3 h. The reaction mixture was concentrated to afford the title compound ethyl 5-(5-cyano-6-oxo-2-thioxo-1,2,3,6-tetrahydropyrimidin-4-yl)picolinate (3, 0.9 g, crude) as a brownish gum. Calculated (M+H): 303.05; Found (M+H): 303.0.

Step-3:

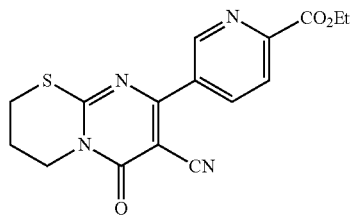 [SMILES: CCOC(=O)c1ccc(-c2nc3n(c(=O)c2C#N)CCCS3)cn1]

Preparation of ethyl 5-(7-cyano-6-oxo-3,4-dihydro-2H,6H-pyrimido[2,1-b][1,3]thiazin-8-yl)picolinate 4

To a solution of ethyl 5-(5-cyano-6-oxo-2-thioxo-1,2,3,6-tetrahydropyrimidin-4-yl)picolinate (3, 0.85 g, 2.81 mmol) in N,N-dimethylformamide (30 mL), 1,3-dibromopropane (0.32 mL, 3.09 mmol) and triethylamine (1.2 mL, 8.43 mmol) were added. The reaction mixture was stirred at 80° C. for 4 h. The reaction mixture was quenched with water (100 mL) and extracted with ethyl acetate (3×50 mL). The Step-1:

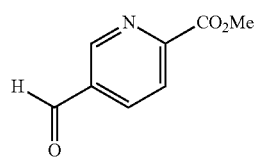

combined organic layer was dried over anhydrous sodium sulfate, filtered and concentrated. The crude product was purified by column chromatography followed by preparative HPLC (analytical conditions: column: Inertsil ODS 3V (250 mm×4.6 mm×5 mic), mobile phase (A): 0.1% ammonia in water, mobile phase (B): acetonitrile, flow rate: 1.0 mL/min, T/% B: 0/20, 10/80, 25/90, 27/20, 30/20) to afford the title compound ethyl 5-(7-cyano-6-oxo-3,4-dihydro-2H,6H-pyrimido[2,1-b][1,3]thiazin-8-yl)picolinate (4 (example 82) 0.25 g, 25% yield) as a white solid. $^1$H NMR (400 MHz, DMSO-$d_6$) δ (ppm): 9.09 (s, 1H), 8.38 (dd, $J_1$=2.0 Hz, $J_2$=8.4 Hz, 1H), 8.20 (d, J=8.0 Hz, 1H), 4.40-4.34 (m, 2H), 4.03 (t, J=5.2 Hz, 2H), 3.27 (bs, 2H), 2.22 (s, 2H), 1.33 (t, J=7.6 Hz, 3H). Calculated (M+H): 343.12; Found (M+H): 343.1, HPLC Purity: 99.23%

Step-4:

Preparation of 8-(6-(2-hydroxypropan-2-yl)pyridin-3-yl)-6-oxo-3,4-dihydro-2H,6H-pyrimido[2,1-b][1,3]thiazine-7-carbonitrile 5

To a solution of ethyl 5-(7-cyano-6-oxo-3,4-dihydro-2H,6H-pyrimido[2,1-b][1,3]thiazin-8-yl)picolinate (4, 0.15 g, 0.45 mmol) in tetrahydrofuran (40 mL), methyl magnesium bromide solution (0.34 mL, 0.68 mmol, 3M in diethyl ether) was added drop wise at 0° C. under nitrogen atmosphere. The reaction mixture was stirred at same temperature for 3 h. The reaction mixture was quenched with ammonium chloride solution (40 mL) and extracted with ethyl acetate (3×30 mL). The combined organic layer was dried over anhydrous sodium sulfate, filtered and concentrated. The crude product was purified by silica gel column chromatography followed by preparative HPLC (analytical conditions: column: Inertsil ODS 3V (250 mm×4.6 mm×5 mic), mobile phase (A): 0.1% ammonia in water, mobile phase (B): acetonitrile, flow rate: 1.0 mL/min, T/% B: 0/20, 10/80, 25/90, 27/20, 30/20) to afford the title compound 8-(6-(2-hydroxypropan-2-yl)pyridin-3-yl)-6-oxo-3,4-dihydro-2H,6H-pyrimido[2,1-b][1,3]thiazine-7-carbonitrile (5 (example 83), 0.1 g, 66% yield) as a white solid. $^1$H NMR (400 MHz, DMSO-$d_6$) δ (ppm): 8.91 (s, 1H), 8.19 (dd, $J_1$=2.4 Hz, $J_2$=8.4 Hz, 1H), 7.82 (d, J=8.4 Hz, 1H), 5.34 (s, 1H), 4.01 (t, J=5.6 Hz, 2H), 2.22 (s, 2H), 1.45 (s, 6H), 2H were merged with DMSO water peak. Calculated (M+H): 329.10; Found (M+H): 329.1. HPLC Purity: 99.34%

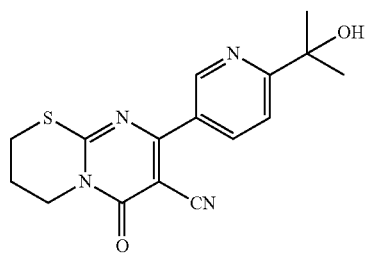 [SMILES: CC(C)(O)c1ccc(-c2nc3n(c(=O)c2C#N)CCCS3)cn1]

TABLE 18

The following compounds were prepared by the method described above:

| Ex. # | Structure | IUPAC Name | Analytical Data |
|---|---|---|---|
| 84 | 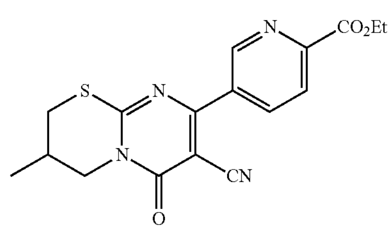 [SMILES: CCOC(=O)c1ccc(-c2nc3n(c(=O)c2C#N)CC(C)CS3)cn1] | ethyl 5-(7-cyano-3-methyl-6-oxo-3,4-dihydro-2H,6H-pyrimido[2,1-b][1,3]thiazin-8-yl)picolinate | $^1$H NMR (400 MHz, DMSO-$d_6$) δ (ppm): 9.09 (d, J = 2.0 Hz, 1H), 8.38 (dd, $J_1$ = 2.4 Hz, $J_2$ = 8.4 Hz, 1H), 8.20 (d, J = 8.4 Hz, 1H), 4.40-4.34 (m, 2H), 4.28 (d, J = 14.0 Hz, 1H), 3.53-3.47 (m, 1H), 3.27 (bs, 1H), 3.11-3.06 (m, 1H), 2.38 (m, 1H), 1.34 (t, J = 7.2 Hz, 3H), 1.16 (d, J = 12.4 Hz, 3H). Calculated (M + H): 357.04; Found (M + H): 357.0, HPLC purity: 99.08% |
| 85 | 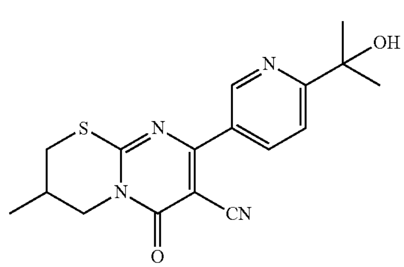 [SMILES: CC1CSc2nc(-c3ccc(C(C)(C)O)nc3)c(C#N)c(=O)n2C1] | 8-(6-(2-hydroxypropan-2-yl)pyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.91 (d, J = 2.4 Hz, 1H), 8.19 (dd, $J_1$ = 2.4 Hz, $J_2$ = 8.4 Hz, 1H), 7.82 (d, J = 8.4 Hz, 1H), 5.34 (s, 1H), 4.28 (d, J = 14.0 Hz, 1H), 3.50-3.44 (m, 1H), 3.23 (bs, 1H), 3.07 (t, J = 9.6 Hz, 1H), 2.33 (m, 1H), 1.45 (s, 6H), 1.13 (d, J = 6.4 Hz, 3H). Calculated (M + H): 343.10, found (M + H): 343.0, HPLC purity: 99.40% |

Examples 86-88

Preparation of methyl 8-(6-(tert-butyl)pyridin-3-yl)-7-cyano-6-oxo-3,4-dihydro-2H,6H-pyrimido[2,1-b][1,3]thiazine-3-carboxylate 2, 8-(6-(tert-butyl)pyridin-3-yl)-3-(hydroxymethyl)-6-oxo-3,4-dihydro-2H,6H-pyrimido[2,1-b][1,3]thiazine-7-carbonitrile 4 & 8-(6-(tert-butyl)pyridin-3-yl)-3-(fluoromethyl)-6-oxo-3,4-dihydro-2H,6H-pyrimido[2,1-b][1,3]thiazine-7-carbonitrile 5

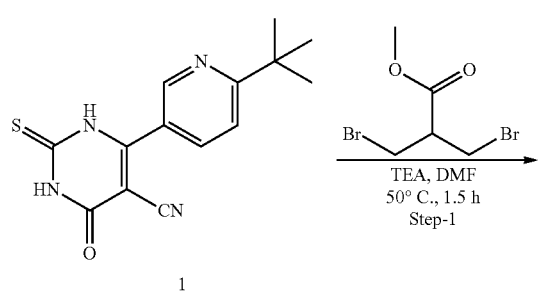

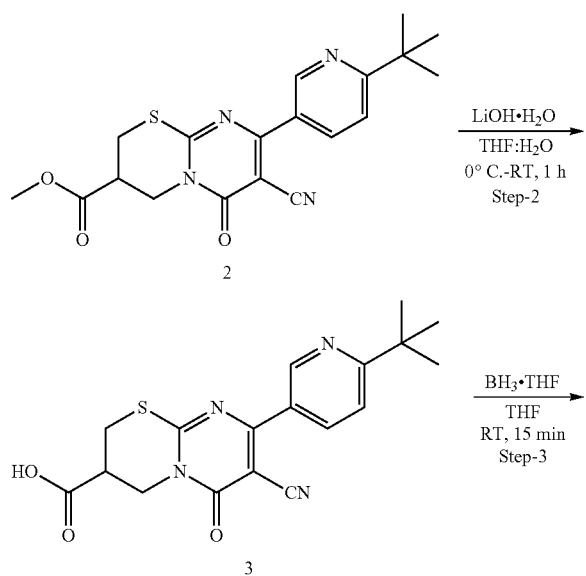

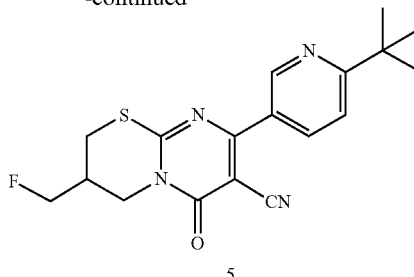

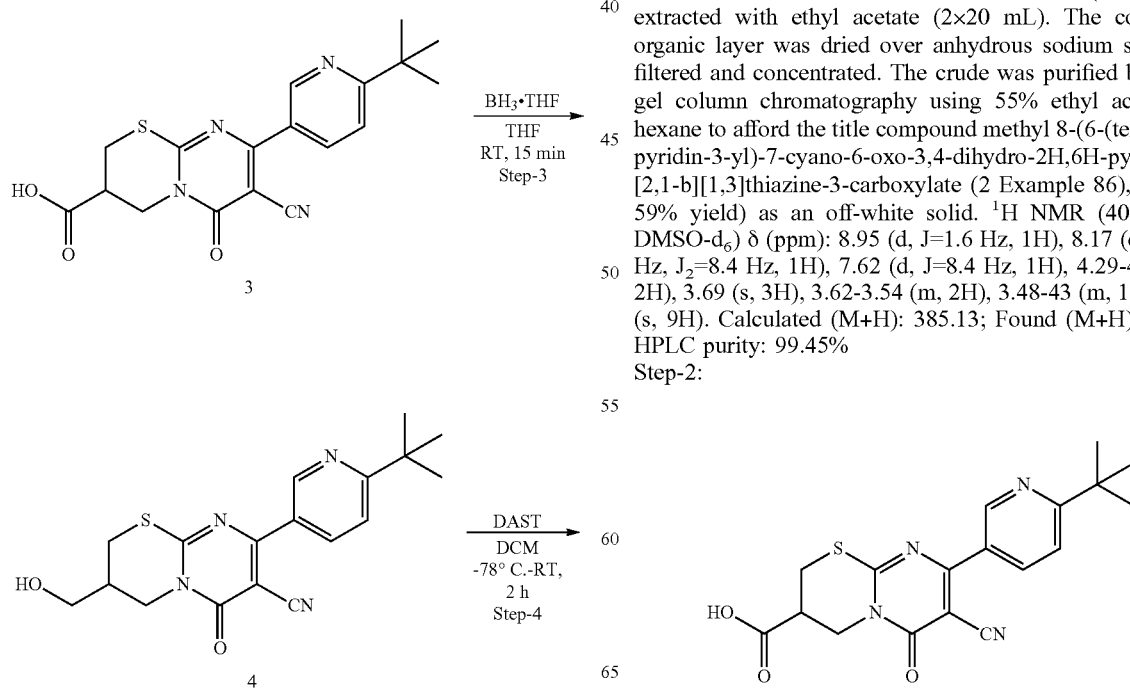

Preparation of methyl 8-(6-(tert-butyl)pyridin-3-yl)-7-cyano-6-oxo-3,4-dihydro-2H,6H-pyrimido[2,1-b][1,3]thiazine-3-carboxylate 2

To a solution of 6-(6-(tert-butyl)pyridin-3-yl)-4-oxo-2-thioxo-1,2,3,4-tetrahydropyrimidine-5-carbonitrile (1, 0.1 g, 0.34 mmol) and methyl 3-bromo-2-(bromomethyl)propanoate (0.049 mL, 0.34 mmol) in N,N-dimethyl formamide (5 mL), triethylamine (0.19 mL, 1.39 mmol) was added and the reaction mixture was heated at 50° C. in a sealed tube for 1.5 h. The reaction mixture was diluted with water (10 mL) and extracted with ethyl acetate (2×20 mL). The combined organic layer was dried over anhydrous sodium sulphate, filtered and concentrated. The crude was purified by silica gel column chromatography using 55% ethyl acetate in hexane to afford the title compound methyl 8-(6-(tert-butyl)pyridin-3-yl)-7-cyano-6-oxo-3,4-dihydro-2H,6H-pyrimido[2,1-b][1,3]thiazine-3-carboxylate (2 Example 86), 0.08 g, 59% yield) as an off-white solid. $^1$H NMR (400 MHz, DMSO-$d_6$) δ (ppm): 8.95 (d, J=1.6 Hz, 1H), 8.17 (dd, $J_1$=2 Hz, $J_2$=8.4 Hz, 1H), 7.62 (d, J=8.4 Hz, 1H), 4.29-4.17 (m, 2H), 3.69 (s, 3H), 3.62-3.54 (m, 2H), 3.48-43 (m, 1H), 1.33 (s, 9H). Calculated (M+H): 385.13; Found (M+H): 385.1. HPLC purity: 99.45%

Step-2:

Preparation of 8-(6-(tert-butyl)pyridin-3-yl)-7-cyano-6-oxo-3,4-dihydro-2H,6H-pyrimido[2,1-b][1,3]thiazine-3-carboxylic acid 3

To a solution of methyl 8-(6-(tert-butyl)pyridin-3-yl)-7-cyano-6-oxo-3,4-dihydro-2H,6H-pyrimido[2,1-b][1,3]thiazine-3-carboxylate (2, 1.3 g, 3.38 mmol) in tetrahydrofuran:water mixture (24 mL, 5:1) cooled to 0° C., was added lithium hydroxide monohydrate (0.42 g, 10.15 mmol) and the reaction mixture was stirred at room temperature for 1 h. The reaction mixture was diluted with water (25 mL), acidified with 1.5N hydrochloric acid and extracted with ethyl acetate (2×50 mL). The combined organic layer was dried over anhydrous sodium sulphate, filtered and concentrated. The crude was purified by silica gel column chromatography using 5% methanol in dichloromethane to afford the title compound 8-(6-(tert-butyl)pyridin-3-yl)-7-cyano-6-oxo-3,4-dihydro-2H,6H-pyrimido[2,1-b][1,3]thiazine-3-carboxylic acid (3, 1.2 g, crude) as an off-white solid. Calculated (M+H): 371.11; Found (M+H): 371.2.
Step-3:

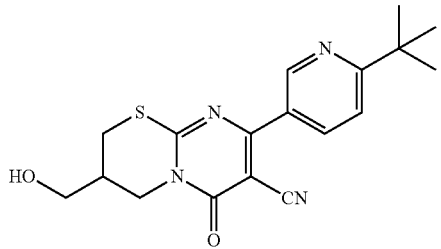 [SMILES: CC(C)(C)c1ccc(-c2nc3n(c(=O)c2C#N)CC(CO)CS3)cn1]

Preparation of 8-(6-(tert-butyl)pyridin-3-yl)-3-(hydroxymethyl)-6-oxo-3,4-dihydro-2H,6H-pyrimido[2,1-b][1,3]thiazine-7-carbonitrile 4

To a solution of 8-(6-(tert-butyl)pyridin-3-yl)-7-cyano-6-oxo-3,4-dihydro-2H,6H-pyrimido[2,1-b][1.3]thiazine-3-carboxylic acid (3, 0.46 g, 1.24 mmol) in tetrahydrofuran (30 mL), borane-tetrahydrofuran complex (4.97 mL, 4.97 mmol, 1M in tetrahydrofuran) was added at room temperature and the reaction mixture was stirred at room temperature for 15 min. The reaction mixture was quenched with saturated ammonium chloride solution (20 mL) and extracted with ethyl acetate (2×50 mL). The combined organic layer was dried over anhydrous sodium sulphate, filtered and concentrated. The crude was purified by silica gel column chromatography using 9% methanol in dichloromethane to afford the title compound 8-(6-(tert-butyl)pyridin-3-yl)-3-(hydroxymethyl)-6-oxo-3,4-dihydro-2H,6H-pyrimido[2,1-b][1,3]thiazine-7-carbonitrile (4 (example 87), 0.14 g, 31% yield) as an off-white solid. $^1$H NMR (400 MHz, DMSO-d$_6$) δ (ppm): 8.94 (bs, 1H), 8.15 (dd, J$_1$=2 Hz, J$_2$=8 Hz, 1H), 7.62 (d, J=8.4 Hz, 1H), 5.02 (t, J=5.2 Hz, 1H), 4.42 (d, J=14 Hz, 1H), 3.54-3.48 (m, 3H), 3.23 (bs, 1H), 3.12 (t, J=10.4 Hz, 1H), 3.28 (bs, 1H), 1.33 (s, 9H). Calculated (M+H): 357.13; Found (M+H): 357.1. HPLC purity: 98.86%
Step-4:

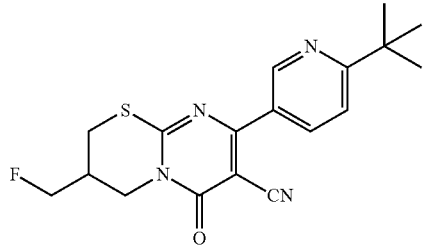 [SMILES: CC(C)(C)c1ccc(-c2nc3n(c(=O)c2C#N)CC(CF)CS3)cn1]

Preparation of 8-(6-(tert-butyl)pyridin-3-yl)-3-(fluoromethyl)-6-oxo-3,4-dihydro-2H,6H-pyrimido[2,1-b][1,3]thiazine-7-carbonitrile 5

To a stirred solution of 8-(6-(tert-butyl)pyridin-3-yl)-3-(hydroxymethyl)-6-oxo-3,4-dihydro-2H,6H-pyrimido[2,1-b][1,3]thiazine-7-carbonitrile (4, 0.1 g, 0.28 mmol) in dichloromethane (10 mL) cooled to −78° C., diethylaminosulfur trifluoride (0.074 mL, 0.56 mmol) was added drop wise and the reaction mixture was stirred at room temperature for 2 h. The reaction mixture was quenched with saturated sodium bicarbonate solution (10 mL) and extracted with dichloromethane (2×20 mL). The combined organic layer was dried over anhydrous sodium sulphate, filtered and concentrated. The crude was purified by silica gel column chromatography using 50% ethyl acetate in hexane to afford the title compound 8-(6-(tert-butyl)pyridin-3-yl)-3-(fluoromethyl)-6-oxo-3,4-dihydro-2H,6H-pyrimido[2,1-b][1,3]thiazine-7-carbonitrile (5 (example 88) 0.015 g, 15% yield) as an off-white solid. $^1$H NMR (400 MHz, DMSO-d$_6$) δ (ppm): 8.95 (d, J=1.6 Hz, 1H), 8.16 (dd, J$_1$=2.4 Hz, J$_2$=8.4 Hz, 1H), 7.63 (d, J=8.4 Hz, 1H), 4.70-4.63 (m, 1H), 4.59-4.51 (m, 1H), 4.42 (d, J=12.8 Hz, 1H), 3.67-3.61 (m, 1H), 3.33-3.30 (m, 1H), 3.23-3.17 (m, 1H), 2.69 (bs, 1H), 1.33 (s, 9H). Calculated (M+H): 359.13; Found (M+H): 359.1, HPLC purity: 99.5%

TABLE 19

The following compounds were prepared by the method described above:

| Ex. # | Structure | IUPAC Name | Analytical Data |
|---|---|---|---|
| 89 | 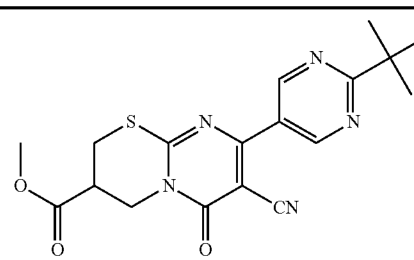 | methyl 8-(2-(tert-butyl)pyrimidin-5-yl)-7-cyano-6-oxo-3,4-dihydro-2H,6H-pyrimido[2,1-b][1,3]thiazine-3-carboxylate | $^1$H NMR (400 MHz, DMSO-d$_6$) δ (ppm): 9.17 (s, 2H), 4.25 (d, J = 5.6 Hz, 2H), 3.69 (s, 3H), 3.63-3.56 (m, 2H), 3.50-3.45 (m, 1H), 1.30 (s, 9H). Calculated (M + H): 386.12; Found (M + H): 386.1, HPLC purity: 99.81% |

TABLE 19-continued

The following compounds were prepared by the method described above:

| Ex. # | Structure | IUPAC Name | Analytical Data |
|---|---|---|---|
| 90 | 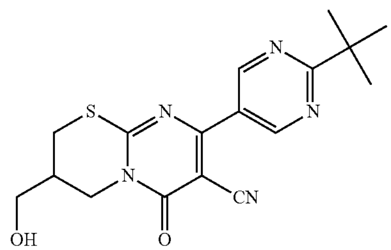 [SMILES: CC(C)(C)c1ncc(-c2nc3n(c(=O)c2C#N)CC(CO)CS3)cn1] | 8-(2-(tert-butyl)pyrimidin-5-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 5.03 (t, J = 5.2 Hz, 1H), 4.43 (d, J = 14.4 Hz, 1H), 3.57-3.51 (m, 3H), 3.16-3.11 (m, 1H), 2.31 (bs, 1H), 1.39 (s, 9H). 1H was merged with DMSO water peak. Calculated (M + H): 358.13; Found (M + H): 358.1, HPLC purity: 99.68% |
| 91 | 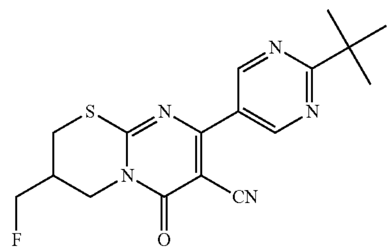 [SMILES: CC(C)(C)c1ncc(-c2nc3n(c(=O)c2C#N)CC(CF)CS3)cn1] | 8-(2-(tert-butyl)pyrimidin-5-yl)-3-(fluoromethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.16 (s, 2H), 4.67 (t, J = 5.6 Hz, 1H), 4.56 (t, J = 5.6 Hz, 1H), 4.43 (d, J = 10 Hz, 1H), 3.69-3.63 (m, 1H), 3.35-3.33 (m, 1H), 3.23-3.19 (m, 1H), 2.65 (bs, 1H), 1.39 (s, 9H). Calculated (M + H): 360.12; Found (M + H): 360.1, HPLC purity: 99.4% |
| 92 | 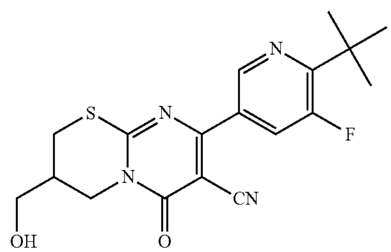 [SMILES: CC(C)(C)c1ncc(-c2nc3n(c(=O)c2C#N)CC(CO)CS3)cc1F] | 8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.81 (s, 1H), 8.00 (dd, $J_1$ = 1.6 Hz, $J_2$ = 12.8 Hz, 1H), 5.03 (bs, 1H), 4.42 (d, J = 14 Hz, 1H), 3.56-350 (m, 3H), 3.24 (bs, 1H), 3.13 (t, J = 10.4 Hz, 1H), 2.31-2.28 (m, 1H), 1.39 (s, 9H). Calculated (M + H): 375.12; Found (M + H): 375.1, HPLC purity: 96.43% |

Example 93

Preparation of 8-(6-(2-cyanopropan-2-yl)pyridin-3-yl)-6-oxo-3,4-dihydro-2H,6H-pyrimido[2,1-b][1,3]thiazine-7-carbonitrile 6

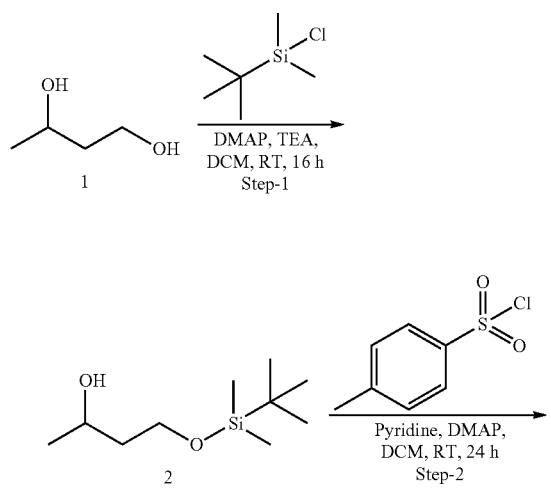

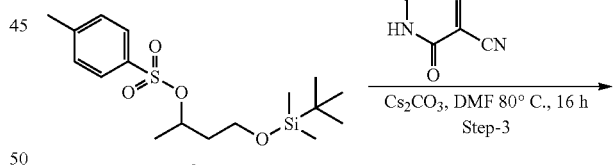

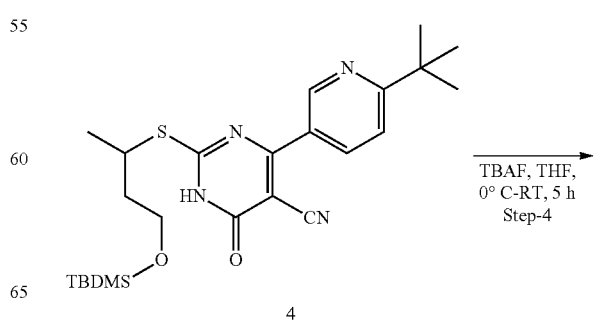

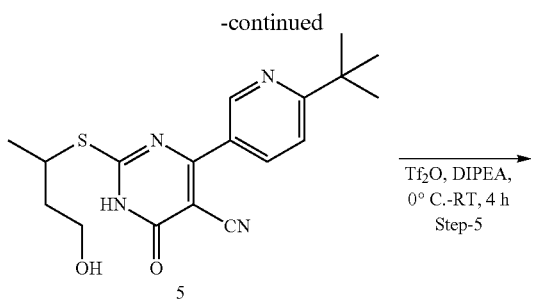

Step-1:

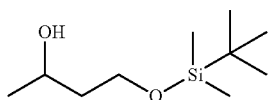

Preparation of
4-((tert-butyldimethylsilyl)oxy)butan-2-ol 2

To a stirred suspension of butane-1,3-diol (1, 5.0 g, 55 mmol), tert-butylchlorodimethylsilane (8.7 g, 58 mmol), triethylamine (23 mL, 165 mmol) in dichloromethane (60 mL) was added 4-dimethylaminopyridine (0.33 g, 2 mmol) and the reaction mixture was stirred at room temperature for 16 h. The reaction mixture was partitioned between water (100 mL) and dichloromethane (100 mL). The organic layer was washed with saturated sodium bicarbonate solution (100 mL), brine (100 mL), dried over anhydrous sodium sulphate, filtered and concentrated. The crude product was purified by silica gel column chromatography using 5% ethyl acetate in hexane to afford the title compound 4-((tert-butyldimethylsilyl)oxy)butan-2-ol (2, 6.2 g, 55% yield) as a pale yellow oil. Calculated (M+H): 205.1; Found (M+H): 205.2.

Step-2:

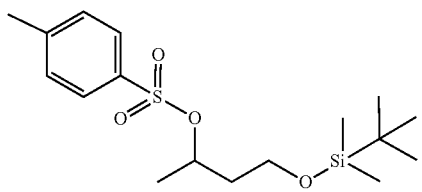 [SMILES: Cc1ccc(S(=O)(=O)OC(C)CCO[Si](C)(C)C(C)(C)C)cc1]

Preparation of
4-((tert-butyldimethylsilyl)oxy)butan-2-yl
4-methylbenzenesulfonate 3

To a solution of 4-((tert-butyldimethylsilyl)oxy)butan-2-ol (2, 6.0 g, 29.35 mmol) in dichloromethane (30 mL), were added pyridine (7.0 mL, 87 mmol), 4-dimethylaminopyridine (0.4 g, 3.27 mmol) and a solution of 4-methylbenzenesulfonyl chloride (0.97 g, 5.08 mmol) in dichloromethane (30 mL) at room temperature. The reaction mixture was stirred at room temperature for 24 h. The reaction mixture was partitioned between water (100 mL) and dichloromethane (150 mL). The organic layer was washed with 1M hydrochloric acid solution (100 mL), brine (150 mL), dried over anhydrous sodium sulphate, filtered and concentrated to afford the title compound 4-((tert-butyldimethylsilyl)oxy)butan-2-yl 4-methylbenzenesulfonate (3, 8.0 g, 76.9% yield) as a pale orange oil. Calculated (M+H): 359.5: Found (M+H): 359.2.

Step-3:

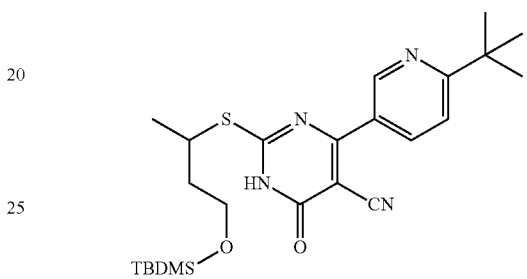

Preparation of 4-(6-(tert-butyl)pyridin-3-yl)-2-((4-((tert-butyldimethylsilyl)oxy)butan-2-yl)thio)-6-oxo-1,6-dihydropyrimidine-5-carbonitrile 4

A mixture of 4-((tert-butyldimethylsilyl)oxy)butan-2-yl 4-methylbenzenesulfonate (3, 0.5 g 1.74 mmol), 6-(6-(tert-butyl)pyridin-3-yl)-4-oxo-2-thioxo-1,2,3,4-tetrahydropyrimidine-5-carbonitrile (0.62 g, 1.74 mmol) and cesium carbonate (0.62 g, 3.42 mmol) in N,N-dimethylformamide (10 mL) was heated at 80° C. for 16 h in a sealed tube. The reaction mixture was cooled to room temperature diluted with water (30 mL) and extracted with ethyl acetate (2×25 mL). The combined organic layer was washed with brine (30 mL), dried over anhydrous sodium sulphate, filtered and concentrated. The crude product was purified by silica gel column chromatography using 40% ethyl acetate in hexane to afford the title compound 4-(6-(tert-butyl)pyridin-3-yl)-2-((4-((tert-butyldimethylsilyl)oxy)butan-2-yl)thio)-6-oxo-1,6-dihydropyrimidine-5-carbonitrile (4, 0.11 g, 13.3% yield) pale yellow gum. Calculated (M+H): 473.2; Found (M+H): 473.2.

Step-4:

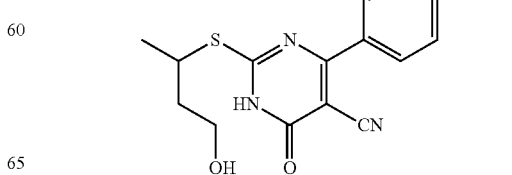

Preparation of 4-(6-(tert-butyl)pyridin-3-yl)-2-((4-hydroxybutan-2-yl)thio)-6-oxo-1,6-dihydropyrimidine-5-carbonitrile 5

To a solution of 4-(6-(tert-butyl)pyridin-3-yl)-2-((4-(((tert-butyldimethylsilyl)oxy)butan-2-yl)thio)-6-oxo-1,6-dihydropyrimidine-5-carbonitrile (4, 0.09 g, 0.19 mmol) in tetrahydrofuran (5 mL), tetra-n-butylammoniumfluoride solution (0.5 mL, 0.48 mmol, 1M in tetrahydrofuran) was added drop wise at 0° C. The reaction mixture was allowed to stir at room temperature for 5 h. The reaction mixture diluted with water (30 mL) and extracted with ethyl acetate (2×25 mL). The combined organic layer was washed with brine (30 mL), dried over anhydrous sodium sulphate, filtered and concentrated. The crude product was washed with diethyl ether to afford the title compound 4-(6-(tert-butyl)pyridin-3-yl)-2-((4-hydroxybutan-2-yl)thio)-6-oxo-1,6-dihydropyrimidine-5-carbonitrile (5, 0.07 g, crude) as yellow gum. Calculated (M+H): 359.1; Found (M+H): 359.1.

Step-5:

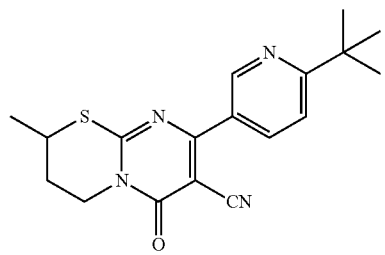 [SMILES: CC1CCn2c(nc(-c3ccc(C(C)(C)C)nc3)c(C#N)c2=O)S1]

Preparation of 8-(6-(tert-butyl)pyridin-3-yl)-2-methyl-6-oxo-3,4-dihydro-2H,6H-pyrimido[2,1-b][1,3]thiazine-7-carbonitrile 6

To a stirred solution of 4-(6-(tert-butyl)pyridin-3-yl)-2-((4-hydroxybutan-2-yl)thio)-6-oxo-1,6-dihydropyrimidine-5-carbonitrile (5, 0.07 g, 0.19 mmol) and N,N-diisopropylethylamine (0.16 mL, 0.97 mmol) in dichloromethane (7 mL), was added triflic anhydride (0.08 mL, 0.48 mmol) at 0 QC. The reaction mixture was allowed to stir at room temperature for 4 h. The reaction mixture was diluted with water (10 mL) and extracted with dichloromethane (2×10 mL). The combined organic layer was dried over anhydrous sodium sulphate, filtered and concentrated. The crude product was purified by silica gel column chromatography using 30% ethyl acetate in hexane to afford the title compound 8-(6-(tert-butyl)pyridin-3-yl)-2-methyl-6-oxo-3,4-dihydro-2H,6H-pyrimido[2,1-b][1,3]thiazine-7-carbonitrile (6 (example 93), 0.014 g, 21% yield) as a brown solid. ¹H NMR (DMSO-d₆, 400 MHz) δ (ppm): 8.93 (s, 1H), 8.15 (d, J=8.4 Hz, 1H), 7.26 (d, J=8.0 Hz, 1H), 4.37 (d, J=14.4 Hz, 1H), 3.79-3.73 (m, 2H), 2.48 (bs, 1H), 1.91-1.83 (m, 1H) 1.38 (d, J=6.4 Hz, 3H), 1.33 (s, 9H). Calculated (M+H): 341.1: Found (M+H): 341.1, HPLC purity: 99.0%

Example 94

Preparation of 8-(6-(tert-butyl)pyridin-3-yl)-1-methyl-6-oxo-1,3,4,6-tetrahydro-2H-pyrimido[1,2-a]pyrimidine-7-carbonitrile 5

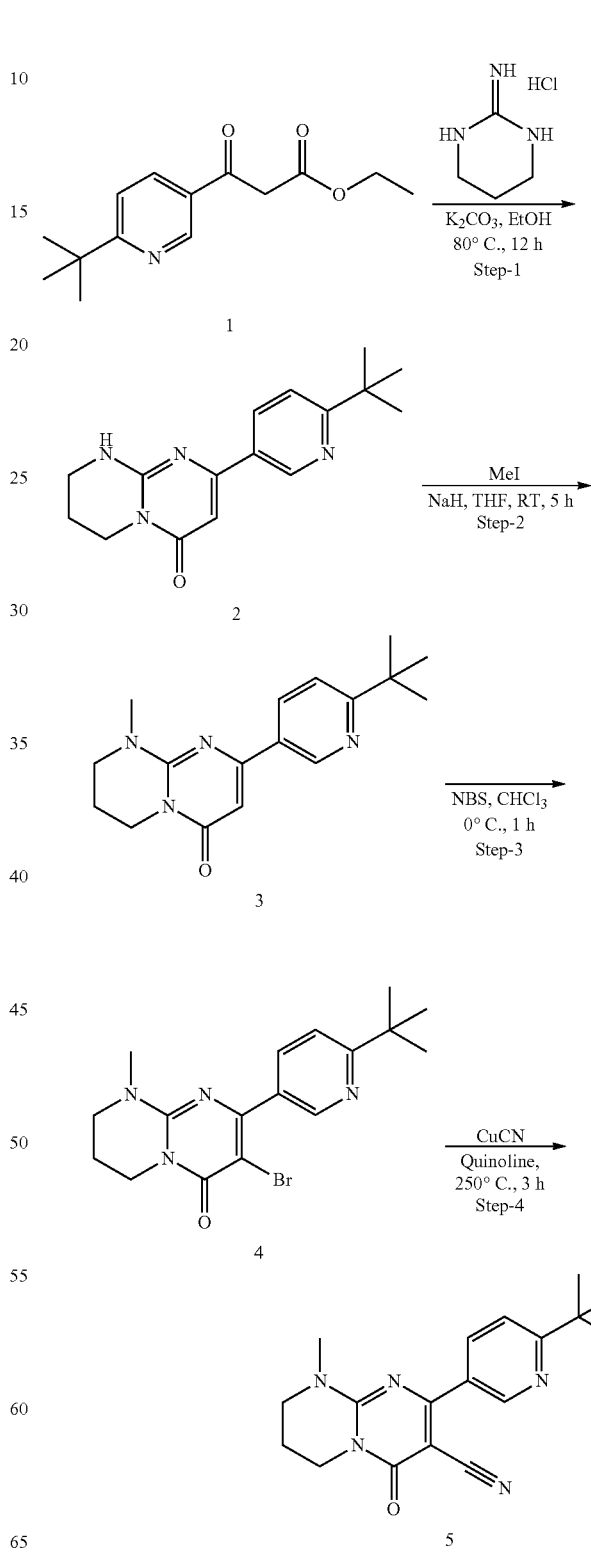

Step-1:

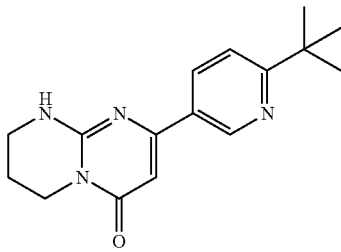 [SMILES: CC(C)(C)c1ccc(-c2cc(=O)n3c(n2)NCCC3)cn1]

Preparation of 2-(6-(tert-butyl)pyridin-3-yl)-6,7,8,9-tetrahydro-4H-pyrimido[1,2-a]pyrimidin-4-one 2

To a solution of ethyl 3-(6-(tert-butyl)pyridin-3-yl)-3-oxopropanoate (1, 0.2 g, 0.8 mmol) in ethanol (10 mL), tetrahydropyrimidin-2(1H)-imine (0.2 g, 1.6 mmol), potassium carbonate (0.33 g, 2.4 mmol) were added and the reaction mixture was stirred at 80° C. for 12 h. The reaction mixture evaporated completely and dried to afford the title compound 2-(6-(tert-butyl)pyridin-3-yl)-6,7,8,9-tetrahydro-4H-pyrimido[1,2-a]pyrimidin-4-one (2, 0.22 g, crude) as pale yellow gum. The crude product was as such taken to next step without any purification. Calculated (M+H): 285.16; Found (M+H): 285.2.

Step-2:

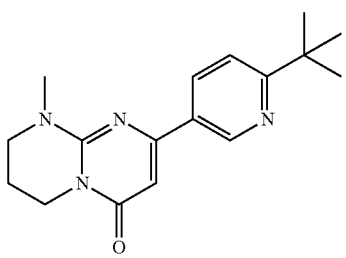 [SMILES: CN1CCCn2c1nc(-c1ccc(C(C)(C)C)nc1)cc2=O]

Preparation of 2-(6-(tert-butyl)pyridin-3-yl)-9-methyl-6,7,8,9-tetrahydro-4H-pyrimido[1,2-a]pyrimidin-4-one 3

To a solution of 2-(6-(tert-butyl)pyridin-3-yl)-6,7,8,9-tetrahydro-4H-pyrimido[1,2-a]pyrimidin-4-one (2, 0.22 g, 0.77 mmol) in tetrahydrofuran (5 mL) was added sodium hydride (0.07 g, 1.7 mmol) at 0° C. and the reaction mixture was stirred at 0° C. for 15 min. Then methyl iodide (0.06 mL, 0.92 mmol) was added and the reaction mixture was stirred at room temperature for 5 h. The reaction mixture was quenched with cold water (30 mL) and extracted with ethyl acetate (2×50 mL). The combined organic layer was dried over anhydrous sodium sulphate, filtered and concentrated. The crude product was purified by silica gel column chromatography using 100% ethyl acetate to afford the title compound 2-(6-(tert-butyl)pyridin-3-yl)-9-methyl-6,7,8,9-tetrahydro-4H-pyrimido[1,2-a]pyrimidin-4-one (3, 0.12 g, 52% yield) as a colorless gum. Calculated (M+H): 299.18; Found (M+H): 299.2.

Step-3:

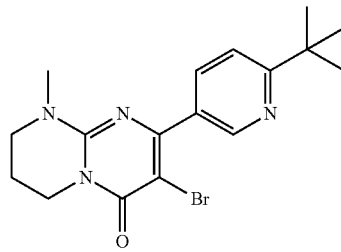

Preparation of 3-bromo-2-(6-(tert-butyl)pyridin-3-yl)-9-methyl-6,7,8,9-tetrahydro-4H-pyrimido[1,2-a]pyrimidin-4-one 4

To a solution of 2-(6-(tert-butyl)pyridin-3-yl)-9-methyl-6,7,8,9-tetrahydro-4H-pyrimido[1,2-a]pyrimidin-4-one (3, 2 g, 6 mmol) in chloroform (30 mL) cooled to 0° C., was added N-bromosuccinimide (1.449, 8 mmol) and the reaction mixture was stirred at 0° C. for 1 h. The reaction mixture was filtered through celite bed and the filtrate was concentrated. The crude product was purified by silica gel column chromatography using 4% methanol in dichloromethane to afford the title compound 3-bromo-2-(6-(tert-butyl)pyridin-3-yl)-9-methyl-6,7,8,9-tetrahydro-4H-pyrimido[1,2-a]pyrimidin-4-one (4, 2.3 g, crude) as pale yellow solid. Calculated (M+H): 377.09; Found (M+H): 377.1.

Step-4:

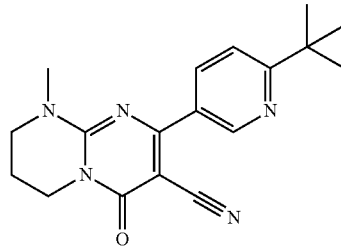

Preparation of 8-(6-(tert-butyl)pyridin-3-yl)-1-methyl-6-oxo-1,3,4,6-tetrahydro-2H-pyrimido[1,2-a]pyrimidine-7-carbonitrile 5

To a stirred solution of 3-bromo-2-(6-(tert-butyl)pyridin-3-yl)-9-methyl-6,7,8,9-tetrahydro-4H-pyrimido[1,2-a]pyrimidin-4-one (4, 0.3 g, 23.9 mmol) in quinoline (10 mL), copper cyanide (0.086 g, 28.7 mmol) was added and the reaction mixture was heated at 250° C. for 3 h. The reaction mixture was cooled to room temperature, quenched with crushed ice and extracted with ethyl acetate (2×50 mL). The combined organic layer was washed with brine (30 mL), dried over sodium sulfate, filtered and concentrated. The crude product was purified by silica gel column chromatography using 3% methanol in dichloromethane to afford the title compound 8-(6-(tert-butyl)pyridin-3-yl)-1-methyl-6-oxo-1,3,4,6-tetrahydro-2H-pyrimido[1,2-a]pyrimidine-7-carbonitrile (5 (example 94), 0.025 g, 9.7% yield) as a pale brown solid. $^1$H NMR (400 MHz, DMSO-$d_6$) δ (ppm): 8.96 (s, 1H), 8.16 (dd, $J_1$=2 Hz, $J_2$=8.4 Hz, 1H), 7.58 (d, J=8.4 Hz, 1H), 3.90-3.87 (m, 2H), 3.52-3.50 (m, 2H), 3.23 (s, 3H), 2.02 (d, J=4.8 Hz, 2H), 1.33 (m, 9H). Calculated (M+H): 324.17; Found (M+H): 324.2. HPLC purity: 99.85%

Example 95

Preparation of 6-oxo-8-(6-(prop-1-en-2-yl)pyridin-3-yl)-3,4-dihydro-2H,6H-pyrimido[2,1-b][1,3]thiazine-7-carbonitrile 2

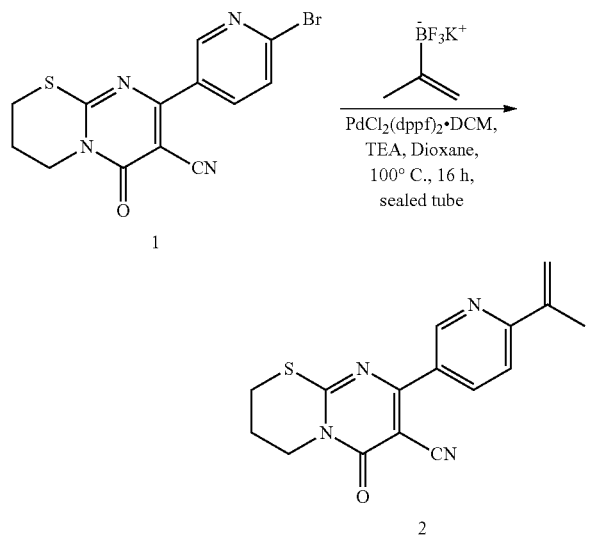

A stirred solution of 8-(6-bromopyridin-3-yl)-6-oxo-3,4-dihydro-2H,6H-pyrimido[2,1-b][1,3]thiazine-7-carbonitrile (1, 0.4 g, 1.15 mmol), potassium isopropenyltrifluoroborate (0.42 g, 2.873 mmol) and triethylamine (0.8 mL, 5.75 mmol) in 1,4-dioxane (20 mL) was purged with argon for 5 min. Then [1,1'-bis(diphenylphosphino)ferrocene]dichloropalladium(II) complex with dichloromethane (0.18 g, 0.23 mmol) was added and the reaction mixture was heated at 100° C. for 16 h in a sealed tube. The reaction mixture was filtered through celite bed and the filtrate was concentrated. The crude was purified by silica gel column chromatography using 60% ethyl acetate in hexane to afford the title compound 6-oxo-8-(6-(prop-1-en-2-yl)pyridin-3-yl)-3,4-dihydro-2H,6H-pyrimido[2,1-b][1,3]thiazine-7-carbonitrile (2 (example 95), 0.35 g, 42% yield) as an off white solid. $^1$H NMR (400 MHz, DMSO-d$_6$) δ (ppm): 8.99 (d, J=2.0 Hz, 1H), 8.21 (dd, J$_1$=2.0 Hz, J$_2$=8.4 Hz, 1H), 7.81 (d, J=8.4 Hz, 1H), 6.06 (s, 1H), 5.44 (s, 1H), 4.02 (t, J=6.0 Hz, 2H), 3.29-3.27 (m, 2H), 2.30-2.22 (m, 2H), 2.19 (s, 3H). Calculated (M+H): 311.09; Found (M+H): 311.1, HPLC purity: 99.0%

Examples 96 and 97

Preparation of (R)-8-(6-(tert-butyl)pyridin-3-yl)-3-methyl-6-oxo-3,4-dihydro-2H,6H-pyrido[2,1-b][1,3]thiazine-7-carbonitrile 2 and (S)-8-(6-(tert-butyl)pyridin-3-yl)-3-methyl-6-oxo-3,4-dihydro-2H,6H-pyrido[2,1-b][1,3]thiazine-7-carbonitrile 3

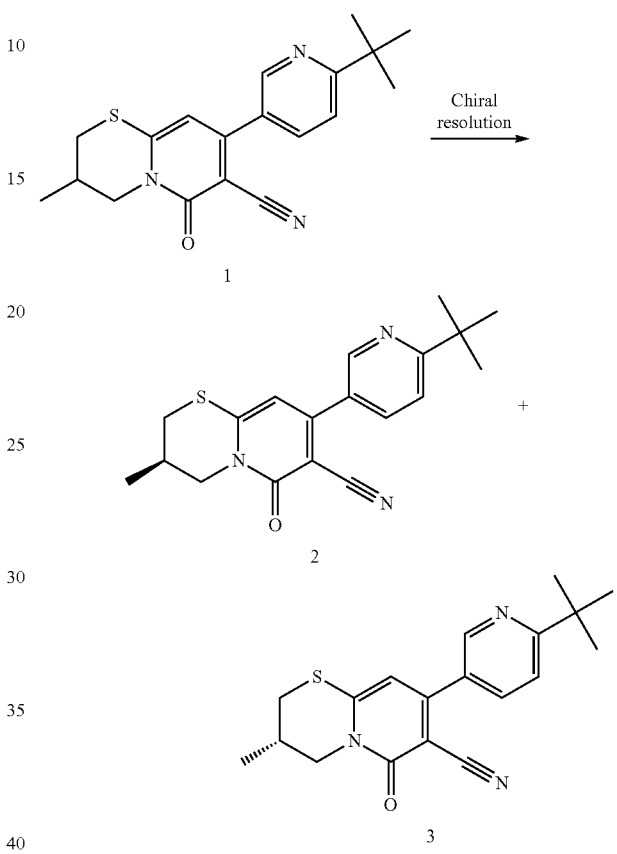

The chiral resolution was performed using the analytical condition: column: CHIRALPAK IA (250 mm×4.6 mm×5 mic), mobile phase: methyl tert-butyl ether: ethanol with 0.1% diethyl amine (50:50), flow rate: 1.0 mL/min. The analytical data for the enantiomers are given below.

TABLE 20

The following compounds were separated by the method described above

| Ex. # | Structure | IUPAC Name | Analytical Data |
|---|---|---|---|
| 96 | 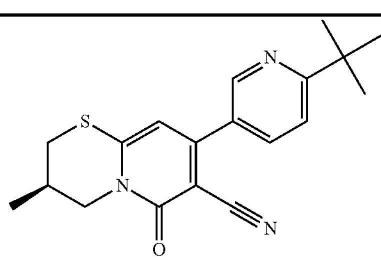 | (R)-8-(6-(tert-butyl)pyridin-3-yl)-3-methyl-6-oxo-3,4-dihydro-2H,6H-pyrido[2,1-b][1,3]thiazine-7-carbonitrile | $^1$H NMR (400 MHz, DMSO-d$_6$) δ (ppm): 8.71 (d, J = 2.0 Hz, 1H), 7.96 (dd, J$_1$ = 2.0 Hz, J$_2$ = 8.4 Hz, 1H), 7.58 (d, J = 8.0 Hz, 1H), 6.58 (s, 1H), 4.34 (d, J = 12.8 Hz, 1H), 3.43 (dd, J$_1$ = 9.6 Hz, J$_2$ = 14.4 Hz, 1H), 3.21 (dd, J$_1$ = 2.8 Hz, J$_2$ = 11.6 Hz, 1H), 2.95 (dd, J$_1$ = 9.6 Hz, J$_2$ = 11.6 Hz, 1H), 2.3-2.26 (m, 1H), 1.33 (s, 9H), 1.11 (d, J = 6.4 Hz, 3H). Calculated (M + H): 340.14, Found (M + H): 340.2, Chiral HPLC purity: 99.99% |

TABLE 20-continued

The following compounds were separated by the method described above

| Ex. # | Structure | IUPAC Name | Analytical Data |
|---|---|---|---|
| 97 | 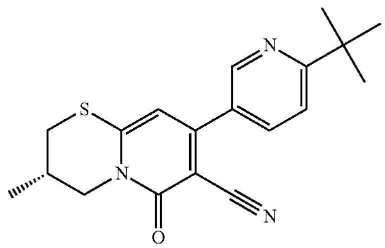 [SMILES: C[C@@H]1CSc2cc(-c3ccc(C(C)(C)C)nc3)c(C#N)c(=O)n2C1] | (S)-8-(6-(tert-butyl)pyridin-3-yl)-3-methyl-6-oxo-3,4-dihydro-2H,6H-pyrido[2,1-b][1,3]thiazine-7-carbonitrile | $^1$H NMR (400 MHz, DMSO-$d_6$) δ (ppm): 8.71 (d, J = 2.0 Hz, 1H), 7.96 (dd, $J_1$ = 2.0 Hz, $J_2$ = 8.4 Hz, 1H), 7.58 (d, J = 8.4 Hz, 1H), 6.58 (s, 1H), 4.34 (d, J = 14.0 Hz, 1H), 3.43 (dd, $J_1$ = 9.6 Hz, $J_2$ = 14.0 Hz, 1H), 3.21 (dd, $J_1$ = 3.2 Hz, $J_2$ = 12.0 Hz, 1H), 2.95 (dd, $J_1$ = 9.6 Hz, $J_2$ = 11.6 Hz, 1H), 2.3-2.26 (m, 1H), 1.33 (s, 9H), 1.11 (d, J = 6.4 Hz, 3H). Calculated (M + H): 340.14, Found (M + H): 340.2, Chiral HPLC purity: 99.99% |

Examples 98 and 99

Preparation of (R)-8-(6-(tert-butyl)-5-fluoropyridin-3-yl)-3-methyl-6-oxo-3,4-dihydro-2H,6H-pyrimido[2,1-b][1,3]thiazine-7-carbonitrile 2 and (S)-8-(6-(tert-butyl)-5-fluoropyridin-3-yl)-3-methyl-6-oxo-3,4-dihydro-2H,6H-pyrimido[2,1-b][1,3]thiazine-7-carbonitrile 3

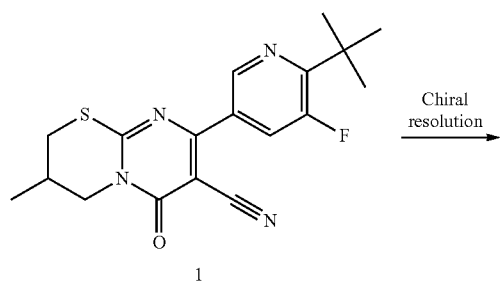

1

Chiral resolution →

-continued

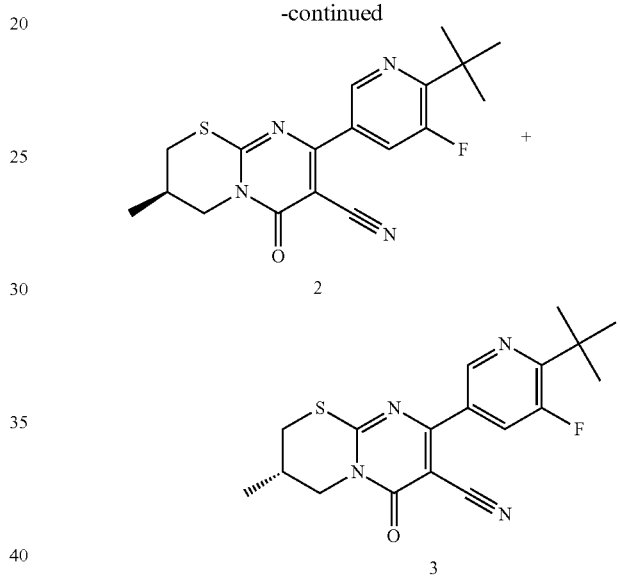

The chiral resolution was performed using the analytical condition: column: CHIRALPAK IA (250 mm×4.6 mm×5 mic), mobile phase A: n-hexane, mobile phase B: 0.1% diethyl amine in isopropyl alcohol (50:50), flow rate: 1.0 mL/min. The analytical data for the enantiomers are given below.

TABLE 21

The following compounds were separated by the method described above

| Ex. # | Structure | IUPAC Name | Analytical Data |
|---|---|---|---|
| 98 | 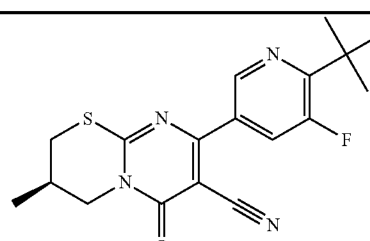 | (R)-8-(6-(tert-butyl)-5-fluoropyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.80 (s, 1H), 8.0 (d, J = 13.2 Hz, 1H), 4.27 (d, J = 14.4 Hz, 1H), 3.51-3.45 (m, 1H), 3.27-3.23 (m, 1H), 3.07 (t, J = 9.6 Hz, 1H), 2.34-2.3 (m, 1H), 1.38 (s, 9H), 1.13 (d, J = 6.4 Hz, 3H). Calculated (M + H): 359.13, Found (M + H): 359.0, Chiral HPLC purity: 99.96% |

TABLE 21-continued

The following compounds were separated by the method described above

| Ex. # | Structure | IUPAC Name | Analytical Data |
|---|---|---|---|
| 99 | 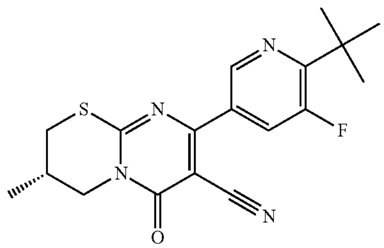 [SMILES: C[C@@H]1CSc2nc(-c3cnc(C(C)(C)C)c(F)c3)c(C#N)c(=O)n2C1] | (S)-8-(6-(tert-butyl)-5-fluoropyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.80 (s, 1H), 8.0 (dd, $J_1$ = 2.0 Hz, $J_2$ = 12.8 Hz, 1H), 4.27 (d, J = 14.0 Hz, 1H), 3.51-3.45 (m, 1H), 3.27-3.23 (m, 1H), 3.1-3.04 (m, 1H), 2.37-2.3 (m, 1H), 1.38 (s, 9H), 1.13 (d, J = 6.4 Hz, 3H). Calculated (M + H): 359.13, Found (M + H): 359.0, Chiral HPLC purity: 98.92% |

Examples 100 and 101

Preparation of (R)-8-(2-(tert-butyl)pyrimidin-5-yl)-6-imino-3-methyl-3,4-dihydro-2H,6H-pyrimido[2,1-b][1,3]thiazine-7-carbonitrile 2 and (S)-8-(2-(tert-butyl)pyrimidin-5-yl)-6-imino-3-methyl-3,4-dihydro-2H,6H-pyrimido[2,1-b][1,3]thiazine-7-carbonitrile 3

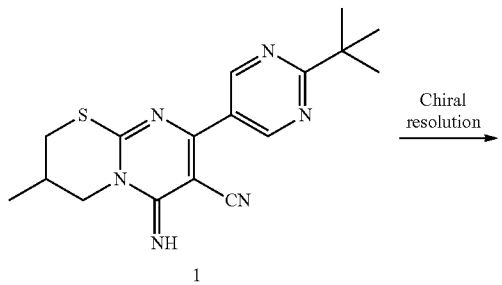

1

Chiral resolution →

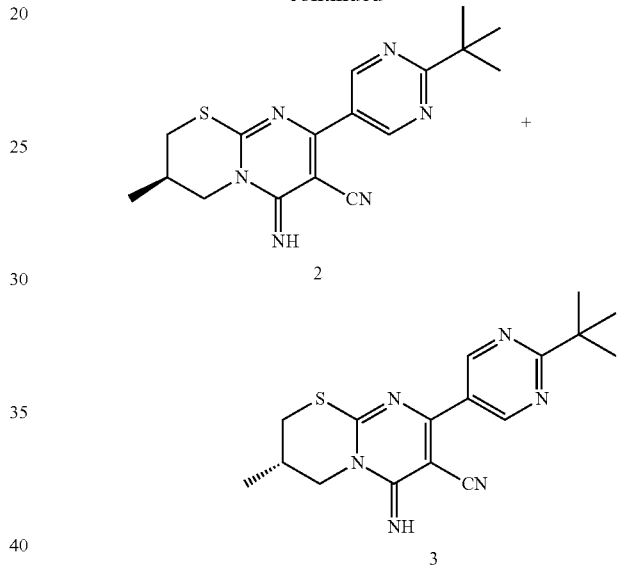

The chiral resolution was performed using analytical condition: column: CHIRALPAK IA (250 mm×4.6 mm×5 mic), mobile phase A: acetonitrile, mobile phase B: 0.10 diethyl amine in methanol, composition: 15:85, flow rate: 1.0 mL/min. The analytical data for the enantiomers are given below.

TABLE 22

The following compounds were separated by the method described above

| Ex. # | Structure | IUPAC Name | Analytical Data |
|---|---|---|---|
| 100 | 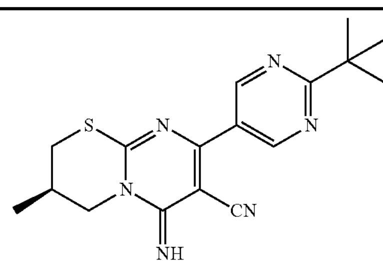 | (R)-8-(2-(tert-butyl)pyrimidin-5-yl)-6-imino-3-methyl-3,4-dihydro-2H,6H-pyrimido[2,1-b][1,3]thiazine-7-carbonitrile | $^1$H NMR (400 MHz, DMSO-$d_6$) δ (ppm): 9.08 (s, 2H), 7.47 (s, 1H), 4.35 (d, J = 14.0 Hz, 1H), 3.49-3.43 (m, 1H), 3.20 (d, J = 18.4, Hz, 1H), 3.05 (t, J = 9.2 Hz, 1H), 2.34 (bs, 1H), 1.37 (s, 9H), 1.13 (d, J = 10.4 Hz, 3H). Calculated (M + H): 341.15; Found (M + H): 341.1, Chiral HPLC purity: 99.41% |

TABLE 22-continued

The following compounds were separated by the method described above

| Ex. # | Structure | IUPAC Name | Analytical Data |
|---|---|---|---|
| 101 | 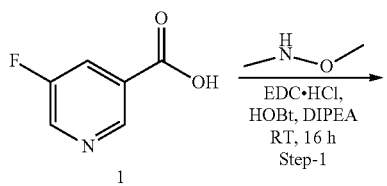 | (S)-8-(2-(tert-butyl)pyrimidin-5-yl)-6-imino-3-methyl-3,4-dihydro-2H,6H-pyrimido[2,1-b][1,3]thiazine-7-carbonitrile | $^1$H-NMR (DMSO-$d_6$, 400 MHz) δ (ppm): 9.08 (s, 2H), 7.47 (s, 1H), 4.35 (d, J = 14.4 Hz, 1H), 3.49-3.43 (m, 1H), 3.20 (d, J = 16.8 Hz, 1H), 3.05 (t, J = 9.6 Hz, 1H), 2.34 (bs, 1H), 1.37 (s, 9H), 1.13 (d, J = 6.4 Hz, 3H). Calculated (M + H): 341.15, Found (M + H): 341.1, Chiral HPLC purity: 99.71% |

Example 102

Preparation of 8-(6-(tert-butyl)-5-fluoropyridin-3-yl)-6-oxo-3,4-dihydro-2H,6H-pyrido[2,1-b][1,3]thiazine-7-carbonitrile 7

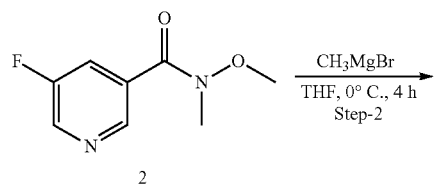

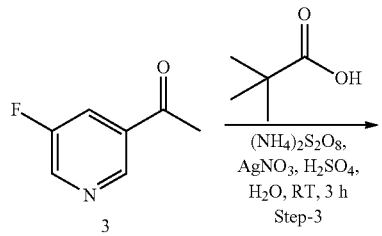

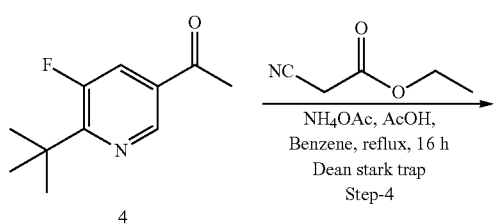

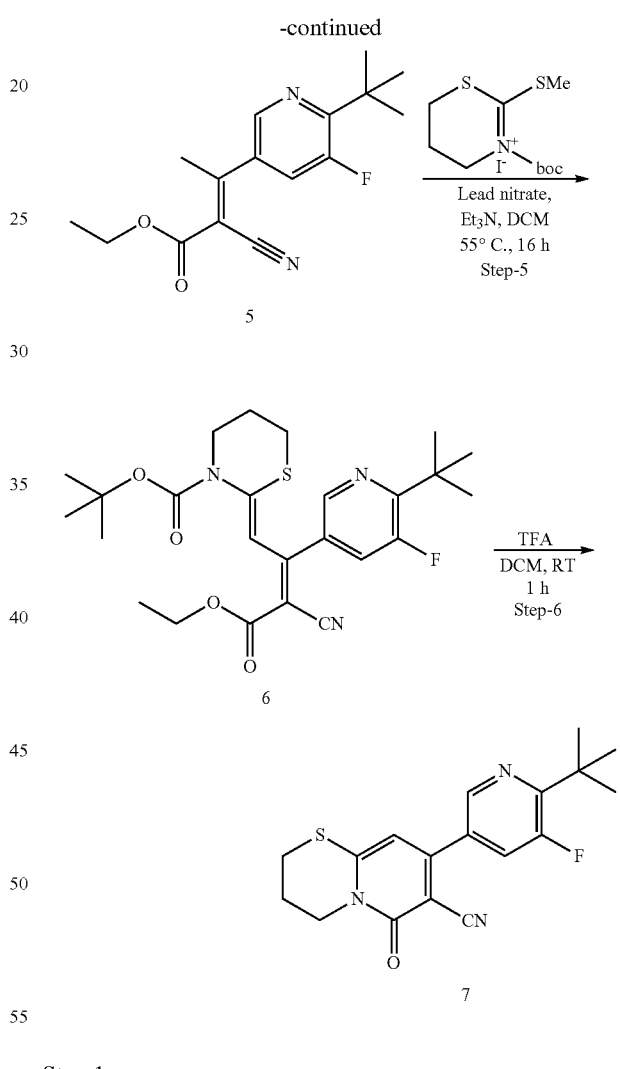

Step-1:

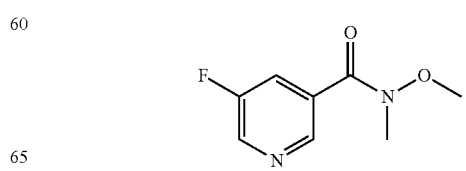

Preparation of 5-fluoro-N-methoxy-N-methylnicotinamide 2

To a solution of 5-fluoronicotinic acid (1, 10.0 g, 70.87 mmol) in N,N-dimethylformamide (100 mL), N,O-dimethylhydroxylamine (7.35 g, 120.48 mmol), 1-(3-dimethylaminopropyl)-3-ethylcarbodiimide hydrochloride (16.5 g, 106.30 mmol) and 1-hydroxybenzotriazole (0.47 g, 3.54 mmol) were added at room temperature. Then N, N-diisopropylethylamine (27.77 mL, 159.51 mmol) was added drop wise at 0° C. The reaction mixture was stirred at room temperature for 16 h. The reaction mixture was quenched with water (100 mL) and extracted with ethyl acetate (3×100 mL). The combined organic layer was dried over anhydrous sodium sulfate, filtered and concentrated. The crude product was purified by silica gel chromatography using 35% ethyl acetate in hexane to afford the title compound 5-fluoro-N-methoxy-N-methylnicotinamide (2, 6.5 g, 50% yield) as an off white solid. Calculated (M+H): 185.06; Found (M+H): 185.1

Step-2:

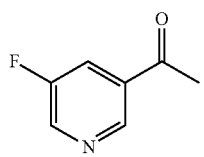

Preparation of 1-(5-fluoropyridin-3-yl)ethan-1-one 3

To a solution of 5-fluoro-N-methoxy-N-methylnicotinamide (2, 6.5 g, 35.29 mmol) in tetrahydrofuran (150 mL), methyl magnesium bromide solution (56.24 mL, 105.82 mmol, 3M in diethyl ether) was added drop wise at 0° C. under nitrogen atmosphere. The reaction mixture was stirred at the same temperature for 4 h. The reaction mixture was quenched with saturated ammonium chloride solution (100 mL) and extracted with ethyl acetate (2×100 mL). The combined organic layer was dried over anhydrous sodium sulfate, filtered and concentrated. The crude product was purified by silica gel column chromatography using 35% ethyl acetate in hexane to afford the title compound 1-(5-fluoropyridin-3-yl)ethan-1-one (3, 3.659, 74% yield) as an off white solid. Calculated (M+H): 140.04; Found (M+H): 140.1.

Step-3:

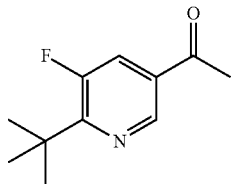

Preparation of 1-(6-(tart-butyl)-5-fluoropyridin-3-yl)ethan-1-one 4

To a solution of 1-(5-fluoropyridin-3-yl)ethan-1-one (3, 3.4 g, 24.45 mmol), pivalic acid (4.99 g, 48.90 mmol) and silver nitrate (0.82 g, 4.88 mmol) in 10% aqueous sulphuric acid (50 mL), ammonium persulphate (11.58 g, 48.91 mmol) dissolved in water (100 mL) was added at room temperature and the reaction mixture was stirred at room temperature for 3 h. The reaction mixture was basified with aqueous ammonia solution to pH 9 and extracted with ethyl acetate (3×100 mL). The combined organic layer was dried over anhydrous sodium sulfate, filtered and concentrated. The crude product was purified by silica gel chromatography using 15% ethyl acetate in hexane to afford the title compound 1-(6-(tert-butyl)-5-fluoropyridin-3-yl)ethan-1-one (4, 3.8 g, 79% yield) as an off white solid. Calculated (M+H): 196.11; Found (M+H): 196.1.

Step-4:

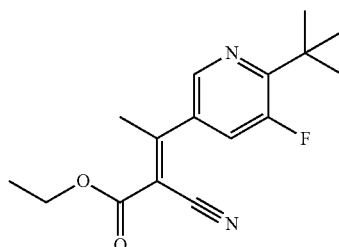

Preparation of ethyl (E)-3-(6-(tert-butyl)-5-fluoropyridin-3-yl)-2-cyanobut-2-enoate 5

To a solution of 1-(6-(tert-butyl)-5-fluoropyridin-3-yl)ethan-1-one (4, 3.3 g, 16.91 mmol), ethyl cyanoacetate (3.96 mL, 37.20 mmol) in benzene (70 mL), acetic acid (1.03 mL, 18.26 mmol) and ammonium acetate (1.3 g, 6.72 mmol) were added. The reaction mixture was stirred at 120° C. using dean stark apparatus for 16 h. The reaction mixture was concentrated to remove benzene, quenched with water (50 mL) and extracted with ethyl acetate (2×100 mL). The combined organic layer was dried over anhydrous sodium sulfate, filtered and concentrated. The crude product was purified by silica gel column chromatography using 30% ethyl acetate in hexane to afford the title compound ethyl (E)-3-(6-(tert-butyl)-5-fluoropyridin-3-yl)-2-cyanobut-2-enoate (5, 3.5 g, 71% yield) as an off white solid. Calculated (M+H): 291.14; Found (M+H): 291.2

Step-5:

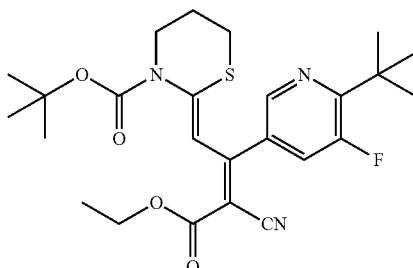

Preparation of tert-butyl (Z)-2-((E)-2-(6-(tert-butyl)-5-fluoropyridin-3-yl)-3-cyano-4-ethoxy-4-oxobut-2-en-1-ylidene)-1,3-thiazinane-3-carboxylate 6

To a solution of ethyl (E)-3-(6-(tert-butyl)-5-fluoropyridin-3-yl)-2-cyanobut-2-enoate (5, 0.25 g, 0.86 mmol) in dichloromethane (30 mL), 3-(tert-butoxycarbonyl)-2-(methylthio)-5,6-dihydro-4H-1,3-thiazin-3-ium iodide (0.45 g, 1.72 mmol), triethylamine (1.98 mL, 8.6 mmol) and lead nitrate (0.85 g, 2.58 mmol) were added. The reaction mixture was stirred at 55° C. for 16 h. The reaction mixture was quenched with water (50 mL) and extracted with dichloromethane (2×50 mL). The combined organic layer was dried over anhydrous sodium sulfate, filtered and concentrated. The crude product was purified by silica gel column chromatography using 30% ethyl acetate in hexane to afford the title compound tert-butyl fluoropyridin-3-yl)-3-cyano-4-ethoxy-4-oxobut-2-en-1-ylidene)-1,3-thiazinane-3-carboxylate (6, 0.33 g, 78% yield) as a colourless liquid. Calculated (M+H): 490.21; Found (M+H): 490.2.

Step-6:

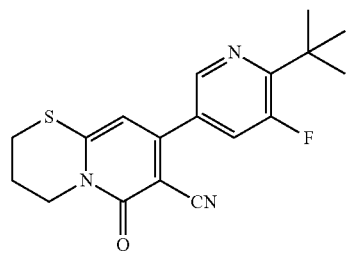

Preparation of 8-(6-(tert-butyl)-5-fluoropyridin-3-yl)-6-oxo-3,4-dihydro-2H,6H-pyrido[2,1-b][1,3]thiazine-7-carbonitrile 7

To a solution of tert-butyl (Z)-2-((E)-2-(6-(tert-butyl)-5-fluoropyridin-3-yl)-3-cyano-4-ethoxy-4-oxobut-2-en-1-ylidene)-1,3-thiazinane-3-carboxylate (6, 0.33 g, 0.67 mmol) in dichloromethane (20 mL), trifluoroacetic acid (10 mL) was added drop wise at 0° C. The reaction mixture was stirred at room temperature for 16 h. The reaction mixture was concentrated, the residue was diluted with saturated sodium bicarbonate solution and extracted with dichloromethane (2×30 mL). The combined organic layer was dried over anhydrous sodium sulfate, filtered and concentrated. The crude product was purified by silica gel chromatography using 60% ethyl acetate in hexane to afford the title compound 8-(6-(tert-butyl)-5-fluoropyridin-3-yl)-6-oxo-3,4-dihydro-2H,6H-pyrido[2,1-b][1,3]thiazine-7-carbonitrile (7 (example 102), 0.07 g, 30% yield) as a yellow solid. $^1$H NMR (400 MHz, DMSO-$d_6$) δ (ppm): 8.57 (s, 1H), 7.91 (d, J=12.0 Hz, 1H), 6.61 (s, 1H), 4.04 (t, J=5.2 Hz, 2H), 3.22 (t, J=6.0 Hz, 2H), 2.20 (s, 2H), 1.38 (s, 9H). Calculated (M+H): 344.12; Found (M+H): 344.0. HPLC purity: 99.66%

TABLE 23

The following compound was prepared by the method described above:

| Ex. # | Structure | IUPAC Name | Analytical Data |
|---|---|---|---|
| 103 | 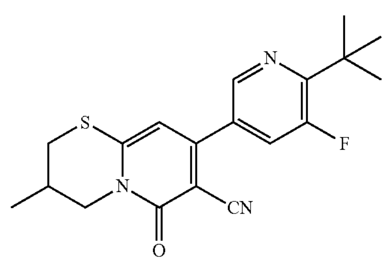 [SMILES: CC1CSc2cc(-c3cnc(C(C)(C)C)c(F)c3)c(C#N)c(=O)n2C1] | 8-(6-(tert-butyl)-5-fluoropyridin-3-yl)-3-methyl-6-oxo-3,4-dihydro-2H,6H-pyrido[2,1-b][1,3]thiazine-7-carbonitrile | $^1$H NMR (400 MHz, DMSO-$d_6$) δ (ppm): 8.57 (s, 1H), 7.92 (dd, $J_1$ = 1.2 Hz, $J_2$ = 13.2 Hz, 1H), 6.63 (s, 1H), 4.34 (d, J = 14.0 Hz, 1H), 3.47-3.41 (m, 1H), 3.24-3.20 (dd, $J_1$ = 3.6 Hz, $J_2$ = 12.4 Hz, 1H), 2.96 (t, J = 9.6 Hz, 1H), 2.30-2.27 (bs, 1H), 1.38 (s, 9H), 1.11 (d, J = 6.4 Hz, 3H). Calculated (M + H): 358.13; Found (M + H): 358.2, HPLC purity: 99.96% |

Examples 104 and 105

Preparation of (R)-8-(2-(tert-butyl)pyrimidin-5-yl)-3-methyl-6-oxo-3,4-dihydro-2H,6H-pyrido[2,1-b][1,3]thiazine-7-carbonitrile 2 and (S)-8-(2-(tert-butyl)pyrimidin-5-yl)-3-methyl-6-oxo-3,4-dihydro-2H,6H-pyrido[2,1-b][1,3]thiazine-7-carbonitrile 3

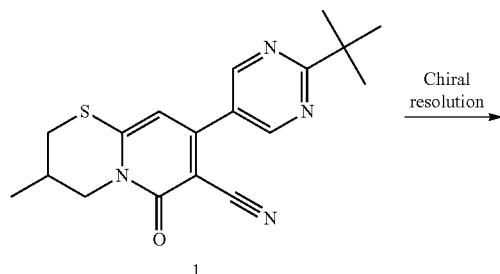

1

Chiral resolution →

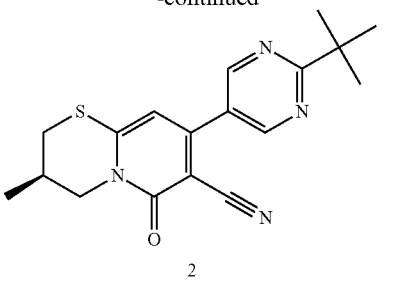

2

+

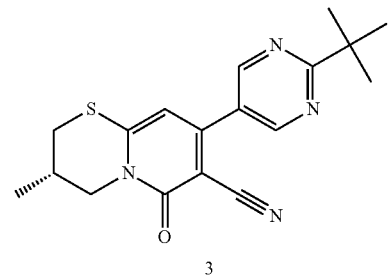

3

The chiral resolution was performed using the analytical condition: column: CHIRALPAK IA (250 mm×4.6 mm×5 mic), mobile phase A: methyl tert-butyl ether, mobile phase B: 0.1% diethyl amine in isopropyl alcohol (70:30), flow rate: 1.0 mL/min. The analytical data for the enantiomers are given below.

TABLE 24

The following compounds were separated by the method described above

| Ex. # | Structure | IUPAC Name | Analytical Data |
|---|---|---|---|
| 104 | 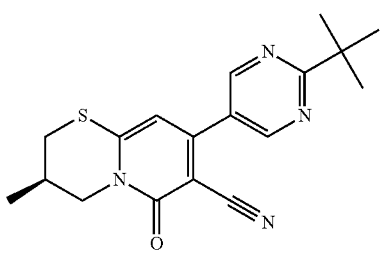 [SMILES: C[C@H]1CSc2cc(-c3cnc(C(C)(C)C)nc3)c(C#N)c(=O)n2C1] | (R)-8-(2-(tert-butyl)pyrimidin-5-yl)-3-methyl-6-oxo-3,4-dihydro-2H,6H-pyrido[2,1-b][1,3]thiazine-7-carbonitrile | $^1$H-NMR (DMSO-$d_6$, 400 MHz) δ (ppm): 8.98 (s, 2H), 6.69 (s, 1H), 4.34 (d, J = 14.0 Hz, 1H), 3.48-3.42 (m, 1H), 3.25-3.21 (m, 1H), 3.0-2.94 (m, 1H), 2.3-2.28 (m, 1H), 1.38 (s, 9H), 1.11 (d, J = 6.4 Hz, 3H). Calculated (M + H): 341.14, Found (M + H): 341.2, Chiral HPLC purity: 99.81% |
| 105 | 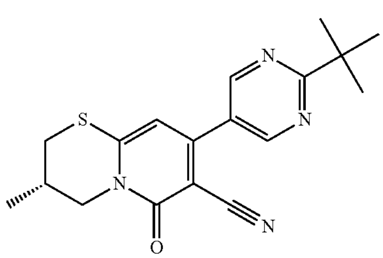 | (S)-8-(2-(tert-butyl)pyrimidin-5-yl)-3-methyl-6-oxo-3,4-dihydro-2H,6H-pyrido[2,1-b][1,3]thiazine-7-carbonitrile | $^1$H-NMR (DMSO-$d_6$, 400 MHz) δ (ppm): 8.98 (s, 2H), 6.69 (s, 1H), 4.34 (d, J = 16.0 Hz, 1H), 3.48-3.42 (m, 1H), 3.25-3.21 (m, 1H), 2.99-2.94 (m, 1H), 2.3-2.28 (m, 1H), 1.38 (s, 9H), 1.11 (d, J = 6.4 Hz, 3H). Calculated (M + H): 341.14, Found (M + H): 341.2, Chiral HPLC purity: 99.49% |

Examples 106 and 107

Preparation of (R)-8-(6-(tert-butyl)-5-fluoropyridin-3-yl)-3-methyl-6-oxo-3,4-dihydro-2H,6H-pyrido[2,1-b][1,3]thiazine-7-carbonitrile 2 and (S)-8-(6-(tert-butyl)-5-fluoropyridin-3-yl)-3-methyl-6-oxo-3,4-dihydro-2H,6H-pyrido[2,1-b][1,3]thiazine-7-carbonitrile 3

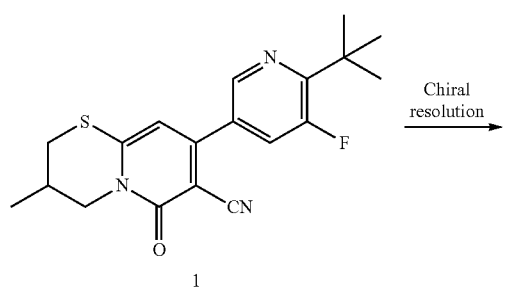

1

Chiral resolution →

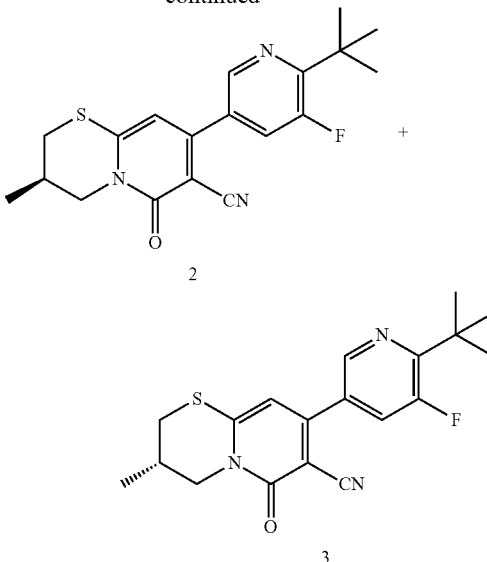

The chiral resolution was performed using the analytical condition: column: CHIRALPAK IA (250 mm×4.6 mm×5 mic), mobile phase A: methyl tertiary butyl ether, mobile phase B: 0.1% diethyl amine in isopropyl alcohol, composition: 70:30, flow rate: 1.0 mL/min. The analytical data for the enantiomers are given below.

TABLE 25

The following compounds were separated by the method described above

| Ex. # | Structure | IUPAC Name | Analytical Data |
|---|---|---|---|
| 106 | 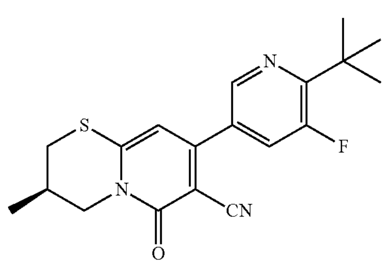 [SMILES: C[C@H]1CSc2cc(-c3cnc(C(C)(C)C)c(F)c3)c(C#N)c(=O)n2C1] | (R)-8-(6-(tert-butyl)-5-fluoropyridin-3-yl)-3-methyl-6-oxo-3,4-dihydro-2H,6H-pyrido[2,1-b][1,3]thiazine-7-carbonitrile | $^1$H NMR (400 MHz, DMSO-$d_6$) δ (ppm): 8.57 (s, 1H), 7.92 (dd, $J_1$ = 1.6 Hz, $J_2$ = 12.8 Hz, 1H), 6.63 (s, 1H), 4.34 (d, J = 14.4 Hz, 1H), 3.47-3.41 (m, 1H), 3.24-3.20 (m, 1H), 2.99-2.94 (m, 1H), 2.30-2.27 (m, 1H), 1.38 (s, 9H), 1.11 (d, J = 6.4 Hz, 3H). Calculated (M + H): 358.13; Found (M + H): 358.1, Chiral HPLC purity: 99.78% |
| 107 | 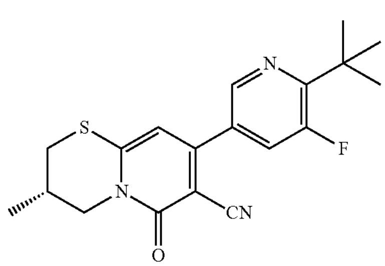 [SMILES: C[C@@H]1CSc2cc(-c3cnc(C(C)(C)C)c(F)c3)c(C#N)c(=O)n2C1] | (S)-8-(6-(tert-butyl)-5-fluoropyridin-3-yl)-3-methyl-6-oxo-3,4-dihydro-2H,6H-pyrido[2,1-b][1,3]thiazine-7-carbonitrile | $^1$H-NMR (DMSO-$d_6$, 400 MHz) δ (ppm): 8.57 (s, 1H), 7.93 (dd, $J_1$ = 2.0 Hz, $J_2$ = 13.6 Hz, 1H), 6.63 (s, 1H), 4.34 (d, J = 14.0 Hz, 1H), 3.47-3.41 (m, 1H), 3.24-3.20 (m, 1H), 2.99-2.93 (m, 1H), 2.30-2.26 (m, 1H), 1.38 (s, 9H), 1.11 (d, J = 6.8 Hz, 3H). Calculated (M + H): 358.13, Found (M + H): 358.1, Chiral HPLC purity: 99.18% |

Example 108

Preparation of 3-methyl-8-(6-(1-methylcyclopropyl)pyridin-3-yl)-6-oxo-3,4-dihydro-2H,6H-pyrimido[2,1-b][1,3]thiazine-7-carbonitrile 5

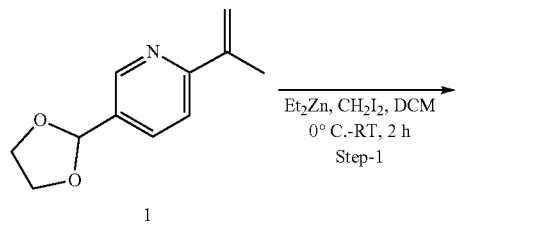

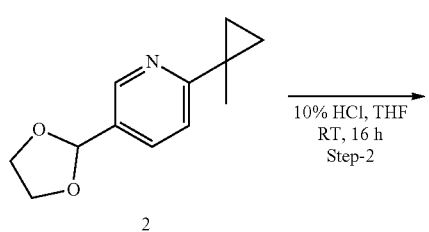

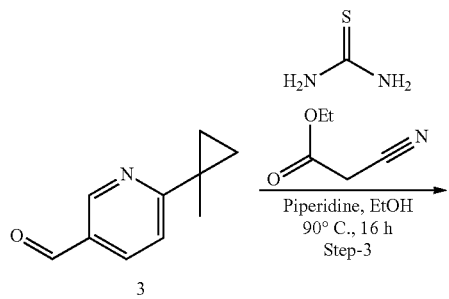

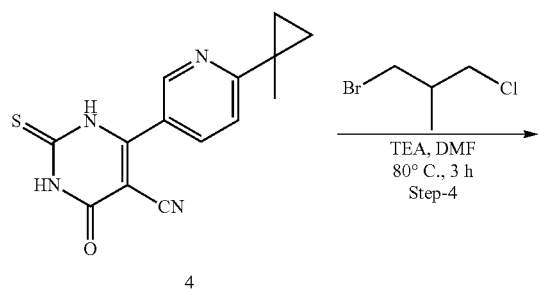

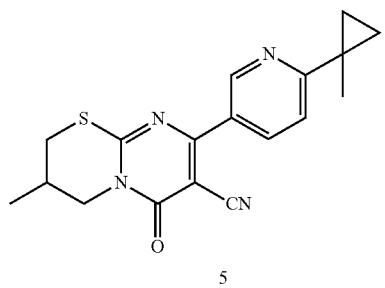

Step-1:

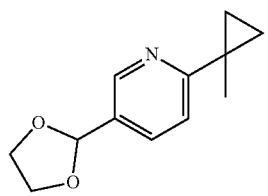

Preparation of 2-(2,2-difluoro-1-methylcyclopropyl)-5-(1,3-dioxolan-2-yl)pyridine 2

Diethyl zinc (32 mL, 31.37 mmol, 1M in hexane) was added to dichloromethane (100 mL) at 0° C., followed by diiodomethane (2.52 mL, 31.3 mmol) drop wise and the reaction mixture was stirred at the same temperature for 30 min. Then a solution of 5-(1,3-dioxolan-2-yl)-2-(prop-1-en-2-yl)pyridine (1, 1.5 g, 7.84 mmol) in dichloromethane (30 mL) was added drop wise at 0° C. and the reaction mixture was allowed to stir at room temperature for 1.5 h. The reaction mixture slowly quenched with saturated ammonium chloride (50 mL) and extracted with dichloromethane (2×50 mL). The combined organic layer was washed with brine (100 mL), dried over anhydrous sodium sulphate, filtered and concentrated to afford the title compound 2-(2,2-difluoro-1-methylcyclopropyl)-5-(1,3-dioxolan-2-yl)pyridine (2, 1.52 g, 94% yield) as a brownish oil. Calculated (M+H): 206.1; Found (M+H): 206.1.

Step-2:

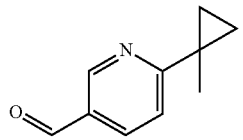

Preparation of 6-(1-methylcyclopropyl)nicotinaldehyde 3

To a stirred solution of 2-(2,2-difluoro-1-methylcyclopropyl)-5-(1,3-dioxolan-2-yl)pyridine (2, 1.6 g) in tetrahydrofuran (20 mL), 10% aqueous hydrochloric acid (20 mL) was added drop wise and the reaction mixture was stirred at room temperature for 16 h. The reaction mixture was basified with saturated sodium bicarbonate solution and extracted with ethyl acetate (2×50 mL). The combined organic layer was dried over anhydrous sodium sulphate, filtered and concentrated to afford the title compound 6-(1-methylcyclopropyl)nicotinaldehyde (3, 1.1 g, 87% yield) as a brown solid. Calculated (M+H): 162.08; Found (M+H): 162.1.

Step-3:

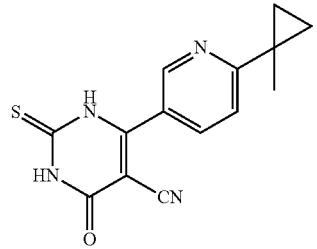 [SMILES: CC1(c2ccc(-c3[nH]c(=S)[nH]c(=O)c3C#N)cn2)CC1]

Preparation of 6-(6-(1-methylcyclopropyl)pyridin-3-yl)-4-oxo-2-thioxo-1,2,3,4-tetrahydropyrimidine-5-carbonitrile 4

To a solution of 6-(1-methylcyclopropyl)nicotinaldehyde (3, 1.0 g, 6.21 mmol) in ethanol (30 mL), ethyl 2-cyanoacetate (0.73 mL, 6.83 mmol), thiourea (0.52 g, 6.83 mmol), piperidine (2.5 mL, 24.82 mmol) were added and the reaction mixture was stirred at 90° C. for 16 h. The reaction mixture was concentrated to afford the title compound 6-(6-(1-methylcyclopropyl)pyridin-3-yl)-4-oxo-2-thioxo-1,2,3,4-tetrahydropyrimidine-5-carbonitrile (4, 1.5 g, crude) as a brown gum. Calculated (M+H): 285.07; Found (M+H): 285.1.

Step-4:

Preparation of 3-methyl-8-(6-(1-methylcyclopropyl)pyridin-3-yl)-6-oxo-3,4-dihydro-2H,6H-pyrimido[2,1-b][1,3]thiazine-7-carbonitrile 5

To a solution of 6-(6-(1-methylcyclopropyl)pyridin-3-yl)-4-oxo-2-thioxo-1,2,3,4-tetrahydropyrimidine-5-carbonitrile (4, 1.0 g, 3.52 mmol), 1-bromo-3-chloro-2-methylpropane (0.67 mL, 5.28 mmol) in N,N-dimethylformamide (15 mL), triethylamine (1.9 mL, 14.06 mmol) was added and the reaction mixture was heated at 80° C. in a sealed tube for 3 h. The reaction mixture was diluted with water (50 mL) and extracted with ethyl acetate (2×50 mL). The combined organic layer was washed with water (2×50 mL), brine (50 mL), dried over anhydrous sodium sulphate, filtered and concentrated. The crude product was purified by silica gel column chromatography using 25% ethyl acetate in hexane, followed by triturating with methanol and n-pentane to afford the title compound 3-methyl-8-(6-(1-methylcyclopropyl)pyridin-3-yl)-6-oxo-3,4-dihydro-2H,6H-pyrimido[2,1-b][1,3]thiazine-7-carbonitrile (5 (example 108), 0.08 g, 6.7% yield) as a white solid. $^1$H NMR (400 MHz, DMSO-d6) δ (ppm): 8.87 (s, 1H), 8.13 (d, J=8.4 Hz, 1H), 7.52 (d, J=8.4 Hz, 1H), 4.26 (d, J=14.0 Hz, 1H), 3.49-343 (m, 1H), 3.22 (bs, 1H), 3.06 (t, J=10.0 Hz, 1H), 2.30 (bs, 1H), 1.50 (s, 3H), 1.24 (s, 2H), 1.12 (d, J=6.8 Hz, 3H), 0.89 (d, J=2.4 Hz, 2H). Calculated (M+H): 339.1; Found (M+H): 339. HPLC purity: 99.80%

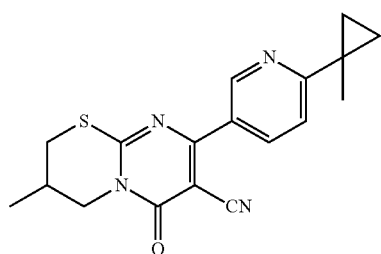 [SMILES: CC1CSc2nc(-c3ccc(C4(C)CC4)nc3)c(C#N)c(=O)n2C1]

TABLE 26

The following compound was prepared by the method described above:

| Ex. # | Structure | IUPAC Name | Analytical Data |
|---|---|---|---|
| 109 | 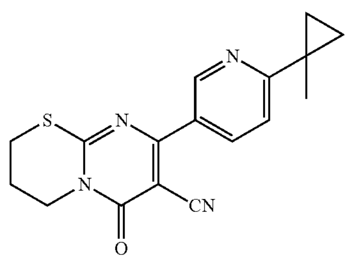 [SMILES: CC1(c2ccc(-c3nc4n(c(=O)c3C#N)CCCS4)cn2)CC1] | 8-(6-(1-methylcyclopropyl)pyridin-3-yl)-6-oxo-3,4-dihydro-2H,6H-pyrimido[2,1-b][1,3]thiazine-7-carbonitrile | $^1$H NMR (400 MHz, DMSO-d$_6$) δ (ppm): 8.87 (s, 1H), 8.12 (d, J = 8.4 Hz, 1H), 7.52 (d, J = 8.4 Hz, 1H), 4.00 (bs, 2H), 2.21 (bs, 2H), 1.50 (bs, 3H), 1.24 (s, 2H), 0.89 (d, J = 2.0 Hz, 2H). 2H were merged with DMSO water peak. Calculated (M + H): 325.10; Found (M + H): 325.1, HPLC purity: 99.83% |

Example 110

Preparation of 8-(6-(2,2-difluoro-1-methylcyclopropyl)pyridin-3-yl)-6-oxo-3,4-dihydro-2H,6H-pyrimido[2,1-b][1,3]thiazine-7-carbonitrile 7

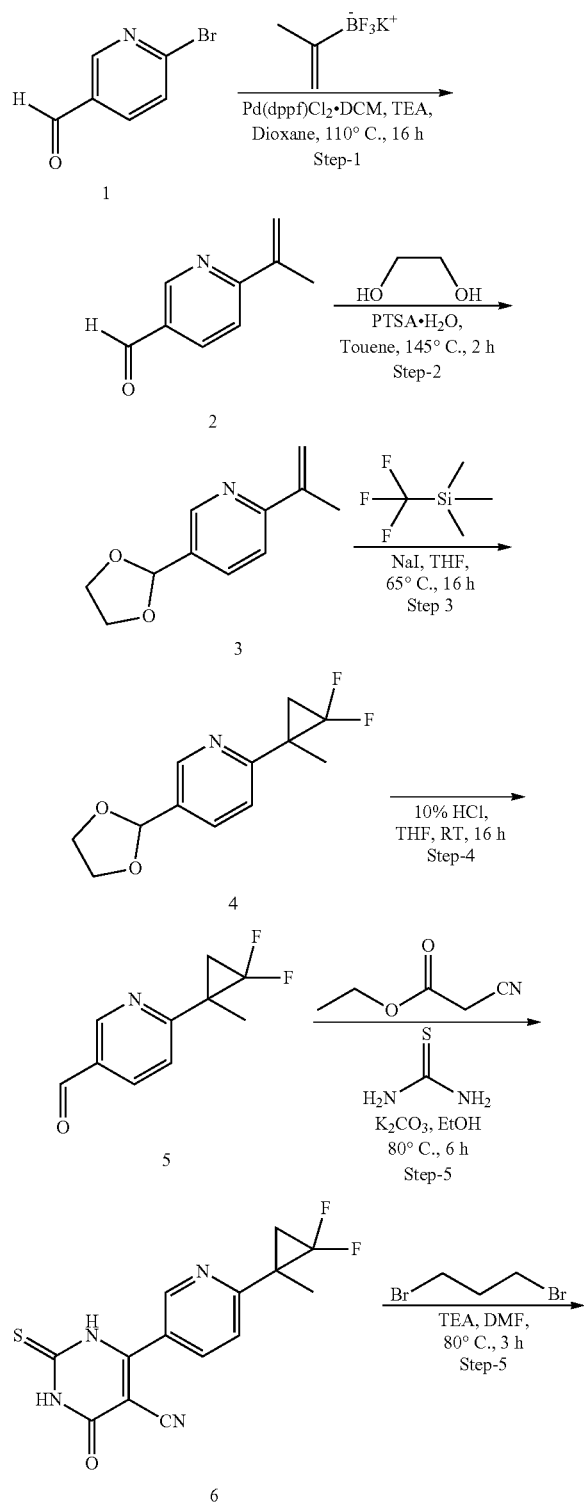

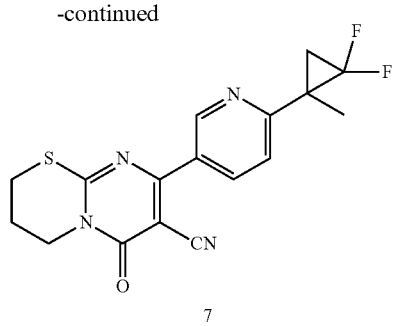

7

Step-1:

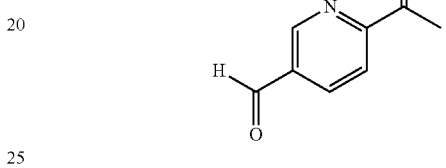

Preparation of 6-(prop-1-en-2-yl)nicotinaldehyde 2

To a solution of 6-bromonicotinaldehyde (1, 6 g, 32.25 mmol), potassium isopropenyl trifluoroborate (9.54 g, 64.51 mmol) and triethylamine (22.49 mL, 161.12 mmol) in dioxane (120 mL), argon was purged for 20 min. Then [1,1'-bis(diphenylphosphino)ferrocene]dichloropalladium (II), complex with dichloromethane (1.31 g, 1.61 mmol) was added and the reaction mixture heated at 110° C. for 16 h. The reaction mixture was filtered through celite bed and the filtrate was concentrated. The crude was purified by silica gel column chromatography using 10% ethyl acetate in hexane to afford the title compound 6-(prop-1-en-2-yl)nicotinaldehyde (2, 3.3 g, 70% yield) as a brownish gum. Calculated (M+H): 148.07; Found (M+H): 148

Step-2:

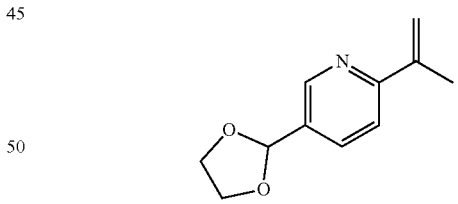

Preparation of 5-(1,3-dioxolan-2-yl)-2-(prop-1-en-2-yl)pyridine 3

To a stirred solution of 6-(prop-1-en-2-yl)nicotinaldehyde (2, 3.3 g, 22.42 mmol) in toluene (60 mL), ethane-1,2-diol (25 mL, 448.43 mmol) and p-toluene sulphonic acid monohydrate (0.213 g, 1.21 mmol) were added and the reaction mixture was refluxed at 145° C. for 2 h using a Dean stark apparatus. The reaction mixture was diluted with 10% aqueous potassium carbonate solution (50 mL) and extracted with ethyl acetate (2×100 mL). The combined organic layer was dried over anhydrous sodium sulphate, filtered and concentrated to afford the title compound 5-(1,3-dioxolan- 2-yl)-2-(prop-1-en-2-yl)pyridine (3, 4.7 g, crude) as a brownish gum. Calculated (M+H): 192.09; Found (M+H): 192.1.

Step-3:

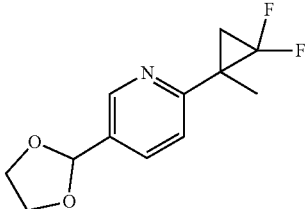 [SMILES: CC1(c2ccc(C3OCCO3)cn2)CC1(F)F]

Preparation of 2-(2,2-difluoro-1-methylcyclopropyl)-5-(1,3-dioxolan-2-yl)pyridine 4

To a stirred solution of 5-(1,3-dioxolan-2-yl)-2-(prop-1-en-2-yl)pyridine (3, 2.5 g, 13.08 mmol) in tetrahydrofuran (30 mL), sodium iodide (0.64 g, 4.31 mmol) was added followed by trimethyl(trifluoromethyl)silane (6.77 mL, 45.81 mmol). The reaction mixture was heated at 65° C. for 16 h in a sealed tube. The reaction mixture was diluted with water (50 mL) and extracted with ethyl acetate (2×100 mL). The combined organic layer was dried over anhydrous sodium sulphate, filtered and concentrated. The crude was purified by silica gel column chromatography using 25% ethyl acetate in hexane to afford the title compound 2-(2,2-difluoro-1-methylcyclopropyl)-5-(1,3-dioxolan-2-yl)pyridine (4, 1.91 g, 60% yield) as a brownish gum. Calculated (M+H): 242.09; Found (M+H): 242.1.

Step-4:

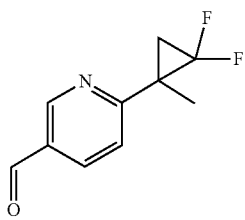

Preparation of 6-(2,2-difluoro-1-methylcyclopropyl)nicotinaldehyde 5

To a stirred solution of 2-(2,2-difluoro-1-methylcyclopropyl)-5-(1,3-dioxolan-2-yl)pyridine (4, 1.95 g) in tetrahydrofuran (20 mL), 10% aqueous hydrochloric acid (20 mL) was added drop wise and the reaction mixture was stirred at room temperature for 16 h. The reaction mixture was basified with saturated sodium bicarbonate solution and extracted with ethyl acetate (2×50 mL). The combined organic layer was dried over anhydrous sodium sulphate, filtered and concentrated to afford the title compound 6-(2,2-difluoro-1-methylcyclopropyl)nicotinaldehyde (5, 1.5 g, 94% yield) as a brown gum. Calculated (M+H): 198.07; Found (M+H): 198

Step-5:

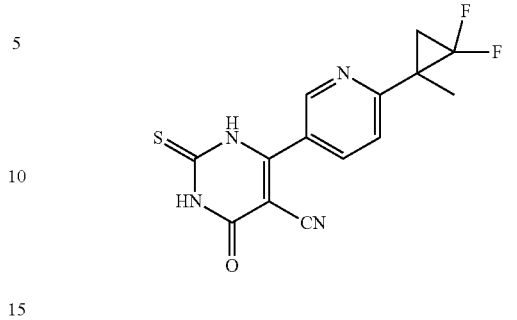

Preparation of 6-(6-(2,2-difluoro-1-methylcyclopropyl)pyridin-3-yl)-4-oxo-2-thioxo-1,2,3,4-tetrahydropyrimidine-5-carbonitrile 6

To a solution of 6-(2,2-difluoro-1-methylcyclopropyl)nicotinaldehyde (5, 1.4 g, 7.10 mmol), ethyl cyano acetate (0.76 mL, 7.10 mmol) and thiourea (0.54 g, 7.10 mmol) in ethanol (25 mL), potassium carbonate (2.94 g, 21.30 mmol) was added and the reaction mixture was refluxed at 80° C. for 6 h. The reaction mixture was concentrated, the residue was diluted with ice water (15 mL) and neutralized with acetic acid. The precipitated solid was filtered and dried under suction to afford the title compound 6-(6-(2,2-difluoro-1-methylcyclopropyl)pyridin-3-yl)-4-oxo-2-thioxo-1,2,3,4-tetrahydropyrimidine-5-carbonitrile (6, 1.1 g, 48% yield) as a brownish solid. Calculated (M+H): 321.05; Found (M+H): 321.1.

Step-6:

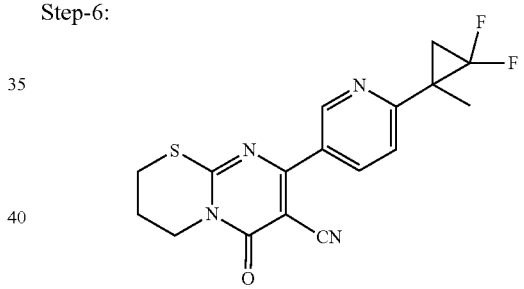

Preparation of 8-(6-(2,2-difluoro-1-methylcyclopropyl)pyridin-3-yl)-6-oxo-3,4-dihydro-2H,6H-pyrimido[2,1-b][1,3]thiazine-7-carbonitrile 7

To a solution of 6-(6-(2,2-difluoro-1-methylcyclopropyl)pyridin-3-yl)-4-oxo-2-thioxo-1,2,3,4-tetrahydropyrimidine-5-carbonitrile (6, 0.2 g, 0.62 mmol) and 1,3-dibromopropane (0.12 g, 0.62 mmol) in N,N-dimethyl formamide (10 mL), triethylamine (0.34 mL, 2.5 mmol) was added and the reaction mixture was heated at 80° C. in a sealed tube for 3 h. The reaction mixture was diluted with water (20 mL) and extracted with ethyl acetate (2×40 mL). The combined organic layer was dried over anhydrous sodium sulphate, filtered and concentrated. The crude was purified by silica gel column chromatography using 55% ethyl acetate in hexane to afford the title compound 8-(6-(2,2-difluoro-1-methylcyclopropyl)pyridin-3-yl)-6-oxo-3,4-dihydro-2H,6H-pyrimido[2,1-b][1,3]thiazine-7-carbonitrile (7 (example 110), 0.062 g, 27.5% yield) as an off-white solid. Calculated (M+H): 361.09; Found (M+H): 361.1, $^1$H NMR (400 MHz, DMSO-$d_6$) δ (ppm): 8.96 (d, J=1.6 Hz, 1H), 8.22 (dd, $J_1$=2.4 Hz, $J_2$=8.4 Hz, 1H), 7.71 (d, J=8.4 Hz, 1H), 4.02 (t, J=5.2 Hz, 2H), 3.29-3.27 (m, 2H), 2.45-2.43 (m, 1H), 2.22 (bs, 2H), 1.75-1.69 (m, 1H), 1.61 (s, 3H). HPLC purity: 99.94%

TABLE 27

The following compound was prepared by the method described above:

| Ex. # | Structure | IUPAC Name | Analytical Data |
|---|---|---|---|
| 111 | 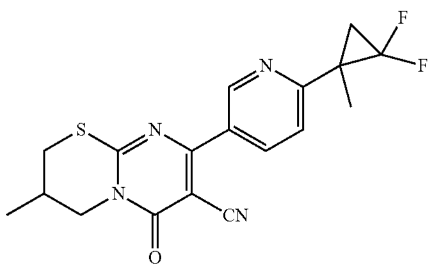 [SMILES: CC1CSc2nc(-c3ccc(C4(C)CC4(F)F)nc3)c(C#N)c(=O)n2C1] | 8-(6-(2,2-difluoro-1-methylcyclopropyl)pyridin-3-yl)-3-methyl-6-oxo-3,4-dihydro-2H,6H-pyrimido[2,1-b][1,3]thiazine-7-carbonitrile | $^1$H NMR (400 MHz, CDCl3) δ (ppm): 9.15 (d, 1.6, 1H), 8.32 (dd, $J_1$ = 2.8 Hz, $J_2$ = 8.4 Hz, 1H), 7.46 (t, J = 8.4 Hz, 1H), 4.55 (d, J = 14.8 Hz, 1H), 3.49-3.43 (m, 1H), 3.18-3.15 (m, 1H), 3.04-2.98 (m, 1H), 2.43-2.31 (m, 2H), 1.62 (s, 3H), 1.50-1.44 (m, 1H), 1.29 (d, J = 6.8 Hz, 3H). Calculated (M + H): 375.10; Found (M + H): 375.2, HPLC purity: 99.59% |

Examples 112 and 113

Preparation of (R)-8-(6-(tert-butyl)-5-fluoropyridin-3-yl)-6-imino-3-methyl-3,4-dihydro-2H,6H-pyrimido[2,1-b][1,3]thiazine-7-carbonitrile 2 and (S)-8-(6-(tert-butyl)-5-fluoropyridin-3-yl)-6-imino-3-methyl-3,4-dihydro-2H,6H-pyrimido[2,1-b][1,3]thiazine-7-carbonitrile 3

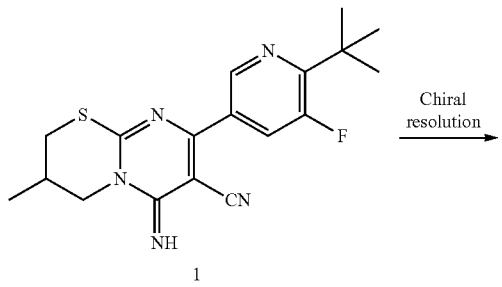

1

Chiral resolution →

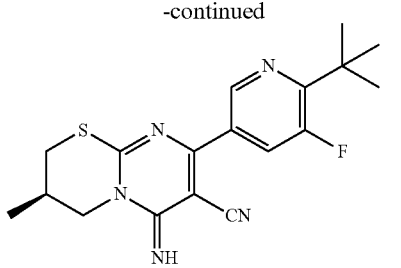

2

-continued

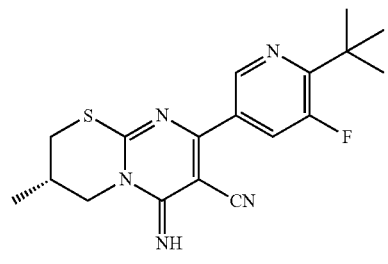 [SMILES: C[C@@H]1CSc2nc(-c3cnc(C(C)(C)C)c(F)c3)c(C#N)c(=N)n2C1]

3

The chiral resolution was performed using the analytical condition: column: CHIRALPAK IA (250 mm×4.6 mm×5 mic), mobile phase A: hexane, mobile phase B: 0.1% diethyl amine in ethanol, composition: 50:50, flow rate: 1.0 mL/min. The analytical data for the enantiomers are given below.

TABLE 28

The following compounds were separated by the method described above

| Ex. # | Structure | IUPAC Name | Analytical Data |
|---|---|---|---|
| 112 | 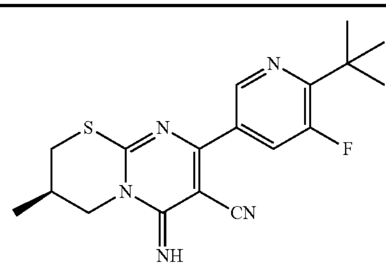 | (R)-8-(6-(tert-butyl)-5-fluoropyridin-3-yl)-6-imino-3-methyl-3,4-dihydro-2H,6H-pyrimido[2,1-b][1,3]thiazine-7-carbonitrile | $^1$H-NMR (DMSO-$d_6$, 400 MHz) δ (ppm): 8.75 (s, 1H), 7.93 (d, J = 12.8 Hz, 1H), 7.46 (bs, 1H), 4.31 (bs, 1H), 3.44 (t, J = 10.4 Hz, 1H), 3.19 (d, J = 12.0 Hz, 1H), 3.05 (t, J = 10.0 Hz, 1H), 2.36-2.31 (m, 1H), 1.37 (s, 9H), 1.13 (d, J = 6.4 Hz, 3H). Calculated (M + H): 358.14, Found (M + H): 358.3, Chiral HPLC purity: 99.94% |

TABLE 28-continued

The following compounds were separated by the method described above

| Ex. # | Structure | IUPAC Name | Analytical Data |
|---|---|---|---|
| 113 | 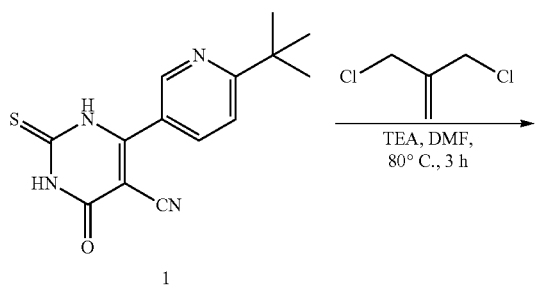 | (S)-8-(6-(tert-butyl)-5-fluoropyridin-3-yl)-6-imino-3-methyl-3,4-dihydro-2H,6H-pyrimido[2,1-b][1,3]thiazine-7-carbonitrile | $^1$H-NMR (DMSO-$d_6$, 400 MHz) δ (ppm): 8.75 (s, 1H), 7.93 (d, J = 16.4 Hz, 1H), 7.49 (bs, 1H), 4.31 (bs, 1H), 3.44 (t, J = 10.4 Hz, 1H), 3.19 (d, J = 12.0 Hz, 1H), 3.05 (t, J = 10.0 Hz, 1H), 2.35-2.31 (m, 1H), 1.37 (s, 9H), 1.13 (d, J = 6.4 Hz, 3H). Calculated (M + H): 358.14, Found (M + H): 358.3, Chiral HPLC purity: 99.39% |

Example 114

Preparation of 8-(6-(tert-butyl)pyridin-3-yl)-3-methylene-6-oxo-3,4-dihydro-2H,6H-pyrimido[2,1-b][1,3]thiazine-7-carbonitrile 2

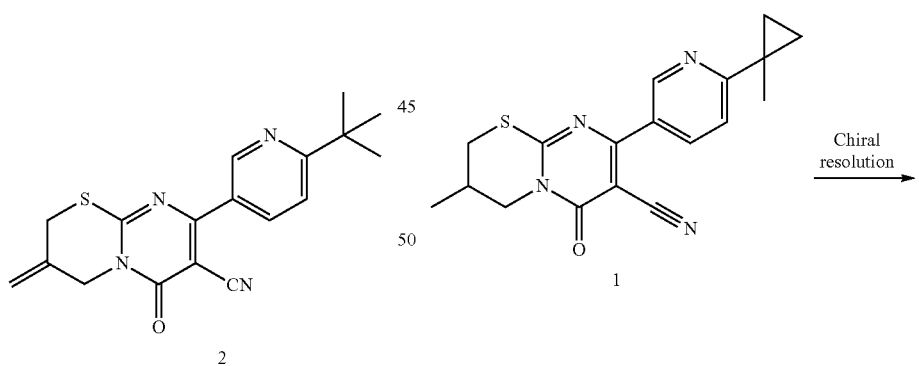

To a solution of 6-(6-(tert-butyl)pyridin-3-yl)-4-oxo-2-thioxo-1,2,3,4-tetrahydropyrimidine-5-carbonitrile (1, 1 g, 3.49 mmol) and 3-chloro-2-(chloromethyl)prop-1-ene (0.43 g, 3.49 mmol) in N,N-dimethyl formamide (25 mL), triethylamine (1.94 mL, 13.96 mmol) was added and the reaction mixture was heated at 80° C. in a sealed tube for 3 h. The reaction mixture was diluted with water (30 mL) and extracted with ethyl acetate (2×60 mL). The combined organic layer was dried over anhydrous sodium sulphate, filtered and concentrated. The crude was purified by silica gel column chromatography using 55% ethyl acetate in hexane to afford the title compound 8-(6-(tert-butyl)pyridin-3-yl)-3-methylene-6-oxo-3,4-dihydro-2H,6H-pyrimido[2,1-b][1,3]thiazine-7-carbonitrile (2 (example 114), 0.61 g, 51% yield) as a brownish solid. $^1$H NMR (400 MHz, DMSO-de) δ (ppm): 8.94 (d, J=2.4 Hz, 1H), 8.15 (dd, $J_1$=2.4 Hz, $J_2$=8.4 Hz, 1H), 7.62 (d, J=8 Hz, 1H), 5.42 (s, 2H), 4.57 (s, 2H), 3.98 (s, 2H), 1.33 (s, 9H). Calculated (M+H): 339.12; Found (M+H): 339.1. HPLC purity: 99.28%

Examples 115 and 116

Preparation of (R)-3-methyl-8-(6-(1-methylcyclopropyl)pyridin-3-yl)-6-oxo-3,4-dihydro-2H,6H-pyrimido[2,1-b][1,3]thiazine-7-carbonitrile 2 and (S)-3-methyl-8-(6-(1-methylcyclopropyl)pyridin-3-yl)-6-oxo-3,4-dihydro-2H,6H-pyrimido[2,1-b][1,3]thiazine-7-carbonitrile 3

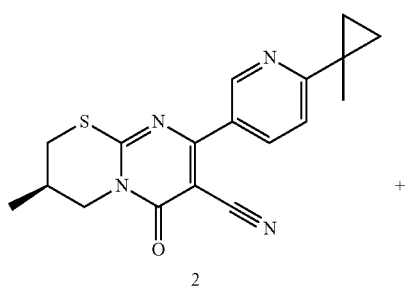

-continued

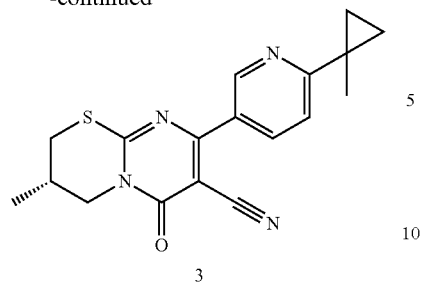
5

The chiral resolution was performed using the analytical condition: column: CHIRALPAK IC (250 mm×4.6 mm×5 mic), mobile phase: methyl tert butyl ether:ethanol with 0.1% diethyl amine (55:45), flow rate: 1.0 mL/min. The analytical data for the enantiomers are given below.

TABLE 29

The following compounds were separated by the method described above

| Ex. # | Structure | IUPAC Name | Analytical Data |
|---|---|---|---|
| 115 | 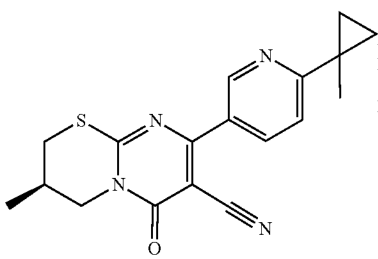 [SMILES: C[C@H]1CSc2nc(-c3ccc(C4(C)CC4)nc3)c(C#N)c(=O)n2C1] | (R)-3-methyl-8-(6-(1-methylcyclopropyl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.88 (s, 1H), 8.13 (dd, $J_1$ = 2.4 Hz, $J_2$ =8.4 Hz, 1H ), 7.52 (d, J = 8.4 Hz, 1H), 4.27 (d, J = 14.0 Hz, 1H), 3.50-344 (m, 1H), 3.23 (bs, 1H), 3.07 (t, J = 10.0 Hz, 1H), 2.31 (bs , 1H), 1.50 (s, 3H), 1.24 (d, J = 2.0 Hz, 2H), 1.13 (d, J = 6.4 Hz, 3H), 0.89 (dd, $J_1$ = 6.0 Hz, $J_2$ = 3.6 Hz, 2H). Calculated (M + H): 340.12; Found (M + H): 340.3, HPLC purity: 99.91% |
| 116 | 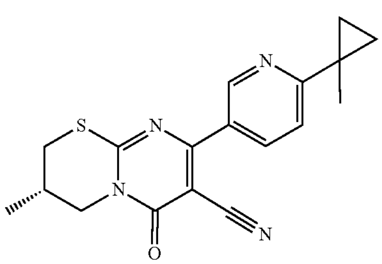 [SMILES: C[C@@H]1CSc2nc(-c3ccc(C4(C)CC4)nc3)c(C#N)c(=O)n2C1] | (S)-3-methyl-8-(6-(1-methylcyclopropyl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.88 (s, 1H), 8.13 (dd, $J_1$ = 2.4 Hz, $J_2$ = 8.4 Hz, 1H), 7.52 (d, J = 8.4 Hz, 1H), 4.27 (d, J = 13.2 Hz, 1H), 3.50-344 (m, 1H), 3.23 (bs, 1H), 3.07 (t, J = 10.0 Hz, 1H), 2.33 (bs , 1H), 1.50 (s, 3H), 1.24 (d, J = 2.0 Hz, 2H), 1.13 (d, J = 6.4 Hz, 3H), 0.89 (dd, $J_1$ = 6.0 Hz, $J_2$ = 3.6 Hz, 2H). Calculated (M + H): 340.12; Found (M + H): 340.3, HPLC purity: 99.24% |

Example 117 and 118

Preparation of (R)-3-methyl-8-(6-(1-methylcyclopropyl)pyridin-3-yl)-6-oxo-3,4-dihydro-2H,6H-pyrido[2,1-b][1,3]thiazine-7-carbonitrile 2 and (S)-3-methyl-8-(6-(1-methylcyclopropyl)pyridin-3-yl)-6-oxo-3,4-dihydro-2H,6H-pyrido[2,1-b][1,3]thiazine-7-carbonitrile 3

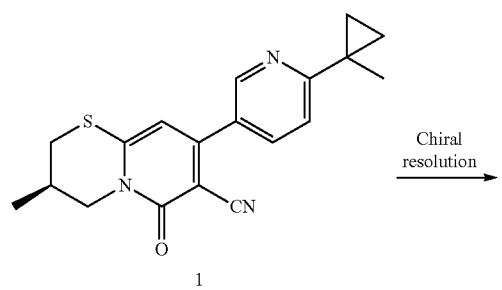

1

Chiral resolution ⟶

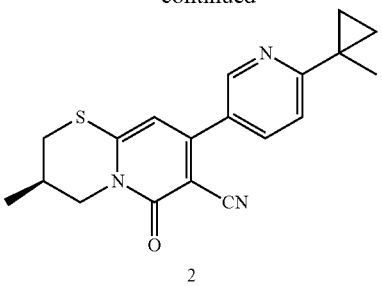

2

+

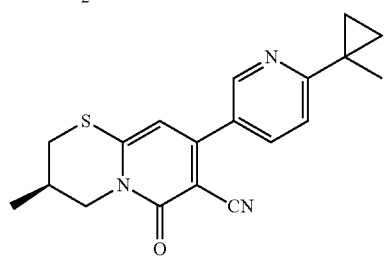

3

The chiral resolution was performed using the analytical condition: column: CHIRALPAK IC (250 mm×4.6 mm×5 mic), mobile phase (A:B): methyl tert butyl ether:ethanol with 0.1% diethyl amine: (55:45), flow rate: 1.0 ml/min. The analytical data for the enantiomers are given below.

TABLE 30

The following compounds were separated by the method described above

| Ex. # | Structure | IUPAC Name | Analytical Data |
|---|---|---|---|
| 117 | (structure) | (R)-3-methyl-8-(6-(1-methylcyclopropyl)pyridin-3-yl)-6-oxo-3,4-dihydro-2H,6H-pyrido[2,1-b][1,3]thiazine-7-carbonitrile | $^1$H NMR (400 MHz, DMSO-$d_6$) δ (ppm): 8.63 (d, J = 1.6 Hz, 1H), 7.92 (dd, $J_1$ = 2 Hz, $J_2$ = 8.4 Hz, 1H), 7.48 (d, J = 8.4 Hz, 1H), 6.55 (s, 1H) 4.34 (d, J = 14.4 Hz, 1H), 3.46-3.40 (m, 1H), 3.24-3.21 (m, 1H), 2.98-2.93 (m, 1H), 2.30-2.27 (m, 1H), 1.49 (s, 3H), 1.22-1.21 (m, 2H), 1.11-1.10 (m, 3H), 0.88-0.86 (m, 2H). Calculated (M + H): 338.12; Found (M + H): 338.0, chiral HPLC purity: 99.98% |
| 118 | (structure) | (S)-3-methyl-8-(6-(1-methylcyclopropyl)pyridin-3-yl)-6-oxo-3,4-dihydro-2H,6H-pyrido[2,1-b][1,3]thiazine-7-carbonitrile | $^1$H NMR (400 MHz, DMSO-$d_6$) δ (ppm): 8.63 (d, J = 1.6 Hz, 1H), 7.92 (dd, $J_1$ = 2 Hz, $J_2$ = 8.4 Hz, 1H), 7.48 (d, $J_2$ = 8.4 Hz, 1H), 6.55 (s, 1H) 4.34 (d, J = 14.4 Hz, 1H), 3.46-3.40 (m, 1H), 3.24-3.21 (m, 1H), 2.98-2.93 (m, 1H), 2.30-2.27 (m, 1H), 1.49 (s, 3H), 1.22-1.21 (m, 2H), 1.11-1.10 (m, 3H), 0.88-0.86 (m, 2H). Calculated (M + H): 338.12; Found (M + H): 338.0, chiral HPLC purity: 98.26% |

Example 119

Preparation of 8-(6-(2-methoxypropan-2-yl)pyridin-3-yl)-3-methyl-6-oxo-3,4-dihydro-2H,6H-pyrimido[2,1-b][1,3]thiazine-7-carbonitrile 6

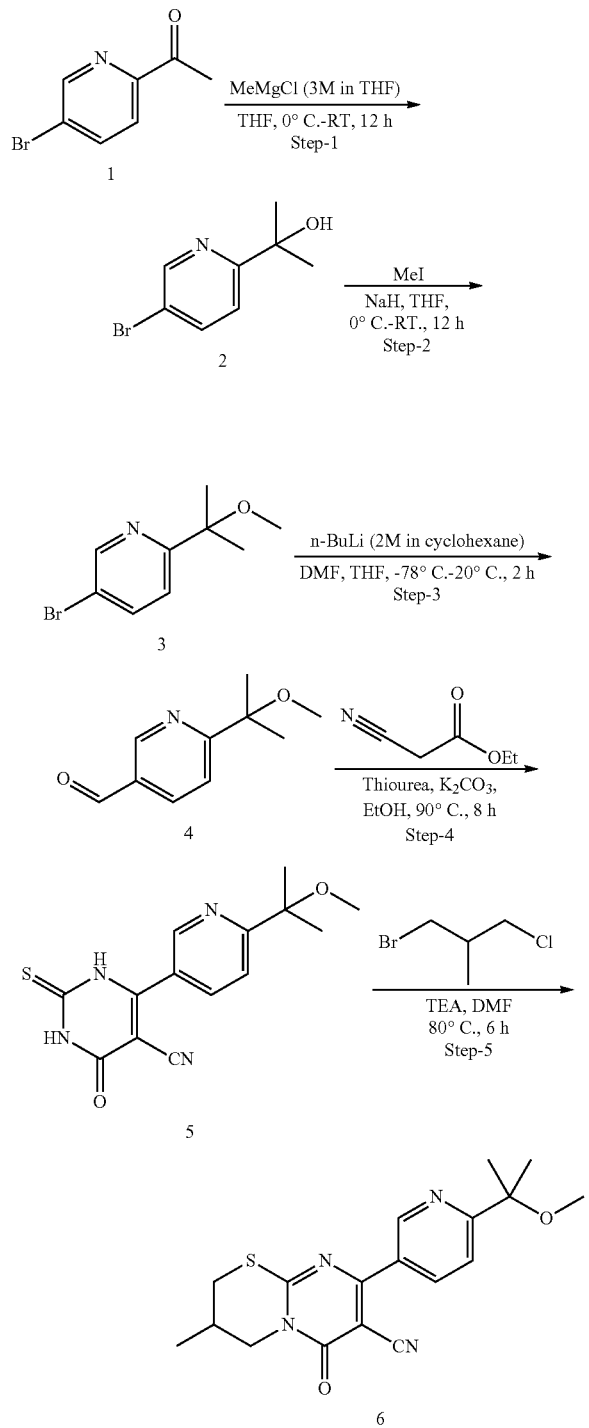

Step-1:

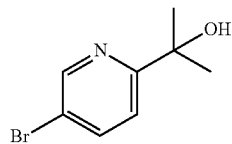

Preparation of 2-(5-bromopyridin-2-yl)propan-2-ol 2

To a stirred solution of 1-(5-bromopyridin-2-yl)ethan-1-one (1, 6.2 g, 30.99 mmol) in tetrahydrofuran (100 mL), was added methyl magnesium chloride solution (18.6 mL, 55.78 mmol, 3.0 M in tetrahydrofuran) at 0° C. and the reaction mixture was then stirred at room temperature for 12 h. The reaction mixture was quenched with saturated ammonium chloride solution (50 mL) and extracted with ethyl acetate (3×100 mL). The combined organic layer was dried over anhydrous sodium sulphate, filtered and concentrated. The crude product was purified by silica gel column chromatography using 10% ethyl acetate in hexane to afford the title compound 2-(5-bromopyridin-2-yl)propan-2-ol (2, 5.8 g, 86% yield) as a yellow oil. Calculated (M+H): 216.0; Found (M+H): 216.1.

Step-2:

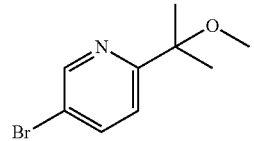

Preparation of 5-bromo-2-(2-methoxypropan-2-yl)pyridine 3

To a stirred suspension of sodium hydride (1.61 g, 40.26 mmol) in tetrahydrofuran (30 mL), was added a solution of 2-(5-bromopyridin-2-yl)propan-2-ol (2, 2.9 g, 13.42 mmol) in tetrahydrofuran (20 mL) at 0° C. and allowed to stir for 20 min. Then methyl iodide (2.5 mL, 40.26 mmol) was added to the reaction mixture and allowed to stir at room temperature for 12 h. The reaction mixture was quenched with crushed ice and extracted with ethyl acetate (3×100 mL). The combined organic layer was dried over anhydrous sodium sulphate, filtered and concentrated. The crude product was purified by silica gel column chromatography using 8% ethyl acetate in hexane to afford the title compound 5-bromo-2-(2-methoxypropan-2-yl)pyridine (3, 2.9 g, 94%) as a pale brown liquid. Calculated (M+H): 231.01; Found (M+H): 231.0.

Step-3:

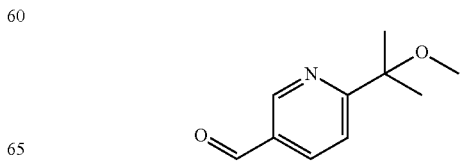

Preparation of 6-(2-methoxypropan-2-yl)nicotinaldehyde 4

To a stirred solution of 5-bromo-2-(2-methoxypropan-2-yl)pyridine (3, 0.2 g, 0.87 mmol) in tetrahydrofuran (3 mL), was added n-butyl lithium solution (0.52 mL, 1.04 mmol, 2.0 M in cyclohexane) at −78° C. and allowed to stir at the same temperature for 10 min. Then N,N-dimethylformamide (0.1 mL, 1.30 mmol) was added to the reaction mixture and allowed to stir at −20° C. for 2 h. The reaction mixture was quenched with crushed ice and extracted with ethyl acetate (3×50 mL). The combined organic layer was dried over anhydrous sodium sulphate, filtered and concentrated. The crude product was purified by silica gel column chromatography using 5% ethyl acetate in hexane to afford the title compound 6-(2-methoxypropan-2-yl)nicotinaldehyde (4, 0.04 g, 26% yield) as a pale brown oil. Calculated (M+H): 180.1: Found (M+H): 180.2

Step-4:

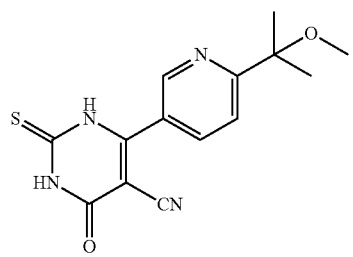 [SMILES: COC(C)(C)c1ccc(-c2[nH]c(=S)[nH]c(=O)c2C#N)cn1]

Preparation of 6-(6-(2-methoxypropan-2-yl)pyridin-3-yl)-4-oxo-2-thioxo-1,2,3,4-tetrahydropyrimidine-5-carbonitrile 5

To a stirred mixture of 6-(2-methoxypropan-2-yl)nicotinaldehyde (4, 0.6 g, 3.35 mmol), thiourea (0.25 g, 3.35 mmol) and ethyl 2-cyanoacetate (0.35 ml, 3.35 mmol) in ethanol (10 mL), was added potassium carbonate (1.38 g, 10.04 mmol) at room temperature. The resulting mixture was stirred at 90 °C for 8 h. The reaction mixture was concentrated and the residue was dissolved in water (10 mL), neutralized with acetic acid and extracted with ethyl acetate (3×50 mL). The combined organic layer was dried over anhydrous sodium sulphate, filtered and concentrated. The crude product was washed with diethyl ether followed by n-pentane to afford the title compound 6-(6-(2-methoxypropan-2-yl)pyridin-3-yl)-4-oxo-2-thioxo-1,2,3,4-tetrahydropyrimidine-5-carbonitrile (5, 0.44 g, 43% yield) as yellow solid. Calculated (M+H): 303.08; Found (M+H): 303.1.

Step-5:

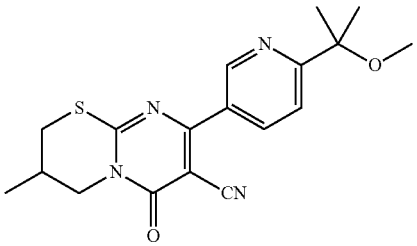

Preparation of 8-(6-(2-methoxypropan-2-yl)pyridin-3-yl)-3-methyl-6-oxo-3,4-dihydro-2H,6H-pyrimido[2,1-b][1,3]thiazine-7-carbonitrile 6

A mixture of 6-(6-(2-methoxypropan-2-yl)pyridin-3-yl)-4-oxo-2-thioxo-1,2,3,4-tetrahydropyrimidine-5-carbonitrile (5, 0.3 g, 0.99 mmol), 1-bromo-3-chloro-2-methylpropane (0.17 mL, 0.99 mmol) and triethylamine (0.55 mL, 3.97 mmol) in N,N-dimethylformamide (5 mL) was heated to 80° C. for 6 h in a sealed tube. The reaction mixture was cooled to room temperature, diluted with water (10 mL) and extracted with ethyl acetate (3×50 mL). The combined organic layer was dried over anhydrous sodium sulphate, filtered and concentrated. The crude product was purified by silica gel column chromatography using 40% ethyl acetate in hexane to afford the title compound 8-(6-(2-methoxypropan-2-yl)pyridin-3-yl)-3-methyl-6-oxo-3,4-dihydro-2H,6H-pyrimido[2,1-b][1,3]thiazine-7-carbonitrile (6 (example 119), 0.025 g, 7% yield) as a white solid. $^1$H NMR (DMSO-$d_6$, 400 MHz) δ (ppm): 8.96 (d, J=1.6 Hz, 1H), 8.22 (dd, $J_1$=2.0 Hz, $J_2$=8.4 Hz, 1H), 7.70 (d, J=8.4 Hz, 1H), 4.28 (d, J=14.0 Hz, 1H), 3.48 (dd, $J_1$=9.2 Hz, $J_2$=14.0 Hz, 1H), 3.24 (bs, 1H), 3.1-3.05 (m, 4H), 2.35-2.31 (m, 1H), 1.48 (s, 6H), 1.13 (d, J=6.8 Hz, 3H). Calculated (M+H): 357.13; Found (M+H): 357.1. HPLC purity: 99.79%

TABLE 31

The following compounds were prepared by the method described above:

| Ex. # | Structure | IUPAC Name | Analytical Data |
| --- | --- | --- | --- |
| 120 | 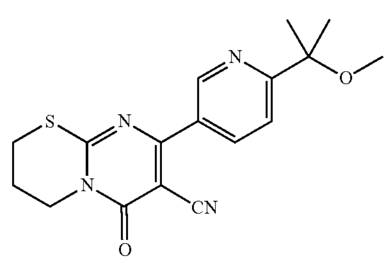 [SMILES: COC(C)(C)c1ccc(-c2nc3n(c(=O)c2C#N)CCCS3)cn1] | 8-(6-(2-methoxypropan-2-pyridin-3-yl)-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.96 (d, J = 1.6 Hz, 1H), 8.22 (dd, $J_1$ = 2.4 Hz, $J_2$ = 8.4 Hz, 1H), 7.70 (d, J = 8.4 Hz, 1H), 4.02 (t, J = 5.2 Hz, 2H), 3.28 (bs, 2H), 3.1 (s, 3H), 2.22 (bs, 2H), 1.48 (s, 6H). Calculated (M + H): 343.12, Found (M + H): 343.0, HPLC purity: 99.3% |

TABLE 31-continued

The following compounds were prepared by the method described above:

| Ex. # | Structure | IUPAC Name | Analytical Data |
|---|---|---|---|
| 121 | 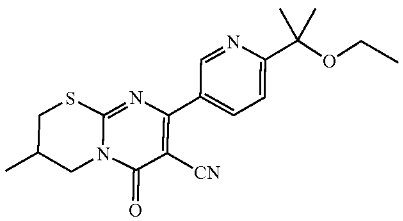 [SMILES: CCOC(C)(C)c1ccc(-c2nc3n(c(=O)c2C#N)CC(C)CS3)cn1] | 8-(6-(2-ethoxypropan-2-yl)pyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.95 (d, J = 2.0 Hz, 1H), 8.22 (dd, $J_1$ = 2.0 Hz, $J_2$ = 8.4 Hz, 1H), 7.71 (d, J = 8.4 Hz, 1H), 4.28 (d, J = 14.4 Hz, 1H), 3.48 (dd, $J_1$ = 9.6 Hz, $J_2$ = 14.0 Hz, 1H), 3.3-3.29 (m, 2H), 3.26-3.24 (m, 1H), 3.08 (t, J = 10.4 Hz, 1H), 2.36-2.31 (m, 1H), 1.49 (s, 6H), 1.14-1.11 (m, 6H); Calculated (M + H): 371.15, Found (M + H): 371.1, HPLC purity: 99.94% |
| 122 | 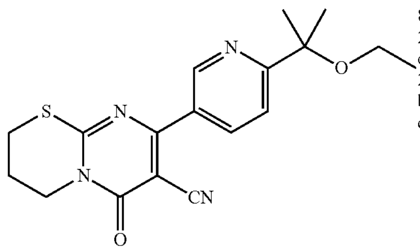 [SMILES: CCOC(C)(C)c1ccc(-c2nc3n(c(=O)c2C#N)CCCS3)cn1] | 8-(6-(2-ethoxypropan-2-yl)pyridin-3-yl)-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.95 (s, 1H), 8.22 (dd, $J_1$ = 2.0 Hz, $J_2$ = 8.0 Hz, 1H), 7.71 (d, J = 8.0 Hz, 1H), 4.02 (t, J = 5.2 Hz, 2H), 2.22 (bs, 2H), 1.49 (s, 6H), 1.13 (t, J = 7.2 Hz, 3H). 4H were merged with DMSO water peak. Calculated (M + H): 357.13, Found (M + H): 357.1, HPLC purity: 99.28% |

Example 123

Preparation of 8-(6-(tert-butyl)pyridin-3-yl)-3-(methoxymethyl)-6-oxo-3,4-dihydro-2H,6H-pyrimido[2,1-b][1,3]thiazine-7-carbonitrile 5

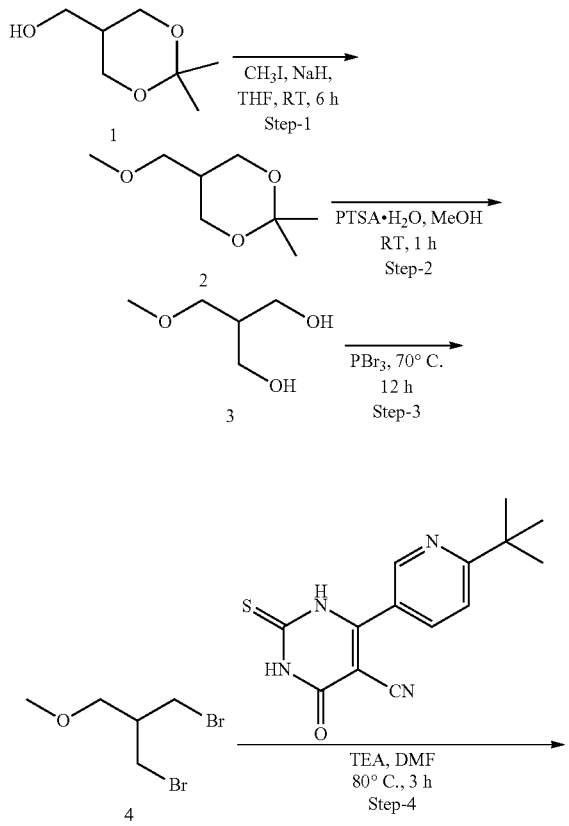

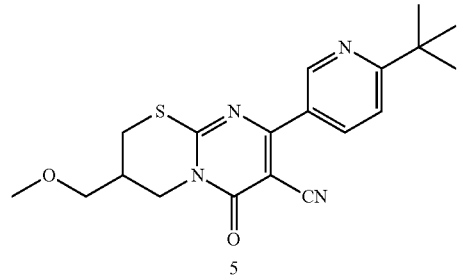

Step-1:

Preparation of 5-(methoxymethyl)-2,2-dimethyl-1,3-dioxane 2

To a suspension of sodium hydride (0.41 g, 10.26 mmol, 60% in mineral oil) in tetrahydrofuran (15 mL), (2,2-dimethyl-1,3-dioxan-5-yl)methanol (1, 1 g, 6.84 mmol) was added and the reaction mixture was stirred at room temperature for 10 min. Then methyl iodide (1.27 mL, 20.52 mmol) was added drop wise at room temperature and the reaction mixture was stirred at room temperature for 6 h. The reaction mixture was quenched with ice water (15 mL) and extracted with ethyl acetate (2×30 mL). The combined organic layer was dried over anhydrous sodium sulphate, filtered and concentrated. The crude was purified by silica gel column chromatography using 60% ethyl acetate in hexane to afford the title compound 5-(methoxymethyl)-2,2-dimethyl-1,3-dioxane (2, 0.65 g, 60% yield) as a colorless oil. $^1$H NMR (400 MHz, CDCl$_3$) δ (ppm): 3.97-3.93 (m, 2H), 3.76-3.72 (m, 2H), 3.42 (d, J=6.8 Hz, 2H), 3.34 (s, 3H), 2.00-1.94 (m, 1H), 1.42 (s, 3H), 1.40 (s, 3H).

Step-2:

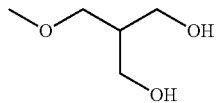

Preparation of 2-(methoxymethyl)propane-1,3-diol 3

To a stirred solution of 5-(methoxymethyl)-2,2-dimethyl-1,3-dioxane (2, 0.65 g, 4.06 mmol) in methanol (8 mL), p-toluene sulphonic acid monohydrate (0.077 g, 0.40 mmol) was added and the reaction mixture was stirred at room temperature for 1 h. The reaction mixture was neutralized with triethylamine and concentrated under reduced pressure. The crude was purified by silica gel column chromatography using 5% methanol in dichloromethane to afford the title compound 2-(methoxymethyl)propane-1,3-diol (3, 0.42 g, 87% yield) as a colorless oil. Calculated (M+H): 121.08; Found (M+H): 121.2.

Step-3:

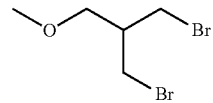

Preparation of 1,3-dibromo-2-(methoxymethyl)propane 4

To stirred 2-(methoxymethyl)propane-1,3-diol (3, 0.2 g, 1.66 mmol), phosphorous tribromide (0.11 mL, 1.23 mmol) was added at 0° C. and the reaction mixture was then heated at 70° C. for 12 h. The reaction mixture was cooled to 0° C., neutralized with saturated sodium bicarbonate solution and extracted with diethyl ether (2×20 mL). The combined organic layer was dried over anhydrous sodium sulphate, filtered and concentrated to afford the crude title compound 1,3-dibromo-2-(methoxymethyl)propane (4, 0.1 g, crude) as a brownish gum. The crude product was as such taken to the next step.

Step-4:

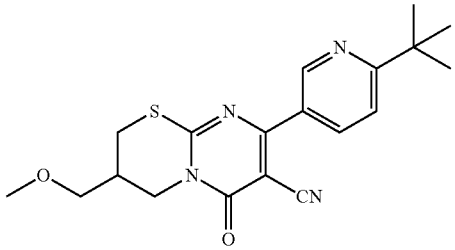 [SMILES: COCC1CSc2nc(-c3ccc(C(C)(C)C)nc3)c(C#N)c(=O)n2C1]

Preparation of 8-(6-(tert-butyl)pyridin-3-yl)-3-(methoxymethyl)-6-oxo-3,4-dihydro-2H,6H-pyrimido[2,1-b][1,3]thiazine-7-carbonitrile 5

To a solution of 6-(6-(tert-butyl)pyridin-3-yl)-4-oxo-2-thioxo-1,2,3,4-tetrahydropyrimidine-5-carbonitrile (0.208 g, 0.72 mmol) and 1,3-dibromo-2-(methoxymethyl)propane (4, 0.179 g, 0.72 mmol) in N,N-dimethyl formamide (10 mL), triethylamine (0.40 mL, 2.90 mmol) was added and the reaction mixture was heated at 80° C. in a sealed tube for 3 h. The reaction mixture was diluted with water (20 mL) and extracted with ethyl acetate (2×40 mL). The combined organic layer was dried over anhydrous sodium sulphate, filtered and concentrated. The crude was purified by silica gel column chromatography using 35% ethyl acetate in hexane to afford the title compound 8-(6-(tert-butyl)pyridin-3-yl)-3-(methoxymethyl)-6-oxo-3,4-dihydro-2H,6H-pyrimido[2,1-b][1,3]thiazine-7-carbonitrile (5 (example 123), 0.03 g, 11% yield) as an off-white solid. $^1$H NMR (400 MHz, DMSO-$d_6$) δ (ppm): 9.15 (d, J=2 Hz, 1H), 8.26 (dd, $J_1$=2 Hz, $J_2$=8.4 Hz, 1H), 7.45 (d, J=8.4 Hz, 1H), 4.62-4.58 (m, 1H), 3.66-3.57 (m, 1H), 3.55-3.49 (m, 2H), 3.39 (s, 3H), 3.25-3.20 (m, 2H), 2.51-2.49 (m, 1H), 1.39 (s, 9H). Calculated (M+H): 371.15; Found (M+H): 371.2. HPLC purity: 97.02%

TABLE 32

The following compounds were prepared by the method described above:

| Ex. # | Structure | IUPAC Name | Analytical Data |
| --- | --- | --- | --- |
| 124 | 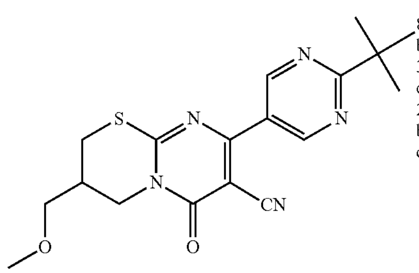 | 8-(2-(tert-butyl)pyrimidin-5-yl)-3-(methoxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 4.39 (d, J = 14 Hz, 1H), 3.60-3.54 (m, 1H), 3.46-3.44 (m, 2H), 3.32 (s, 3H), 3.22-3.12 (m, 2H), 1.39 (s, 9H). 1H was merged with DMSO residual peak. Calculated (M + H): 372.14; Found (M + H): 372.1, HPLC purity: 97.91% |

TABLE 32-continued

The following compounds were prepared by the method described above:

| Ex. # | Structure | IUPAC Name | Analytical Data |
|---|---|---|---|
| 125 | 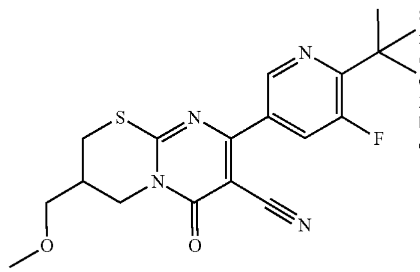 | 8-(6-(tert-butyl)-5-fluoropyridin-3-yl)-3-(methoxymethyl)-6-oxo-3,4-dihydro-2H,6H-pyrimido[2,1-b][1,3]thiazine-7-carbonitrile | $^1$H NMR (400 MHz, CDCl$_3$) δ (ppm): 8.99 (s, 1H), 7.93 (d, J = 12.0 Hz, 1H), 4.6 (dd, J$_1$ = 2.8 Hz, J$_2$ = 14.8 Hz, 1H), 3.63 (dd, J$_1$ = 10.0 Hz, J$_2$ = 14.8 Hz, 1H), 3.57-3.49 (m, 2H), 3.39 (s, 3H), 3.21 (d, J = 7.6 Hz, 2H), 2.5 (bs, 1H), 1.43 (s, 9H). Calculated (M + H): 389.14; Found (M + H): 389.3, HPLC purity: 99.41% |

Example 126

Preparation of 8-(6-(tert-butyl)-5-hydroxypyridin-3-yl)-3-methyl-6-oxo-3,4-dihydro-2H,6H-pyrimido[2,1-b][1,3]thiazine-7-carbonitrile 5

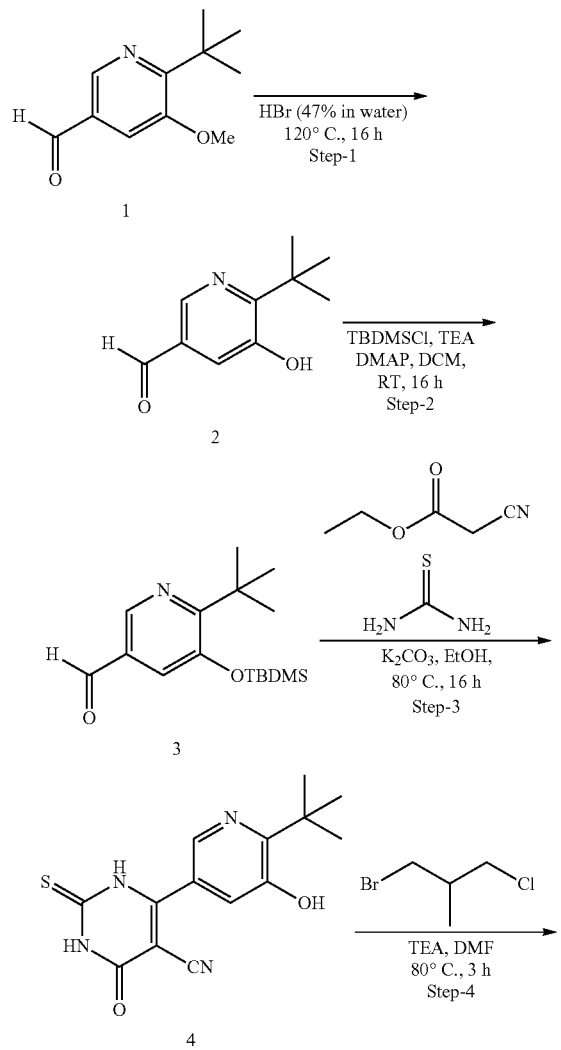

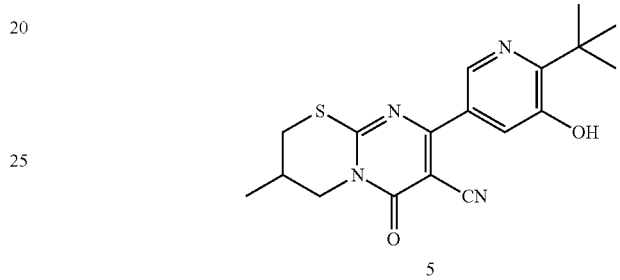

Step-1:

Preparation of 6-(tert-butyl)-5-hydroxynicotinaldehyde 2

A solution of 6-(tert-butyl)-5-methoxynicotinaldehyde (1, 1.2 g, 6.21 mmol) in hydrobromic acid (60 mL, 47% in water) was refluxed at 120° C. for 16 h. The reaction mixture was cooled to room temperature, neutralized with saturated sodium bicarbonate solution (180 mL) and extracted with ethyl acetate (2×50 mL). The combined organic layer was washed with brine (100 mL), dried over anhydrous sodium sulphate, filtered and concentrated. The crude product was purified by silica gel column chromatography using 15% ethyl acetate in hexane to afford the title compound 6-(tert-butyl)-5-hydroxynicotinaldehyde (2, 0.5 g, 45% yield) as a white solid. Calculated (M+H): 180.09; Found (M+H): 180.0.

Step-2:

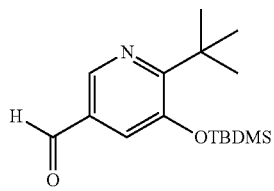 [SMILES: CC(C)(C)c1ncc(C=O)cc1O[Si](C)(C)C(C)(C)C]

Preparation of 6-(tert-butyl)-5-((tert-butyldimethyl-silyl)oxy)nicotinaldehyde 3

A mixture of 6-(tert-butyl)-5-hydroxynicotinaldehyde (2, 0.45 g, 2.51 mmol), tert-butylchlorodimethylsilane (0.75 g, 5.02 mmol), triethylamine (2.0 mL, 15.06 mmol) and 4-dimethylaminopyridine (0.06 g, 0.50 mmol) in dichloromethane (20 mL) was stirred at room temperature for 16 h. The reaction mixture was partitioned between water (30 mL) and dichloromethane (30 mL). The organic layer was washed with saturated sodium bicarbonate solution (30 mL), brine (30 mL), dried over anhydrous sodium sulphate, filtered and concentrated. The crude product was purified by silica gel column chromatography using 5% ethyl acetate in hexane to afford the title compound 6-(tert-butyl)-5-((tert-butyldimethylsilyl)oxy)nicotinaldehyde (3, 0.6 g, 81.4% yield) as a greenish oil. Calculated (M+H): 294.18; Found (M+H): 294.2.

Step-3:

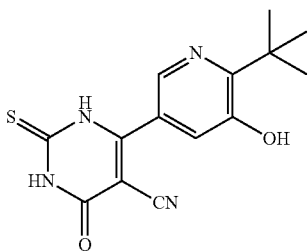 [SMILES: CC(C)(C)c1ncc(-c2[nH]c(=S)[nH]c(=O)c2C#N)cc1O]

Preparation of 6-(6-(tert-butyl)-5-hydroxypyridin-3-yl)-4-oxo-2-thioxo-1,2,3,4-tetrahydropyrimidine-5-carbonitrile 4

A mixture of 6-(tert-butyl)-5-((tert-butyldimethylsilyl)oxy)nicotinaldehyde (3, 0.60 g, 2.04 mmol), thiourea (0.17 g, 2.24 mmol), ethyl 2-cyanoacetate (0.23 mL, 2.24 mmol) and potassium carbonate (0.85 g, 6.13 mmol) in ethanol (10 mL) was heated at 80° C. for 16 h. The reaction mixture was filtered and the filtrate was concentrated. The residue was diluted with water (10 mL) and neutralized with acetic acid. The precipitated solid was filtered, washed with cold water (10 mL) and n-pentane (20 mL) to afford the title compound 6-(6-(tert-butyl)-5-hydroxypyridin-3-yl)-4-oxo-2-thioxo-1,2,3,4-tetrahydropyrimidine-5-carbonitrile (4, 0.25 g, 40.4% yield) as a yellow solid. Calculated (M+H): 303.08; Found (M+H): 303.1.

Step-4:

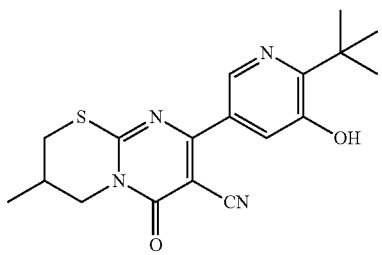 [SMILES: CC1CSc2nc(-c3cnc(C(C)(C)C)c(O)c3)c(C#N)c(=O)n2C1]

Preparation of 8-(6-(tert-butyl)-5-hydroxypyridin-3-yl)-3-methyl-6-oxo-3,4-dihydro-2H,6H-pyrimido[2,1-b][1,3]thiazine-7-carbonitrile 5

To a solution of 6-(6-(tert-butyl)-5-hydroxypyridin-3-yl)-4-oxo-2-thioxo-1,2,3,4-tetrahydropyrimidine-5-carbonitrile (4, 0.15 g, 0.49 mmol) and 1-bromo-3-chloro-2-methylpropane (0.12 g, 0.74 mmol) in N,N-dimethyl formamide (3 mL), triethylamine (0.3 mL, 1.98 mmol) was added and the reaction mixture was heated at 80° C. for 3 h in a sealed tube. The reaction mixture was diluted with water (30 mL) and extracted with ethyl acetate (2×20 mL). The combined organic layer was washed with water (2×30 mL), brine (30 mL), dried over anhydrous sodium sulphate, filtered and concentrated. The crude was purified by silica gel column chromatography using 40% ethyl acetate in hexane, followed by preparative HPLC purification (analytical conditions: column: Inertsil ODS 3V (250 mm×4.6 mm×5 mic), mobile phase (A): 0.1% ammonia in water, mobile phase (B): acetonitrile, flow rate: 1.0 mL/min, T/% B: 0/10, 10/80, 25/90, 27/10, 30/10) to afford the title compound 8-(6-(tert-butyl)-5-hydroxypyridin-3-yl)-3-methyl-6-oxo-3,4-dihydro-2H,6H-pyrimido[2,1-b][1,3]thiazine-7-carbonitrile (5 (example 126), 0.03 g, 16.9% yield) as a white solid. $^1$H NMR (400 MHz, DMSO-d$_6$) δ (ppm): 10.32 (s, 1H), 8.45 (d, J=1.6 Hz, 1H), 7.58 (d, J=1.2 Hz, 1H), 4.27 (d, J=13.6 Hz, 1H), 3.42-3.48 (m, 1H), 3.22 (bs, 1H), 3.06 (t, J=9.6 Hz, 1H), 2.31-2.35 (m, 1H), 1.37 (s, 9H), 1.13 (d, J=6.4 Hz, 3H). Calculated (M+H): 357.13; Found (M+H): 357.1. HPLC purity: 99.42%

TABLE 33

The following compounds were prepared by the method described above:

| Ex. # | Structure | IUPAC Name | Analytical Data |
|---|---|---|---|
| 127 | 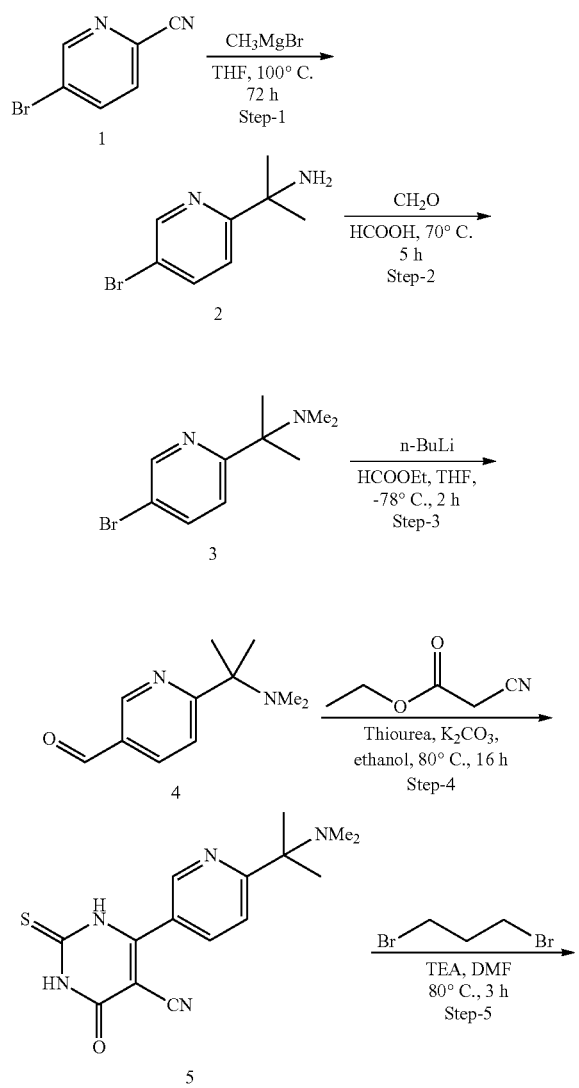 | 8-(6-(tert-butyl)-5-hydroxypyridin-3-yl)-6-oxo-3,4-dihydro-2H,6H-pyrimido[2,1-b][1,3]thiazine-7-carbonitrile | $^{1}$H NMR (400 MHz, DMSO-$d_6$) δ (ppm): 10.27 (bs, 1H) 8.4 (d, J = 2.0 Hz, 1H), 7.58 (d, J = 1.6 Hz, 1H), 4.00 (t, J = 5.2 Hz, 2H), 3.25 (bs, 2H), 2.22 (bs, 2H), 1.37 (s, 9H). Calculated (M + H): 343.12, Found (M + H): 343.1, HPLC purity: 99.97% |

Example 128

Preparation of 8-(6-(2-(dimethylamino)propan-2-yl)pyridin-3-yl)-6-oxo-3,4-dihydro-2H,6H-pyrimido[2,1-b][1,3]thiazine-7-carbonitrile 6

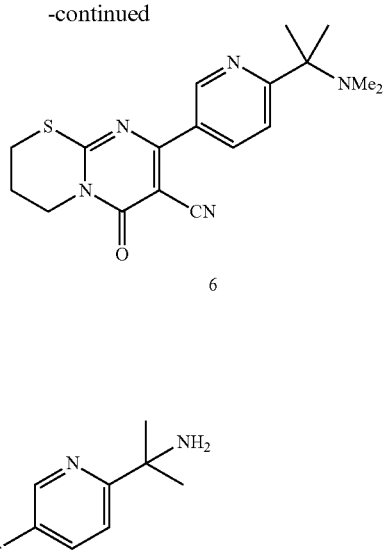

Step-1:

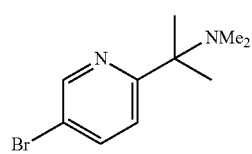

Preparation of 2-(5-bromopyridin-2-yl)propan-2-amine 2

To a solution of 5-bromopicolinonitrile (1, 15.0 g, 82.44 mmol) in tetrahydrofuran (500 mL), methyl magnesium bromide solution (131.43 mL, 247.32 mmol, 3M in diethyl ether) was added drop wise at 0° C. under nitrogen atmosphere. The reaction mixture was stirred at 100° C. for 72 h. The reaction mixture was quenched with saturated ammonium chloride solution (200 mL) and extracted with ethyl acetate (3×100 mL). The combined organic layer was dried over anhydrous sodium sulfate, filtered and concentrated. The crude product was purified by silica gel column chromatography using 35% ethyl acetate in hexane to afford the title compound 2-(5-bromopyridin-2-yl)propan-2-amine (2, 6.0 g, 34% yield) as a brown liquid. Calculated (M+H): 215.01; Found (M+H): 215.1.

Step-2:

Preparation of 2-(5-bromopyridin-2-yl)-N,N-dimethylpropan-2-amine 3

To a solution of 2-(5-bromopyridin-2-yl)propan-2-amine (2, 2.0 g, 9.28 mmol) in formic acid (2.77 mL, 73.67 mmol), formaline solution (1.98 mL, 24.5 mmol) was added drop wise at 0° C. The reaction mixture was stirred at 70° C. for 5 h. The reaction mixture was quenched with water (50 mL), basified using 5% sodium hydroxide solution and extracted with ethyl acetate (3×50 mL). The combined organic layer was dried over anhydrous sodium sulfate, filtered and concentrated. The crude product was purified by silica gel chromatography using 100% ethyl acetate to afford the title compound 2-(5-bromopyridin-2-yl)-N,N-dimethylpropan-2-amine (3, 2.0 g, 88% yield) as a brown liquid. Calculated (M+H): 243.04; Found (M+H): 243.1.

Step-3:

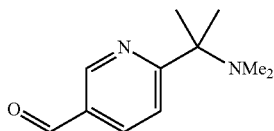

Preparation of 6-(2-(dimethylamino)propan-2-yl)nicotinaldehyde 4

To a solution of 2-(5-bromopyridin-2-yl)-N,N-dimethyl-propan-2-amine (3, 1.35 g, 5.57 mmol) in tetrahydrofuran (50 mL), n-butyllithium (3.25 mL, 6.1 mmol, 2M in cyclohexane) was added drop wise at −78° C. under nitrogen atmosphere. The reaction mixture was stirred at the same temperature for 30 min. Then ethyl formate (0.66 mL, 8.25 mmol) was added and the reaction mixture was stirred at same temperature for 2 h. The reaction mixture was quenched with saturated ammonium chloride solution (50 mL) and extracted with ethyl acetate (2×50 mL). The combined organic layer was dried over anhydrous sodium sulfate, filtered and concentrated. The crude product was purified by silica gel chromatography using 60% ethyl acetate in hexane to afford the title compound 6-(2-(dimethylamino)propan-2-yl)nicotinaldehyde (4, 0.75 g, 70% yield) as a brown gum. Calculated (M+H): 193.13; Found (M+H): 193.2.

Step-4:

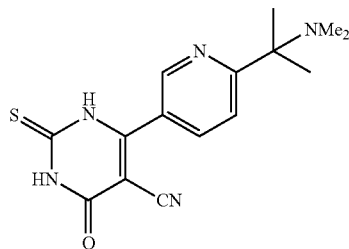 [SMILES: CN(C)C(C)(C)c1ccc(-c2[nH]c(=S)[nH]c(=O)c2C#N)cn1]

Preparation of 6-(6-(2-(dimethylamino)propan-2-yl) pyridin-3-yl)-4-oxo-2-thioxo-1,2,3,4-tetrahydropyrimidine-5-carbonitrile 5

To a solution of 6-(2-(dimethylamino)propan-2-yl)nicotinaldehyde (4, 0.75 g, 3.90 mmol) in ethanol (40 mL), thiourea (0.29 g, 3.90 mmol), ethyl cyanoacetate (0.41 mL, 3.90 mmol) and potassium carbonate (1.61, 11.70 mmol) were added. The reaction mixture was stirred at 80° C. for 16 h. The reaction mixture was concentrated to remove ethanol and dried to afford the title compound 6-(6-(2-(dimethylamino)propan-2-yl)pyridin-3-yl)-4-oxo-2-thioxo-1,2,3,4-tetrahydropyrimidine-5-carbonitrile (5, 1.1 g, crude) as a brownish solid. Calculated (M+H): 316.12; Found (M+H): 316.0.

Step-5:

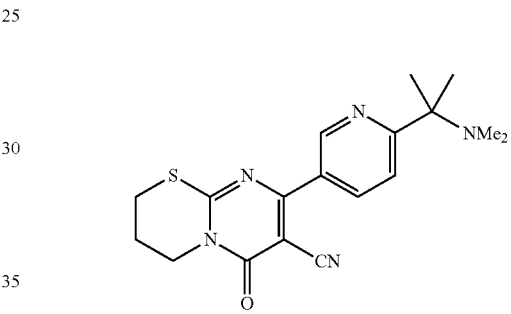

Preparation of 8-(6-(2-(dimethylamino)propan-2-yl) pyridin-3-yl)-6-oxo-3,4-dihydro-2H,6H-pyrimido[2, 1-b][1,3]thiazine-7-carbonitrile 6

To a solution of 6-(6-(2-(dimethylamino)propan-2-yl) pyridin-3-yl)-4-oxo-2-thioxo-1,2,3,4-tetrahydropyrimidine-5-carbonitrile (5, 0.4 g, 1.26 mmol) in N,N-dimethylformamide (30 mL), 1,3-dibromopropane (0.13 mL, 1.39 mmol) and triethylamine (0.5 mL, 3.6 mmol) were added. The reaction mixture was stirred at 80° C. for 3 h. The reaction mixture was quenched with water (100 mL) and extracted with ethyl acetate (2×100 mL). The combined organic layer was dried over anhydrous sodium sulfate, filtered and concentrated. The crude product was purified by silica gel chromatography using 50% ethyl acetate in hexane to afford the title compound 8-(6-(2-(dimethylamino)propan-2-yl)pyridin-3-yl)-6-oxo-3,4-dihydro-2H,6H-pyrimido[2,1-b][1,3]thiazine-7-carbonitrile (6 (example 128), 0.038 g, 8% yield) as an off white solid. $^1$H NMR (400 MHz, DMSO-$d_6$) δ (ppm): 8.93 (s, 1H), 8.17 (d, J=7.2 Hz, 1H), 7.84 (d, J=8.4 Hz, 1H), 4.02 (t, J=4.8 Hz, 2H), 2.31 (s, 2H), 2.12 (s, 6H), 1.31 (s, 6H), 2H merged with DMSO residual peak. Calculated (M+H): 356.15; Found (M+H): 356.2, HPLC Purity: 98.55%

Examples 129 and 130

Preparation of (S)-8-(6-(tert-butyl)pyridin-3-yl)-3-(hydroxymethyl)-6-oxo-3,4-dihydro-2H,6H-pyrimido[2,1-b][1,3]thiazine-7-carbonitrile 2 and (R)-8-(6-(tert-butyl)pyridin-3-yl)-3-(hydroxymethyl)-6-oxo-3,4-dihydro-2H,6H-pyrimido[2,1-b][1,3]thiazine-7-carbonitrile 3

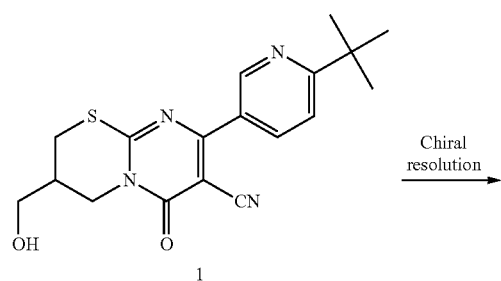
1

Chiral resolution
⟶

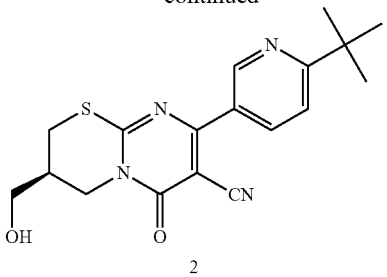
2

+

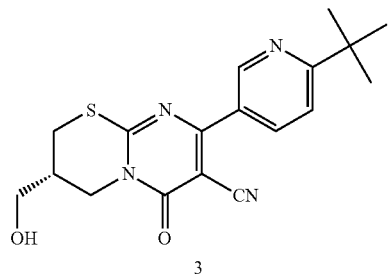
3

The chiral resolution was performed using the analytical condition: column: CHIRALPAK IA (250 mm×4.6 mm×5 mic), mobile phase A: methyl tert-butyl ether, mobile phase B: 100% isopropyl alcohol, composition: 70:30, flow rate: 1.0 mL/min. The analytical data for the enantiomers are given below.

TABLE 34

The following compounds were separated by the method described above

| Ex. # | Structure | IUPAC Name | Analytical Data |
|---|---|---|---|
| 129 | 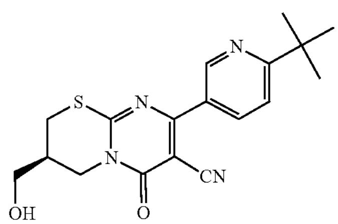 [SMILES: CC(C)(C)c1ccc(-c2nc3n(c(=O)c2C#N)C[C@@H](CO)CS3)cn1] | (S)-8-(6-(tert-butyl)pyridin-3-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.95 (d, J = 1.6 Hz, 1H), 8.16 (dd, $J_1$ = 2 Hz, $J_2$ = 8.4 Hz, 1H), 7.62 (d, J = 8.4 Hz, 1H), 5.02 (t, J = 5.2 Hz, 1H), 4.42 (d, J = 13.6 Hz, 1H), 3.55-3.49 (m, 3H), 3.24 (bs, 1H), 3.13 (t, J = 10 Hz, 1H), 3.28 (bs, 1H), 1.34 (s, 9H). Calculated (M + H): 357.13; Found (M + H): 357.3, chiral HPLC purity: 99.94% |
| 130 | 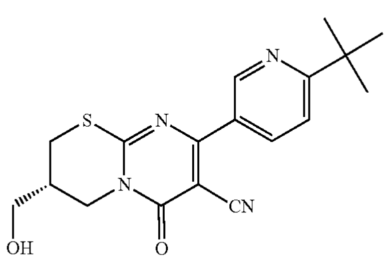 [SMILES: CC(C)(C)c1ccc(-c2nc3n(c(=O)c2C#N)C[C@H](CO)CS3)cn1] | (R)-8-(6-(tert-butyl)pyridin-3-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.95 (s, 1H), 8.16 (dd, $J_1$ = 2 Hz, $J_2$ = 8.4 Hz, 1H), 7.62 (d, J = 8.4 Hz, 1H), 5.03 (t, J = 5.2 Hz, 1H), 4.42 (d, J = 14 Hz, 1H), 3.55-3.49 (m, 3H), 3.23 (bs, 1H), 3.13 (t, J = 10 Hz, 1H), 3.28 (bs, 1H), 1.34 (s, 9H). Calculated (M + H): 357.13; Found (M + H): 357.3, chiral HPLC purity: 99.06% |

Examples 131 and 132

Preparation of (S)-8-(6-(tert-butyl)pyridin-3-yl)-3-(fluoromethyl)-6-oxo-3,4-dihydro-2H,6H-pyrimido[2,1-b][1,3]thiazine-7-carbonitrile 2 and (R)-8-(6-(tert-butyl)pyridin-3-yl)-3-(fluoromethyl-6-oxo-3,4-dihydro-2H,6H-pyrimido[2,1-b][1,3]thiazine-7-carbonitrile 3

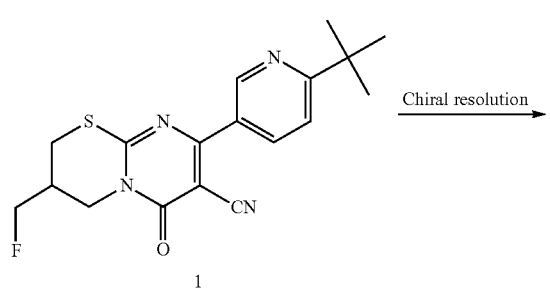

Chiral resolution →

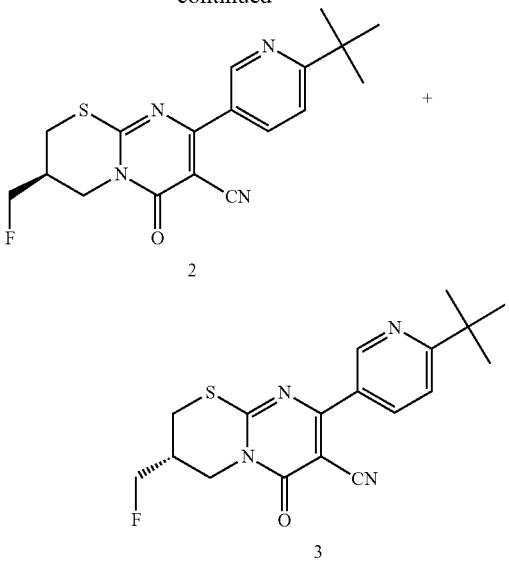

The chiral resolution was performed using the analytical condition: column: CHIRALPAK IA (250 mm×4.6 mm×5 mic), mobile phase A: methyl tert-butyl ether, mobile phase B: 100% isopropyl alcohol, composition: 70:30, flow rate: 1.0 mL/min. The analytical data for the enantiomers are given below.

TABLE 35

The following compounds were separated by the method described above

| Ex. # | Structure | IUPAC Name | Analytical Data |
|---|---|---|---|
| 131 | 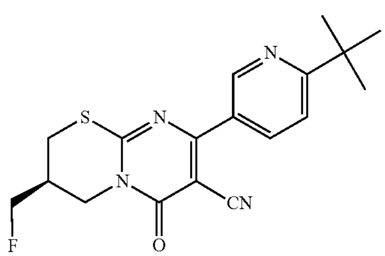 [SMILES: CC(C)(C)c1ccc(-c2nc3n(c(=O)c2C#N)C[C@@H](CF)CS3)cn1] | (S)-8-(6-(tert-butyl)pyridin-3-yl)-3-(fluoromethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.95 (d, J = 2 Hz, 1H), 8.17 (dd, $J_1$ = 2 Hz, $J_2$ = 8.4 Hz, 1H), 7.63 (d, J = 8 Hz, 1H), 4.67 (t, J = 5.6 Hz, 1H), 4.55 (t, J = 5.6, 1H), 4.42 (d, J = 13.6 Hz, 1H), 3.67-3.61 (m, 1H), 3.34-3.27 (m, 1H), 3.23-3.18 (m, 1H), 2.65 (bs, 1H), 1.34 (s, 9H). Calculated (M + H): 359.13; Found (M + H): 359.1, chiral HPLC purity: 99.72% |
| 132 | 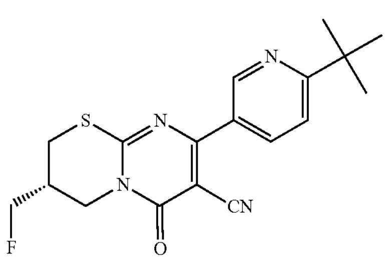 | (R)-8-(6-(tert-butyl)pyridin-3-yl)-3-(fluoromethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.95 (d, J = 1.6 Hz, 1H), 8.17 (dd, $J_1$ = 2 Hz, $J_2$ = 8.4 Hz, 1H), 7.63 (d, J = 8.4 Hz, 1H), 4.67 (bs, 1H), 4.55 (bs, 1H), 4.42 (d, J = 14.4 Hz, 1H), 3.67-3.61 (m, 1H), 3.34-3.27 (bs, 1H), 3.23-3.21 (m, 1H), 2.65 (bs, 1H), 1.34 (s, 9H). Calculated (M + H): 359.13; Found (M + H): 359.1, chiral HPLC purity: 97.8% |

Examples 133 and 134

Preparation of (R)-8-(6-(2-(dimethylamino)propan-2-yl)pyridin-3-yl)-3-methyl-6-oxo-3,4-dihydro-2H,6H-pyrimido[2,1-b][1,3]thiazine-7-carbonitrile 2 and (S)-8-(6-(2-(dimethylamino)propan-2-yl)pyridin-3-yl)-3-methyl-6-oxo-3,4-dihydro-2H,6H-pyrimido[2,1-b][1,3]thiazine-7-carbonitrile 3

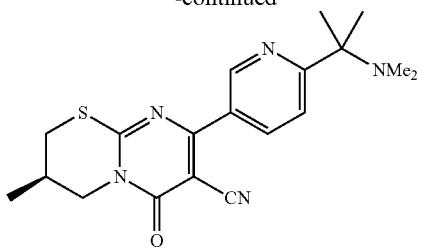

2

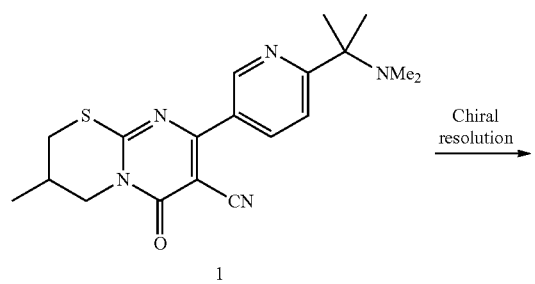

1

Chiral resolution →

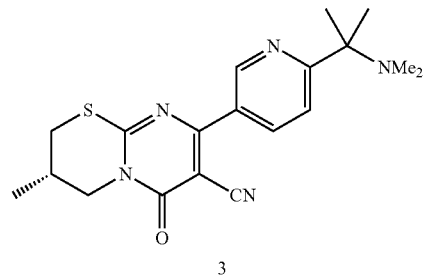

3

The chiral resolution was performed using the analytical condition: column: CHIRALPAK IA (250 mm×4.6 mm×5 mic), mobile phase A: n-hexane, mobile phase B: 0.1% diethyl amine in ethanol, composition: 50:50, flow rate: 1.0 mL/min. The analytical data for the enantiomers are given below.

TABLE 36

The following compounds were separated by the method described above

| Ex. # | Structure | IUPAC Name | Analytical Data |
|---|---|---|---|
| 133 | 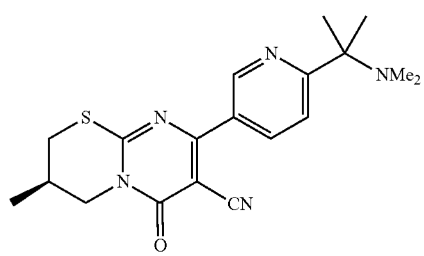 [SMILES: C[C@H]1CSc2nc(-c3ccc(C(C)(C)N(C)C)nc3)c(C#N)c(=O)n2C1] | (R)-8-(6-(2-(dimethylamino)propan-2-yl)pyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.94 (s, 1H), 8.17 (s, 1H), 7.84 (d, J = 8.4 Hz, 1H), 4.28 (d, J = 14.0 Hz, 1H), 3.51-3.45 (m, 1H), 3.32-3.24 (m, 1H), 3.08 (t, J = 9.6 Hz, 1H), 2.35-2.31 (m, 1H), 2.12 (s, 6H), 1.33(s, 6H), 1.13 (d, J = 6.8 Hz, 3H). Calculated (M + H): 370.12, found (M + H): 370.2, chiral HPLC purity: 99.42% |
| 134 | 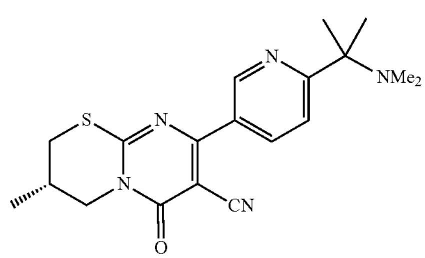 [SMILES: C[C@@H]1CSc2nc(-c3ccc(C(C)(C)N(C)C)nc3)c(C#N)c(=O)n2C1] | (S)-8-(6-(2-(dimethylamino)propan-2-yl)pyridin-3-yl)-3-methyl-6-oxo-3,4-dihydro-2H,6H-pyrimido[2,1-b][1,3]thiazine-7-carbonitrile | $^1$H-NMR (DMSO-$d_6$, 400 MHz) δ (ppm): 8.93 (s, 1H), 8.17 (d, J = 7.6 Hz, 1H), 7.84 (d, J = 8.4 Hz, 1H), 4.28 (d, J = 14.4 Hz, 1H), 3.51-3.45 (m, 1H), 3.23 (s, 1H), 3.07 (t, J = 10.0 Hz, 1H), 2.35-2.31 (m, 1H), 2.11 (s, 6H), 1.32 (s, 6H), 1.13 (d, J = 6.8 Hz, 3H). Calculated (M + H): 370.12, found (M + H): 370.2, chiral HPLC purity: 99.29% |

Example 135

Preparation of 8-(5-fluoro-6-(1-methylcyclopropyl)pyridin-3-yl)-3-methyl-6-oxo-3,4-dihydro-2H,6H-pyrido[2,1-b][1,3]thiazine-7-carbonitrile 5

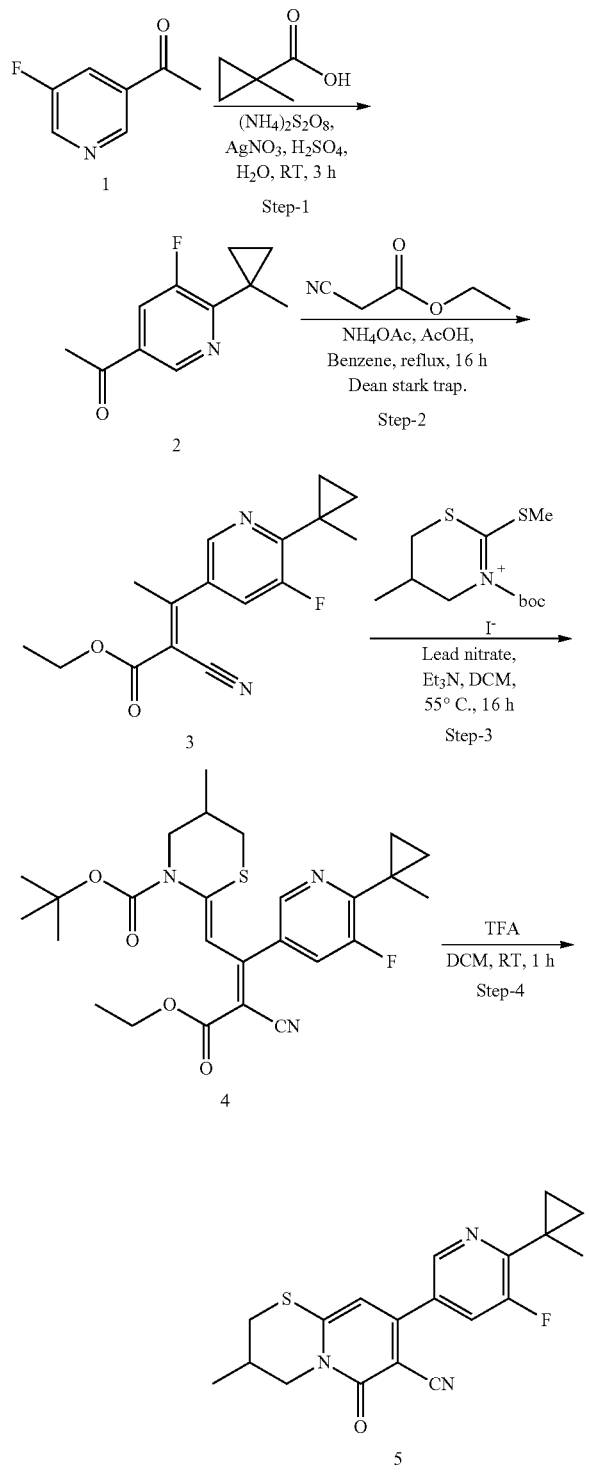

Step-1:

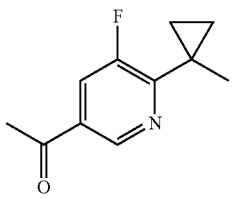

Preparation of 1-(5-fluoro-6-(1-methylcyclopropyl)pyridin-3-yl)ethan-1-one 2

To a solution of 1-(5-fluoropyridin-3-yl)ethan-1-one (1, 5.2 g, 37.39 mmol), 1-methylcyclopropane-1-carboxylic acid (7.48 g, 74.79 mmol) and silver nitrate (1.269, 7.47 mmol) in 10% aqueous sulphuric acid (100 mL), ammonium persulphate (11.58 g, 48.91 mmol) dissolved in water (200 mL) was added at room temperature. The reaction mixture was stirred at room temperature for 3 h. The reaction mixture was basified using aqueous ammonia solution to pH 9 and extracted with ethyl acetate (3×100 mL). The combined organic layer was dried over anhydrous sodium sulfate, filtered and concentrated. The crude product was purified by silica gel chromatography using 15% ethyl acetate in hexane to afford the title compound 1-(5-fluoro-6-(1-methylcyclopropyl)pyridin-3-yl)ethan-1-one (2, 2.0 g, 27% yield) as a white solid. Calculated (M+H): 194.09; Found (M+H): 194.1.

Step-2:

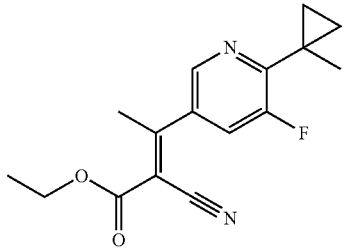 [SMILES: CCOC(=O)/C(C#N)=C(\C)c1cnc(C2(C)CC2)c(F)c1]

Preparation of ethyl (E)-2-cyano-3-(5-fluoro-6-(1-methylcyclopropyl)pyridin-3-yl)but-2-enoate 3

To a solution of 1-(5-fluoro-6-(1-methylcyclopropyl)pyridin-3-yl)ethan-1-one (2, 2.0 g, 10.35 mmol) and ethyl cyanoacetate (2.07 mL, 22.77 mmol) in benzene (40 mL), acetic acid (0.62 mL, 11.17 mmol), ammonium acetate (0.31 g, 4.14 mmol) were added. The reaction mixture was stirred at 120° C. using dean stark apparatus for 16 h. The reaction mixture was concentrated to remove benzene, the residue was quenched with water (50 mL) and extracted with ethyl acetate (2×100 mL). The combined organic layer was dried over anhydrous sodium sulfate, filtered and concentrated. The crude product was purified by silica gel chromatography using 40% ethyl acetate in hexane to afford the title compound ethyl (E)-2-cyano-3-(5-fluoro-6-(1-methylcyclopropyl)pyridin-3-yl)but-2-enoate (3, 1.5 g, 50% yield) as a colourless liquid. Calculated (M+H): 289.13; Found (M+H): 289.1.

Step-3:

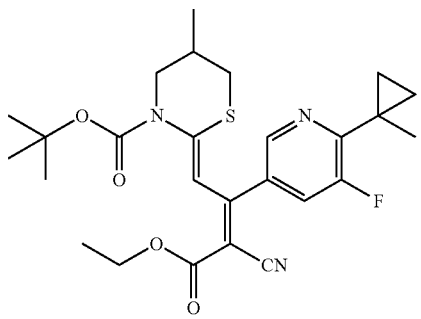 [SMILES: CCOC(=O)/C(C#N)=C(\C=C1/SCC(C)CN1C(=O)OC(C)(C)C)c1cnc(C2(C)CC2)c(F)c1]

Preparation of tert-butyl (Z)-2-((E)-3-cyano-4-ethoxy-2-(5-fluoro-6-(1-methyl cyclopropyl)pyridin-3-yl)-4-oxobut-2-en-1-ylidene)-5-methyl-1,3-thiazinane-3-carboxylate 4

To a solution of ethyl (E)-2-cyano-3-(5-fluoro-6-(1-methylcyclopropyl)pyridin-3-yl)but-2-enoate (3, 0.7 g, 2.42 mmol) in dichloromethane (50 mL), 3-(tert-butoxycarbonyl)-5-methyl-2-(methylthio)-5,6-dihydro-4H-1,3-thiazin-3-ium iodide (1.27 g, 4.85 mmol), triethylamine (3.37 mL, 2.42 mmol) and lead nitrate (2.4 g, 7.26 mmol) were added. The reaction mixture was stirred at 55° C. for 16 h. The reaction mixture was quenched with water (50 mL) and extracted with dichloromethane (2×50 mL). The combined organic layer was dried over anhydrous sodium sulfate, filtered and concentrated. The crude product was purified by silica gel column chromatography using 30% ethyl acetate in hexane to afford the title compound tert-butyl (Z)-2-((E)-3-cyano-4-ethoxy-2-(5-fluoro-6-(1-methylcyclopropyl)pyridin-3-yl)-4-oxobut-2-en-1-ylidene)-5-methyl-1,3-thiazinane-3-carboxylate (4, 0.1 g, crude) as a yellow gum. Calculated (M+H): 502.21; Found (M+H): 502.2.

Step-4:

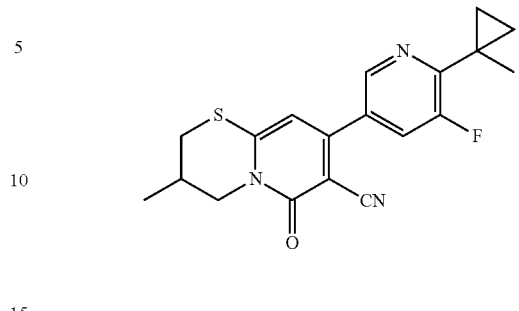

Preparation of 8-(5-fluoro-6-(1-methylcyclopropyl)pyridin-3-yl)-3-methyl-6-oxo-3,4-dihydro-2H,6H-pyrido[2,1-b][1,3]thiazine-7-carbonitrile 5

To a solution of tert-butyl (Z)-2-((E)-3-cyano-4-ethoxy-2-(5-fluoro-6-(1-methylcyclopropyl)pyridin-3-yl)-4-oxobut-2-en-1-ylidene)-5-methyl-1,3-thiazinane-3-carboxylate (4, 0.1 g, 0.19 mmol) in dichloromethane (3 mL), trifluoroacetic acid (3 ml) was added drop wise at 0° C. The reaction mixture was stirred at room temperature for 1 h. The reaction mixture was concentrated to remove trifluoroacetic acid, the residue was diluted with dichloromethane (40 mL), washed with sodium bicarbonate solution (20 mL), dried over anhydrous sodium sulfate, filtered and concentrated. The crude product was purified by silica gel column chromatography using 60% ethyl acetate in hexane to afford the title compound 8-(5-fluoro-6-(1-methylcyclopropyl)pyridin-3-yl)-3-methyl-6-oxo-3,4-dihydro-2H,6H-pyrido[2,1-b][1,3]thiazine-7-carbonitrile (5 (example 135), 0.05 g, 7% yield) as a yellow solid. $^1$H NMR (400 MHz, DMSO-$d_6$) δ (ppm): 8.53 (s, 1H), 7.92 (d, J=11.6 Hz, 1H), 6.61 (s, 1H), 4.34 (d, J=13.6 Hz, 1H), 3.47-3.41 (m, 1H), 2.97 (t, J=9.6 Hz, 1H), 2.31 (bs, 1H), 1.45 (s, 3H), 1.11 (d, J=6.8 Hz, 5H), 0.80 (s, 2H), 1H was merged with DMSO water peak. Calculated (M+H): 356.12; Found (M+H): 356.1. HPLC purity: 99.62%

TABLE 37

The following compound was prepared by the method described above:

| Ex. # | Structure | IUPAC Name | Analytical Data |
|---|---|---|---|
| 136 | 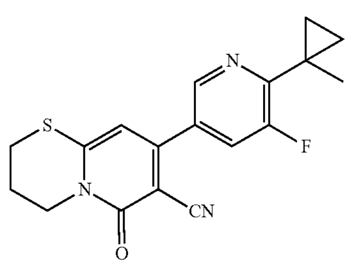 [SMILES: CC1(c2ncc(-c3cc4n(c(=O)c3C#N)CCCS4)cc2F)CC1] | 8-(5-fluoro-6-(1-methylcyclopropyl)pyridin-3-yl)-6-oxo-3,4-dihydro-2H,6H-pyrido[2,1-b][1,3]thiazine-7-carbonitrile | $^1$H NMR (400 MHz, DMSO-$d_6$) δ (ppm): 8.52 (s, 1H), 7.91 (d, J = 12.0 Hz, 1H), 6.59 (s, 1H), 4.04 (t, J = 5.6 Hz, 2H), 3.22 (t, J = 6.0 Hz, 2H), 2.2 (bs, 2H), 1.45 (s, 3H), 1.12 (s, 2H). 0.80 (s, 2H). Calculated (M + H): 342.10; Found (M + H): 342, HPLC purity: 99.53% |

Examples 137 and 138

Preparation of (S)-8-(2-(tert-butyl)pyrimidin-5-yl)-3-(hydroxymethyl)-6-oxo-3,4-dihydro-2H,6H-pyrimido[2,1-b][1,3]thiazine-7-carbonitrile 2 and (R)-8-(2-(tert-butyl)pyrimidin-5-yl)-3-(hydroxymethyl)-6-oxo-3,4-dihydro-2H,6H-pyrimido[2,1-b][1,3]thiazine-7-carbonitrile 3

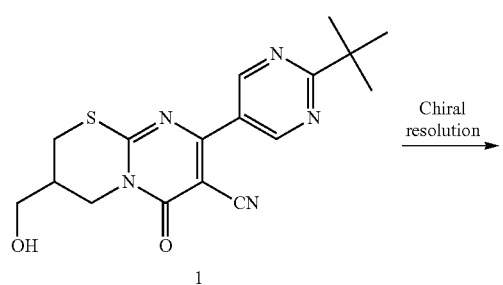

1

Chiral resolution →

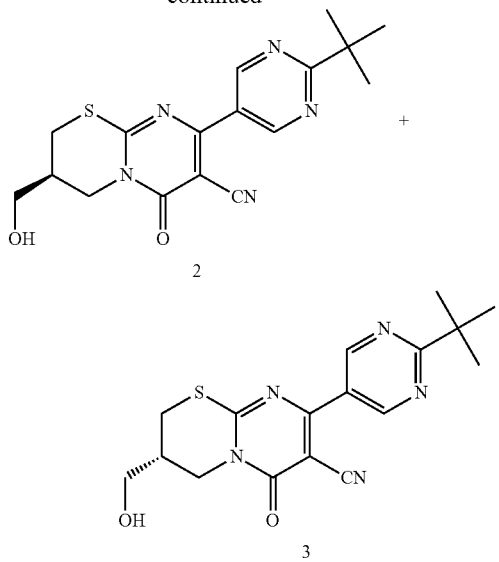

2

3

The chiral resolution was performed using the analytical condition: column: CHIRALPAK IC (250 mm×4.6 mm×5 mic), mobile phase: methyl tert-butyl ether:ethanol with 0.1% diethyl amine (50:50), flow rate: 1.0 mL/min. The analytical data for the enantiomers are given below.

TABLE 38

The following compounds were separated by the method described above

| Ex. # | Structure | IUPAC Name | Analytical Data |
|---|---|---|---|
| 137 | 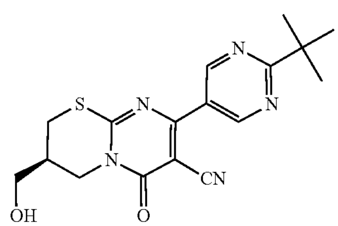 [SMILES: CC(C)(C)c1ncc(-c2nc3n(c(=O)c2C#N)C[C@@H](CO)CS3)cn1] | (S)-8-(2-(tert-butyl)pyrimidin-5-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 5.03 (t, J = 5.2 Hz, 1H), 4.43 (d, J = 13.6 Hz, 1H), 3.57-3.51 (m, 3H), 3.16-3.11 (m, 1H), 2.31 (bs, 1H), 1.39 (s, 9H). 1H was merged with DMSO water peak. Calculated (M + H): 358.13; Found (M + H): 358.1, chiral HPLC purity: 99.65% |
| 138 | 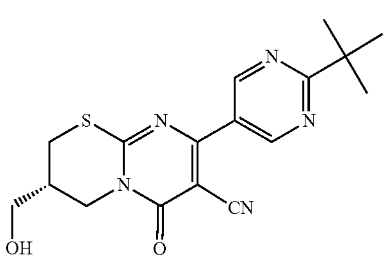 [SMILES: CC(C)(C)c1ncc(-c2nc3n(c(=O)c2C#N)C[C@H](CO)CS3)cn1] | (R)-8-(2-(tert-butyl)pyrimidin-5-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.15 (s, 2H), 5.03 (t, J = 5.2 Hz, 1H), 4.43 (d, J = 14.4 Hz, 1H), 3.57-3.51 (m, 3H), 3.16-3.11 (m, 1H), 2.31 (bs, 1H), 1.39 (s, 9H). 1H merged with DMSO water peak. Calculated (M + H): 358.13; Found (M + H): 358.1, chiral HPLC purity: 99.86% |

Examples 139 and 140

Preparation of (R)-8-(6-(tert-butyl)-5-hydroxypyridin-3-yl)-3-methyl-6-oxo-3,4-dihydro-2H,6H-pyrimido[2,1-b][1,3]thiazine-7-carbonitrile 2 and (S)-8-(6-(tert-butyl)-5-hydroxypyridin-3-yl)-3-methyl-6-oxo-3,4-dihydro-2H,6H-pyrimido[2,1-b][1,3]thiazine-7-carbonitrile 3

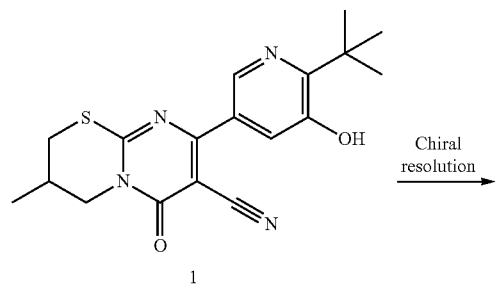

1

Chiral resolution →

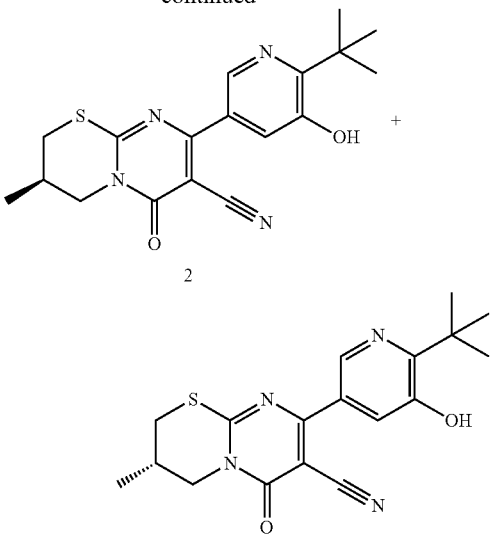

The chiral resolution was performed using the analytical conditions: column: CHIRALPAK IA (250 mm×4.6 mm×5 μm) mobile phase: n-hexane:ethanol with 0.1% diethyl amine (50:50) flow rate: 1.0 mL/min. The analytical data for the enantiomers are given below.

TABLE 39

The following compounds were separated by the method described above

| Ex. # | Structure | IUPAC Name | Analytical Data |
|---|---|---|---|
| 139 | 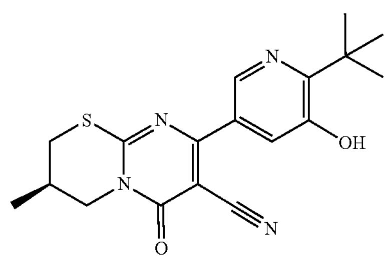 [SMILES: C[C@H]1CSc2nc(-c3cnc(C(C)(C)C)c(O)c3)c(C#N)c(=O)n2C1] | (R)-8-(6-(tert-butyl)-5-hydroxypyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 10.32 (bs, 1H), 8.45 (s, 1H), 7.58 (s, 1H), 4.27 (d, J = 14.0 Hz, 1H), 3.42-3.48 (m, 1H), 3.22 (bs, 1H), 3.06 (t, J = 10.0 Hz, 1H), 2.31 (bs, 1H), 1.37 (s, 9H), 1.13 (d, J = 6.4 Hz, 3H). Calculated (M + H): 357.13; Found (M + H): 357.1, chiral HPLC purity: 99.61% |
| 140 | 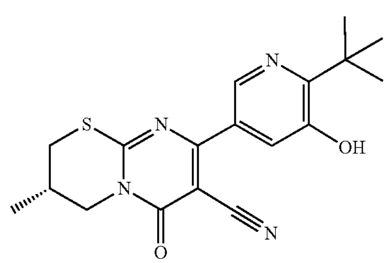 [SMILES: C[C@@H]1CSc2nc(-c3cnc(C(C)(C)C)c(O)c3)c(C#N)c(=O)n2C1] | (S)-8-(6-(tert-butyl)-5-hydroxypyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 10.32 (bs, 1H), 8.45 (d, J = 2.0 Hz, 1H), 7.58 (d, J = 1.2 Hz, 1H), 4.27 (d, J = 13.6 Hz, 1H), 3.42-3.48 (m, 1H), 3.22 (bs, 1H), 3.06 (t, J = 9.6 Hz, 1H), 2.34 (bs, 1H), 1.37 (s, 9H) , 1.13 (d, J = 6.4 Hz, 3H); Calculated (M + H): 357.13, Found (M + H): 357.0, chiral HPLC purity: 99.02% |

Examples 141 and 142

Preparation of (S)-8-(2-(tert-butyl)pyrimidin-5-yl)-3-(fluoromethyl)-6-oxo-3,4-dihydro-2H,6H-pyrimido[2,1-b][1,3]thiazine-7-carbonitrile 2 and (R)-8-(2-(tert-butyl)pyrimidin-5-yl)-3-(fluoromethyl)-6-oxo-3,4-dihydro-2H,6H-pyrimido[2,1-b][1,3]thiazine-7-carbonitrile 3

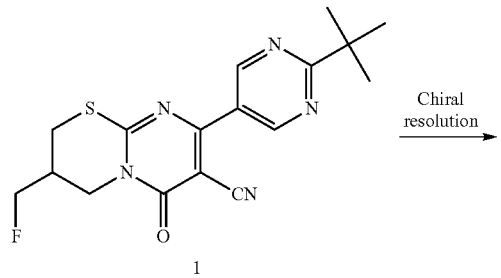

1

Chiral resolution →

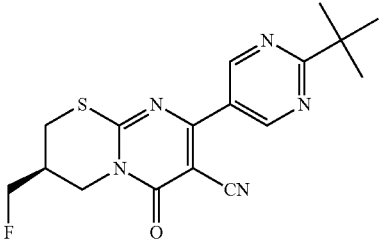 [SMILES: CC(C)(C)c1ncc(-c2nc3n(c(=O)c2C#N)C[C@@H](CF)CS3)cn1]

2

+

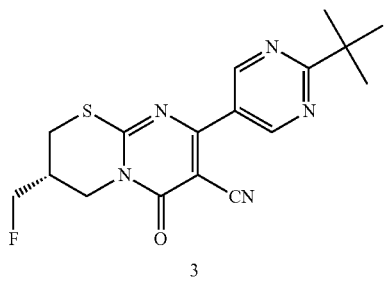

3

The chiral resolution was performed using the analytical condition: column: CHIRALPAK IA (250 mm×4.6 mm×5 μm), mobile phase: methyl tert-butyl ether: methanol with 0.1% diethyl amine (95:05), flow rate: 1.0 mL/min. The analytical data for the enantiomers are given below.

TABLE 40

The following compounds were separated by the method described above

| Ex. # | Structure | IUPAC Name | Analytical Data |
|---|---|---|---|
| 141 | 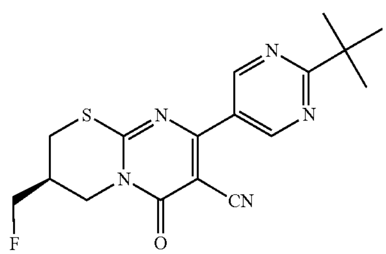 | (S)-8-(2-(tert-butyl)pyrimidin-5-yl)-3-(fluoromethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.16 (s, 2H), 4.67 (t, J = 5.6 Hz, 1H), 4.56 (t, J = 5.6 Hz, 1H), 4.44 (d, J = 14 Hz, 1H), 3.69-3.63 (m, 1H), 3.35-3.27 (m, 1H), 3.25-3.19 (m, 1H), 2.65 (bs, 1H), 1.39 (s, 9H). Calculated (M + H): 360.12; Found (M + H): 360.1, chiral HPLC purity: 99.99% |
| 142 | 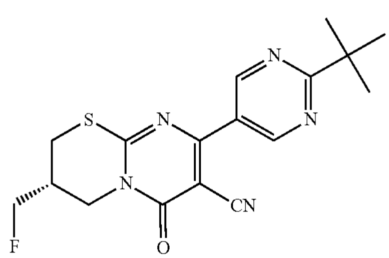 [SMILES: CC(C)(C)c1ncc(-c2nc3n(c(=O)c2C#N)C[C@H](CF)CS3)cn1] | (R)-8-(2-(tert-butyl)pyrimidin-5-yl)-3-(fluoromethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 9.16 (s, 2H), 4.67 (t, J = 5.6 Hz, 1H), 4.56 (t, J = 5.6 Hz, 1H), 4.44 (d, J = 14.4 Hz, 1H), 3.69-3.63 (m, 1H), 3.35-3.27 (m, 1H), 3.25-3.19 (m, 1H), 2.65 (bs, 1H), 1.39 (s, 9H). Calculated (M + H): 360.12; Found (M + H): 360.1, chiral HPLC purity: 96.75% |

Example 143

Preparation of 8-(6-(tert-butyl)pyridin-3-yl)-6-oxo-3-(trifluoromethyl)-3,4-dihydro-2H,6H-pyrimido[2,1-b][1,3]thiazine-7-carbonitrile 2

Examples 144 and 145

Preparation of tert-butyl ((8-(6-(tert-butyl)pyridin-3-yl)-7-cyano-6-oxo-3,4-dihydro-2H,6H-pyrimido[2,1-b][1,3]thiazin-3-yl)methyl)carbamate 4 & 3-(aminomethyl)-8-(6-(tert-butyl)pyridin-3-yl)-6-oxo-3,4-dihydro-2H,6H-pyrimido[2,1-b][1,3]thiazine-7-carbonitrile hydrochloride 5

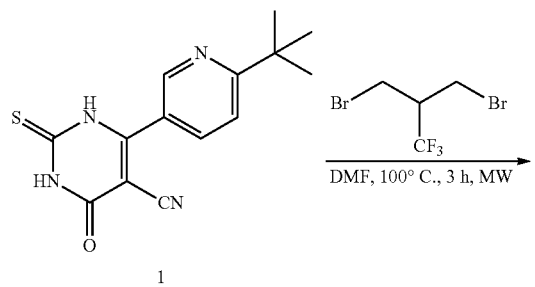

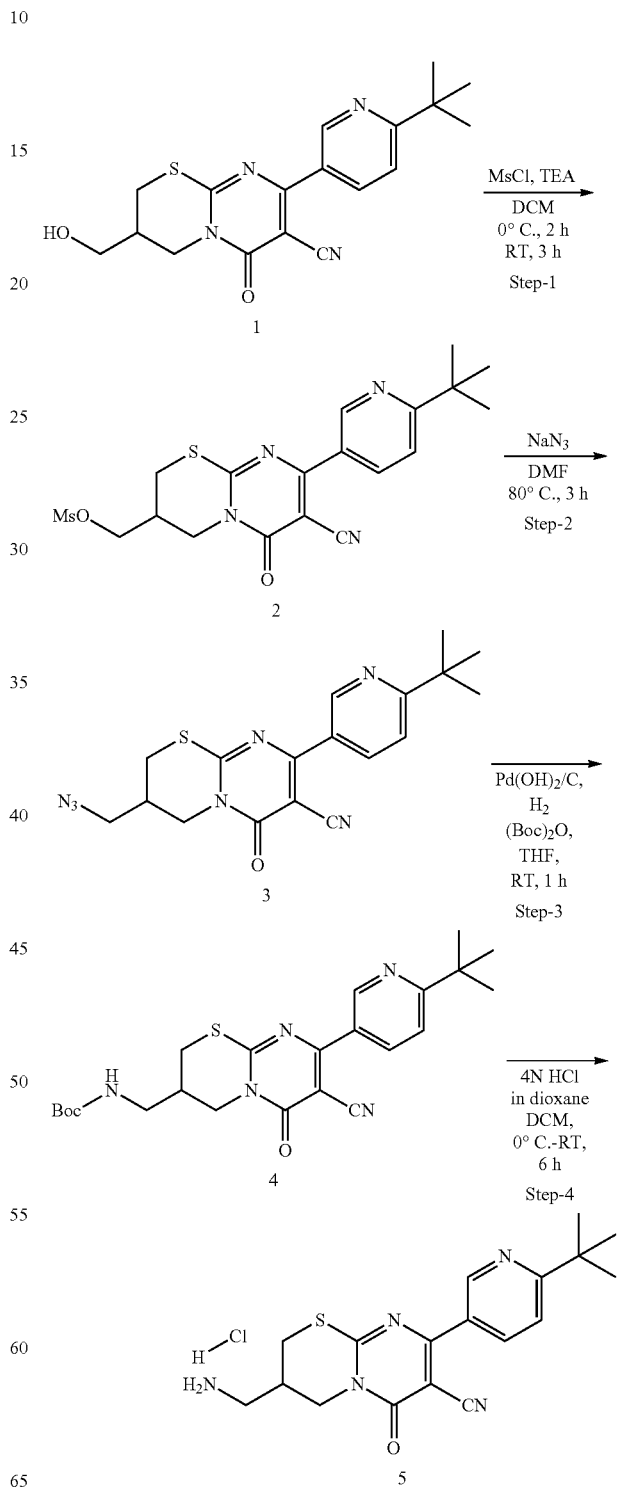

A stirred solution of 6-(6-(tert-butyl)pyridin-3-yl)-4-oxo-2-thioxo-1,2,3,4-tetrahydropyrimidine-5-carbonitrile (1, 0.1 g, 0.34 mmol) and 3-bromo-2-(bromomethyl)-1,1,1-trifluoropropane (0.94 g, 0.34 mmol) in N,N-dimethyl formamide (3 mL) was subjected to microwave irradiation for 3 h at 100° C. The reaction mixture was diluted with water (10 mL) and extracted with ethyl acetate (2×20 mL). The combined organic layer was dried over anhydrous sodium sulphate, filtered and concentrated. The crude was purified by silica gel preparative thin layer chromatography using 30% ethyl acetate in hexane to afford the title compound 8-(6-(tert-butyl)pyridin-3-yl)-6-oxo-3-(trifluoromethyl)-3,4-dihydro-2H,6H-pyrimido[2,1-b][1,3]thiazine-7-carbonitrile (2 (example 143), 0.008 g, 6% yield) as a pale brown solid. $^1$H NMR (400 MHz, DMSO-$d_6$) δ (ppm): 8.98 (bs, 1H), 8.19 (d, J=8.4 Hz, 1H), 7.64 (d, J=8.4 Hz, 1H), 4.57 (d, J=13.6 Hz, 1H), 3.89-3.83 (m, 1H), 3.55-3.44 (m, 3H), 1.34 (s, 9H). Calculated (M+H): 395.11; Found (M+H): 395.1. HPLC purity: 99.32%

Step-1:

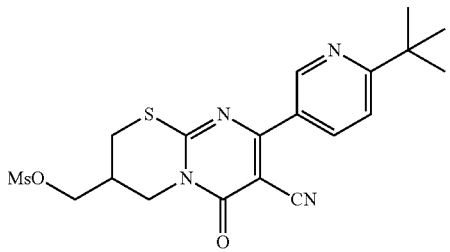 [SMILES: CC(C)(C)c1ccc(-c2nc3n(c(=O)c2C#N)CC(COS(C)(=O)=O)CS3)cn1]

Preparation of (8-(6-(tert-butyl)pyridin-3-yl)-7-cyano-6-oxo-3,4-dihydro-2H,6H-pyrimido[2,1-b][1,3]thiazin-3-yl)methyl methanesulfonate 2

To a solution of 8-(6-(tert-butyl)pyridin-3-yl)-3-(hydroxymethyl)-6-oxo-3,4-dihydro-2H,6H-pyrimido[2,1-b][1,3]thiazine-7-carbonitrile (1, 0.398 g, 1.11 mmol) in tetrahydrofuran (20 mL) cooled to 0° C., triethylamine (0.62 mL, 4.46 mmol) and methane sulphonyl chloride (0.22 mL, 2.79 mmol) were added. The reaction mixture was stirred at 0° C. for 2 h and then at room temperature for 3 h. The reaction mixture was neutralized with saturated sodium bicarbonate solution and extracted with ethyl acetate (2×30 mL). The combined organic layer was dried over anhydrous sodium sulphate, filtered and concentrated. The crude was purified by silica gel column chromatography using 40% ethyl acetate in hexane to afford the title compound (8-(6-(tert-butyl)pyridin-3-yl)-7-cyano-6-oxo-3,4-dihydro-2H,6H-pyrimido[2,1-b][1,3]thiazin-3-yl)methyl methanesulfonate (2, 0.38 g, 78% yield) as a brownish solid. Calculated (M+H): 435.11; Found (M+H): 435.1

Step-2:

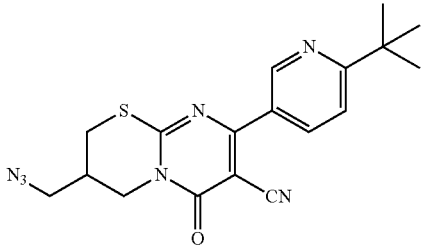 [SMILES: CC(C)(C)c1ccc(-c2nc3n(c(=O)c2C#N)CC(CN=[N+]=[N-])CS3)cn1]

Preparation of 3-(azidomethyl)-8-(6-(tert-butyl)pyridin-3-yl)-6-oxo-3,4-dihydro-2H,6H-pyrimido[2,1-b][1,3]thiazine-7-carbonitrile 3

To a solution of (8-(6-(tert-butyl)pyridin-3-yl)-7-cyano-6-oxo-3,4-dihydro-2H,6H-pyrimido[2,1-b][1,3]thiazin-3-yl)methyl methanesulfonate (2, 0.38 g, 0.88 mmol) in N,N-dimethyl formamide (15 mL), sodium azide (0.086 g, 1.32 mmol) was added and the reaction mixture was heated at 80° C. for 3 h. The reaction mixture was diluted with water (30 mL) and extracted with ethyl acetate (2×50 mL). The combined organic layer was dried over anhydrous sodium sulphate, filtered and concentrated. The crude was purified by silica gel column chromatography using 40% ethyl acetate in hexane to afford the title compound 3-(azidomethyl)-8-(6-(tert-butyl)pyridin-3-yl)-6-oxo-3,4-dihydro-2H,6H-pyrimido[2,1-b][1,3]thiazine-7-carbonitrile (3, 0.32 g, 95% yield) as a brownish solid. Calculated (M+H): 382.14; Found (M+H): 382.1.

Step-3:

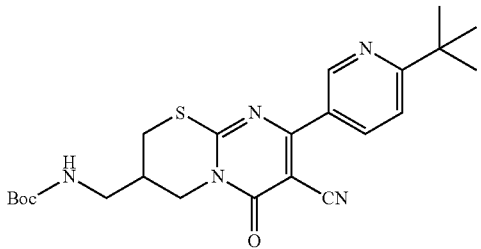 [SMILES: CC(C)(C)OC(=O)NCC1CSc2nc(-c3ccc(C(C)(C)C)nc3)c(C#N)c(=O)n2C1]

Preparation of tert-butyl ((8-(6-(tert-butyl)pyridin-3-yl)-7-cyano-6-oxo-3,4-dihydro-2H,6H-pyrimido[2,1-b][1,3]thiazin-3-yl)methyl)carbamate 4

To a solution of 3-(azidomethyl)-8-(6-(tert-butyl)pyridin-3-yl)-6-oxo-3,4-dihydro-2H,6H-pyrimido[2,1-b][1,3]thiazine-7-carbonitrile (3, 0.15 g, 0.39 mmol) in tetrahydrofuran (15 mL), di-tert-butyl dicarbonate (0.11 mL, 0.47 mmol) and palladium hydroxide on carbon (0.03 g) were added and the reaction mixture was stirred at room temperature for 1 h under hydrogen atmosphere using a balloon. The reaction mixture was filtered through celite bed and the filtrate was concentrated. The crude was purified by silica gel column chromatography using 50% ethyl acetate in hexane to afford the title compound tert-butyl ((8-(6-(tert-butyl)pyridin-3-yl)-7-cyano-6-oxo-3,4-dihydro-2H,6H-pyrimido[2,1-b][1,3]thiazin-3-yl)methyl)carbamate (4 (example 144), 0.075 g, 42% yield) as an off-white solid. $^1$H NMR (400 MHz, DMSO-de) δ (ppm): 8.95 (s, 1H), 8.16 (d, J=8 Hz, 1H), 7.63 (d, J=8.4 Hz, 1H), 7.13 (s, 1H), 4.29 (d, J=13.6 Hz, 1H), 3.61-3.55 (m, 1H), 3.1 (s, 3H), 2.31 (bs, 2H), 1.38 (s, 9H), 1.34 (s, 9H). Calculated (M+H): 456.20; Found (M+H): 456.1. HPLC purity: 99.58%

Step-4:

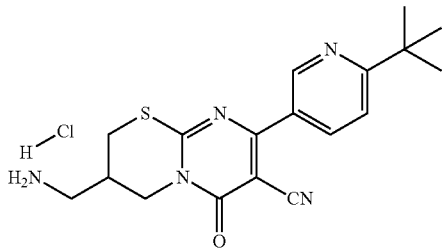

Preparation of 3-(aminomethyl)-8-(6-(tert-butyl)pyridin-3-yl)-6-oxo-3,4-dihydro-2H,6H-pyrimido[2,1-b][1,3]thiazine-7-carbonitrile hydrochloride To a solution of tert-butyl ((8-(6-(tert-butyl)pyridin-3-yl)-7-cyano-6-oxo-3,4-dihydro-2H,6H-pyrimido[2,1-b][1,3]thiazin-3-yl)methyl)carbamate (4, 0.035 g, 0.07 mmol) in dichloromethane (4 mL) cooled to 0° C. was added 4N hydrochloric acid in dioxane (0.2 mL) drop wise and the reaction mixture was stirred at room temperature for 6 h. The supernatant liquid was decanted off. The solid was triturated with diethyl ether and pentane to afford the title compound 3-(aminomethyl)-8-(6-(tert-butyl)pyridin-3-yl)-6-oxo-3,4-dihydro-2H,6H-pyrimido[2,1-b][1,3]thiazine-7-carbonitrile hydrochloride (5 (example 145), 0.021 g, 70% yield) as an off-white solid which is highly hygroscopic. $^1$H NMR (400 MHz, DMSO-de) δ (ppm): 8.96 (s, 1H), 8.30 (bs, 2H), 8.21 (d, J=7.6 Hz, 1H), 7.67 (d, J=7.6 Hz, 1H), 5.70 (bs, 1H), 4.37 (d, J=14.4 Hz, 1H), 3.77-3.71 (m, 1H), 3.44 (d, J=12 Hz, 1H), 3.25 (t, J=9.2 Hz, 1H), 3.07-2.99 (m, 2H), 2.65 (bs, 1H), 1.34 (s, 9H). Calculated (M+H): 392.12; Found (M+H): 356.2. (free base mass was observed), HPLC purity: 98.44%

TABLE 41

The following compounds were prepared by the method described above:

| Ex. # | Structure | IUPAC Name | Analytical Data |
|---|---|---|---|
| 146 | 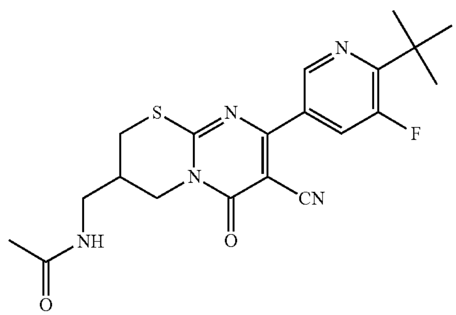 [SMILES: CC(=O)NCC1CSc2nc(-c3cnc(C(C)(C)C)c(F)c3)c(C#N)c(=O)n2C1] | N-((8-(6-(tert-butyl)-5-fluoropyridin-3-yl)-7-cyano-6-oxo-3,4-dihydro-2H,6H-pyrimido[2,1-b][1,3]thiazin-3-yl)methyl)acetamide | $^1$H NMR (400 MHz, DMSO-d$_6$) δ (ppm): 8.81 (s, 1H), 8.10 (bs, 1H), 8.00 (d, J = 11.2 Hz, 1H), 4.31 (d, J = 14 Hz, 1H), 3.60-3.49 (m, 1H), 3.25-3.19 (m, 3H), 3.11 (t, J = 9.6 Hz, 1H), 2.36 (bs, 1H), 1.83 (s, 3H), 1.39 (s, 9H). Calculated (M + H): 416.15; Found (M + H): 416.2, HPLC purity: 97.63% |
| 147 | 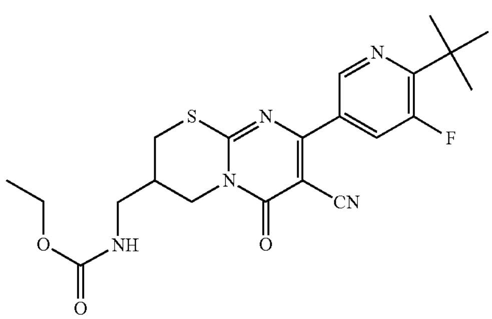 [SMILES: CCOC(=O)NCC1CSc2nc(-c3cnc(C(C)(C)C)c(F)c3)c(C#N)c(=O)n2C1] | ethyl ((8-(6-(tert-butyl)-5-fluoropyridin-3-yl)-7-cyano-6-oxo-3,4-dihydro-2H,6H-pyrimido[2,1-b][1,3]thiazin-3-yl)methyl)carbamate | $^1$H NMR (400 MHz, DMSO-d$_6$) δ (ppm): 8.81 (s, 1H), 8.00 (dd, J$_1$ = 1.6 Hz, 4.12 = 12.4 Hz, 1H), 7.38 (bs, 1H), 4.31 (d, J = 14.4 Hz, 1H), 3.99-3.96 (m, 2H), 3.61-3.32 (m, 1H), 3.21-3.08 (m, 4H), 2.36-2.31 (m, 1H), 1.39 (s, 9H), 1.15 (t, J = 7.2 Hz, 3H). Calculated (M + H): 446.16; Found (M + H): 446, HPLC purity: 99.1% |

Examples 148-150

Preparation of 8-(6-(bicyclo[1.1.1]pentan-1-yl)pyridin-3-yl)-3-methyl-6-oxo-3,4-dihydro-2H,6H-pyrimido[2,1-b][1.3]thiazine-7-carbonitrile 2

8-(2-(bicyclo[1.1.1]pentan-1-yl)pyridin-3-yl)-3-methyl-6-oxo-3,4-dihydro-2H,6H-pyrimido[2,1-b][1,3]thiazine-7-carbonitrile 3 and 8-(2,6-di(bicyclo[1.1.1]pentan-1-yl)pyridin-3-yl)-3-methyl-6-oxo-3,4-dihydro-2H,6H-pyrimido[2,1-b][1,3]thiazine-7-carbonitrile 4

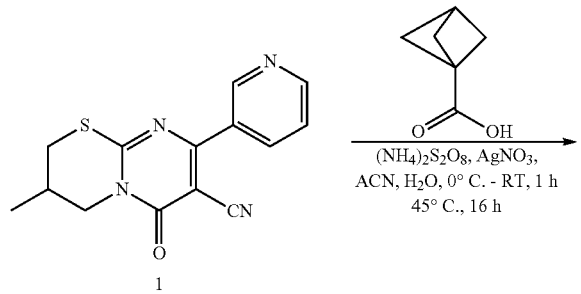

To a stirred suspension of 3-methyl-6-oxo-8-(pyridin-3-yl)-3,4-dihydro-2H,6H-pyrimido[2,1-b][1,3]thiazine-7-carbonitrile (1, 0.15 g, 0.53 mmol), bicyclo[1.1.1]pentane-1-carboxylic acid (0.05 g, 0.44 mmol) and silver nitrate (0.09 g, 0.53 mmol) in acetonitrile:water mixture (5 mL, 1:1), was added a solution of ammonium persulfate (0.20 g, 0.89 mmol) in acetonitrile:water mixture (5 mL, 1:1) drop wise over 10 min at 0° C. The resulting mixture was brought to room temperature over 30 min (reaction mixture changed into clear solution). Then the reaction mixture was stirred at 45° C. for 16 h in a sealed tube. The reaction mixture was basified to pH 9 with saturated sodium bicarbonate solution and extracted with ethyl acetate (20 mL×2). The combined organic layer was dried over anhydrous sodium sulphate, filtered and concentrated. The crude product was purified by silica gel column chromatography to afford the title compounds 8-(6-(bicyclo[1.1.1]pentan-1-yl)pyridin-3-yl)-3-methyl-6-oxo-3,4-dihydro-2H,6H-pyrimido[2,1-b][1,3]thiazine-7-carbonitrile (2 (example 148), 0.01 g, 6.3% yield) as a white solid, 8-(2-(bicyclo[1.1.1]pentan-1-yl)pyridin-3-yl)-3-methyl-6-oxo-3,4-dihydro-2H,6H-pyrimido[2,1-b][1,3]thiazine-7-carbonitrile (3 (example 149), 0.09 g, 5.7% yield) as a white solid and 8-(2,6-di(bicyclo[1.1.1]pentan-1-yl)pyridin-3-yl)-3-methyl-6-oxo-3,4-dihydro-2H,6H-pyrimido[2,1-b][1,3]thiazine-7-carbonitrile (4 (example 150), 0.07 g, 3.7% yield) as a white solid.

TABLE 42

The analytical data for the title compounds are given in the below table

| Ex. # | Structure | IUPAC Name | Analytical Data |
|---|---|---|---|
| 148 | 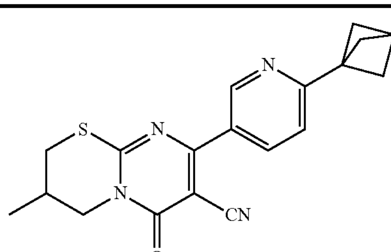 | (8-(6-(bicyclo[1.1.1]pentan-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-$d_6$) δ (ppm): 8.91 (s, 1H), 8.15 (d, J = 6.4 Hz, 1H), 7.44 (d, J = 8.0 Hz, 1H), 4.27 (d, J = 14.4 Hz, 1H), 3.49-3.43 (m, 1H), 3.22 (bs, 1H), 3.06 (t, J = 10.0 Hz, 1H), 2.56 (bs, 2H), 2.13 (s, 6H), 1.12 (d, J = 6.4 Hz, 3H). Calculated (M + H): 351.12; Found (M + H): 351.1, HPLC purity: 98.79% |

TABLE 42-continued

The analytical data for the title compounds are given in the below table

| Ex. # | Structure | IUPAC Name | Analytical Data |
|---|---|---|---|
| 149 | 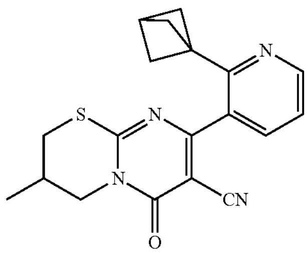 [SMILES: CC1CSc2nc(-c3cccnc3C34CC(C3)C4)c(C#N)c(=O)n2C1] | 8-(2-(bicyclo[1.1.1]pentan-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-d$_6$) δ (ppm): 8.62 (bs, 1H), 7.71 (d, J = 7.6 Hz, 1H), 7.38 (t, J = 5.6 Hz, 1H), 4.29 (d, J = 14.0 Hz, 1H), 3.59-3.54 (m, 1H), 3.25 (bs, 1H), 3.09 (t, J = 10.0 Hz, 1H), 2.39 (bs, 2H), 1.99 (s, 6H), 1.13 (d, J = 5.2 3H). Calculated (M + H): 351.12; Found (M + H): 351.1, HPLC purity: 99.09% |
| 150 | 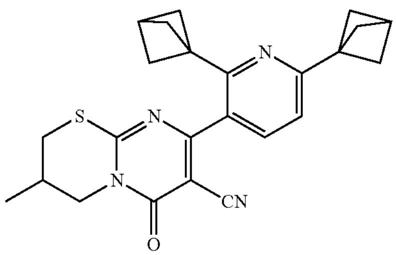 [SMILES: CC1CSc2nc(-c3ccc(C45CC(C4)C5)nc3C34CC(C3)C4)c(C#N)c(=O)n2C1] | 8-(2,6-di(bicyclo[1.1.1]pentan-1-yl)pyridin-3-yl)-3-methyl-6-oxo-3,4-dihydro-2H,6H-pyrimido[2,1-b][1,3]thiazine-7-carbonitrile | $^1$H NMR (400 MHz, DMSO-d$_6$) δ (ppm): 7.64 (d, J = 7.6 Hz, 1H), 7.44 (d, J = 7.2 Hz, 1H), 4.29 (d, J = 14.4 Hz, 1H), 3.56 (t, J = 10.4 Hz, 1H), 3.28 (bs, 1H), 3.09 (t, J = 10.0 Hz, 1H), 2.31 (bs, 1H), 2.11 (s, 6H), 1.98 (s, 6H), 1.13 (bs, 3H). 2H were merged with DMSO water peak. Calculated; (M + H): 417.17; Found (M + H): 417.2, HPLC purity: 99.0% |

TABLE 43

The following compounds were prepared by the method described above:

| Ex. # | Structure | IUPAC Name | Analytical Data |
|---|---|---|---|
| 151 | 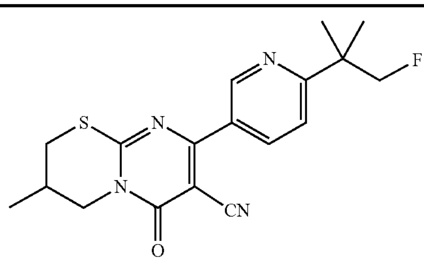 | 8-(6-(1-fluoro-2-methylpropan-2-yl)pyridin-3-yl)-3-methyl-6-oxo-3 4-dihydro-2H,6H-pyrimido[2,1-b][1,3]thiazine-7-carbonitrile | 1H NMR (400 MHz, DMSO-d$_6$) δ (ppm): 8.97 (bs, 1H), 8.15 (d, J = 6.4 Hz, 1H), 7.65 (d, J = 8.4 Hz, 1H), 4.68 (s, 1H), 4.56 (s, 1H), 4.28 (d, J = 14.4 Hz, 1H), 3.44-3.50 (m, 1H), 3.23 (bs, 1H), 3.07 (t, J = 10.0 Hz, 1H), 2.34 (bs, 1H), 1.34 (s, 6H), 1.13 (d, J = 6.0 Hz, 3H). Calculated (M + H): 359.13; Found (M + H): 359.0, HPLC purity: 98.52% |
| 152 | 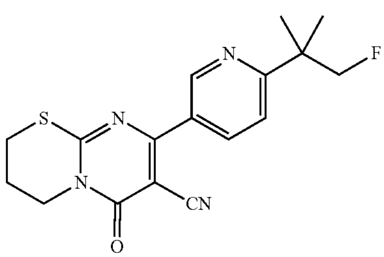 [SMILES: CC(C)(CF)c1ccc(-c2nc3n(c(=O)c2C#N)CCCS3)cn1] | 8-(6-(1-fluoro-2-methylpropan-2-yl)pyridin-3-yl)-6-oxo-3,4-dihydro-2H,6H-pyrimido[2,1-b][1,3]thiazine-7-carbonitrile | $^1$H NMR (400 MHz, DMSO-d$_6$) δ (ppm): 8.96 (bs, 1H), 8.19 (dd, J$_1$ = 6.0 Hz, J$_2$ = 3.6 Hz, 1H), 7.65 (d, J = 8.4 Hz, 1H), 4.68 (s, 1H), 4.56 (s, 1H), 4.02 (t, J = 4.8 Hz, 2H), 3.28 (t, J = 5.6 Hz, 2H), 2.22 (bs, 2H), 1.34 (s, 6H). Calculated (M + H): 345.11; Found (M + H): 345.1, HPLC purity: 98.72% |
| 153 | 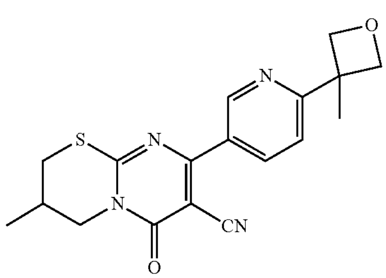 [SMILES: CC1CSc2nc(-c3ccc(C4(C)COC4)nc3)c(C#N)c(=O)n2C1] | 3-methyl-8-(6-(3-methyloxetan-3-yl)pyridin-3-yl)-6-oxo-3,4-dihydro-2H,6H-pyrimido[2,1-b][1,3]thiazine-7-carbonitrile | $^1$H NMR (400 MHz, DMSO-d$_6$) δ (ppm): 8.98 (bs, 1H), 8.22 (d, J = 7.6 Hz, 1H), 7.56 (d, J = 8.4 Hz, 1H), 4.93 (d, J = 5.6 Hz, 2H), 4.53 (d, J = 5.2 Hz, 2H), 4.27 (d, J = 14.4 Hz, 1H), 3.44-3.50 (m, 1H), 3.23 (bs, 1H), 3.07 (t, J = 10.8 Hz, 1H), 2.34 (bs, 1H), 1.67 (s, 3H), 1.13 (d, J = 6.4 Hz, 3H). Calculated (M + H): 355.12; Found (M + H): 355.3, HPLC purity: 99.0% |

TABLE 43-continued

The following compounds were prepared by the method described above:

| Ex. # | Structure | IUPAC Name | Analytical Data |
|---|---|---|---|
| 154 | 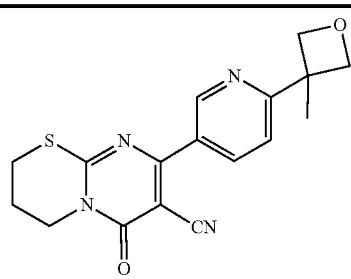 | 8-(6-(3-methyloxetan-3-yl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.98 (bs, 1H), 8.22 (d, J = 8.4 Hz, 1H), 7.57 (d, J = 8.0 Hz, 1H), 4.94 (d, J = 5.2 Hz, 2H), 4.54 (d, J = 5.6 Hz, 2H), 4.02 (d, J = 4.8 Hz, 2H), 2.28 (bs, 2H), 1.68 (s, 3H). 2H were merged with DMSO water peak. Calculated (M + H): 341.1; Found (M + H): 341.1, HPLC purity: 98.07% |

Example 155

Preparation of 8-(6-(1,3-difluoro-2-methylpropan-2-yl)pyridin-3-yl)-3-methyl-6-oxo-3,4-dihydro-2H,6H-pyrimido[2,1-b][1,3]thiazine-7-carbonitrile 2

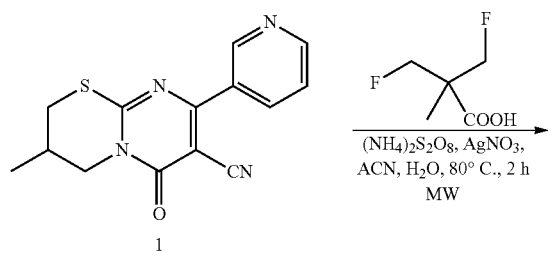

To a stirred suspension of 3-methyl-6-oxo-8-(pyridin-3-yl)-3,4-dihydro-2H,6H-pyrimido[2,1-b][1,3]thiazine-7-carbonitrile (1, 0.10 g, 0.35 mmol), 3-fluoro-2-(fluoromethyl)-2-methylpropanoic acid (0.19 g, 1.41 mmol) and silver nitrate (0.23 g, 1.41 mmol) in acetonitrile:water mixture (3 mL, 1:1), was added a solution of ammonium persulfate (0.48 g, 2.11 mmol) in acetonitrile:water mixture (3 mL, 1:1) drop wise. The resulting mixture was subjected to microwave irradiation for 2 h at 80° C. The reaction mixture was basified to pH 9 with saturated sodium bicarbonate solution and extracted with ethyl acetate (20 mL×2). The combined organic layer was dried over anhydrous sodium sulphate, filtered and concentrated. The crude was purified by silica gel column chromatography using 40% ethyl acetate in hexane to afford the title compound 8-(6-(1,3-difluoro-2-methylpropan-2-yl)pyridin-3-yl)-3-methyl-6-oxo-3,4-dihydro-2H,6H-pyrimido[2,1-b][1,3]thiazine-7-carbonitrile (2 (example 155), 0.013 g, 9.8% yield) as a yellow solid. $^1$H NMR (400 MHz, DMSO-$d_6$) δ (ppm): 8.97 (bs, 1H), 8.22 (d, J=8.0 Hz, 1H), 7.71 (d, J=8.4 Hz, 1H), 4.85 (s, 2H), 4.73 (s, 2H), 4.28 (d, J=14.4 Hz, 1H), 3.45-3.51 (m, 1H), 3.27 (bs, 1H), 3.07 (t, J=12 Hz, 1H), 2.35 (bs, 1H), 1.35 (s, 3H), 1.13 (d, J=6.4 Hz, 3H). Calculated (M+H): 377.12; Found (M+H): 377.1. HPLC purity: 98.39%

TABLE 44

The following compound was prepared by the method described above:

| Ex. # | Structure | IUPAC Name | Analytical Data |
|---|---|---|---|
| 156 | 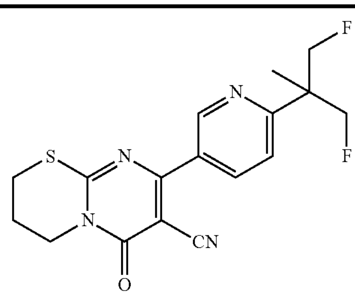 | 8-(6-(1,3-difluoro-2-methylpropan-2-yl)pyridin-3-yl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.97 (bs, 1H), 8.24 (d, J = 8.4 Hz, 1H), 7.72 (d, J = 8.0 Hz, 1H), 4.85 (t, J = 10 Hz, 2H), 4.73 (t, J = 10 Hz, 2H), 4.02 (s, 2H), 3.34 (bs, 2H), 2.22 (bs, 2H) 1.35 (s, 3H). Calculated (M + H): 363.1; Found (M + H): 363.1, HPLC purity: 98.07% |

Examples 157 and 158

Preparation of (S)-8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile 2 and (R)-8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile 3

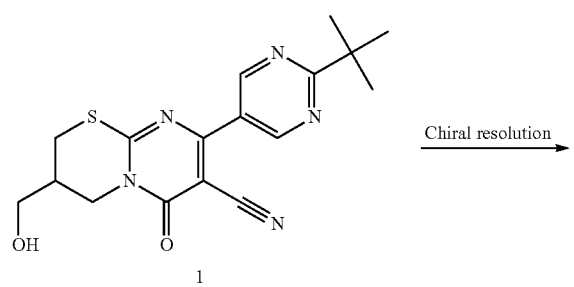

1

Chiral resolution →

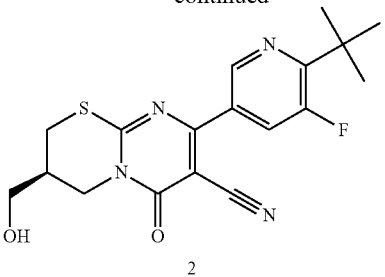

2

+

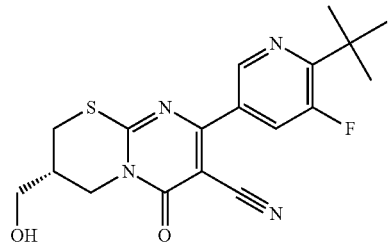

3

The chiral resolution was performed using the analytical condition: column: CHIRALPAK IA (250 mm×4.6 mm×5 mic), mobile phase A: methyl tert-butyl ether, mobile phase B: 0.1% diethyl amine in isopropyl alcohol, composition (A:B): (70:30), flow rate: 1.0 mL/min. The analytical data for the enantiomers are given below.

TABLE 45

The following compounds were separated by the method described above

| Ex. # | Structure | IUPAC Name | Analytical Data |
|---|---|---|---|
| 157 | 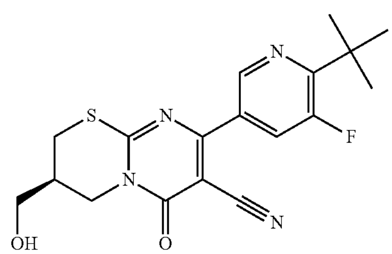 [SMILES: CC(C)(C)c1ncc(-c2nc3n(c(=O)c2C#N)C[C@@H](CO)CS3)cc1F] | (S)-8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.81 (s, 1H), 8.0 (d, J = 12.8 Hz, 1H), 5.03 (t, J = 5.6 Hz, 1H), 4.42 (d, J = 14.0 Hz, 1H), 3.56-3.47 (m, 3H), 3.24 (bs, 1H), 3.13 (t, J = 10.0 Hz, 1H), 2.31-2.28 (m, 1H), 1.39 (s, 9H). Calculated (M + H): 375.12; Found (M + H): 375.1, Chiral HPLC purity: 99.8% |
| 158 | 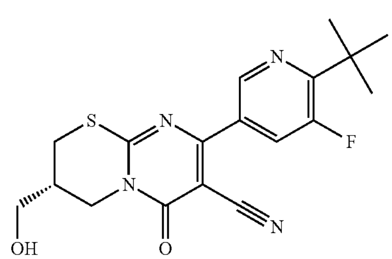 [SMILES: CC(C)(C)c1ncc(-c2nc3n(c(=O)c2C#N)C[C@H](CO)CS3)cc1F] | (R)-8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.81 (s, 1H), 8.0 (d, J = 12.8 Hz, 1H), 5.03 (t, J = 5.6 Hz, 1H), 4.42 (d, J = 14.0 Hz, 1H), 3.56-3.5 (m, 3H), 3.24 (bs, 1H), 3.13 (t, J = 10.4 Hz, 1H), 2.31-2.28 (m, 1H), 1.39 (s, 9H). Calculated (M + H): 375.12; Found (M + H): 375.1, Chiral HPLC purity: 99.9% |

Example 159

Preparation of 8-(6-(tert-butyl)-5-fluoropyridin-3-yl)-6-oxo-3-(pyrrolidin-1-ylmethyl)-3,4-dihydro-2H,6H-pyrimido[2,1-b][1,3]thiazine-7-carbonitrile 2

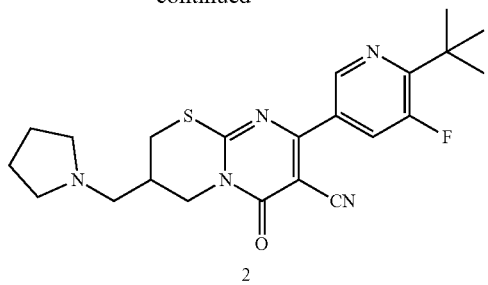

2

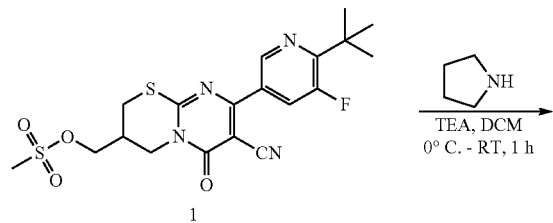

To a stirred solution of (8-(6-(tert-butyl)-5-fluoropyridin-3-yl)-7-cyano-6-oxo-3,4-dihydro-2H,6H-pyrimido[2,1-b][1,3]thiazin-3-yl)methyl methanesulfonate (1, 0.10 g, 0.22 mmol) and triethylamine (0.12 mL, 0.88 mmol) in dichloromethane (5 mL) was added pyrrolidine (0.07 mL, 0.8839 mmol) at 0° C. The reaction mixture was allowed to stir at room temperature for 1 h. The reaction mixture was partitioned between water (20 mL) and dichloromethane (20 mL). The organic layer was washed with brine (30 mL), dried over anhydrous sodium sulphate, filtered and concentrated. The crude product was purified by silica gel column chromatography using 50% ethyl acetate in hexane to afford the title compound 8-(6-(tert-butyl)-5-fluoropyridin-3-yl)-6-oxo-3-(pyrrolidin-1-ylmethyl)-3,4-dihydro-2H,6H-pyrimido[2,1-b][1,3]thiazine-7-carbonitrile (2 (example 159), 0.012 g, 10.5% yield) as a white solid. $^1$H NMR (400 MHz, DMSO-de) δ (ppm): 8.87 (s, 1H), 8.06 (d, J=13.2 Hz, 1H), 4.28 (d, J=7.2 Hz, 2H), 3.67 (bs, 4H), 3.58-3.48 (m, 1H), 3.05 (t, J=8.8 Hz, 2H), 2.98 (t. J=7.6 Hz, 2H), 1.90 (bs, 4H), 1.38 (s, 9H). Calculated (M+H): 428.18; Found (M+H): 428.2. HPLC purity: 98.42%

TABLE 46

The following compound was prepared by the method described above:

| Ex. # | Structure | IUPAC Name | Analytical Data |
|---|---|---|---|
| 160 | 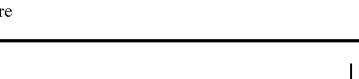 | 8-(6-(tert-butyl)-5-fluoropyridin-3-yl)-3-((dimethylamino)methyl)-6-oxo-3,4-dihydro-2H,6H-pyrimido[2,1-b][1,3]thiazine-7-carbonitrile | $^1$H NMR (400 MHz, DMSO-d$_6$) δ δ (ppm): 8.88 (s, 1H), 8.07 (d, J = 12.4 Hz, 1H), 4.16 (d, J = 6.4 Hz, 2H), 3.56-3.60 (m, 1H), 3.12 (s, 6H), 2.95-3.03 (m, 4H), 1.38 (s, 9H). Calculated (M + H): 402.17; Found (M + H): 402.2, HPLC purity: 99.76% |

Example 161

Preparation of 8-(6-(tert-butyl)-5-fluoropyridin-3-yl)-7-cyano-N,N-dimethyl-6-oxo-3,4-dihydro-2H,6H-pyrimido[2,1-b][1,3]thiazine-3-carboxamide 2

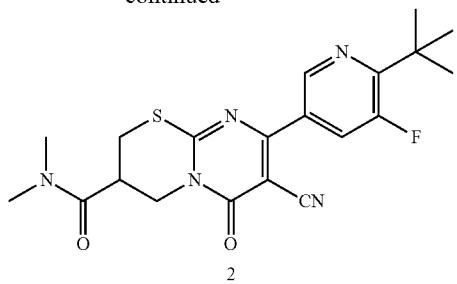

2

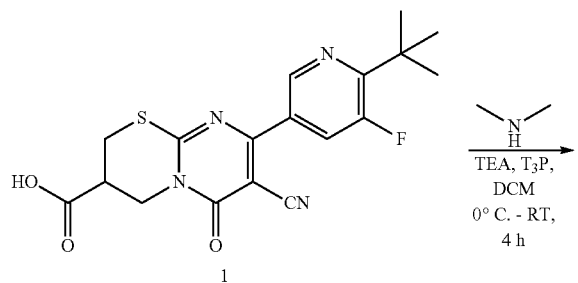

To a stirred solution of 8-(6-(tert-butyl)-5-fluoropyridin-3-yl)-7-cyano-6-oxo-3,4-dihydro-2H,6H-pyrimido[2,1-b][1,3]thiazine-3-carboxylic acid (1, 0.1 g, 0.25 mmol), dimethylamine (0.03 mL, 0.51 mmol, 2M in tetrahydrofuran) in dichloromethane (30 mL) was added triethylamine (0.25 mL, 1.80 mmol) at room temperature and the reaction mixture was cooled to 0° C. Then 1-propanephosphonic anhydride solution ($T_3P$) (0.62 mL, 0.51 mmol, 50% in ethyl acetate) was added and the reaction mixture was stirred at room temperature for 4 h. The reaction mixture was diluted with dichloromethane (30 mL) and washed with water (2×30 mL). The organic layer was dried over anhydrous sodium sulfate, filtered and concentrated to get the crude compound which was purified by silica gel column chromatography using 4% methanol in dichloromethane to afford the title compound 8-(6-(tert-butyl)-5-fluoropyridin-3-yl)-7-cyano-N,N-dimethyl-6-oxo-3,4-dihydro-2H,6H-pyrimido[2,1-b][1,3]thiazine-3-carboxamide (2 (example 161), 0.041 g, 38% yield) as an off white solid. $^1$H NMR (400 MHz, DMSO-$d_6$) δ (ppm): 8.82 (s, 1H), 8.02 (d, J=12.8 Hz, 1H), 4.37 (d, J=14.4 Hz, 1H), 3.77-3.72 (m, 1H), 3.60 (d, J=6.0 Hz, 1H), 3.39 (d, J=6.4 Hz, 2H), 3.07 (s, 3H), 2.85 (s, 3H), 1.39 (s, 9H). Calculated (M+H): 416.15; Found (M+H): 416.1. HPLC purity: 99.66%

TABLE 47

The following compounds were prepared by the method described above:

| Ex. # | Structure | IUPAC Name | Analytical Data |
|---|---|---|---|
| 162 | 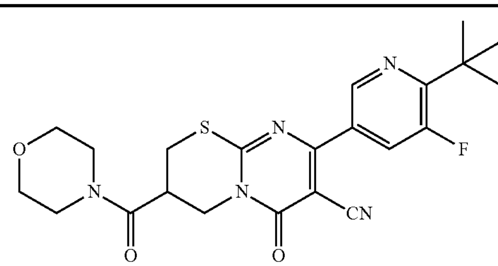 | 8-(6-(tert-butyl)-5-fluoropyridin-3-yl)-3-(morpholine-4-carbonyl)-6-oxo-3,4-dihydro-2H,6H-pyrimido[2,1-b][1,3]thiazine-7-carbonitrile | $^1$H NMR (400 MHz, DMSO-$d_6$) δ (ppm): 8.82 (bs, 1H), 8.03 (d, J = 12.8 Hz, 1H), 4.34 (d, J = 14 Hz, 1H), 3.85-3.80 (m, 1H), 3.45-361 (m, 7H), 3.40-3.47 (m, 2H), 3.38-3.28 (m, 2H), 1.39 (s, 9H). Calculated (M + H): 458.16; Found (M + H): 458.0, HPLC purity: 99.82% |
| 163 | 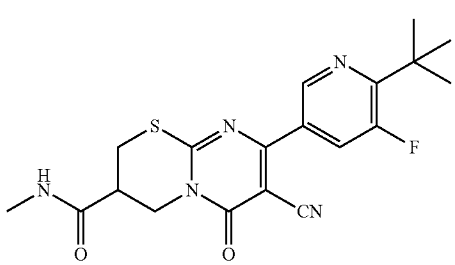 [SMILES: CNC(=O)C1CSc2nc(-c3cnc(C(C)(C)C)c(F)c3)c(C#N)c(=O)n2C1] | 8-(6-(tert-butyl)-5-fluoropyridin-3-yl)-7-cyano-N-methyl-6-oxo-3,4-dihydro-2H,6H-pyrimido[2,1-b][1,3]thiazine-3-carboxamide | $^1$H NMR (400 MHz, DMSO-$d_6$) δ (ppm): 8.82 (s, 1H), 8.20 (d, J = 4.0 Hz, 1H), 8.01 (d, J = 12.8 Hz, 1H), 4.28 (dd, $J_1$ = 2.4 Hz, $J_2$ = 14.4 Hz, 1H), 3.98-3.92 (m, 1H), 3.45-3.37 (m, 2H), 3.16-3.13 (m, 1H), 2.62 (t, J = 12.0 Hz, 3H), 1.39 (s, 9H). Calculated (M + H): 402.13; Found (M + H): 402.2, HPLC purity: 99.50% |

Example 164

Preparation of 8-(6-(tert-butyl)-5-fluoropyridin-3-yl)-3-((methylthio)methyl)-6-oxo-3,4-dihydro-2H,6H-pyrimido[2,1-b][1,3]oxazine-7-carbonitrile 2

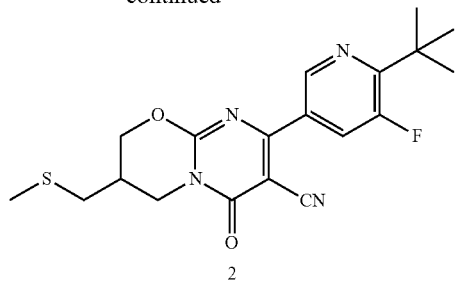

2

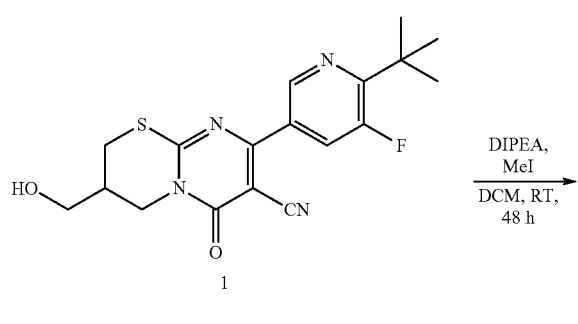

A solution of 8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile (1, 0.09 g, 0.24 mmol) in dichloromethane (6 mL), N,N-diisopropyl ethylamine (0.21 mL, 1.20 mmol) and methyl iodide (0.074 mL, 1.20 mmol) were added and the reaction mixture was stirred at room temperature for 48 h. The reaction mixture was diluted with dichloromethane (30 mL) and washed with water (2×15 mL). The organic layer was dried over anhydrous sodium sulphate, filtered and concentrated. The crude was purified by silica gel column chromatography using 40% ethyl acetate in hexane to afford the title compound 8-(6-(tert-butyl)-5-fluoropyridin-3-yl)-3-((methylthio)methyl)-6-oxo-3,4-dihydro-2H,6H-pyrimido[2,1-b][1,3]oxazine-7-carbonitrile (2 (example 164), 0.03 g, 32% yield) as an off-white solid. $^1$H NMR (400 MHz, DMSO-$d_6$) δ (ppm): 8.83 (s, 1H), 8.01 (d, J=12.8 Hz, 1H), 4.65 (d, J=10.4 Hz, 1H), 4.37 (t, J=7.6 Hz, 1H), 4.16-4.12 (m, 1H), 3.67 (m, 1H), 2.64-2.60 (m, 3H), 2.09 (s, 3H), 1.39 (s, 9H). Calculated (M+H): 389.14; Found (M+H): 389.1. HPLC purity: 99.24%

TABLE 48

The following compounds were prepared by the method described above:

| Ex. # | Structure | IUPAC Name | Analytical Data |
|---|---|---|---|
| 165 | 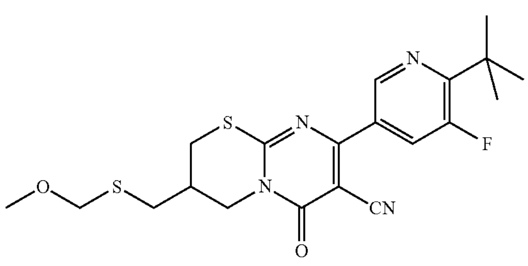 | 8-(6-(tert-butyl)-5-fluoropyridin-3-yl)-3-(((methoxymethyl)thio)methyl)-6-oxo-3,4-dihydro-2H,6H-pyrimido[2,1-b][1,3]oxazine-7-carbonitrile | $^1$H NMR (400 MHz, DMSO-$d_6$) δ (ppm): 8.81 (s, 1H), 8.01 (d, J = 12.8 Hz, 1H), 4.73-4.59 (m, 2H), 4.41 (d, J = 13.6 Hz, 1H), 3.65-3.53 (m, 2H), 3.32-3.15 (m, 6H), 1.39 (s, 9H). 1H merged with DMSO residual peak. Calculated (M + H): 419.15; Found (M + H): 419.1, HPLC purity: 99% |

Examples 166 and 167

Preparation of (S)-8-(6-(tert-butyl)-5-fluoropyridin-3-yl)-3-(methoxymethyl)-6-oxo-3,4-dihydro-2H,6H-pyrimido[2,1-b][1,3]thiazine-7-carbonitrile 2 and (R)-8-(6-(tert-butyl)-5-fluoropyridin-3-yl)-3-(methoxymethyl)-6-oxo-3,4-dihydro-2H,6H-pyrimido[2,1-b][1,3]thiazine-7-carbonitrile 3

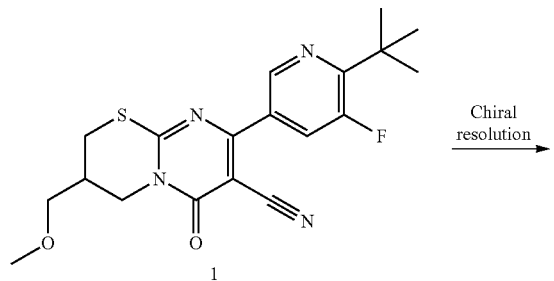

1

→ Chiral resolution

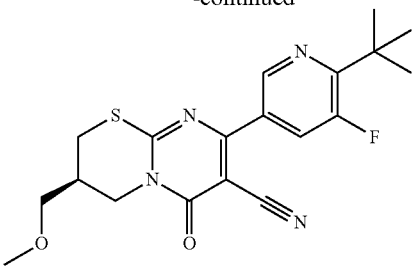

2

+

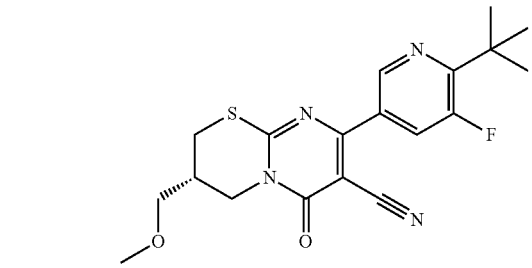

3

The chiral resolution was performed using the analytical condition: column: CHIRALPAK IA (250 mm×4.6 mm×5 mic), mobile phase A: n-hexane, mobile phase B: 0.1% diethyl amine in isopropyl alcohol, composition: 70:30, flow rate: 1.0 mL/min. The analytical data for the enantiomers are given below.

TABLE 49

The following compounds were separated by the method described above

| Ex. # | Structure | IUPAC Name | Analytical Data |
|---|---|---|---|
| 166 | 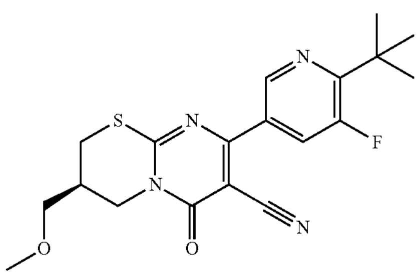 [SMILES: COC[C@H]1CSc2nc(-c3cnc(C(C)(C)C)c(F)c3)c(C#N)c(=O)n2C1] | (S)-8-(6-(tert-butyl)-5-fluoropyridin-3-yl)-3-(methoxymethyl)-6-oxo-3,4-dihydro-2H,6H-pyrimido[2,1-b][1,3]thiazine-7-carbonitrile | 1H NMR (400 MHz, CDCl$_3$) δ (ppm): 9.0 (s, 1H), 7.95 (dd, J = 2.0 Hz, J$_2$ = 12.4 Hz, 1H), 4.6 (dd, J$_1$ = 2.8 Hz, J$_2$ = 15.2 Hz, 1H), 3.64 (dd, J$_1$ = 10.0 Hz, J$_2$ = 14.8 Hz, 1H), 3.56-3.52 (m, 2H), 3.39 (s, 3H), 3.22 (d, J = 8.0 Hz, 2H), 2.5 (bs, 1H), 1.44 (d, J = 0.8 Hz, 9H). Calculated (M + H): 389.14; Found (M + H): 389.3, chiral HPLC purity: 96.16% |
| 167 | 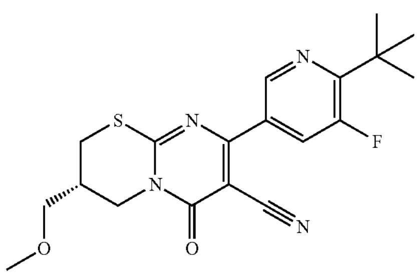 [SMILES: COC[C@@H]1CSc2nc(-c3cnc(C(C)(C)C)c(F)c3)c(C#N)c(=O)n2C1] | (R)-8-(6-(tert-butyl)-5-fluoropyridin-3-yl)-3-(methoxymethyl)-6-oxo-3,4-dihydro-2H,6H-pyrimido[2,1-b][1,3]thiazine-7-carbonitrile | $^1$H NMR (400 MHz, CDCl$_3$) δ (ppm): 8.99 (s, 1H), 7.93 (dd, J$_1$ = 1.6 Hz, J$_2$ = 12.0 Hz, 1H), 4.6 (dd, J$_1$ = 2.8 Hz, J$_2$ = 15.2 Hz, 1H), 3.63 (dd, J$_1$ = 9.6 Hz, J$_2$ = 14.4 Hz, 1H), 3.57-3.49 (m, 2H), 3.39 (s, 3H), 3.21 (d, J = 8.0 Hz, 2H), 2.53-2.48 (m, 1H), 1.43 (d, J = 0.8 Hz, 9H). Calculated (M + H): 389.14; Found (M + H): 389.3, chiral HPLC purity: 98.75% |

Examples 168 and 169

Preparation of (R)—N-((8-(6-(tert-butyl)-5-fluoro-pyridin-3-yl)-7-cyano-6-oxo-3,4-dihydro-2H,6H-pyrimido[2,1-b][1,3]thiazin-3-yl)methyl)acetamide 2 and (S)—N-((8-(6-(tert-butyl)-5-fluoropyridin-3-yl)-7-cyano-6-oxo-3,4-dihydro-2H,6H-pyrimido[2,1-b][1,3]thiazin-3-yl)methyl)acetamide 3

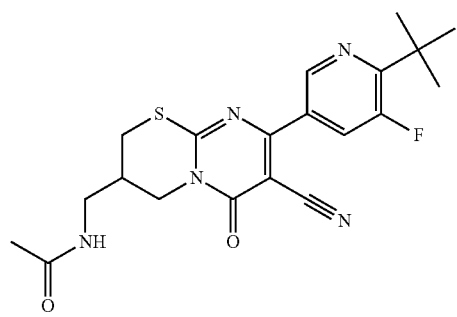

1

→ Chiral resolution

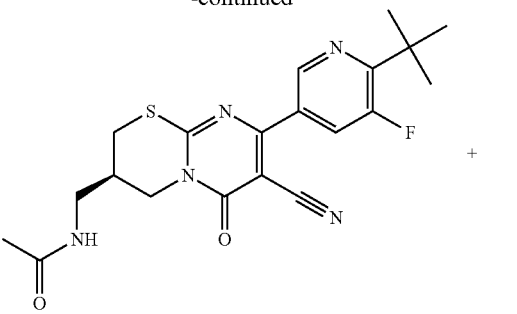

2

+

3

The chiral resolution was performed using the analytical condition: column: CHIRALPAK IC (250 mm×4.6 mm×5 mic), mobile phase: methyl tert-butyl ether:ethanol with 0.1% diethyl amine (70:30), flow rate: 1.0 mL/min. The analytical data for the enantiomers are given below.

TABLE 50

The following compounds were separated by the method described above

| Ex. # | Structure | IUPAC Name | Analytical Data |
|---|---|---|---|
| 168 | 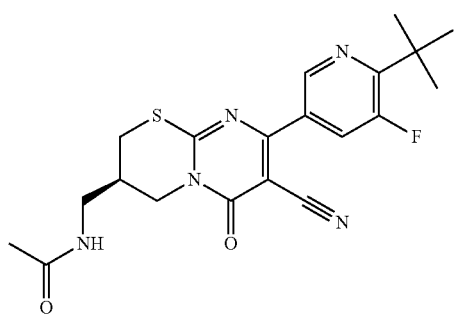 [SMILES: CC(=O)NC[C@H]1CSc2nc(-c3cnc(C(C)(C)C)c(F)c3)c(C#N)c(=O)n2C1] | (R)-N-((8-(6-(tert-butyl)-5-fluoropyridin-3-yl)-7-cyano-6-oxo-3,4-dihydro-2H,6H-pyrimido[2,1-b][1,3]thiazin-3-yl)methyl)acetamide | $^1$H NMR (400 MHz, DMSO-$d_6$) δ (ppm): 8.81 (s, 1H), 8.10 (t, J = 5.6, 1H), 8.01-7.98 (m, 1H), 4.30 (d, J = 14.4 Hz, 1H), 3.60-3.54 (m, 1H), 3.25-3.08 (m, 4H), 2.36 (bs, 1H), 1.83 (s, 3H), 1.39 (s, 9H). Calculated (M + H): 416.15; Found (M + H): 416.3, chiral HPLC purity: 99.99% |

TABLE 50-continued

The following compounds were separated by the method described above

| Ex. # | Structure | IUPAC Name | Analytical Data |
|---|---|---|---|
| 169 | 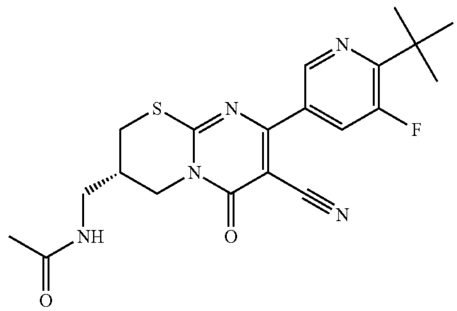 [SMILES: CC(=O)NC[C@@H]1CSc2nc(-c3cnc(C(C)(C)C)c(F)c3)c(C#N)c(=O)n2C1] | (S)-N-((8-(6-(tert-butyl)-5-fluoropyridin-3-yl)-7-cyano-6-oxo-3,4-dihydro-2H,6H-pyrimido[2,1-b][1,3]thiazin-3-yl)methyl)acetamide | $^1$NMR (400 MHz, DMSO-$d_6$) δ (ppm): 8.81 (s, 1H), 8.13-8.08 (m, 1H), 8.00 (dd, $J_1$ = 1.6 Hz, $J_2$ =12.4 Hz, 1H), 4.30 (d, J = 13.2 Hz, 1H), 3.60-3.53 (m, 1H), 3.25-3.08 (m, 4H), 2.36 (bs, 1H), 1.80 (s, 3H), 1.38 (s, 9H). Calculated (M + H): 416.15; Found (M + H): 416.3, chiral HPLC purity: 98.68% |

Example 170

Preparation of 8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile 2

Examples 171 and 172

Preparation of (S)-8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile 2 and (R)-8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile 3

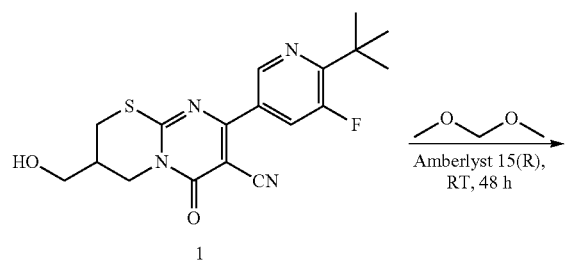

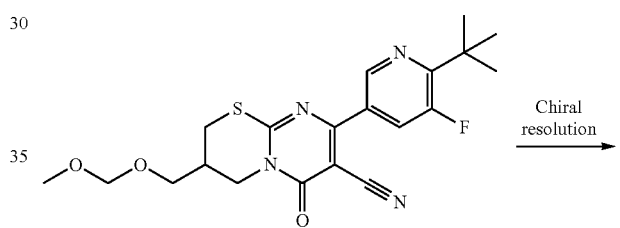

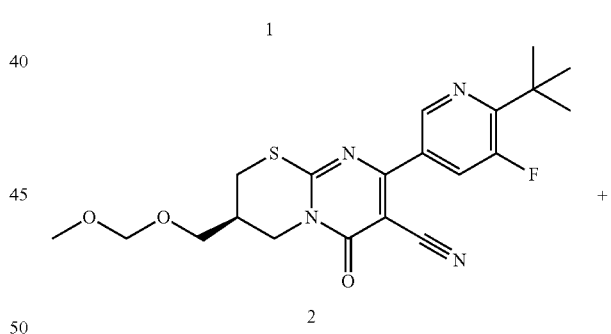

A mixture of 8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile (1, 0.2 g, 0.53 mmol), dimethoxymethane (5 mL) and amberlyst 15(R) (0.1 g) was stirred at room temperature for 48 h. The reaction mixture was filtered, filtrate was concentrated under reduced pressure and the residue was purified by silica gel column chromatography using 25% ethyl acetate in hexane to afford the title compound 8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile (2 (example 170), 0.06 g, 27% yield) as a white solid. $^1$H NMR (400 MHz, CDCl$_3$) δ (ppm): 9.01 (s, 1H), 7.95 (d, J=12.4 Hz, 1H), 4.65-4.62 (m, 3H), 3.69-3.64 (m, 3H), 3.38 (s, 3H), 3.23 (d, J=6.4 Hz, 2H), 2.55 (bs, 1H), 1.44 (s, 9H). Calculated (M+H): 419.15; Found (M+H): 419.0. HPLC purity: 99.21%

The chiral resolution was performed using the analytical condition: Column: CHIRALPAK IC (250 mm×4.6 mm×5 mic), mobile phase: methyl tert-butyl ether: ethanol with 0.1% diethyl amine (50:50), flow rate: 1.0 mL/min. The analytical data for the enantiomers are given below.

TABLE 51

The following compounds were separated by the method described above

| Ex. # | Structure | IUPAC Name | Analytical Data |
|---|---|---|---|
| 171 | 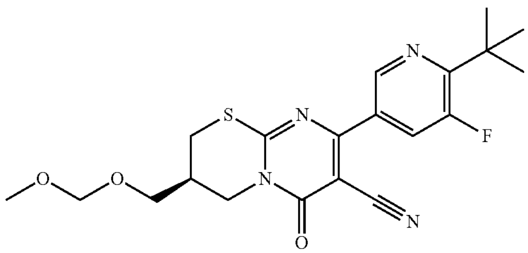 [SMILES: COCOC[C@H]1CSc2nc(-c3cnc(C(C)(C)C)c(F)c3)c(C#N)c(=O)n2C1] | (S)-8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile | $^1$H NMR (400 MHz, CDCl3) δ (ppm): 9.0 (s, 1H), 7.94 (dd, $J_1$ = 2.0 Hz, $J_2$ = 12.4 Hz, 1H), 4.65-4.59 (m, 3H), 3.71-3.65 (m, 3H), 3.38 (s, 3H), 3.23 (d, J = 8.0 Hz, 2H), 2.56-2.55 (m, 1H), 1.43 (s, 9H); Calculated (M + H): 419.14; Found (M + H): 419.0, chiral HPLC purity: 99.78% |
| 172 | 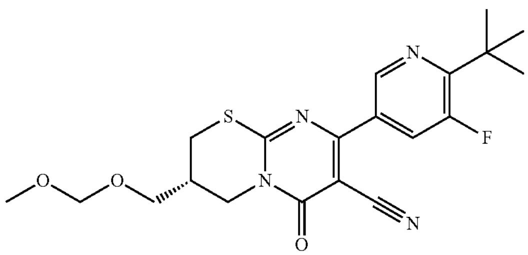 [SMILES: COCOC[C@@H]1CSc2nc(-c3cnc(C(C)(C)C)c(F)c3)c(C#N)c(=O)n2C1] | (R)-8-(6-(tert-butyl)-5-fluoropyridin-3-yl)-3-((methoxymethoxy)methyl)-6-oxo-3,4-dihydro-2H,6H-pyrimido[2,1-b][1,3]thiazine-7-carbonitrile | $^1$H NMR (400 MHz, CDCl3) δ (ppm): 9.0 (s, 1H), 7.94 (dd, $J_1$ = 2.0 Hz, $J_2$ = 12.4 Hz, 1H), 4.65-4.59 (m, 3H), 3.71-3.65 (m, 3H), 3.38 (s, 3H), 3.23 (d, J = 8.0 Hz, 2H), 2.6-2.52 (m, 1H), 1.43 (s, 9H); Calculated (M + H): 419.14; Found (M + H): 419.0, chiral HPLC purity: 97.26% |

Example 173

Preparation of 3-(tert-butoxymethyl)-8-(6-(tert-butyl)-5-fluoropyridin-3-yl)-6-oxo-3,4-dihydro-2H,6H-pyrimido[2,1-b][1,3]thiazine-7-carbonitrile 2

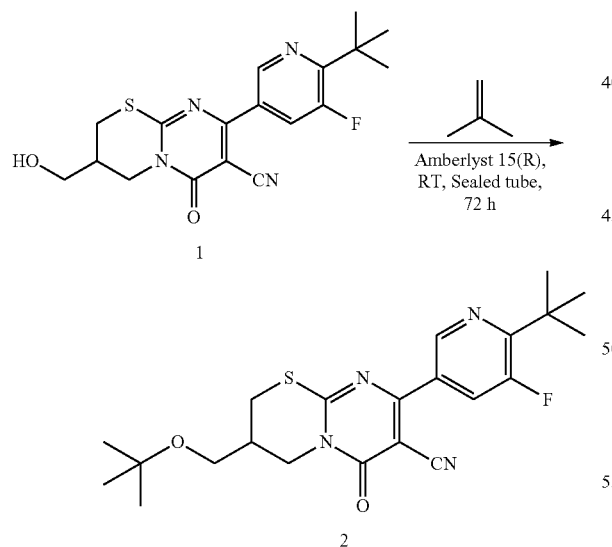

A mixture of 8-(6-(tert-butyl)-5-fluoropyridin-3-yl)-3-(hydroxymethyl)-6-oxo-3,4-dihydro-2H,6H-pyrimido[2,1-b][1,3]thiazine-7-carbonitrile (1, 0.25 g, 0.667 mmol), 2-methylprop-1-ene (50 mL, 15% in tetrahydrofuran) and amberlyst 15(R) (0.2 g) was stirred at room temperature for 72 h in a sealed tube. The reaction mixture was filtered, the filtrate was concentrated under reduced pressure and the residue was purified by silica gel column chromatography using 30% ethyl acetate in hexane followed by preparative TLC (mobile phase: 30% ethyl acetate in hexane) to afford the title compound 3-(tert-butoxymethyl)-8-(6-(tert-butyl)-5-fluoropyridin-3-yl)-6-oxo-3,4-dihydro-2H,6H-pyrimido[2,1-b][1,3]thiazine-7-carbonitrile (2 (example 173), 0.03 g, 109/6 yield) as a white solid. $^1$H NMR (400 MHz, CDCl$_3$) δ (ppm): 8.99 (s, 1H), 7.94 (d, J=12.8 Hz, 1H), 4.56 (d, J=15.2 Hz, 1H), 3.69 (dd, $J_1$=9.6 Hz, $J_2$=14.8 Hz, 1H), 3.54-3.46 (m, 2H), 3.26-3.21 (m, 2H), 2.43 (bs, 1H), 1.43 (s, 9H), 1.19 (s, 9H). Calculated (M+H): 431.19; Found (M+H): 431.1. HPLC purity: 99.9%

Example 174: Synthesis of 8-(6-tert-butyl-3-pyridinyl)-3,4-dihydro-6-oxo-2H,6H-pyrimido[2,1-b][1,3]thiazine-7-carbonitrile 3

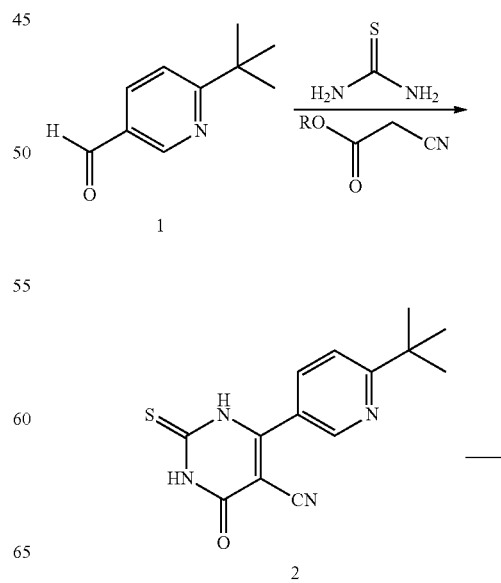

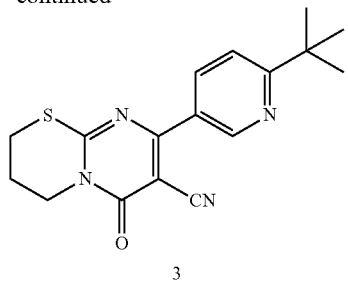

3

To a solution of 6-tert-butylpyridine-3-carbaldehyde (1.22 g, 7.5 mmol), ethyl cyanoacetate (0.85 g, 7.5 mmol) and thiourea (0.57 g, 7.5 mmol) in absolute ethanol (10 mL), potassium carbonate (1.03 g, 7.5 mmol) was added. The reaction mixture was refluxed for 12 hrs. Following completion, the solvent was removed and the residue was poured into ice-cold water with stirring. The solution was neutralized with glacial acetic acid. The precipitated solid was filtered and washed with water and dried to give 1,2,3,4-tetrahydro-4-oxo-6-(6-tert-butyl-3-pyridinyl)-2-thioxo-5-pyrimidinecarbonitrile 2 as a light yellow solid (1.7 g). MS: m/z=287.1 (M+1), retention time: 1.49 min. The material was used for next step without further purification.

A mixture of 1,2,3,4-tetrahydro-4-oxo-6-(6-tert-butyl-3-pyridinyl)-2-thioxo-5-pyrimidinecarbonitrile (69 mg, 0.24 mmol), 1,3-dibromopropane (52 mg, 0.26 mmol) and triethylamine (50 mg, 0.49 mmol) in DMF (5 mL) was heated at 80° C. for three hours. The mixture was cooled to room temperature and water was added (10 mL) to form a solid. The solid was filtered and purified by preparative TLC with hexane and ethyl acetate to give product 3 (example 174) (50 mg, 60%). $^{1}$H NMR (400 MHz, CDCl$_3$): 1.40 (s, 9H), 2.36 (m, 2H), 3.24 (t, 2H), 4.20 (t, 2H), 7.42 (d, 1H), 8.22 (d, 1H), 9.16 (s, 1H). MS: m/z=327.2 (M+1), retention time: 1.75 min.

Examples 175-183

TABLE 52

The following compounds were prepared by the method described above:

| Ex. # | Structure | IUPAC Name | Analytical Data |
|---|---|---|---|
| 175 | 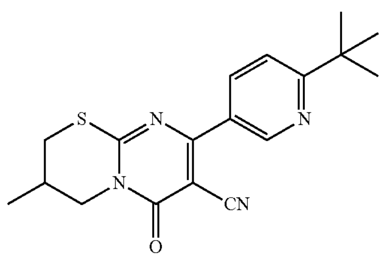 [SMILES: CC1CSc2nc(-c3ccc(C(C)(C)C)nc3)c(C#N)c(=O)n2C1] | 8-(6-tert-butylpyridin-3-yl)-3-methyl-6-oxo-2H,3H,4H,6H-pyrimido[2,1-b][1,3]thiazine-7-carbonitrile | 1.27 (d, 3H), 1.38 (s, 9H), 2.40 (m, 1H), 3.00 (m, 1H), 3.18 (m, 1H), 3.44 (m,1H), 4.56 (m, 1H), 7.42 (d, 1H), 8.24 (d, 1H), 9.16 (s, 1H). MW = 340.44; MS = 341: HPLC = 1.85 min |
| 176 | 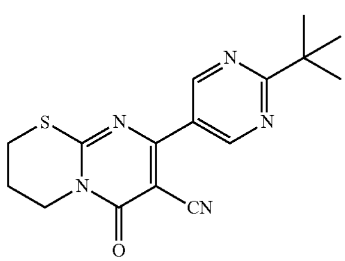 [SMILES: CC(C)(C)c1ncc(-c2nc3n(c(=O)c2C#N)CCCS3)cn1] | 8-(2-tert-butylpyrimidin-5-yl)-6-oxo-2H,3H,4H,6H-pyrimido[2,1-b][1,3]thiazine-7-carbonitrile | 1.42 (s, 9H), 2.38 (m, 2H), 3.26 (t, 2H), 4.20 (t, 2H), 9.24 (s, 2H). MW = 327.4; MS = 328: HPLC |
| 177 | 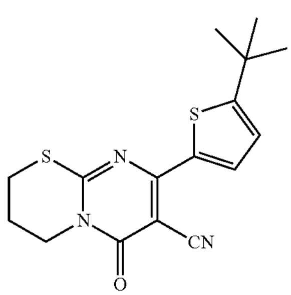 [SMILES: CC(C)(C)c1ccc(-c2nc3n(c(=O)c2C#N)CCCS3)s1] | 8-(5-tert-butylthiophen-2-yl)-6-oxo-2H,3H,4H,6H-pyrimido[2,1-b][1,3]thiazine-7-carbonitrile | MW = 331.46; MS = 332: HPLC = 1.56 min |

TABLE 52-continued

The following compounds were prepared by the method described above:

| Ex. # | Structure | IUPAC Name | Analytical Data |
|---|---|---|---|
| 178 | 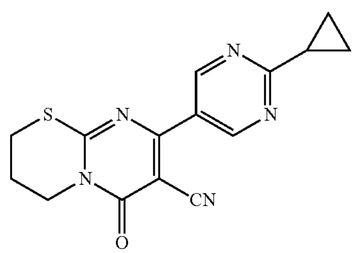 [SMILES: N#Cc1c(-c2cnc(C3CC3)nc2)nc2n(c1=O)CCCS2] | 8-(2-cyclopropylpyrimidin-5-yl)-6-oxo-2H,3H,4H,6H-pyrimido[2,1-b][1,3]thiazine-7-carbonitrile | MW = 311.36; MS = 312: HPLC = 1.99 min |
| 179 | 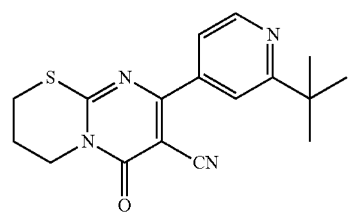 [SMILES: CC(C)(C)c1cc(-c2nc3n(c(=O)c2C#N)CCCS3)ccn1] | 8-(2-tert-butylpyridin-4-yl)-6-oxo-2H,3H,4H,6H-pyrimido[2,1-b][1,3]thiazine-7-carbonitrile | MW = 326.42; MS = 327: HPLC = 1.65 min |
| 180 | 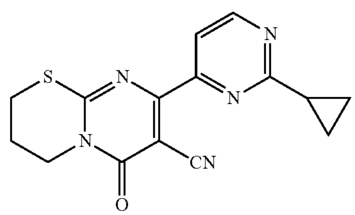 [SMILES: N#Cc1c(-c2ccnc(C3CC3)n2)nc2n(c1=O)CCCS2] | 8-(2-cyclopropylpyrimidin-4-yl)-6-oxo-2H,3H,4H,6H-pyrimido[2,1-b][1,3]thiazine-7-carbonitrile | MW = 311.36; MS = 312: HPLC = 1.56 min |
| 181 | 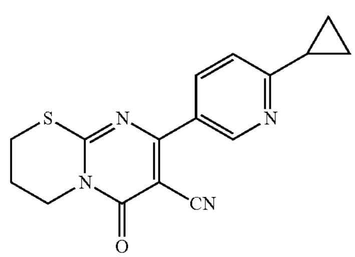 [SMILES: N#Cc1c(-c2ccc(C3CC3)nc2)nc2n(c1=O)CCCS2] | 8-(6-cyclopropylpyridin-3-yl)-6-oxo-2H,3H,4H,6H-pyrimido[2,1-b][1,3]thiazine-7-carbonitrile | MW = 310.37; MS = 311: HPLC = 1.57 min |
| 182 | 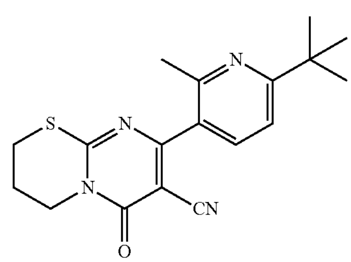 [SMILES: Cc1nc(C(C)(C)C)ccc1-c1nc2n(c(=O)c1C#N)CCCS2] | 8-(6-tert-butyl-2-methylpyridin-3-yl)-6-oxo-2H,3H,4H,6H-pyrimido[2,1-b][1,3]thiazine-7-carbonitrile | MW = 340.44; MS = 341: HPLC = 1.78 min |
| 183 | 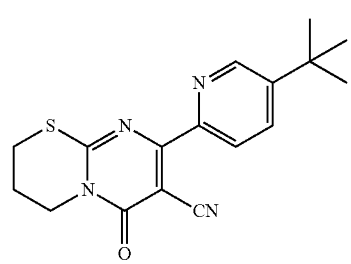 [SMILES: CC(C)(C)c1ccc(-c2nc3n(c(=O)c2C#N)CCCS3)nc1] | 8-(5-tert-butylpyridin-2-yl)-6-oxo-2H,3H,4H,6H-pyrimido[2,1-b][1,3]thiazine-7-carbonitrile | MW = 326.42; MS = 327: HPLC = 1.80 min |

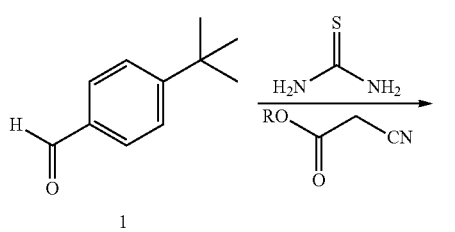

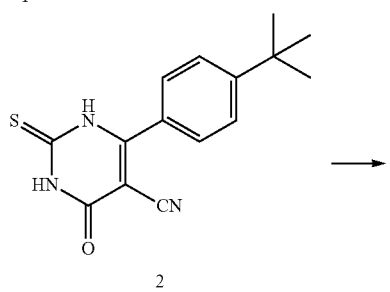

Example 184: Synthesis of 8-(4-tert-butylphenyl)-3,4-dihydro-6-oxo-2H,6H-pyrimido[2,1-b][1,3]thiazine-7-carbonitrile 3

Step 1. Preparation of 6-(4-tert-butylphenyl)-1,2,3,4-tetrahydro-4-oxo-2-thioxo-5-pyrimidinecarbonitrile 2

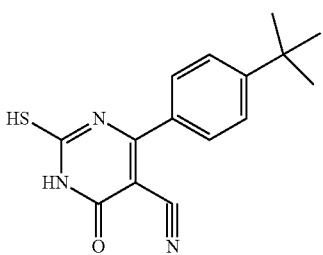 [SMILES: CC(C)(C)c1ccc(-c2nc(S)[nH]c(=O)c2C#N)cc1]

To a solution of 4-tert-butylbenzaldehyde 1 (20.0 g, 0.123 mol), ethyl cyanoacetate (13.9 g, 0.123 mol) and thiourea (9.4 g, 0.123 mol) in absolute ethanol, potassium carbonate (17.1 g, 0.123 mol) was added. The reaction mixture was refluxed for 12 hrs. Following completion, the solvent was removed and the residue was poured into ice-cold water with stirring. The solution was neutralized with glacial acetic acid. The precipitated solid was filtered and washed with water and dried to give 6-(4-tert-butylphenyl)-1,2,3,4-tetrahydro-4-oxo-2-thioxo-5-pyrimidinecarbonitrile 2 as a light yellow solid (29 g, 82%). $^1$H NMR (400 MHz, DMSO-$d_6$): 1.30 (s, 9H), 7.48 (d, 2H), 7.22 (d, 2H), 11.60 (s, 1H), 11.93 (bs, 1H). MS: m/z=286.1 (M+1), retention time: 1.63 min.

Step 2. Preparation of 8-(4-tert-butylphenyl)-3,4-dihydro-6-oxo-2H,6H-pyrimido[2,1-b][1,3]thiazine-7-carbonitrile 3

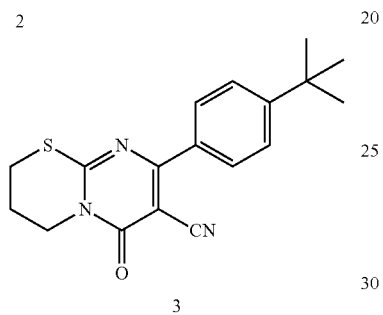

A mixture of 6-(4-tert-butylphenyl)-1,2,3,4-tetrahydro-4-oxo-2-thioxo-5-pyrimidinecarbonitrile 2 (8.2 g, 28.8 mmol), 1,3-dibromopropane (6.1 g, 30.2 mmol) and triethylamine (5.8 g, 60.4 mmol) in DMF (50 mL) was heated at 80° C. for three hours. The mixture was cooled to room temperature and water was added (100 mL) to form a solid. The solid was filtered and washed with a mixture of hexane and ethyl acetate (4:1, 20 mL) to give product 3 (example 184) (6 g, 65%). $^1$H NMR (400 MHz, CDCl$_3$): 7.88 (d, 2H), 7.50 (d, 2H), 4.18 (t, 2H), 3.24 (t, 2H), 2.36 (m, 2H), 1.34 (s, 9J). MS: m/z=326.2 (M+1), retention time: 1.93 min.

Examples 185-193

TABLE 53 the following compounds were prepared by the method described above:

| Ex. # | Structure | IUPAC Name | Analytical Data |
|---|---|---|---|
| 185 | 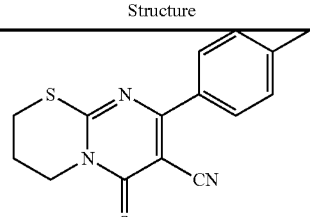 | 8-(4-methylphenyl)-6-oxo-2H,3H,4H,6H-pyrimido[2,1-b][1,3]thiazine-7-carbonitrile | MW = 283.35 |

TABLE 53-continued the following compounds were prepared by the method described above:

| Ex. # | Structure | IUPAC Name | Analytical Data |
|---|---|---|---|
| 186 | 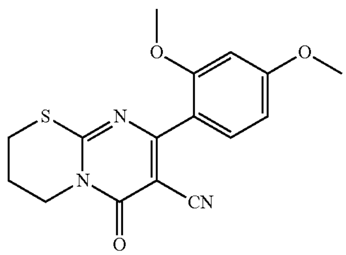 [SMILES: COc1ccc(-c2nc3n(c(=O)c2C#N)CCCS3)c(OC)c1] | 8-(2,4-dimethoxyphenyl)-6-oxo-2H,3H,4H,6H-pyrimido[2,1-b][1,3]thiazine-7-carbonitrile | MW = 329.37; MS = 330: HPLC = 1.55 min |
| 187 | 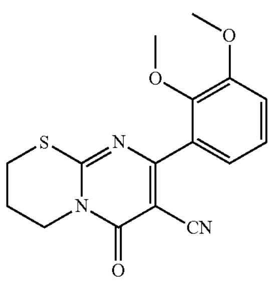 [SMILES: COc1cccc(-c2nc3n(c(=O)c2C#N)CCCS3)c1OC] | 8-(2,3-dimethoxyphenyl)-6-oxo-2H,3H,4H,6H-pyrimido[2,1-b][1,3]thiazine-7-carbonitrile | MW = 329.37; MS = 330: HPLC = 1.54 min |
| 188 | 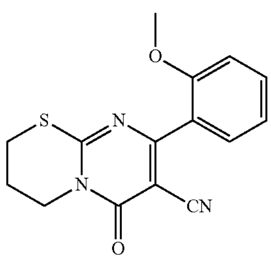 [SMILES: COc1ccccc1-c1nc2n(c(=O)c1C#N)CCCS2] | 8-(2-methoxyphenyl)-6-oxo-2H,3H,4H,6H-pyrimido[2,1-b][1,3]thiazine-7-carbonitrile | MW = 299.35; MS = 300: HPLC = 1.54 min |
| 189 | 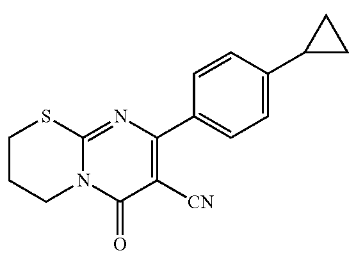 | 8-(4-cyclopropylphenyl)-6-oxo-2H,3H,4H,6H-pyrimido[2,1-b][1,3]thiazine-7-carbonitrile | MW = 309.39; MS = 310: HPLC = 1.79 min |
| 190 | 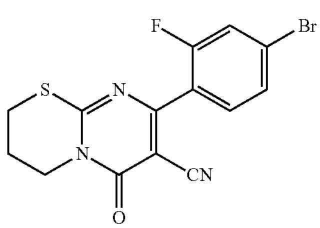 [SMILES: N#Cc1c(-c2ccc(Br)cc2F)nc2n(c1=O)CCCS2] | 8-(4-bromo-2-fluorophenyl)-6-oxo-2H,3H,4H,6H-pyrimido[2,1-b][1,3]thiazine-7-carbonitrile | 2.38 (m, 2H), 3.24 (m, 2H), 4.20 (m, 2H), 7.44 (m, 3H).MW = 366.21; MS = 366: HPLC = 1.74 min |
| 191 | 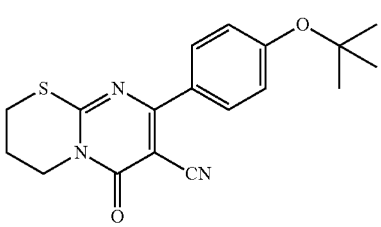 [SMILES: CC(C)(C)Oc1ccc(-c2nc3n(c(=O)c2C#N)CCCS3)cc1] | 8-[4-(tert-butoxy)phenyl]-6-oxo-2H,3H,4H,6H-pyrimido[2,1-b][1,3]thiazine-7-carbonitrile | MW = 341.43; MS = 342: HPLC = 1.86 min |

TABLE 53-continued the following compounds were prepared by the method described above:

| Ex. # | Structure | IUPAC Name | Analytical Data |
|---|---|---|---|
| 192 | 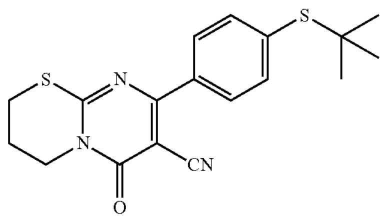 [SMILES: CC(C)(C)Sc1ccc(-c2nc3n(c(=O)c2C#N)CCCS3)cc1] | 8-[4-(tert-butylsulfanyl)phenyl]-6-oxo-2H,3H,4H,6H-pyrimido[2,1-b][1,3]thiazine-7-carbonitrile | MW = 357.49; MS = 358: HPLC = 1.99 min |
| 193 | 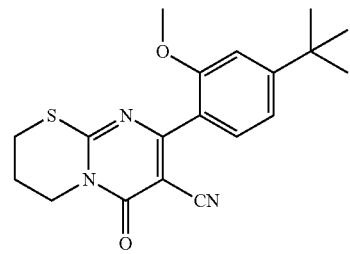 [SMILES: COc1cc(C(C)(C)C)ccc1-c1nc2n(c(=O)c1C#N)CCCS2] | 8-(4-tert-butyl-2-methoxyphenyl)-6-oxo-2H,3H,4H,6H-pyrimido[2,1-b][1,3]thiazine-7-carbonitrile | MW = 355.45; MS = 356: HPLC = 1.88 min |

Example 194: Synthesis of 3,4-dihydro-8-(2-fluoro-4-phenylphenyl)-6-oxo-2H,6H-pyrimido[2,1-b][1,3]thiazine-7-carbonitrile

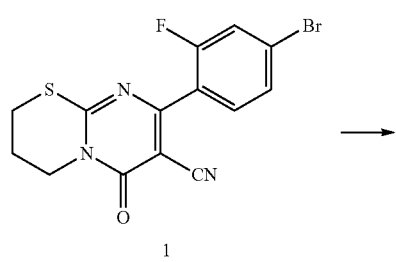

1

-continued

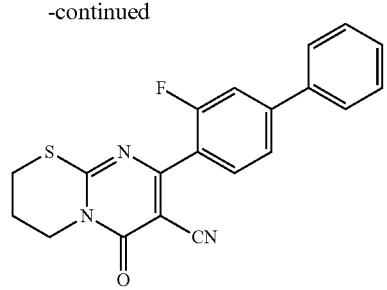

2

To a mixture of 8-(4-bromo-2-fluorophenyl)-3,4-dihydro-6-oxo-2H,6H-pyrimido[2,1-b][1,3]thiazine-7-carbonitrile 1 (50 mg, 0.154 mmol) and phenylboronic acid (24.4 mg, 0.2 mmol) in dioxane (4 mL) was added Pd(PPh$_3$)$_4$ (8.9 mg, 0.07 mmol) and 2M Na$_2$CO$_3$ solution (0.5 mL). The mixture was degassed for 5 min. and heated at 80° C. for three hours. The reaction mixture was cooled to room temperature and diluted with ethyl acetate. The solution was washed with water, dried, and purified by preparative TLC with hexane and ethyl acetate (2:1) to give the product 2 (example 194) (15 mg). MS: m/z=364.0 (M+1), retention time: 1.85 min.

Examples 195-198

TABLE 54

The following compounds were prepared by the method described above:

| Example Number | Structure | IUPAC Name | Analytical Data |
|---|---|---|---|
| 195 | 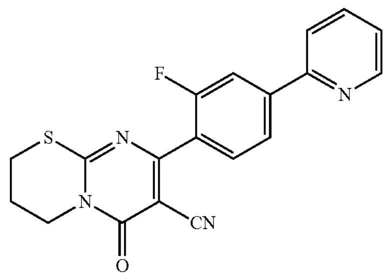 [SMILES: N#Cc1c(-c2ccc(-c3ccccn3)cc2F)nc2n(c1=O)CCCS2] | 8-[2-fluoro-4-(pyridin-2-yl)phenyl]-6-oxo-2H,3H,4H,6H-pyrimido[2,1-b][1,3]thiazine-7-carbonitrile | MW = 364.4; MS = 365: HPLC = 1.61 min |
| 196 | 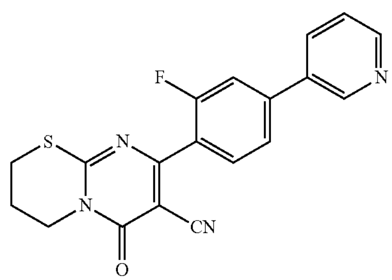 [SMILES: N#Cc1c(-c2ccc(-c3cccnc3)cc2F)nc2n(c1=O)CCCS2] | 8-[2-fluoro-4-(pyridin-3-yl)phenyl]-6-oxo-2H,3H,4H,6H-pyrimido[2,1-b][1,3]thiazine-7-carbonitrile | MW = 364.4; MS = 365: HPLC = 1.33 min |
| 197 | 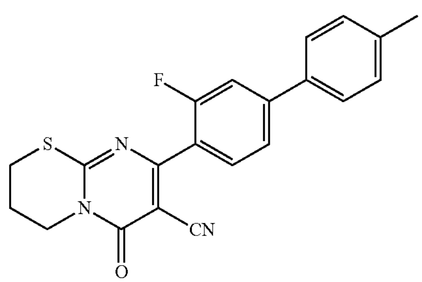 [SMILES: Cc1ccc(-c2ccc(-c3nc4n(c(=O)c3C#N)CCCS4)c(F)c2)cc1] | 8-[2-fluoro-4-(4-methylphenyl)phenyl]-6-oxo-2H,3H,4H,6H-pyrimido[2,1-b][1,3]thiazine-7-carbonitrile | MW = 377.44; MS = 378: HPLC = 1.95 min |
| 198 | 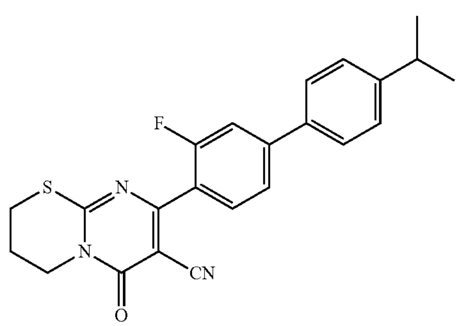 [SMILES: CC(C)c1ccc(-c2ccc(-c3nc4n(c(=O)c3C#N)CCCS4)c(F)c2)cc1] | 8-{2-fluoro-4[4-(propan-2-yl)phenyl]phenyl}-6-oxo-2H,3H,4H,6H-pyrimido[2,1-b][1,3]thiazine-7-carbonitrile | MW = 405.49; MS = 406: HPLC = 2.08 min |

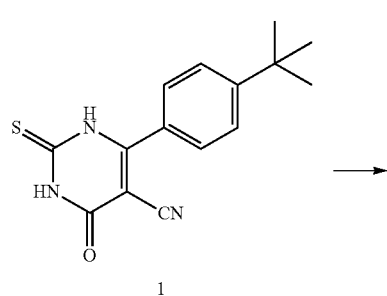

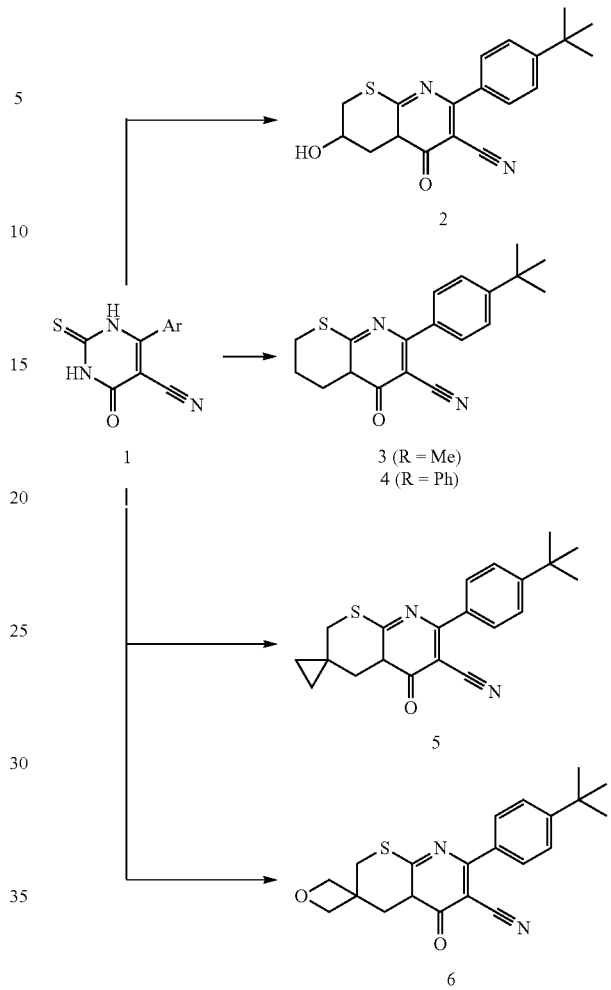

Example 199: Synthesis of 8-(4-tert-butylphenyl)-3,4-dihydro-3-methyl-6-oxo-2H,6H-pyrimido[2,1-b][1,3]thiazine-7-carbonitrile

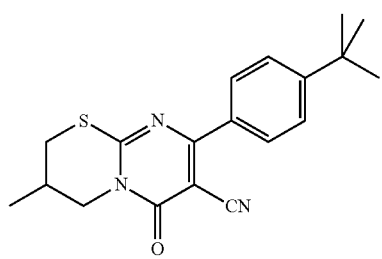 [SMILES: CC1CSc2nc(-c3ccc(C(C)(C)C)cc3)c(C#N)c(=O)n2C1]

A mixture of 6-(4-tert-butylphenyl)-1,2,3,4-tetrahydro-4-oxo-2-thioxo-5-pyrimidinecarbonitrile 1 (100 mg, 0.35 mmol), 1-bromo-3-chloro-2-methylpropane (63 mg, 0.37 mmol) and triethylamine (72 mg, 0.71 mmol) in DMF (5 mL) was heated at 80° C. for three hours. The mixture was cooled to room temperature and water was added (10 mL) to form a solid. The solid was filtered and washed with water, and purified by preparative TLC with hexane and ethyl acetate (1:1) to give product 2 (example 199) (15 mg). $^1$H NMR (400 MHz, CDCl$_3$): 1.27 (d, 3H), 1.32 (s, 9H), 2.40 (m, 1H), 2.98 (m, 1H), 3.14 (m, 1H), 3.42 (m, 1H), 4.56 (m, 1H), 7.50 (d, 2H), 7.94 (d, 2H). MS: m/z=340.1 (M+1), retention time: 2.02 min.

Examples 200-204: The following compounds 2-6 were prepared by the method described above:

Example 200: Synthesis of 8-(4-tert-butylphenyl)-3,4-dihydro-3-hydroxy-6-oxo-2H,6H-pyrimido[2,1-b][1,3]thiazine-7-carbonitrile 2

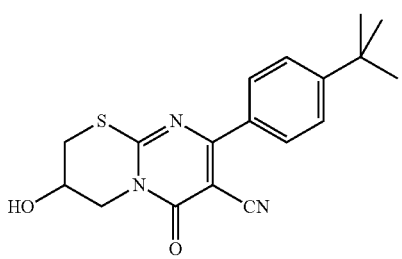 [SMILES: CC(C)(C)c1ccc(-c2nc3n(c(=O)c2C#N)CC(O)CS3)cc1]

A mixture of 6-(4-tert-butylphenyl)-1,2,3,4-tetrahydro-4-oxo-2-thioxo-5-pyrimidinecarbonitrile (1000 mg, 3.5 mmol), epichlorohydrin (351 mg, 3.7 mmol) and triethylamine (720 mg, 7.1 mmol) in DMF (5 mL) was heated at 80° C. for three hours. The mixture was cooled to room temperature and water was added (10 mL) to form a solid. The solid was filtered and washed with water, and purified by column chromatography with hexane and ethyl acetate (1:1) to give product 2 (example 200) (500 mg). ¹H NMR (400 MHz, CDCl₃): 1.40 (s, 9H), 2.42 (m, 2H), 3.24 (m, 1H), 3.86 (m, 1HO, 4.42 (m, 1H), 7.60 (d, 2H), 7.78 (d, 2H), 9.18 (m, 1H). MS: m/z=342.1 (M+1), retention time: 1.78 min.

Example 201: Synthesis of 8-(4-tert-butylphenyl)-3, 4-dihydro-4-methyl-6-oxo-2H,6H-pyrimido[2,1-b][1,3]thiazine-7-carbonitrile 3

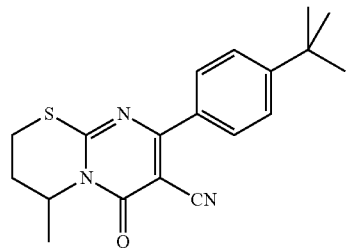 [SMILES: CC1CCSc2nc(-c3ccc(C(C)(C)C)cc3)c(C#N)c(=O)n21]

A mixture of 6-(4-tert-butylphenyl)-1,2,3,4-tetrahydro-4-oxo-2-thioxo-5-pyrimidinecarbonitrile (100 mg, 0.35 mmol), crotyl chloride (35 mg, 0.37 mmol) and triethylamine (72 mg, 0.71 mmol) in DMF (5 mL) was heated at 80° C. for three hours. The mixture was cooled to room temperature and water was added (10 mL) to form a solid. The solid was filtered and washed with water, and purified by preparative TLC with hexane and ethyl acetate (1:1) to give product 3 (example 201) (20 mg). MS: m/z=340.1 (M+1), retention time: 2.07 min.

Example 202: Synthesis of 8-(4-tert-butylphenyl)-3, 4-dihydro-4-phenyl-6-oxo-2H,6H-pyrimido[2,1-b][1.3]thiazine-7-carbonitrile 4

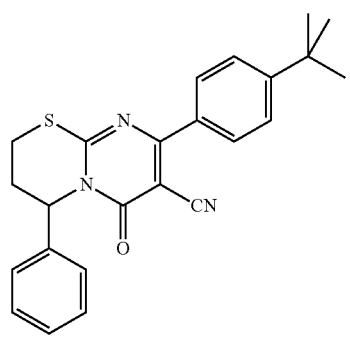 [SMILES: CC(C)(C)c1ccc(-c2nc3n(c(=O)c2C#N)C(c2ccccc2)CCS3)cc1]

A mixture of 6-(4-tert-butylphenyl)-1,2,3,4-tetrahydro-4-oxo-2-thioxo-5-pyrimidinecarbonitrile (100 mg, 0.35 mmol), cinnamyl chloride (56.2 mg, 0.37 mmol) and triethylamine (72 mg, 0.71 mmol) in DMF (5 mL) was heated at 80° C. for three hours. The mixture was cooled to room temperature and water was added (10 mL) to form a solid. The solid was filtered and washed with water, and purified by preparative TLC with hexane and ethyl acetate (1:1) to give product 4 (example 202) (20 mg). MS: m/z=402.1 (M+1), retention time: 2.15 min.

Example 203: Synthesis of 8'-(4-tert-butylphenyl)-6'-oxo-4',6'-dihydro-2'H-spiro[cyclopropane-1,3'-pyrimido[2,1-b][1,3]thiazine]-7'-carbonitrile 5

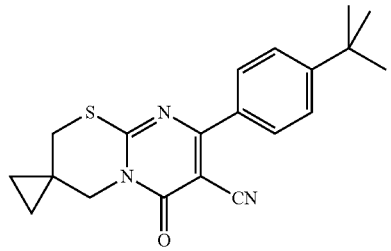 [SMILES: CC(C)(C)c1ccc(-c2nc3n(c(=O)c2C#N)CC2(CC2)CS3)cc1]

A mixture of 6-(4-tert-butylphenyl)-1,2,3,4-tetrahydro-4-oxo-2-thioxo-5-pyrimidinecarbonitrile (100 mg, 0.35 mmol), 1,1-bis(bromomethyl)cyclopropane (83.9 mg, 0.37 mmol) and triethylamine (72 mg, 0.71 mmol) in DMF (5 mL) was heated at 80° C. for three hours. The mixture was cooled to room temperature and water was added (10 mL) to form a solid. The solid was filtered and washed with water, and purified by preparative TLC with hexane and ethyl acetate (1:1) to give product 5 (example 203) (25 mg). MS: m/z=352.1 (M+1), retention time: 2.03 min.

Example 204: Synthesis of 8'-(4-tert-butylphenyl)-6'-oxo-4',6'-dihydro-2'H-spiro[oxetane-3,3'-pyrimido[2,1-b][1,3]thiazine]-7'-carbonitrile 6

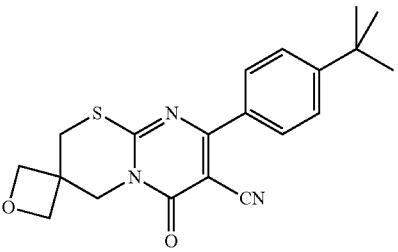 [SMILES: CC(C)(C)c1ccc(-c2nc3n(c(=O)c2C#N)CC2(COC2)CS3)cc1]

A mixture of 6-(4-tert-butylphenyl)-1,2,3,4-tetrahydro-4-oxo-2-thioxo-5-pyrimidinecarbonitrile (100 mg, 0.35 mmol), 3,3-bis(chloromethyl)oxetane (57.1 mg, 0.37 mmol) and triethylamine (72 mg, 0.71 mmol) in DMF (5 mL) was heated at 80° C. for three hours. The mixture was cooled to room temperature and water was added (10 mL) to form a solid. The solid was filtered and washed with water, and purified by preparative TLC with hexane and ethyl acetate (1:1) to give product 6 (example 204) (21 mg). MS: m/z=368.1 (M+1), retention time: 1.87 min.

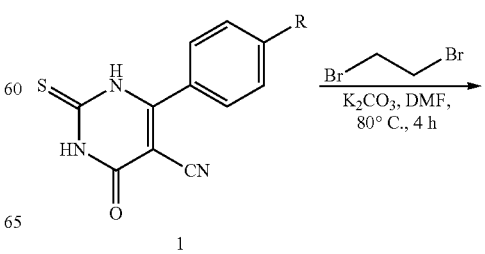

-continued

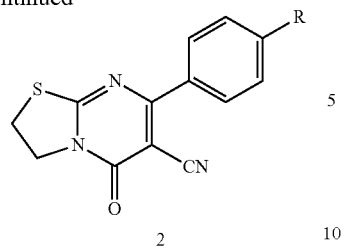

Examples 205-209

TABLE 55

The following compounds were prepared by the method described above: (see example 1 for conditions)

| Example Number | Structure | IUPAC Name | Analytical Data |
|---|---|---|---|
| 205 | 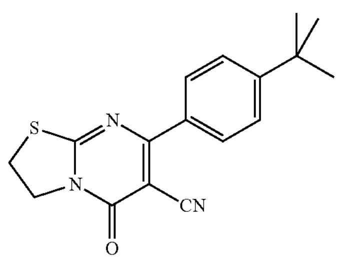 [SMILES: CC(C)(C)c1ccc(-c2nc3n(c(=O)c2C#N)CCS3)cc1] | 7-(4-tert-butylphenyl)-5-oxo-2H,3H,5H-[1,3]thiazolo[3,2-a]pyrimidine-6-carbonitrile | MW = 311.4 |
| 206 | 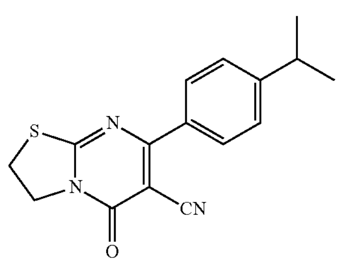 [SMILES: CC(C)c1ccc(-c2nc3n(c(=O)c2C#N)CCS3)cc1] | 5-oxo-7-[4-(propan-2-yl)phenyl]-2H,3H,5H-[1,3]thiazolo[3,2-a]pyrimidine-6-carbonitrile | MW = 297.38 |
| 207 | 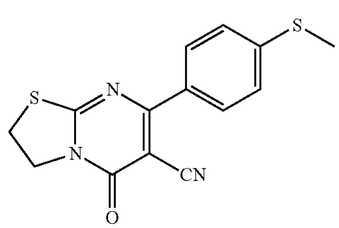 [SMILES: CSc1ccc(-c2nc3n(c(=O)c2C#N)CCS3)cc1] | 7-[4-(methylsulfanyl)phenyl]-5-oxo-2H,3H,5H-[1,3]thiazolo[3,2-a]pyrimidine-6-carbonitrile | MW = 301.39 |
| 208 | 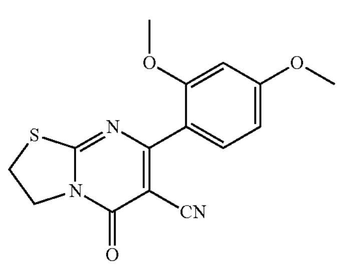 [SMILES: COc1ccc(-c2nc3n(c(=O)c2C#N)CCS3)c(OC)c1] | 7-(2,4-dimethoxyphenyl)-5-oxo-2H,3H,5H-[1,3]thiazolo[3,2-a]pyrimidine-6-carbonitrile | MW = 315.35 |

TABLE 55-continued

The following compounds were prepared by the method described above: (see example 1 for conditions)

| Example Number | Structure | IUPAC Name | Analytical Data |
|---|---|---|---|
| 209 | 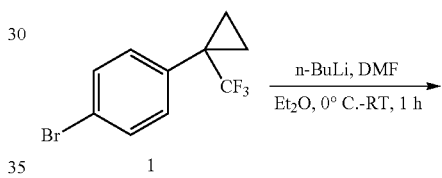 | 7-(4-chlorophenyl)-5-oxo-2H,3H,5H-[1,3]thiazolo[3,2-a]pyrimidine-6-carbonitrile | MW = 289.74 |

Example 210: Synthesis of 3-amino-7-(4-tert-butylphenyl)-5-oxo-5H-thiazolo[3,2-a]pyrimidine-6-carbonitrile 2

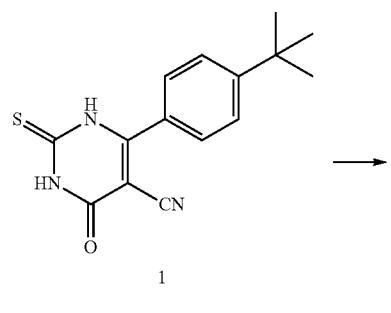

A mixture of 6-(4-tert-butylphenyl)-1,2,3,4-tetrahydro-4-oxo-2-thioxo-5-pyrimidinecarbonitrile 1 (100 mg, 0.35 mmol), chloroacetonitrile (26.4 mg, 0.35 mmol) and triethylamine (36 mg, 0.4 mmol) in ethanol (5 mL) was heated at reflux for three hours. The solvent was removed. Water was added to the residue. The mixture was acidified with concentrated HCl solution. The solid obtained was filtered and purified by preparative TLC to give 3-amino-7-(4-tert-butylphenyl)-5-oxo-5H-Thiazolo[3,2-a]pyrimidine-6-carbonitrile 2 (example 210) as a yellow solid (30 mg). MS: m/z=325.1, retention time: 1.79 min.

Intermediate Synthesis

Preparation of 1-(6-(tert-butyl)pyridin-3-yl)ethan-1-one

Preparation of 4-(1-(trifluoromethyl)cyclopropyl)benzaldehyde

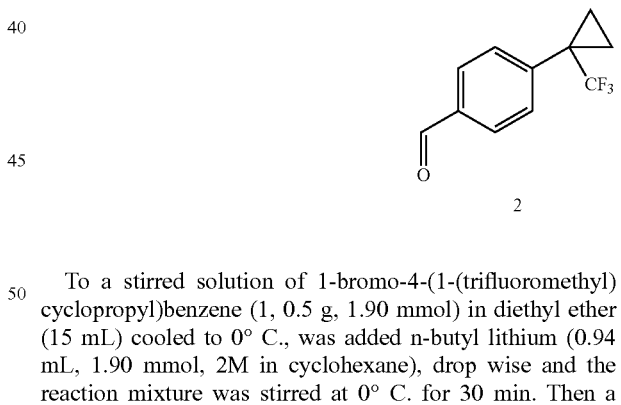

To a stirred solution of 1-bromo-4-(1-(trifluoromethyl)cyclopropyl)benzene (1, 0.5 g, 1.90 mmol) in diethyl ether (15 mL) cooled to 0° C., was added n-butyl lithium (0.94 mL, 1.90 mmol, 2M in cyclohexane), drop wise and the reaction mixture was stirred at 0° C. for 30 min. Then a solution of N,N-dimethyl formamide (0.23 mL, 3.04 mmol) in diethyl ether (5 mL) was added drop wise and the reaction mixture was stirred at 0° C. for 30 min. The reaction mixture was warmed to room temperature, 10% hydrochloric acid solution (10 mL) was added and the layers were separated. The aqueous layer was extracted with diethyl ether (2×50 mL). The combined organic layer was washed with saturated sodium bicarbonate solution, brine, dried over anhydrous sodium sulphate, filtered and concentrated to under not too strong vacuum to afford the title compound 4-(1-(trifluoromethyl)cyclopropyl)benzaldehyde (2, 0.38 g, crude) as colorless liquid. The crude product was as such taken for next step.

Preparation of 6-(3-fluoro-3-methylazetidin-1-yl)nicotinaldehyde

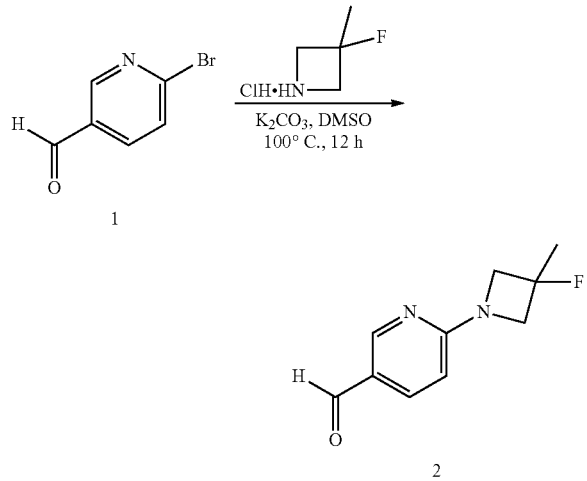

To a solution of 6-bromonicotinaldehyde (1, 1.5 g, 8 mmol) in dimethyl sulphoxide (30 mL), 3-fluoro-3-methyl-azetidine hydrochloride (1.52 g, 12 mmol), potassium carbonate (4.45 g, 32.2 mmol) were added and the reaction mixture was stirred at 100° C. for 12 h. The reaction mixture was cooled to room temperature and diluted with water (100 mL) and extracted with ethyl acetate (2×200 mL). The combined organic layer was washed with brine (100 mL), dried over anhydrous sodium sulfate, filtered and concentrated. The crude product was purified by silica gel column chromatography using 100% ethyl acetate to afford the title compound 6-(3-fluoro-3-methylazetidin-1-yl)nicotinaldehyde (2, 1.1 g, 70% yield) as a brownish solid. Calculated (M+H): 195.09; Found (M+H): 195

Preparation of 1-(6-(1-methylcyclopropyl)pyridin-3-yl)ethan-1-one 2

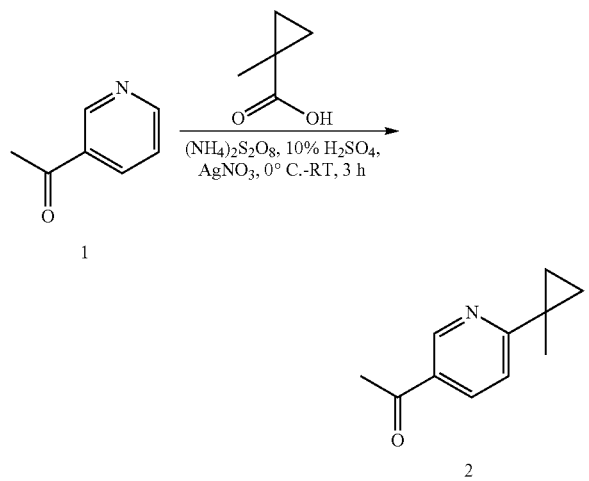

To a solution of 1-(pyridin-3-yl)ethan-1-one (1, 12 g, 99 mmol) in 10% aqueous sulphuric acid solution (150 mL) were added 1-methylcyclopropane-1-carboxylic acid (9.91 g, 99 mmol) and silver nitrate (3.4 g, 19.8 mmol). Then a solution of ammonium persulphate (34 g, 12.39 mmol) in water (150 mL) was added drop wise at 0° C. Then the reaction mixture was stirred at room temperature for 3 h. The reaction mixture was basified with aqueous ammonia and extracted with ethyl acetate (2×500 mL). The combined organic layer was dried over anhydrous sodium sulphate, filtered and concentrated. The crude product was purified by silica gel column chromatography using 10% ethyl acetate in hexane to afford the title compound 1-(6-(1-methylcyclopropyl)pyridin-3-yl)ethan-1-one (2, 1.8 g, 10% yield) as a pale yellow liquid. Calculated (M+H): 176.10; Found (M+H): 176.2.

Preparation of 6-(tert-butyl)-5-methoxynicotinaldehyde 2

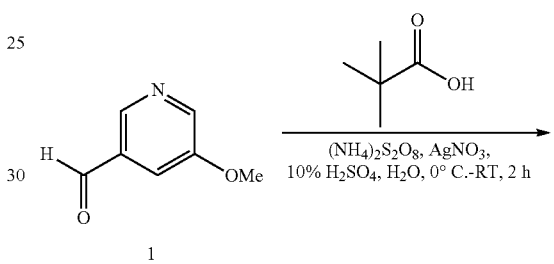

To a stirred solution of 5-methoxynicotinaldehyde (1, 5.0 g, 36.4 mmol), trimethylacetic acid (7.4 g, 72.9 mmol) and silver nitrate (1.2 g, 7.2 mmol) in 10% aqueous sulfuric acid (40 mL), was added a solution of ammonium persulfate (16.6 g, 72.9 mmol) in water (80 mL) drop wise for 30 min at 0° C. The resulting mixture was allowed to stir at room temperature for 2 h (colorless suspension changed into yellow clear solution). The reaction mixture was basified to pH 9 with aqueous ammonia and extracted with ethyl acetate (100 mL×2). The combined organic layer was dried over anhydrous sodium sulphate, filtered and concentrated. The crude product was purified by silica gel column chromatography using 7% ethyl acetate in hexane to afford the title compound 6-(tert-butyl)-5-methoxynicotinaldehyde (2, 2.0 g, 28.4%) as a pale yellow oil. Calculated (M+H): 194.1; Found (M+H): 194.2.

Preparation of 6-(tert-butyl)-5-(methylthio)nicotinaldehyde 4

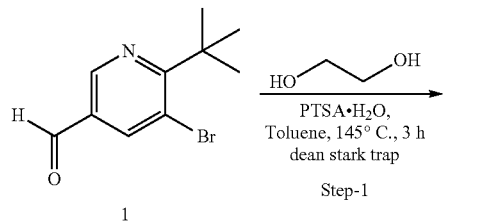

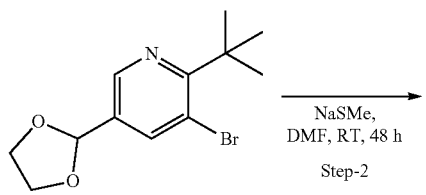

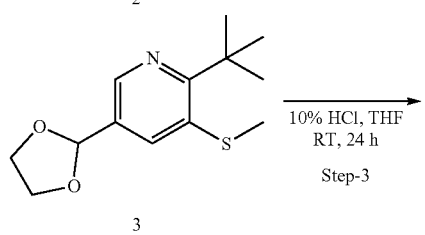

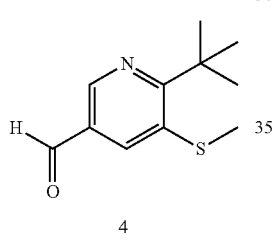

Step-1:

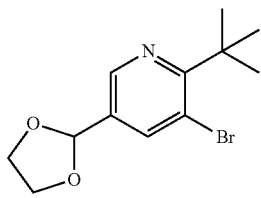 [SMILES: CC(C)(C)c1ncc(C2OCCO2)cc1Br]

Preparation of 3-bromo-2-(tert-butyl)-5-(1,3-dioxolan-2-yl)pyridine

To a stirred solution of 5-bromo-6-(tert-butyl)nicotinaldehyde (1, 2.0 g, 8.26 mmol) in toluene (60 mL), ethane-1,2-diol (9.2 mL, 165.2 mmol), p-toluene sulphonic acid monohydrate (0.78 g, 0.41 mmol) were added and the reaction mixture was refluxed at 145° C. tor 2 h using a Dean stark apparatus. The reaction mixture was diluted with 10% aqueous potassium carbonate solution (50 mL) and extracted with ethyl acetate (2×100 mL). The combined organic layer was dried over anhydrous sodium sulphate, filtered and concentrated. The crude product was purified by silica gel column chromatography using 8% ethyl acetate in hexane to afford the title compound 3-bromo-2-(tert-butyl)-5-(1,3-dioxolan-2-yl)pyridine (2, 2.1 g, 89% yield) as a yellow oil. Calculated (M+H): 288.03; Found (M+H): 288.0.

Step-2:

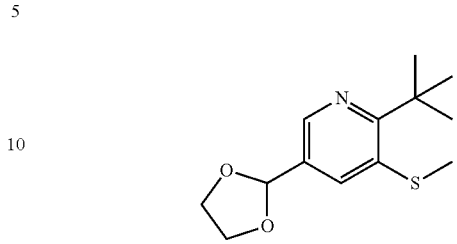

Preparation of 2-(tert-butyl)-5-(1,3-dioxolan-2-yl)-3-(methylthio)pyridine 3

A mixture of 3-bromo-2-(tert-butyl)-5-(1,3-dioxolan-2-yl)pyridine (2, 2.0 g, 1.74 mmol) and sodium methanethiolate (2.5 g, 34.94 mmol) in N,N-dimethylformamide (10 mL) was stirred at room temperature for 48 h. The reaction mixture was diluted with water (30 mL) and extracted with ethyl acetate (2×50 mL). The combined organic layer was washed with brine (50 mL), dried over anhydrous sodium sulphate, filtered and concentrated. The crude product was purified by silica gel column chromatography using 10% ethyl acetate in hexane to afford the title compound 2-(tert-butyl)-5-(1,3-dioxolan-2-yl)-3-(methylthio)pyridine (3, 0.45 g, 25.4% yield) as a colorless oil. Calculated (M+H): 254.1; Found (M+H): 254.1.

Step-3:

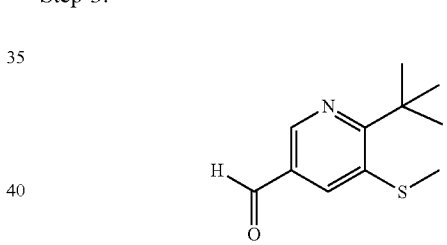

Preparation of 6-(tert-butyl)-5-(methylthio)nicotinaldehyde 4

To a stirred solution of 2-(tert-butyl)-5-(1,3-dioxolan-2-yl)-3-(methylthio)pyridine (3, 0.8 g, 3.15 mmol) in tetrahydrofuran (30 mL), 10% aqueous hydrochloric acid (30 mL) was added drop wise and the reaction mixture was stirred at room temperature for 24 h. The reaction mixture was basified with potassium carbonate and extracted with ethyl acetate (2×100 mL). The combined organic layer was dried over anhydrous sodium sulphate, filtered and concentrated. The crude product was purified by silica gel column chromatography using 5% ethyl acetate in hexane to afford the title compound 6-(tert-butyl)-5-(methylthio)nicotinaldehyde (4, 0.4 g, 60% yield) as a pale green oil. Calculated (M+H): 210.09: Found (M+H): 209.9.

GluN2D PAM CIQ Flourescence Assay HEK293 cells were transfected to express human GRIN1 (variant NR1-3, Origene, SKU #: SC115601, Rockville, MD) and GRIN2D (NCBI locus NM_000836, sequence optimized and synthesized by GenScript) and grown as an adherent monolayer at 37° C., 5% COP in DMEM/Ham's F12+10% FBS (Hyclone SH3007.03T in the presence of 2.5 mM ARL-15896

(AdooQ Bioscience, Irvine CA). To prepare the cells for an experiment, they were rinsed with Dulbecco's PBS ($Ca^{2+}$ and $Mg^{2+}$ free) and detached from the flask with TrypLE™ Express (Life Technologies, Carlsbad, CA) using the manufacturer's recommended methods. Cells collected from the flask were washed twice in $Ca^{2+}/Mg^{2+}$-free Hanks Balanced Salt Solution+20 mM HEPES (HBSS), and counted and assessed for viability with trypan blue. Washed cells were then dye-loaded by resuspending in Fluo-8/AM calcium sensitive dye plus Component B (AAT Bioquest, Sunnyvale, CA) diluted in HBSS. To allow cells to take up fluo-8 dye, they were incubated in the dark for 15 min at 37° C., followed by 30 min at 22-25° C. After dye-loading, cells were washed and resuspended in HBSS and plated in 384-well plates (Falcon 353962; Corning, Big Flats. NY) at 20,000-30,000 cells/well in a final volume of 25 µl/well. The cell plates were centrifuged at 200×g, for 2 minutes at 21° C., to create a monolayer of cells at the bottom of the wells.

To initiate an assay, 10 µl of test compound or buffer was added to each well of the cell plate and pre-incubated for 10 minutes in the dark. After 10 minutes, the cell plate was placed in a FDSS 6000 plate reader (Hamamatsu Photonics, Middlesex, NJ); baseline fluorescence readings were collected for 20 seconds. Next, 25 µl□ of agonist solution (3 µM□ glutamate, 3 µM□ glycine, and 1 mM $Ca^{2+}$ in HBSS) was added and the change in fluorescence was recorded for 3 minutes.

Results were calculated by comparing the effects of test compounds to that of the literature standard GluN2C/D PAM CIQ (100 uM). The increase in fluorescence in the presence of CIQ minus the increase induced by glutamate+glycine alone was set to 100%. Responses induced by compounds that were larger than that ain the presence of the standard concentration of CIQ were greater than 100% and lesser responses were less than 100%.

NR2D Oocyte Potentiation Assay. Xenopus oocytes (*Xenopus* 1, Dexter, MI) were initially separated from the lobes of an ovary using surgical forceps; they were then defolliculated by constant agitation at room temperature in OR-2 buffer (82.5 mM NaCl; 2.5 mM KCl; 1 mM $MgCl_2$; 5 mM HEPES; pH 7.4) containing 2 mg/ml collagenase Type 1 (Fisher Scientific, USA) for 1.5-2 hours. The cells were then gently aspirated with a Pasteur pipette to remove the follicular tissue; this was followed by washing three times with OR-2 to remove all traces of collagenase. The oocytes were then washed in ND-96 (96 mM NaCl, 2 mM KCl, 1.8 mM $CaCl2$, 1 mM $MgCl2$, 5 mM HEPES, 50 ng/L gentamycin, 100 units/ml penicillin and 100 µg/ml streptomycin; pH 7.6) three times and this was followed by incubation in ND-96 at room temperature with mild agitation for 15 minutes; subsequently they were stored for at least 2 hours at 16° C. before sorting and selection for injection. Oocytes selected for injection were incubated overnight in ND-96 at 16° C.

The human GRIN1 (transcript variant NR1-3 (Origene, SKU #: SC115601, Rockville, MD) and GRIN2D (NCBI locus NM_000836, sequence optimized and synthesized by GenScript) were linearized and transcribed using the mMessage mMachine kit (Life Technologies) and promoters SP6 (for GluN1) and T7 (for GluN2D). cRNAs were mixed together at a ratio of 1 GluN1:2 GluN2. Each oocyte was injected with 50 nL of cRNA and stored in ND96 (96 mM NaCl, 2 mM KCl, 1.8 mM $CaCl_2$, 1 mM $MgCl_2$, 5 mM HEPES, 50 ng/L gentamycin, 100 units/ml penicillin and 100 □g/ml streptomycin; pH 7.6) at 16° C.; for 72 h prior to recording.

Currents were recorded using a two-electrode voltage-clamp amplifier (Oocyte Clamp OC-725C; Warner Instrument Corp, Hamden, CT), and digitized using Digidata 1550A and pClamp (v.10) software (Molecular Devices, Sunnyvale, CA). Electrodes were filled with 3 M KCl and had resistances that ranged from 0.2-1 MO. All measurements were made at a holding potential of −40 mV. Cells were continuously perfused with oocyte recording solution containing 90 mM NaCl, 1 mM KCl, 0.5 mM $BaCl_2$, and 10 mM HEPES (Ph 7.4). Glutamate and Glycine (co-agonists) were applied at respective concentrations of 10 µM□ each. Co-agonists were applied until a plateau was reached, and test compounds were then added in the continued presence of co-agonists until a new plateau was reached. After the addition of the last test compound concentration, the oocyte was washed with oocyte recording buffer. Fraction of current remaining was calculated as [(current in presence of test compound−background current)/(co-agonist current−background current)] and $IC_{50}$ values were computed using Prism 6.0 (Graphpad).

The results of the above assay are shown in the ActivityTable

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 1 | (structure shown) | 7-(6-tert-butylpyridin-3-yl)-5-oxo-2H,3H,5H-[1,3]thiazolo[3,2-a]pyrimidine-6-carbonitrile | C16H16N4OS | 312.1045 | ** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 2 | 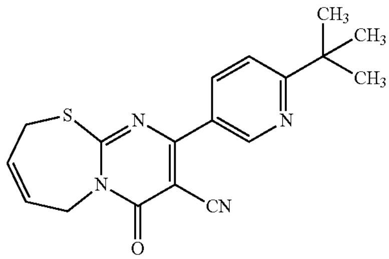 [SMILES: CC(C)(C)c1ccc(-c2nc3n(c(=O)c2C#N)CC=CCS3)cn1] | 2-(6-tert-butylpyridin-3-yl)-4-oxo-4H,6H,9H-pyrimido[2,1-b][1,3]thiazepine-3-carbonitrile | C18H18N4OS | 338.1201 | * | NT |
| 3 | 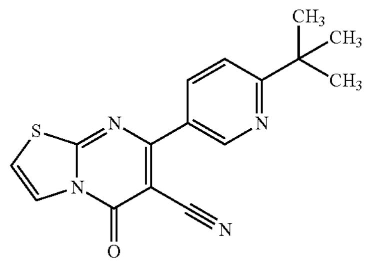 [SMILES: CC(C)(C)c1ccc(-c2nc3sccn3c(=O)c2C#N)cn1] | 7-(6-tert-butylpyridin-3-yl)-5-oxo-5H-[1,3]thiazolo[3,2-a]pyrimidine-6-carbonitrile | C16H14N4OS | 310.0888 | ** | NT |
| 4 | 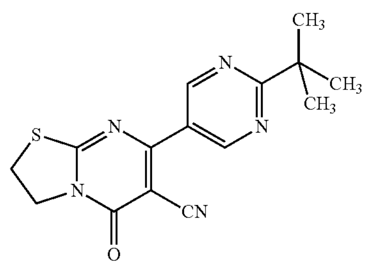 [SMILES: CC(C)(C)c1ncc(-c2nc3n(c(=O)c2C#N)CCS3)cn1] | 7-(2-tert-butylpyrimidin-5-yl)-5-oxo-2H,3H,5H-[1,3]thiazolo[3,2-a]pyrimidine-6-carbonitrile | C15H15N5OS | 313.0997 | ** | NT |
| 5 | 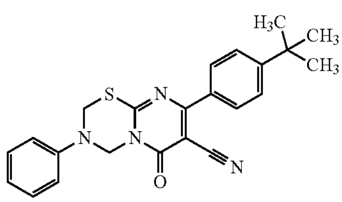 [SMILES: CC(C)(C)c1ccc(-c2nc3n(c(=O)c2C#N)CN(c2ccccc2)CS3)cc1] | 8-(4-tert-butylphenyl)-6-oxo-3-phenyl-2H,3H,4H,6H-pyrimido[2,1-b][1,3,5]thiadiazine-7-carbonitrile | C23H22N4OS | 402.1514 | * | NT |
| 6 | 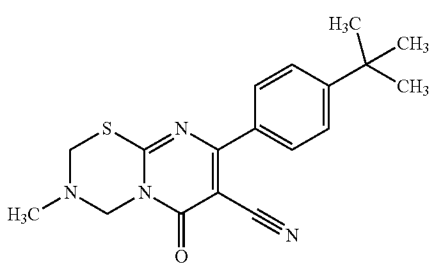 [SMILES: CN1CSc2nc(-c3ccc(C(C)(C)C)cc3)c(C#N)c(=O)n2C1] | 8-(4-tert-butylphenyl)-3-methyl-6-oxo-2H,3H,4H,6H-pyrimido[2,1-b][1,3,5]thiadiazine-7-carbonitrile | C18H20N4OS | 340.1358 | * | NT |
| 7 | 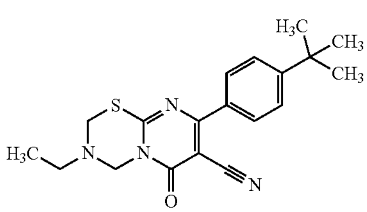 [SMILES: CCN1CSc2nc(-c3ccc(C(C)(C)C)cc3)c(C#N)c(=O)n2C1] | 8-(4-tert-butylphenyl)-3-ethyl-6-oxo-2H,3H,4H,6H-pyrimido[2,1-b][1,3,5]thiadiazine-7-carbonitrile | C19H22N4OS | 354.1514 | * | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 8 | 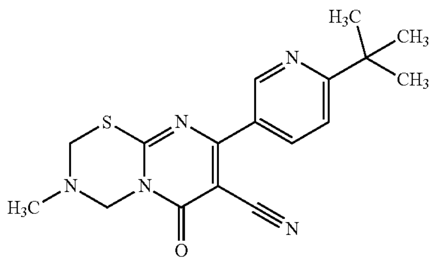 [SMILES: CN1CSc2nc(-c3ccc(C(C)(C)C)nc3)c(C#N)c(=O)n2C1] | 8-(6-tert-butylpyridin-3-yl)-3-methyl-6-oxo-2H,3H,4H,6H-pyrimido[2,1-b][1,3,5]thiadiazine-7-carbonitrile | C17H19N5OS | 341.131 | * | NT |
| 9 | 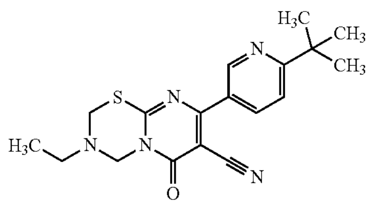 [SMILES: CCN1CSc2nc(-c3ccc(C(C)(C)C)nc3)c(C#N)c(=O)n2C1] | 8-(6-tert-butylpyridin-3-yl)-3-ethyl-6-oxo-2H,3H,4H,6H-pyrimido[2,1-b][1,3,5]thiadiazine-7-carbonitrile | C18H21N5OS | 355.1467 | * | NT |
| 10 | 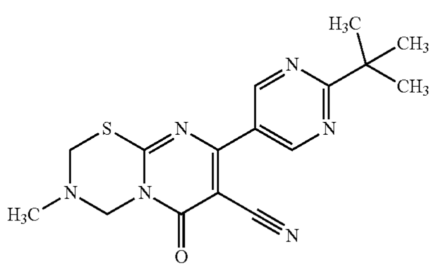 [SMILES: CN1CSc2nc(-c3cnc(C(C)(C)C)nc3)c(C#N)c(=O)n2C1] | 8-(2-tert-butylpyrimidin-5-yl)-3-methyl-6-oxo-2H,3H,4H,6H-pyrimido[2,1-b][1,3,5]thiadiazine-7-carbonitrile | C16H18N6OS | 342.1263 | * | NT |
| 11 | 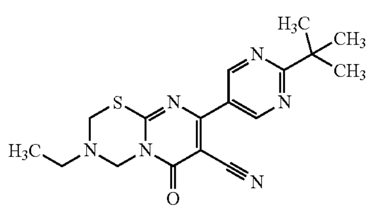 [SMILES: CCN1CSc2nc(-c3cnc(C(C)(C)C)nc3)c(C#N)c(=O)n2C1] | 8-(2-tert-butylpyrimidin-5-yl)-3-ethyl-6-oxo-2H,3H,4H,6H-pyrimido[2,1-b][1,3,5]thiadiazine-7-carbonitrile | C17H20N6OS | 356.1419 | * | NT |
| 12 | 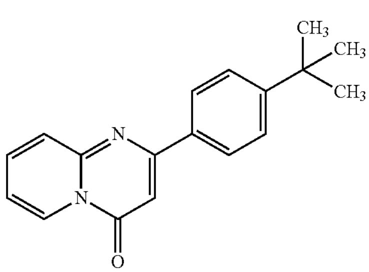 [SMILES: CC(C)(C)c1ccc(-c2cc(=O)n3ccccc3n2)cc1] | 2-(4-tert-butylphenyl)-4H-pyrido[1,2-a]pyrimidin-4-one | C18H18N2O | 278.1419 | * | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 13 | 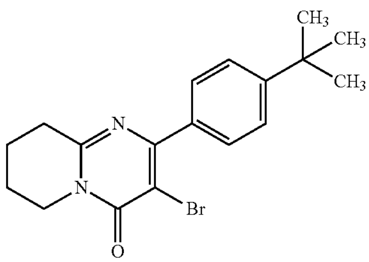 [SMILES: CC(C)(C)c1ccc(-c2nc3n(c(=O)c2Br)CCCC3)cc1] | 3-bromo-2-(4-tert-butylphenyl)-4H,6H,7H,8H,9H-pyrido[1,2-a]pyrimidin-4-one | C18H21BrN2O | 360.0837 | NA | NT |
| 14 | 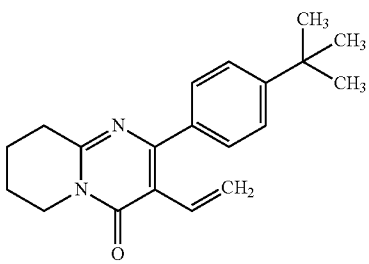 [SMILES: C=Cc1c(-c2ccc(C(C)(C)C)cc2)nc2n(c1=O)CCCC2] | 2-(4-tert-butylphenyl)-3-ethenyl-4H,6H,7H,8H,9H-pyrido[1,2-a]pyrimidin-4-one | C20H24N2O | 308.1889 | NA | NT |
| 15 | 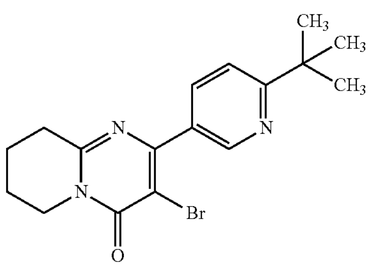 [SMILES: CC(C)(C)c1ccc(-c2nc3n(c(=O)c2Br)CCCC3)cn1] | 3-bromo-2-(6-tert-butylpyridin-3-yl)-4H,6H,7H,8H,9H-pyrido[1,2-a]pyrimidin-4-one | C17H20BrN3O | 361.079 | * | NT |
| 16 | 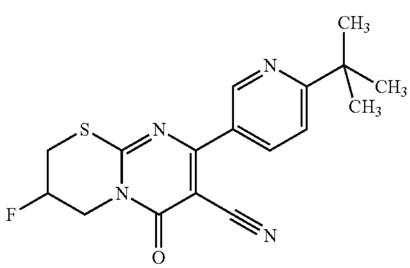 [SMILES: CC(C)(C)c1ccc(-c2nc3n(c(=O)c2C#N)CC(F)CS3)cn1] | 8-(6-tert-butylpyridin-3-yl)-3-fluoro-6-oxo-2H,3H,4H,6H-pyrimido[2,1-b][1,3]thiazine-7-carbonitrile | C17H17FN4OS | 344.1107 | * | NT |
| 17 | 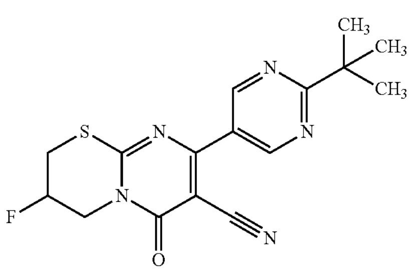 [SMILES: CC(C)(C)c1ncc(-c2nc3n(c(=O)c2C#N)CC(F)CS3)cn1] | 8-(2-tert-butylpyrimidin-5-yl)-3-fluoro-6-oxo-2H,3H,4H,6H-pyrimido[2,1-b][1,3]thiazine-7-carbonitrile | C16H16FN5OS | 345.106 | ** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 18 | 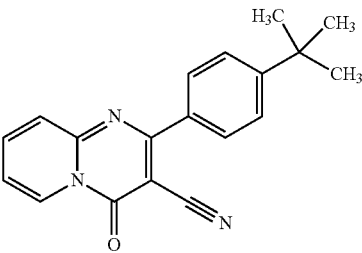 [SMILES: CC(C)(C)c1ccc(-c2nc3ccccn3c(=O)c2C#N)cc1] | 2-(4-tert-butylphenyl)-4-oxo-4H-pyrido[1,2-a]pyrimidine-3-carbonitrile | C19H17N3O | 303.1372 | ** | NT |
| 19 | 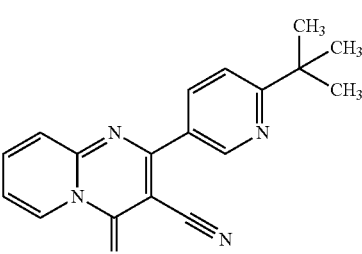 | 2-(6-tert-butylpyridin-3-yl)-4-oxo-4H-pyrido[1,2-a]pyrimidine-3-carbonitrile | C18H16N4O | 304.1324 | ** | NT |
| 20 | 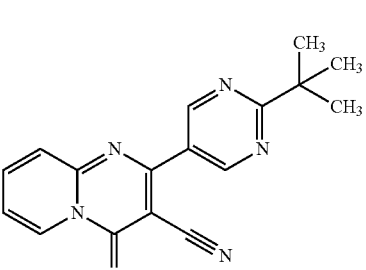 | 2-(2-tert-butylpyrimidin-5-yl)-4-oxo-4H-pyrido[1,2-a]pyrimidine-3-carbonitrile | C17H15N5O | 305.1277 |  | * |
| 21 | 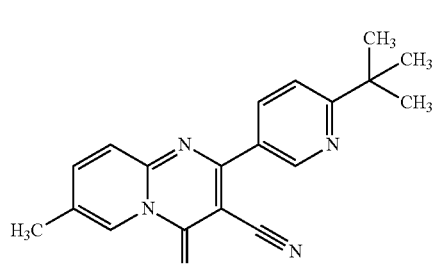 | 2-(6-tert-butylpyridin-3-yl)-7-methyl-4-oxo-4H-pyrido[1,2-a]pyrimidine-3-carbonitrile | C19H18N4O | 318.1481 | ** | NT |
| 22 | 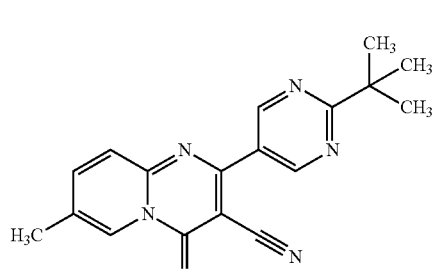 | 2-(2-tert-butylpyrimidin-5-yl)-7-methyl-4-oxo-4H-pyrido[1,2-a]pyrimidine-3-carbonitrile | C18H17N5O | 319.1433 | ** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 23 | 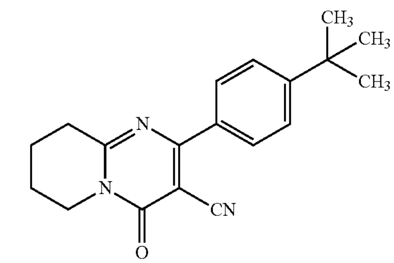 [SMILES: CC(C)(C)c1ccc(-c2nc3n(c(=O)c2C#N)CCCC3)cc1] | 2-(4-tert-butylphenyl)-4-oxo-4H,6H,7H,8H,9H-pyrido[1,2-a]pyrimidine-3-carbonitrile | C19H21N3O | 307.1685 | * | NT |
| 24 | 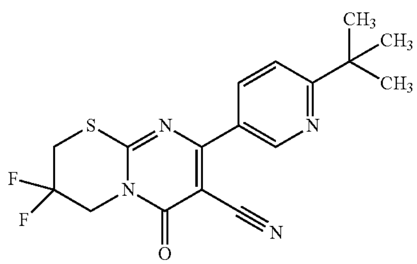 [SMILES: CC(C)(C)c1ccc(-c2nc3n(c(=O)c2C#N)CC(F)(F)CS3)cn1] | 8-(6-tert-butylpyridin-3-yl)-3,3-difluoro-6-oxo-2H,3H,4H,6H-pyrimido[2,1-b][1,3]thiazine-7-carbonitrile | C17H16F2N4OS | 362.1013 | ** | NT |
| 25 | 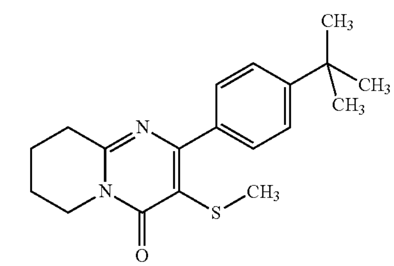 [SMILES: CSc1c(-c2ccc(C(C)(C)C)cc2)nc2n(c1=O)CCCC2] | 2-(4-tert-butylphenyl)-3-(methylsulfanyl)-4H,6H,7H,8H,9H-pyrido[1,2-a]pyrimidin-4-one | C19H24N2OS | 328.1609 | NA | NT |
| 26 | 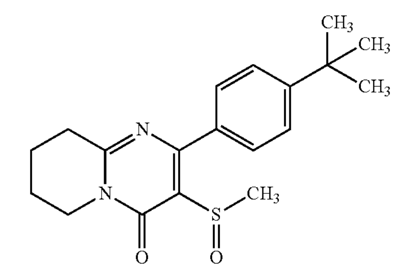 [SMILES: CS(=O)c1c(-c2ccc(C(C)(C)C)cc2)nc2n(c1=O)CCCC2] | 2-(4-tert-butylphenyl)-3-methanesulfinyl-4H,6H,7H,8H,9H-pyrido[1,2-a]pyrimidin-4-one | C19H24N2O2S | 344.1558 | NA | NT |
| 27 | 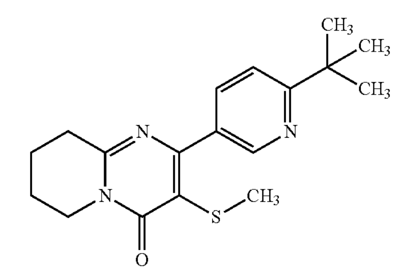 [SMILES: CSc1c(-c2ccc(C(C)(C)C)nc2)nc2n(c1=O)CCCC2] | 2-(6-tert-butylpyridin-3-yl)-3-(methylsulfanyl)-4H,6H,7H,8H,9H-pyrido[1,2-a]pyrimidin-4-one | C18H23N3OS | 329.1562 | NA | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 28 | 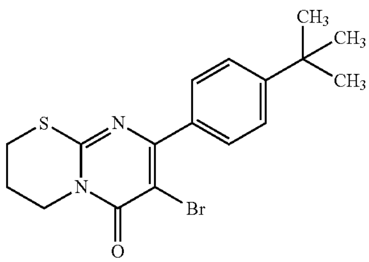 [SMILES: CC(C)(C)c1ccc(-c2nc3n(c(=O)c2Br)CCCS3)cc1] | 7-bromo-8-(4-tert-butylphenyl)-2H,3H,4H,6H-pyrimido[2,1-b][1,3]thiazin-6-one | C17H19BrN2OS | 378.0401 | ** | NT |
| 29 | 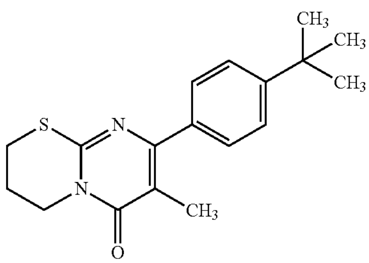 [SMILES: Cc1c(-c2ccc(C(C)(C)C)cc2)nc2n(c1=O)CCCS2] | 8-(4-tert-butylphenyl)-7-methyl-2H,3H,4H,6H-pyrimido[2,1-b][1,3]thiazin-6-one | C18H22N2OS | 314.1453 | * | NT |
| 30 | 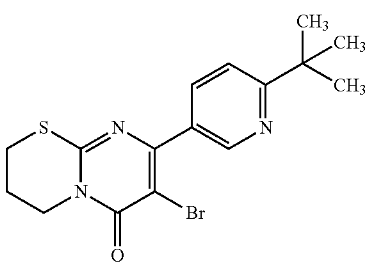 [SMILES: CC(C)(C)c1ccc(-c2nc3n(c(=O)c2Br)CCCS3)cn1] | 7-bromo-8-(6-tert-butylpyridin-3-yl)-2H,3H,4H,6H-pyrimido[2,1-b][1,3]thiazin-6-one | C16H18BrN3OS | 379.0354 | ** | NT |
| 31 | 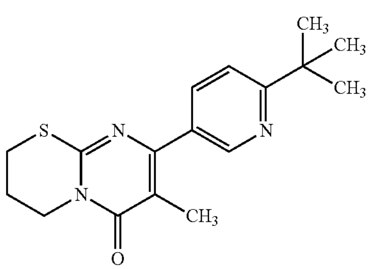 [SMILES: Cc1c(-c2ccc(C(C)(C)C)nc2)nc2n(c1=O)CCCS2] | 8-(6-tert-butylpyridin-3-yl)-7-methyl-2H,3H,4H,6H-pyrimido[2,1-b][1,3]thiazin-6-one | C17H21N3OS | 315.1405 | * | NT |
| 32 | 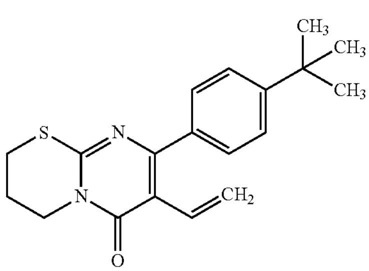 [SMILES: C=Cc1c(-c2ccc(C(C)(C)C)cc2)nc2n(c1=O)CCCS2] | 8-(4-tert-butylphenyl)-7-ethenyl-2H,3H,4H,6H-pyrimido[2,1-b][1,3]thiazin-6-one | C19H22N2OS | 326.1453 | * | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 33 | 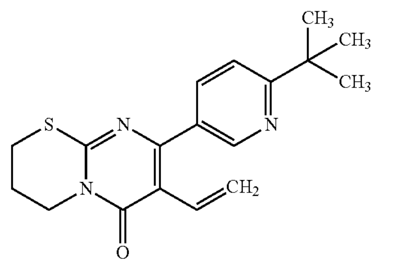 [SMILES: C=Cc1c(-c2ccc(C(C)(C)C)nc2)nc2n(c1=O)CCCS2] | 8-(6-tert-butylpyridin-3-yl)-7-ethenyl-2H,3H,4H,6H-pyrimido[2,1-b][1,3]thiazin-6-one | C18H21N3OS | 327.1405 | * | NT |
| 34 | 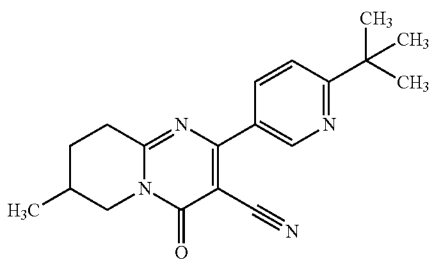 [SMILES: CC1CCc2nc(-c3ccc(C(C)(C)C)nc3)c(C#N)c(=O)n2C1] | 2-(6-tert-butylpyridin-3-yl)-7-methyl-4-oxo-4H,6H,7H,8H,9H-pyrido[1,2-a]pyrimidine-3-carbonitrile | C19H22N4O | 322.1794 | * | NT |
| 35 | 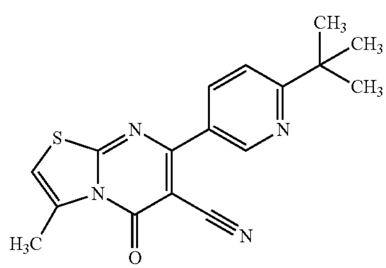 [SMILES: Cc1csc2nc(-c3ccc(C(C)(C)C)nc3)c(C#N)c(=O)n12] | 7-(6-tert-butylpyridin-3-yl)-3-methyl-5-oxo-5H-[1,3]thiazolo[3,2-a]pyrimidine-6-carbonitrile | C17H16N4OS | 324.1045 | ** | NT |
| 36 | 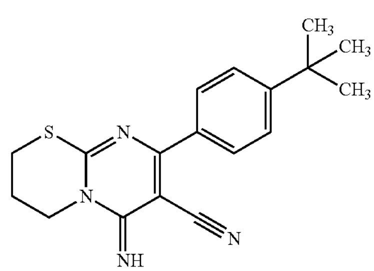 [SMILES: CC(C)(C)c1ccc(-c2nc3n(c(=N)c2C#N)CCCS3)cc1] | 8-(4-tert-butylphenyl)-6-imino-2H,3H,4H,6H-pyrimido[2,1-b][1,3]thiazine-7-carbonitrile | C18H20N4S | 324.1409 | * | * |
| 37 | 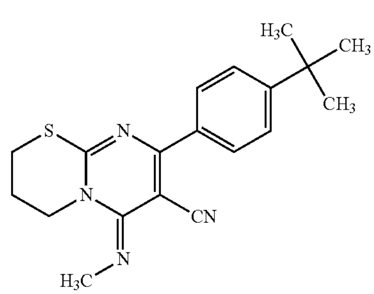 [SMILES: C/N=c1/c(C#N)c(-c2ccc(C(C)(C)C)cc2)nc2n1CCCS2] | (6Z)-8-(4-tert-butylphenyl)-6-(methylimino)-2H,3H,4H,6H-pyrimido[2,1-b][1,3]thiazine-7-carbonitrile | C19H22N4S | 338.1565 | * | ** |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 38 | 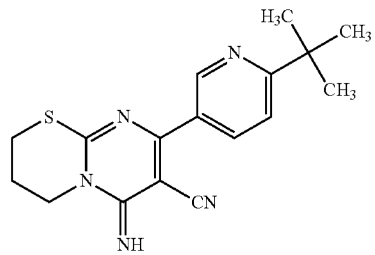 [SMILES: CC(C)(C)c1ccc(-c2nc3n(c(=N)c2C#N)CCCS3)cn1] | 8-(6-tert-butylpyridin-3-yl)-6-imino-2H,3H,4H,6H-pyrimido[2,1-b][1,3]thiazine-7-carbonitrile | C17H19N5S | 325.1361 | ** | * |
| 39 | 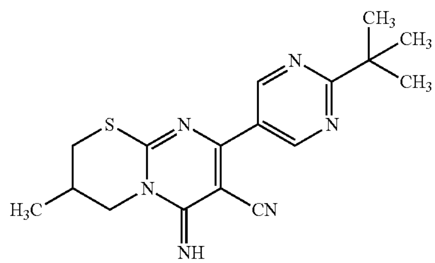 [SMILES: CC1CSc2nc(-c3cnc(C(C)(C)C)nc3)c(C#N)c(=N)n2C1] | 8-(2-tert-butylpyrimidin-5-yl)-6-imino-3-methyl-2H,3H,4H,6H-pyrimido[2,1-b][1,3]thiazine-7-carbonitrile | C17H20N6S | 340.147 | ** | ** |
| 40 | 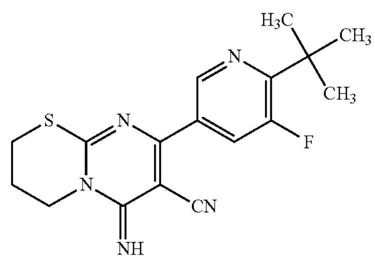 [SMILES: CC(C)(C)c1ncc(-c2nc3n(c(=N)c2C#N)CCCS3)cc1F] | 8-(6-tert-butyl-5-fluoropyridin-3-yl)-6-imino-2H,3H,4H,6H-pyrimido[2,1-b][1,3]thiazine-7-carbonitrile | C17H18FN5S | 343.1267 | **** | NT |
| 41 | 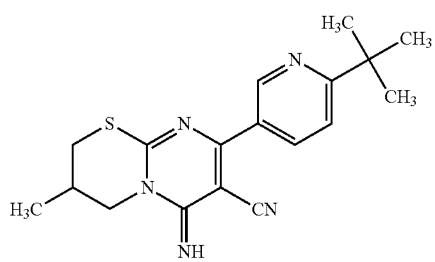 [SMILES: CC1CSc2nc(-c3ccc(C(C)(C)C)nc3)c(C#N)c(=N)n2C1] | 8-(6-tert-butyl-5-fluoropyridin-3-yl)-6-imino-3-methyl-2H,3H,4H,6H-pyrimido[2,1-b][1,3]thiazine-7-carbonitrile | C18H20FN5S | 357.1423 | **** | NT |
| 42 | 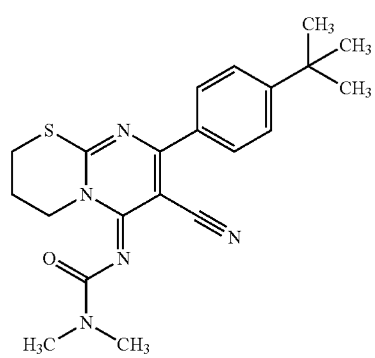 [SMILES: CN(C)C(=O)/N=c1/c(C#N)c(-c2ccc(C(C)(C)C)cc2)nc2n1CCCS2] | 1-[(6Z)-8-(4-tert-butylphenyl)-7-cyano-2H,3H,4H,6H-pyrimido[2,1-b][1,3]thiazin-6-ylidene]-3,3-dimethylurea | C21H25N5OS | 395.178 |  | * |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 43 | 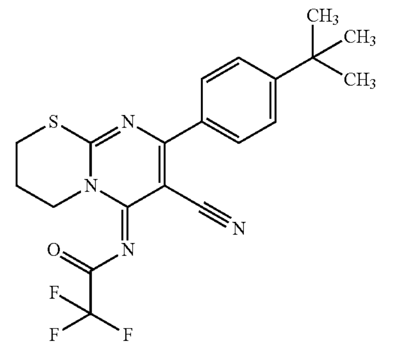 [SMILES: CC(C)(C)c1ccc(-c2nc3n(/c(=N\C(=O)C(F)(F)F)c2C#N)CCCS3)cc1] | N-[(6Z)-8-(4-tert-butylphenyl)-7-cyano-2H,3H,4H,6H-pyrimido[2,1-b][1,3]thiazin-6-ylidene]-2,2,2-trifluoro-acetamide | C20H19F3N4OS | 420.1232 | ** | * |
| 44 | 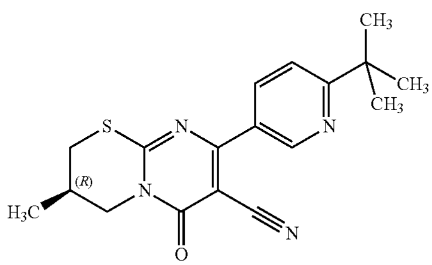 | (3R)-8-(6-tert-butylpyridin-3-yl)-3-methyl-6-oxo-2H,3H,4H,6H-pyrimido[2,1-b][1,3]thiazine-7-carbonitrile | C18H20N4OS | 340.1358 |  | * |
| 45 | 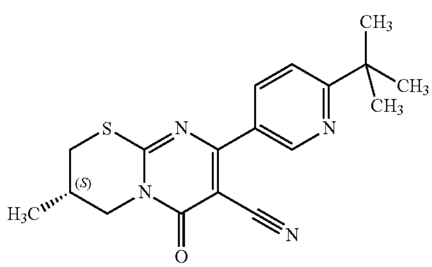 | (3S)-8-(6-tert-butylpyridin-3-yl)-3-methyl-6-oxo-2H,3H,4H,6H-pyrimido[2,1-b][1,3]thiazine-7-carbonitrile | C18H20N4OS | 340.1358 | ** | ** |
| 46 | 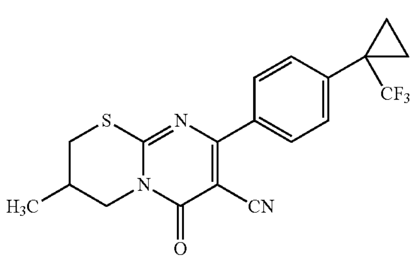 [SMILES: CC1CSc2nc(-c3ccc(C4(C(F)(F)F)CC4)cc3)c(C#N)c(=O)n2C1] | 3-methyl-6-oxo-8-[4-[1-(trifluoromethyl)cyclopropyl]phenyl}-2H,3H,4H,6H-pyrimido[2,1-b][1,3]thiazine-7-carbonitrile | C19H16F3N3OS | 391.0966 | ** | NT |
| 47 | 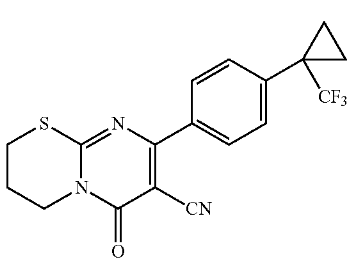 [SMILES: N#Cc1c(-c2ccc(C3(C(F)(F)F)CC3)cc2)nc2n(c1=O)CCCS2] | 6-oxo-8-1{4-[1-(trifluoromethyl)cyclopropyl]phenyl}-2H,3H,4H,6H-pyrimido[2,1-b][1,3]thiazine-7-carbonitrile | C18H14F3N3OS | 377.081 | *** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 48 | 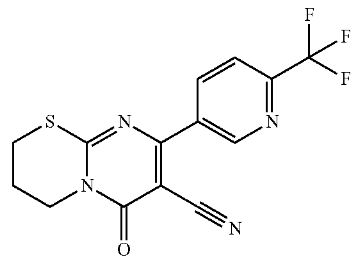 [SMILES: N#Cc1c(-c2ccc(C(F)(F)F)nc2)nc2n(c1=O)CCCS2] | 6-oxo-8-[6-(trifluoromethyl)pyridin-3-yl]-2H,3H,4H,6H-pyrimido[2,1-b][1,3]thiazine-7-carbonitrile | C14H9F3N4OS | 338.0449 | NA | * |
| 49 | 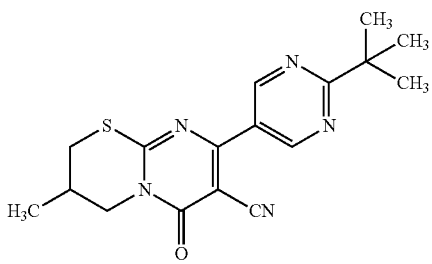 [SMILES: CC1CSc2nc(-c3cnc(C(C)(C)C)nc3)c(C#N)c(=O)n2C1] | 8-(2-tert-butylpyrimidin-5-yl)-3-methyl-6-oxo-2H,3H,4H,6H-pyrimido[2,1-b][1,3]thiazine-7-carbonitrile | C17H19N5OS | 341.131 | ** | ** |
| 50 | 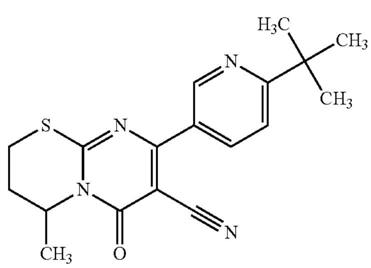 [SMILES: CC1CCSc2nc(-c3ccc(C(C)(C)C)nc3)c(C#N)c(=O)n21] | 8-(6-tert-butylpyridin-3-yl)-4-methyl-6-oxo-2H,3H,4H,6H-pyrimido[2,1-b][1,3]thiazine-7-carbonitrile | C18H20N4OS | 340.1358 |  | * |
| 51 | 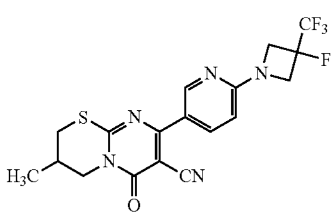 [SMILES: CC1CSc2nc(-c3ccc(N4CC(F)(C(F)(F)F)C4)nc3)c(C#N)c(=O)n2C1] | 8-[6-(3-fluoro-3-methylazetidin-1-yl)pyridin-3-yl]-3-methyl-6-oxo-2H,3H,4H,6H-pyrimido[2,1-b][1,3]thiazine-7-carbonitrile | C18H18FN5OS | 371.1216 | Inhibitor | NT |
| 52 | 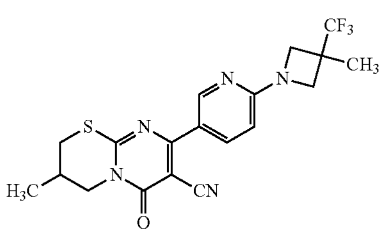 | 8-[6-(3,3-dimethylazetidin-1-yl)pyridin-3-yl]-3-methyl-6-oxo-2H,3H,4H,6H-pyrimido[2,1-b][1,3]thiazine-7-carbonitrile | C19H21N5OS | 367.1467 | Inhibitor | NT |

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 53 | 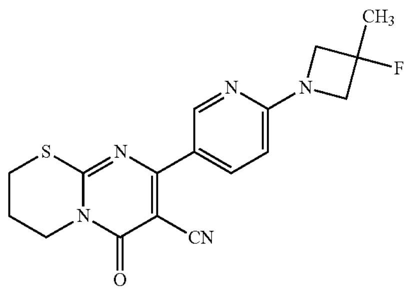 [SMILES: CC1(F)CN(c2ccc(-c3nc4n(c(=O)c3C#N)CCCS4)cn2)C1] | 8-[6-(3-fluoro-3-methylazetidin-1-yl)pyridin-3-yl]-6-oxo-2H,3H,4H,6H-pyrimido[2,1-b][1,3]thiazine-7-carbonitrile | C17H16FN5OS | 357.106 | Inhibitor | NT |
| 54 | 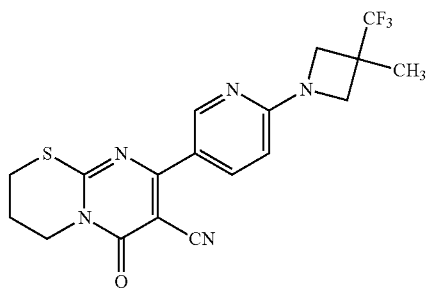 [SMILES: CC1(C(F)(F)F)CN(c2ccc(-c3nc4n(c(=O)c3C#N)CCCS4)cn2)C1] | 8-[6-(3,3-dimethylazetidin-1-yl)pyridin-3-yl]-6-oxo-2H,3H,4H,6H-pyrimido[2,1-b][1,3]thiazine-7-carbonitrile | C18H19N5OS | 353.131 | Inhibitor | NT |
| 55 | 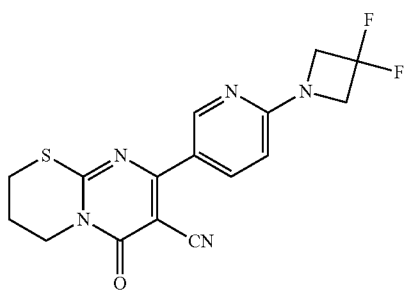 [SMILES: N#Cc1c(-c2ccc(N3CC(F)(F)C3)nc2)nc2n(c1=O)CCCS2] | 8-[6-(3,3-difluoroazetidin-1-yl)pyridin-3-yl]-6-oxo-2H,3H,4H,6H-pyrimido[2,1-b][1,3]thiazine-7-carbonitrile | C16H13F2N5OS | 361.0809 | Inhibitor | NT |
| 56 | 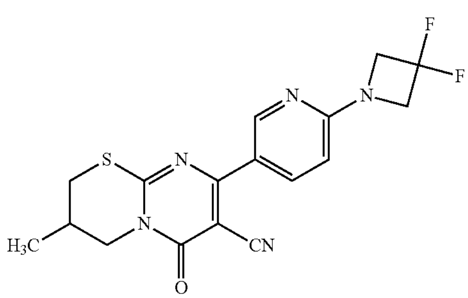 [SMILES: CC1CSc2nc(-c3ccc(N4CC(F)(F)C4)nc3)c(C#N)c(=O)n2C1] | 8-[6-(3,3-difluoroazetidin-1-yl)pyridin-3-yl]-3-methyl-6-oxo-2H,3H,4H,6H-pyrimido[2,1-b][1,3]thiazine-7-carbonitrile | C17H15F2N5OS | 375.0965 | Inhibitor | NT |
| 57 | 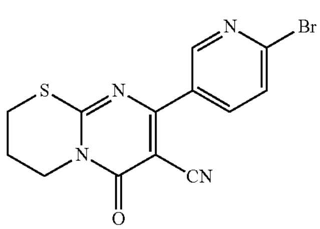 [SMILES: N#Cc1c(-c2ccc(Br)nc2)nc2n(c1=O)CCCS2] | 8-(6-bromopyridin-3-yl)-6-oxo-2H,3H,4H,6H-pyrimido[2,1-b][1,3]thiazine-7-carbonitrile | C13H9BrN4OS | 347.968 | * | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 58 | 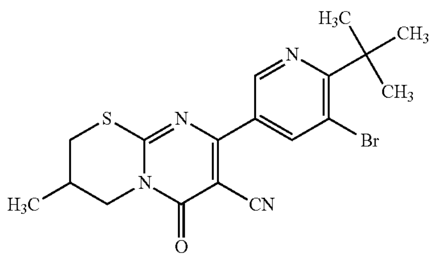 [SMILES: CC1CSc2nc(-c3cnc(C(C)(C)C)c(Br)c3)c(C#N)c(=O)n2C1] | 8-(5-bromo-6-tert-butylpyridin-3-yl)-3-methyl-6-oxo-2H,3H,4H,6H-pyrimido[2,1-b][1,3]thiazine-7-carbonitrile | C18H19BrN4OS | 418.0463 | **** | NT |
| 59 | 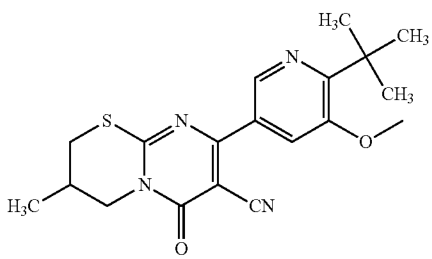 | 8-(6-tert-butyl-5-methoxypyridin-3-yl)-3-methyl-6-oxo-2H,3H,4H,6H-pyrimido[2,1-b][1,3]thiazine-7-carbonitrile | C19H22N4O2S | 370.1463 | **** | NT |
| 60 | 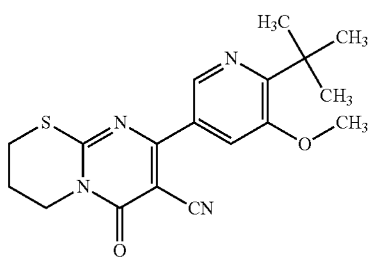 [SMILES: COc1cc(-c2nc3n(c(=O)c2C#N)CCCS3)cnc1C(C)(C)C] | 8-(6-tert-butyl-5-methoxypyridin-3-yl)-6-oxo-2H,3H,4H,6H-pyrimido[2-1-b][1,3]thiazine-7-carbonitrile | C18H20N4O2S | 356.1307 | *** | NT |
| 61 | 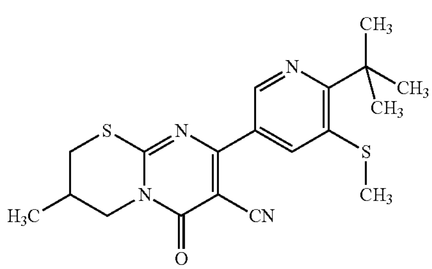 [SMILES: CSc1cc(-c2nc3n(c(=O)c2C#N)CC(C)CS3)cnc1C(C)(C)C] | 8-[6-tert-butyl-5-(methylsulfanyl)pyridin-3-yl]-3-methyl-6-oxo-2H,3H,4H,6H-pyrimido[2,1-b][1,3]thiazine-7-carbonitrile | C19H22N4OS2 | 386.1235 | **** | NT |
| 62 | 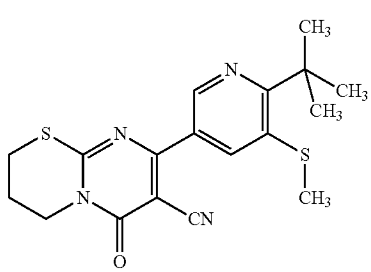 [SMILES: CSc1cc(-c2nc3n(c(=O)c2C#N)CCCS3)cnc1C(C)(C)C] | 8-[6-tert-butyl-5-(methylsulfanyl)pyridin-3-yl]-6-oxo-2H,3H,4H,6H-pyrimido[2,1-b][1,3]thiazine-7-carbonitrile | C18H20N4OS2 | 372.1079 | **** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 63 | 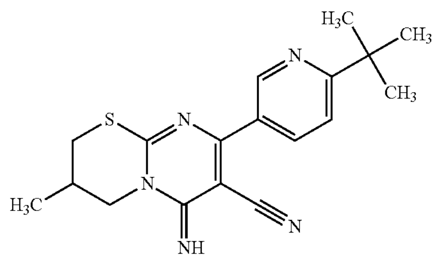 [SMILES: CC1CSc2nc(-c3ccc(C(C)(C)C)nc3)c(C#N)c(=N)n2C1] | 8-(6-tert-butylpyridin-3-yl)-6-imino-3-methyl-2H,3H,4H,6H-pyrimido[2,1-b][1,3]thiazine-7-carbonitrile | C18H21N5S | 339.1518 | ** | ** |
| 64 | 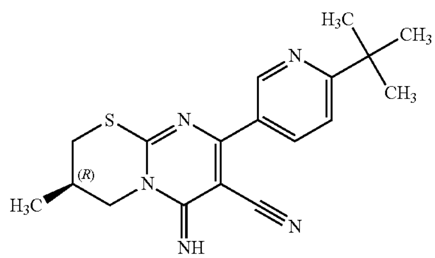 | (3R)-8-(6-tert-butylpyridin-3-yl)-6-imino-3-methyl-2H,3H,4H,6H-pyrimido[2,1-b][1,3]thiazine-7-carbonitrile | C18H21N5S | 339.1518 |  | * |
| 65 | 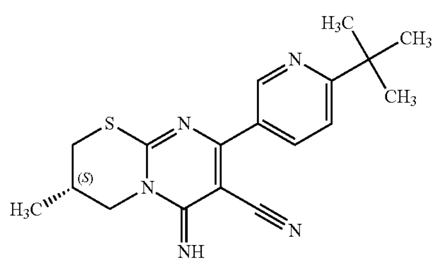 | (3S)-8-(6-tert-butylpyridin-3-yl)-6-imino-3-methyl-2H,3H,4H,6H-pyrimido[2,1-b][1,3]thiazine-7-carbonitrile | C18H21N5S | 339.1518 | ** | ** |
| 66 | 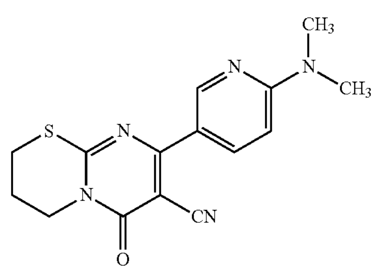 [SMILES: CN(C)c1ccc(-c2nc3n(c(=O)c2C#N)CCCS3)cn1] | 8-[6-(dimethylamino)pyridin-3-yl]-6-oxo-2H,3H,4H,6H-pyrimido[2,1-b][1,3]thiazine-7-carbonitrile | C15H15N5OS | 313.0997 | * | NT |
| 67 | 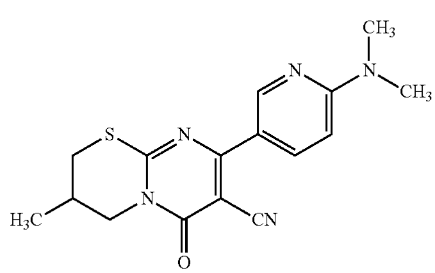 | 8-[6-(dimethylamino)pyridin-3-yl]-3-methyl-6-oxo-2H,3H,4H,6H-pyrimido[2,1-b][1,3]thiazine-7-carbonitrile | C16H17N5OS | 327.1154 |  |  |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 68 | 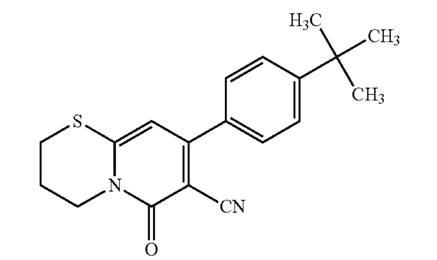 [SMILES: CC(C)(C)c1ccc(-c2cc3n(c(=O)c2C#N)CCCS3)cc1] | 8-(4-tert-butylphenyl)-6-oxo-2H,3H,4H,6H-pyrido[2,1-b][1,3]thiazine-7-carbonitrile | C19H20N2OS | 324.1296 | **** | NT |
| 69 | 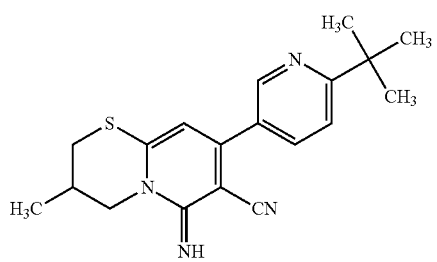 [SMILES: CC1CSc2cc(-c3ccc(C(C)(C)C)nc3)c(C#N)c(=N)n2C1] | 8-(6-tert-butylpyridin-3-yl)-3-methyl-6-oxo-2H,3H,4H,6H-pyrido[2,1-b][1,3]thiazine-7-carbonitrile | C19H21N3OS | 339.1405 | **** | NT |
| 70 | 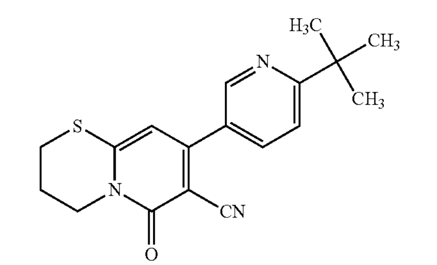 [SMILES: CC(C)(C)c1ccc(-c2cc3n(c(=O)c2C#N)CCCS3)cn1] | 8-(6-tert-butylpyridin-3-yl)-6-oxo-2H,3H,4H,6H-pyrido[2,1-b][1,3]thiazine-7-carbonitrile | C18H19N3OS | 325.1249 | **** | NT |
| 71 | 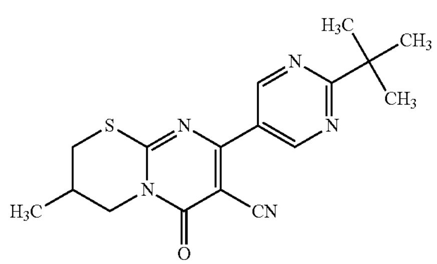 [SMILES: CC1CSc2nc(-c3cnc(C(C)(C)C)nc3)c(C#N)c(=O)n2C1] | 8-(2-tert-butylpyrimidin-5-yl)-3-methyl-6-oxo-2H,3H,4H,6H-pyrido[2,1-b][1,3]thiazine-7-carbonitrile | C18H20N4OS | 340.1358 | **** | NT |
| 72 | 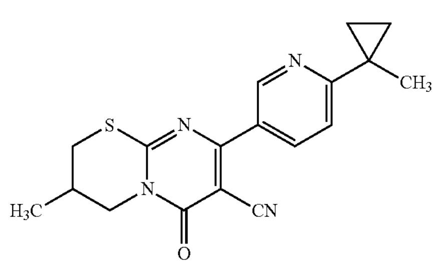 | 3-methyl-8-[6-(1-methylcyclopropyl)pyridin-3-yl]-6-oxo-2H,3H,4H,6H-pyrido[2,1-b][1,3]thiazine-7-carbonitrile | C19H19N3OS | 337.1249 | **** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 73 | 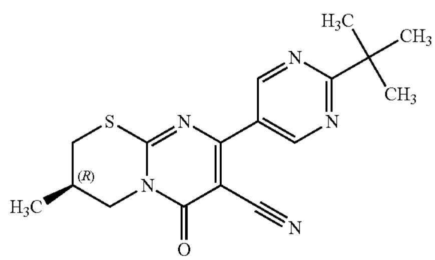 | (3R)-8-(2-tert-butylpyrimidin-5-yl)-3-methyl-6-oxo-2H,3H,4H,6H-pyrimido[2,1-b][1,3]thiazine-7-carbonitrile | C17H19N5OS | 341.131 | **** | NT |
| 74 | 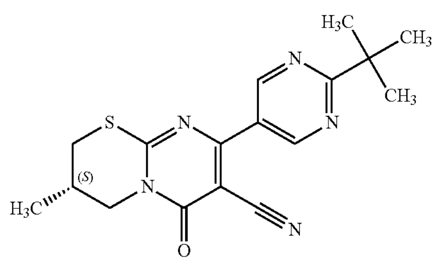 | (3S)-8-(2-tert-butylpyrimidin-5-yl)-3-methyl-6-oxo-2H,3H,4H,6H-pyrimido[2,1-b][1,3]thiazine-7-carbonitrile | C17H19N5OS | 341.131 | *** | NT |
| 75 | 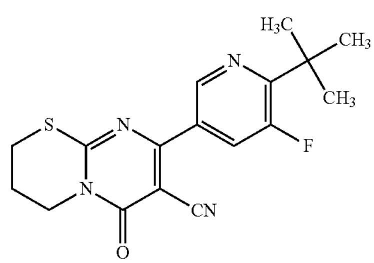 [SMILES: CC(C)(C)c1ncc(-c2nc3n(c(=O)c2C#N)CCCS3)cc1F] | 8-(6-tert-butyl-5-fluoropyridin-3-yl)-6-oxo-2H,3H,4H,6H-pyrimido[2,1-b][1,3]thiazine-7-carbonitrile | C17H17FN4OS | 344.1107 | **** | NT |
| 76 | 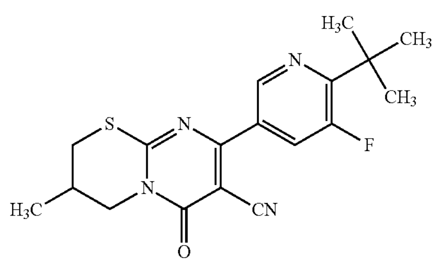 [SMILES: CC1CSc2nc(-c3cnc(C(C)(C)C)c(F)c3)c(C#N)c(=O)n2C1] | 8-(6-tert-butyl-5-fluoropyridin-3-yl)-3-methyl-6-oxo-2H,3H,4H,6H-pyrimido[2,1-b][1,3]thiazine-7-carbonitrile | C18H19FN4OS | 358.1264 | **** | NT |
| 77 | 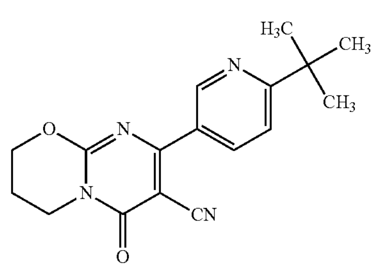 [SMILES: CC(C)(C)c1ccc(-c2nc3n(c(=O)c2C#N)CCCO3)cn1] | 8-(6-tert-butylpyridin-3-yl)-6-oxo-2H,3H,4H,6H-pyrimido[2,1-b][1,3]oxazine-7-carbonitrile | C17H18N4O2 | 310.143 | * | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 78 | 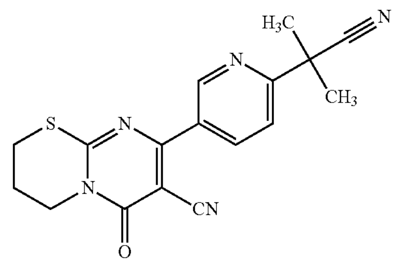 [SMILES: CC(C)(C#N)c1ccc(-c2nc3n(c(=O)c2C#N)CCCS3)cn1] | 8-[6-(1-cyano-1-methylethyl)pyridin-3-yl)-6-oxo-2H,3H,4H,6H-pyrimido[2,1-b][1,3]thiazine-7-carbonitrile | C17H15N5OS | 337.0997 | * | NT |
| 79 | 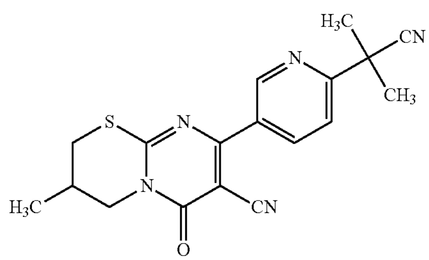 [SMILES: CC1CSc2nc(-c3ccc(C(C)(C)C#N)nc3)c(C#N)c(=O)n2C1] | 8-[6-(1-cyano-1-methylethyl)pyridin-3-yl]-3-methyl-6-oxo-2H,3H,4H,6H-pyrimido[2,1-b][1,3]thiazine-7-carbonitrile | C18H17N5OS | 351.1154 | ** | NT |
| 80 | 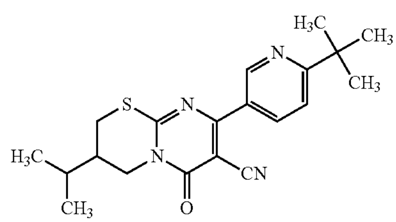 [SMILES: CC(C)C1CSc2nc(-c3ccc(C(C)(C)C)nc3)c(C#N)c(=O)n2C1] | 8-(6-tert-butylpyridin-3-yl)-6-oxo-3-(propan-2-yl)-2H,3H,4H,6H-pyrimido[2,1-b][1,3]thiazine-7-carbonitrile | C20H24N4OS | 368.1671 | ** | NT |
| 81 | 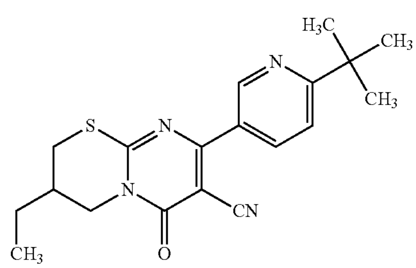 | 8-(6-tert-butylpyridin-3-yl)-3-ethyl-6-oxo-2H,3H,4H,6H-pyrimido[2,1-b][1,3]thiazine-7-carbonitrile | C19H22N4OS | 354.1514 | **** | NT |
| 82 | 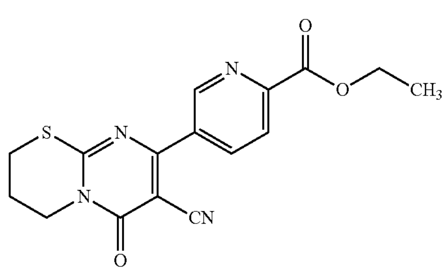 [SMILES: CCOC(=O)c1ccc(-c2nc3n(c(=O)c2C#N)CCCS3)cn1] | ethyl 5-{7-cyano-6-oxo-2H,3H,4H,6H-pyrimido[2,1-b][1,3]thiazin-8-yl}pyridine-2-carboxylate | C16H14N4O3S | 342.0787 | Inhibitor | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 83 | 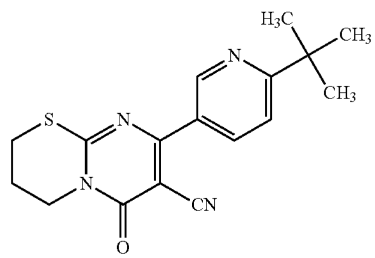 | 8-[6-(2-hydroxypropan-2-yl)pyridin-3-yl]-6-oxo-2H,3H,4H,6H-pyrimido[2,1-b][1,3]thiazine-7-carbonitrile | C16H16N4O2S | 328.0994 | * | NT |
| 84 | 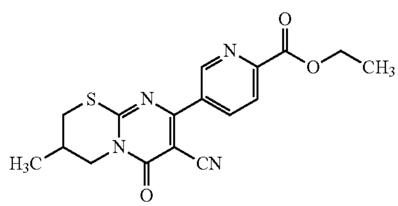 [SMILES: CCOC(=O)c1ccc(-c2nc3n(c(=O)c2C#N)CC(C)CS3)cn1] | ethyl 5-{7-cyano-3-methyl-6-oxo-2H,3H,4H,6H-pyrimido[2,1-b][1,3]thiazin-8-yl}pyridine-2-carboxylate | C17H16N4O3S | 356.0943 | NA | NT |
| 85 | 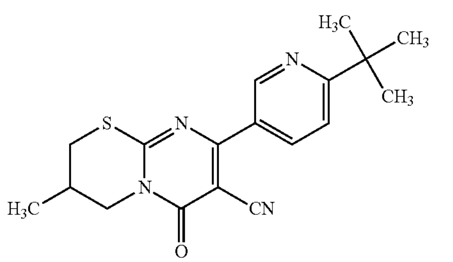 [SMILES: CC1CSc2nc(-c3ccc(C(C)(C)C)nc3)c(C#N)c(=O)n2C1] | 8-[6-(2-hydroxypropan-2-yl)pyridin-3-yl]-3-methyl-6-oxo-2H,3H,4H,6H-pyrimido[2,1-b][1,3]thiazine-7-carbonitrile | C17H18N4O2S | 342.115 | * | NT |
| 86 | 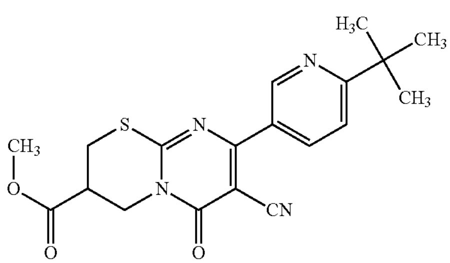 [SMILES: COC(=O)C1CSc2nc(-c3ccc(C(C)(C)C)nc3)c(C#N)c(=O)n2C1] | methyl 8-(6-tert-butylpyridin-3-yl)-7-cyano-6-oxo-2H,3H,4H,6H-pyrimido[2,1-b][1,3]thiazine-3-carboxylate | C19H20N4O3S | 384.1256 | ** | NT |
| 87 | 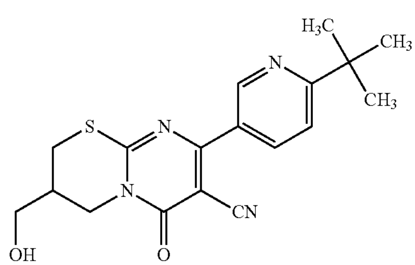 [SMILES: CC(C)(C)c1ccc(-c2nc3n(c(=O)c2C#N)CC(CO)CS3)cn1] | 8-(6-tert-butylpyridin-3-yl)-3-(hydroxymethyl)-6-oxo-2H,3H,4H,6H-pyrimido[2,1-b][1,3]thiazine-7-carbonitrile | C18H20N4O2S | 356.1307 | *** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 88 | 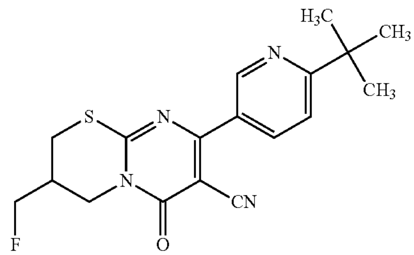 [SMILES: CC(C)(C)c1ccc(-c2nc3n(c(=O)c2C#N)CC(CF)CS3)cn1] | 8-(6-tert-butylpyridin-3-yl)-3-(fluoromethyl)-6-oxo-2H,3H,4H,6H-pyrimido[2,1-b][1,3]thiazine-7-carbonitrile | C18H19FN4OS | 358.1264 | *** | NT |
| 89 | 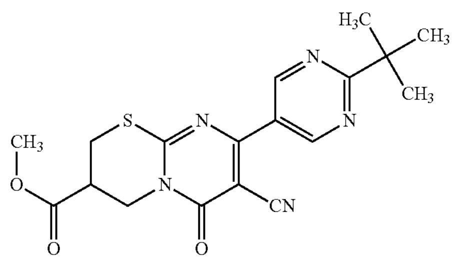 [SMILES: COC(=O)C1CSc2nc(-c3cnc(C(C)(C)C)nc3)c(C#N)c(=O)n2C1] | methyl 8-(2-tert-butylpyrimidin-5-yl)-7-cyano-6-oxo-2H,3H,4H,6H-pyrimido[2,1-b][1,3]thiazine-3-carboxylate | C18H19N5O3S | 385.1209 | ** | NT |
| 90 | 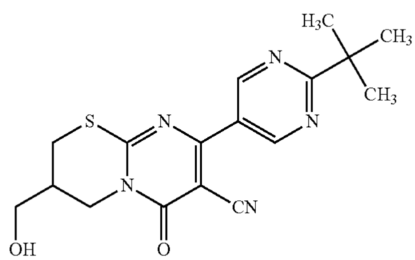 [SMILES: CC(C)(C)c1ncc(-c2nc3n(c(=O)c2C#N)CC(CO)CS3)cn1] | 8-(2-tert-butylpyrimidin-5-yl)-3-(hydroxymethyl)-6-oxo-2H,3H,4H,6H-pyrimido[2,1-b][1,3]thiazine-7-carbonitrile | C17H19N5O2S | 357.1259 | *** | NT |
| 91 | 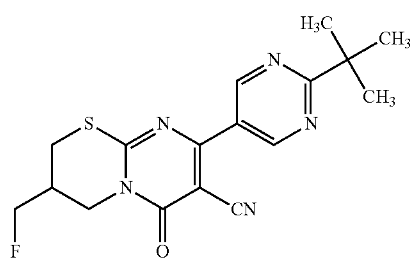 [SMILES: CC(C)(C)c1ncc(-c2nc3n(c(=O)c2C#N)CC(CF)CS3)cn1] | 8-(2-tert-butylpyrimidin-5-yl)-3-(fluoromethyl)-6-oxo-2H,3H,4H,6H-pyrimido[2,1-b][1,3]thiazine-7-carbonitrile | C17H18FN5OS | 359.1216 | *** | NT |
| 92 | 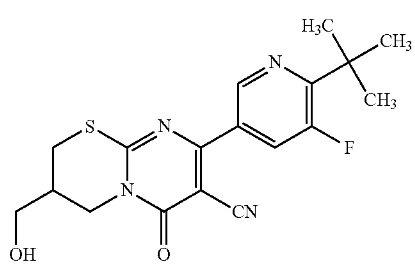 [SMILES: CC(C)(C)c1ncc(-c2nc3n(c(=O)c2C#N)CC(CO)CS3)cc1F] | 8-(6-tert-butyl-5-fluoropyridin-3-yl)-3-(hydroxymethyl)-6-oxo-2H,3H,4H,6H-pyrimido[2,1-b][1,3]thiazine-7-carbonitrile | C18H19FN4O2S | 374.1213 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 93 | 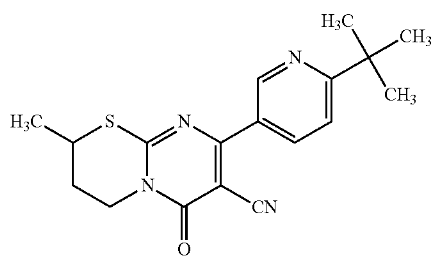 [SMILES: CC1CCn2c(nc(-c3ccc(C(C)(C)C)nc3)c(C#N)c2=O)S1] | 8-(6-tert-butylpyridin-3-yl)-2-methyl-6-oxo-2H,3H,4H,6H-pyrimido[2,1-b][1,3]thiazine-7-carbonitrile | C18H20N4OS | 340.1358 | *** | NT |
| 94 | 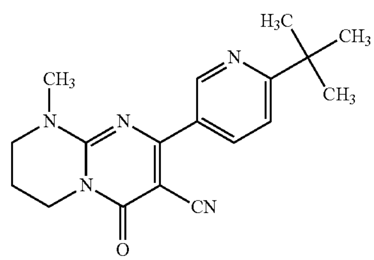 [SMILES: CN1CCCn2c1nc(-c1ccc(C(C)(C)C)nc1)c(C#N)c2=O] | 8-(6-tert-butylpyridin-3-yl)-1-methyl-6-oxo-1H,2H,3H,4H,6H-[1,3]diazino[1,2-a]pyrimidine-7-carbonitrile | C18H21N5O | 323.1746 | ** | NT |
| 95 | 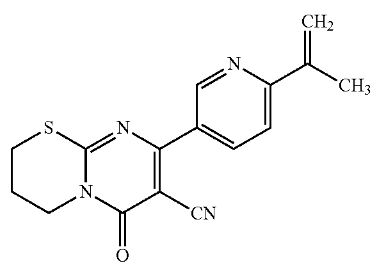 [SMILES: C=C(C)c1ccc(-c2nc3n(c(=O)c2C#N)CCCS3)cn1] | 6-oxo-8-[6-(prop-1-en-2-yl)pyridin-3-yl]-2H,3H,4H,6H-pyrimido[2,1-b][1,3]thiazine-7-carbonitrile | C16H14N4OS | 310.0888 | ** | NT |
| 96 | 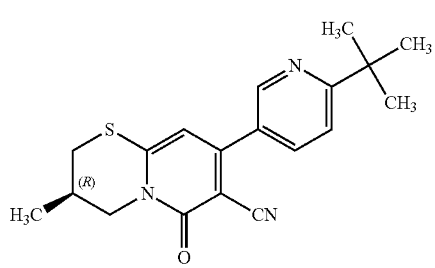 | (3R)-8-(6-tert-butylpyridin-3-yl)-3-methyl-6-oxo-2H,3H,4H,6H-pyrido[2,1-b][1,3]thiazine-7-carbonitrile | C19H21N3OS | 339.1405 | **** | NT |
| 97 | 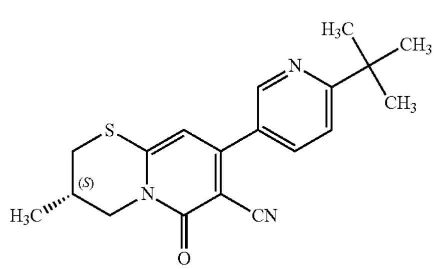 | (3S)-8-(6-tert-butylpyridin-3-yl)-3-methyl-6-oxo-2H,3H,4H,6H-pyrido[2,1-b][1,3]thiazine-7-carbonitrile | C19H21N3OS | 339.1405 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 98 | 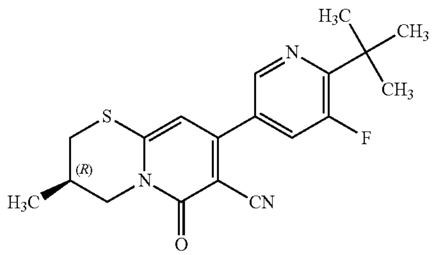 | (3R)-8-(6-tert-butyl-5-fluoropyridin-3-yl)-3-methyl-6-oxo-2H,3H,4H,6H-pyrimido[2,1-b][1,3]thiazine-7-carbonitrile | C18H19FN4OS | 358.1264 | **** | NT |
| 99 | 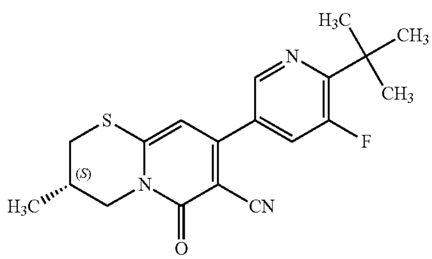 | (3S)-8-(6-tert-butyl-5-fluoropyridin-3-yl)-3-methyl-6-oxo-2H,3H,4H,6H-pyrimido[2,1-b][1,3]thiazine-7-carbonitrile | C18H19FN4OS | 358.1264 | **** | NT |
| 100 | 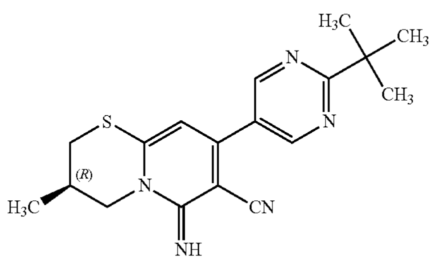 | (3R)-8-(2-tert-butylpyrimidin-5-yl)-6-imino-3-methyl-2H,3H,4H,6H-pyrimido[2,1-b][1,3]thiazine-7-carbonitrile | C17H20N6S | 340.147 | **** | NT |
| 101 | 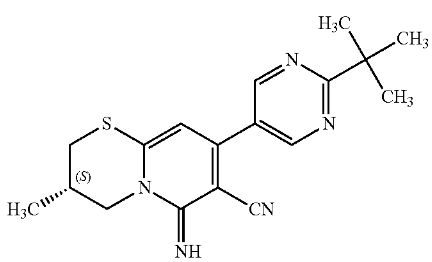 | (3S)-8-(2-tert-butylpyrimidin-5-yl)-6-imino-3-methyl-2H,3H,4H,6H-pyrimido[2,1-b][1,3]thiazine-7-carbonitrile | C17H20N6S | 340.147 | **** | NT |
| 102 | 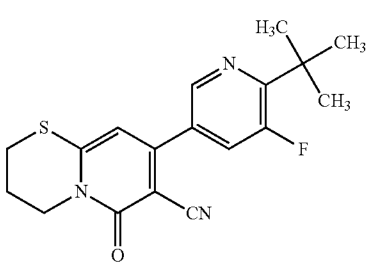 [SMILES: CC(C)(C)c1ncc(-c2cc3n(c(=O)c2C#N)CCCS3)cc1F] | 8-(6-tert-butyl-5-fluoropyridin-3-yl)-6-oxo-2H,3H,4H,6H-pyrido[2,1-b][1,3]thiazine-7-carbonitrile | C18H18FN3OS | 343.1155 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 103 | 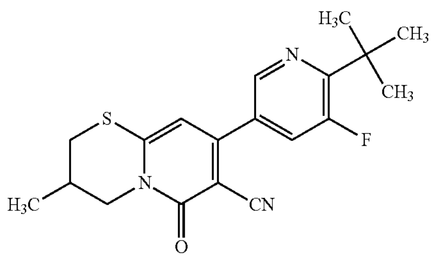 [SMILES: CC1CSc2cc(-c3cnc(C(C)(C)C)c(F)c3)c(C#N)c(=O)n2C1] | 8-(6-tert-butyl-5-fluoropyridin-3-yl)-3-methyl-6-oxo-2H,3H,4H,6H-pyrido[2,1-b][1,3]thiazine-7-carbonitrile | C19H20FN3OS | 357.1311 | **** | NT |
| 104 | 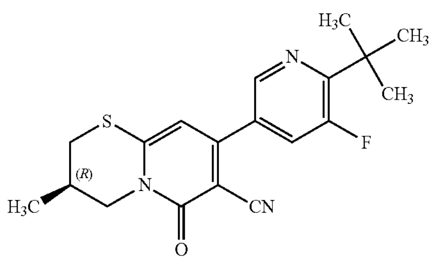 | (3R)-8-(2-tert-butylpyrimdin-5-yl)-3-methyl-6-oxo-2H,3H,4H,6H-pyrido[2,1-b][1,3]thiazine-7-carbonitrile | C18H20N4OS | 340.1358 | **** | NT |
| 105 | 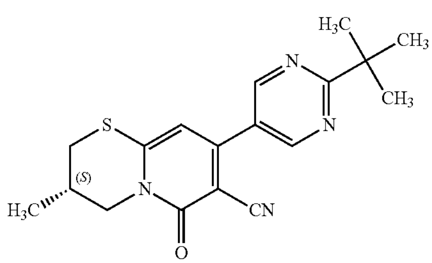 | (3S)-8-(2-tert-butylpyrimidin-5-yl)-3-methyl-6-oxo-2H,3H,4H,6H-pyrido[2,1-b][1,3]thiazine-7-carbonitrile | C18H20N4OS | 340.1358 | **** | NT |
| 106 | 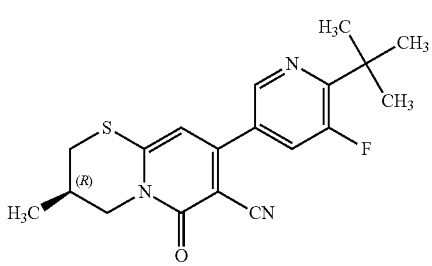 | (3R)-8-(6-tert-butyl-5-fluoropyridn-3-yl)-3-methyl-6-oxo-2H,3H,4H,6H-pyrido[2,1-b][1,3]thiazine-7-carbonitrile | C19H20FN3OS | 357.1311 | **** | NT |
| 107 | 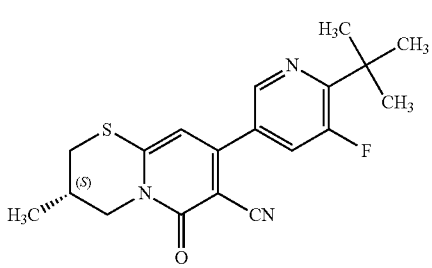 | (3S)-8-(6-tert-butyl-5-fluoropyridin-3-yl)-3-methyl-6-oxo-2H,3H,4H,6H-pyrido[2,1-b][1,3]thiazine-7-carbonitrile | C19H20FN3OS | 357.1311 | *** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 108 | 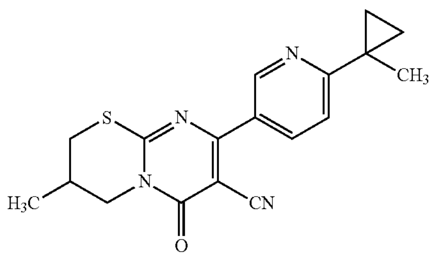 [SMILES: CC1CSc2nc(-c3ccc(C4(C)CC4)nc3)c(C#N)c(=O)n2C1] | 3-methyl-8-[6-(1-methyl-cyclopropyl)pyridin-3-yl]-6-oxo-2H,3H,4H,6H-pyrimido[2,1-b][1,3]thiazine-7-carbonitrile | C18H18N4OS | 338.1201 | *** | NT |
| 109 | 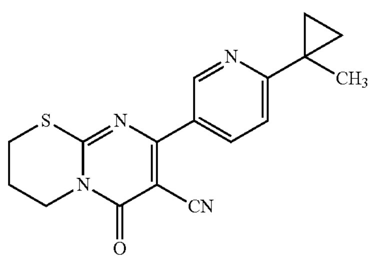 [SMILES: CC1(c2ccc(-c3nc4n(c(=O)c3C#N)CCCS4)cn2)CC1] | 8-[6-(1-methyl-cyclopropyl)pyridin-3-yl]-6-oxo-2H,3H,4H,6H-pyrimido[2,1-b][1,3]thiazine-7-carbonitrile | C17H16N4OS | 324.1045 | *** | NT |
| 110 | 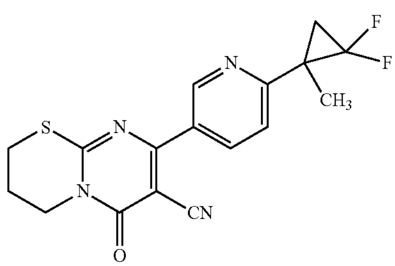 [SMILES: CC1(c2ccc(-c3nc4n(c(=O)c3C#N)CCCS4)cn2)CC1(F)F] | 8-[6-(2,2-difluoro-1-methyl-cyclopropyl)pyridin-3-yl]-6-oxo-2H,3H,4H,6H-pyrimido[2,1-b][1,3]thiazine-7-carbonitrile | C17H14F2N4OS | 360.0856 | *** | NT |
| 111 | 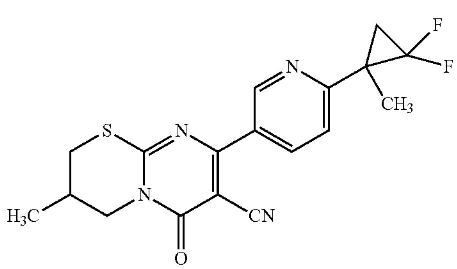 [SMILES: CC1CSc2nc(-c3ccc(C4(C)CC4(F)F)nc3)c(C#N)c(=O)n2C1] | 8-[6-(2,2-difluoro-1-methyl-cyclopropyl)pyridin-3-yl]-3-methyl-6-oxo-2H,3H,4H,6H-pyrimido[2,1-b][1,3]thiazine-7-carbonitrile | C18H16F2N4OS | 374.1013 | *** | NT |
| 112 | 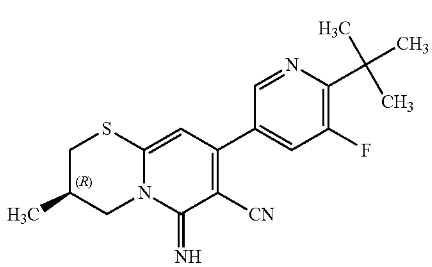 | (3R)-8-(6-tert-butyl-5-fluoropyridin-3-yl)-6-imino-3-methyl-2H,3H,4H,6H-pyrimido[2,1-b][1,3]thiazine-7-carbonitrile | C18H20FN5S | 357.1423 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 113 | 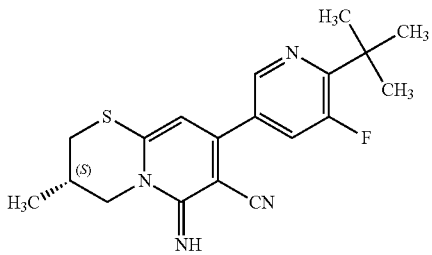 | (3S)-8-(6-tert-butyl-5-fluoropyridin-3-yl)-6-imino-3-methyl-2H,3H,4H,6H-pyrimido[2,1-b][1,3]thiazine-7-carbonitrile | C18H20FN5S | 357.1423 | **** | NT |
| 114 | 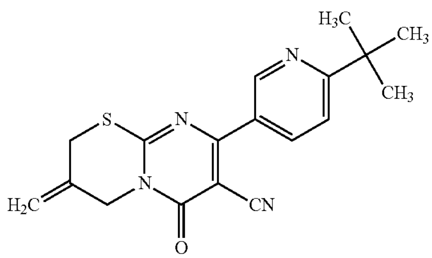 [SMILES: C=C1CSc2nc(-c3ccc(C(C)(C)C)nc3)c(C#N)c(=O)n2C1] | 8-(6-tert-butylpyridin-3-yl)-3-methylidene-6-oxo-2H,3H,4H,6H-pyrimido[2,1-b][1,3]thiazine-7-carbonitrile | C18H18N4OS | 338.1201 | **** | NT |
| 115 | 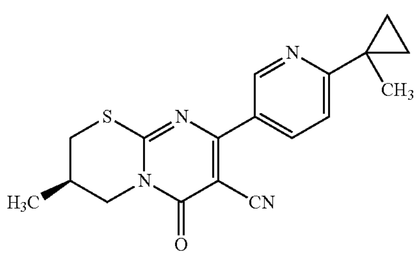 [SMILES: C[C@H]1CSc2nc(-c3ccc(C4(C)CC4)nc3)c(C#N)c(=O)n2C1] | (3R)-3-methyl-8-[6-(1-methyl-cyclopropyl)pyridin-3-yl]-6-oxo-2H,3H,4H,6H-pyrimido[2,1-b][1,3]thiazine-7-carbonitrile | C18H18N4OS | 338.1201 | ** | NT |
| 116 | 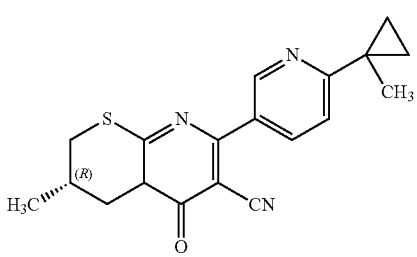 | (3S)-3-methyl-8-[6-(1-methyl-cyclopropyl)pyridin-3-yl]-6-oxo-2H,3H,4H,6H-pyrimido[2,1-b][1,3]thiazine-7-carbonitrile | C18H18N4OS | 338.1201 | **** | NT |
| 117 | 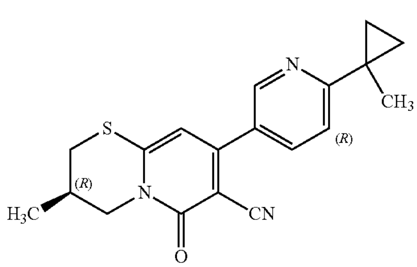 | (3R)-3-methyl-8-[6-(1-methyl-cyclopropyl)pyridin-3-yl]-6-oxo-2H,3H,4H,6H-pyrido[2,1-b][1,3]thiazine-7-carbonitrile | C19H19N3OS | 337.1249 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 118 | 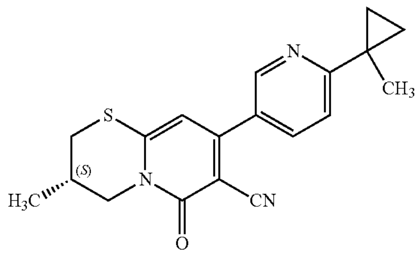 | (3S)-3-methyl-8-[6-(1-methyl-cyclopropyl)pyridin-3-yl]-6-oxo-2H,3H,4H,6H-pyrido[2,1-b][1,3]thiazine-7-carbonitrile | C19H19N3OS | 337.1249 | **** | NT |
| 119 | 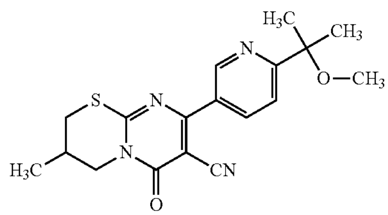 | 8-[6-(2-methoxypropan-2-yl)pyridin-3-yl]-3-methyl-6-oxo-2H,3H,4H,6H-pyrimido[2,1-b][1,3]thiazine-7-carbonitrile | C18H20N4O2S | 356.1307 | * | NT |
| 120 | 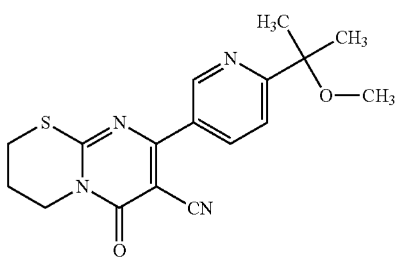 [SMILES: COC(C)(C)c1ccc(-c2nc3n(c(=O)c2C#N)CCCS3)cn1] | 8-[6-(2-methoxypropan-2-yl)pyridin-3-yl]-6-oxo-2H,3H,4H,6H-pyrimido[2,1-b][1,3]thiazine-7-carbonitrile | C17H18N4O2S | 342.115 | * | NT |
| 121 | 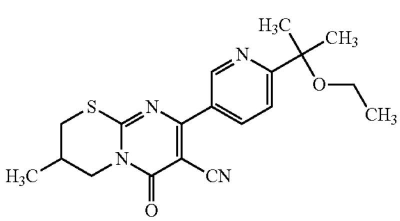 [SMILES: CCOC(C)(C)c1ccc(-c2nc3n(c(=O)c2C#N)CC(C)CS3)cn1] | 8-[6-(2-ethoxypropan-2-yl)pyridin-3-yl]-3-methyl-6-oxo-2H,3H,4H,6H-pyrimido[2,1-b][1,3]thiazine-7-carbonitrile | C19H22N4O2S | 370.1463 | Inhibitor | NT |
| 122 | 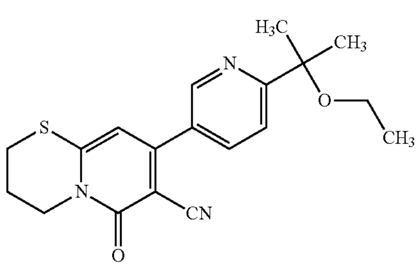 [SMILES: CCOC(C)(C)c1ccc(-c2cc3n(c(=O)c2C#N)CCCS3)cn1] | 8-[6-(2-ethoxypropan-2-yl)pyridin-3-yl]-6-oxo-2H,3H,4H,6H-pyrimido[2,1-b][1,3]thiazine-7-carbonitrile | C18H20N4O2S | 356.1307 | Inhibitor | NT |
| 123 | 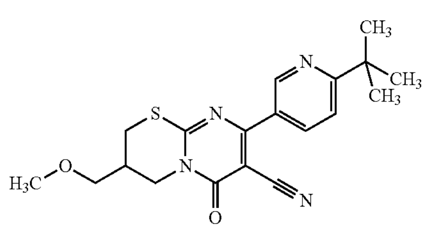 [SMILES: COCC1CSc2nc(-c3ccc(C(C)(C)C)nc3)c(C#N)c(=O)n2C1] | 8-(6-tert-butylpyridin-3-yl)-3-(methoxymethyl)-6-oxo-2H,3H,4H,6H-pyrimido[2,1-b][1,3]thiazine-7-carbonitrile | C19H22N4O2S | 370.1463 | *** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 124 | 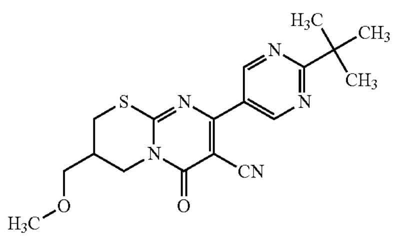 [SMILES: COCC1CSc2nc(-c3cnc(C(C)(C)C)nc3)c(C#N)c(=O)n2C1] | 8-(2-tert-butylpyrimidin-5-yl)-3-(methoxymethyl)-6-oxo-2H,3H,4H,6H-pyrimido[2,1-b][1,3]thiazine-7-carbonitrile | C18H21N5O2S | 371.1416 | *** | NT |
| 125 | 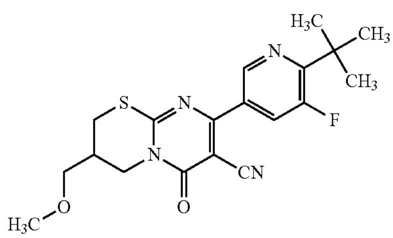 [SMILES: COCC1CSc2nc(-c3cnc(C(C)(C)C)c(F)c3)c(C#N)c(=O)n2C1] | 8-(6-tert-butyl-5-fluoropyridin-3-yl)-3-(methoxymethyl)-6-oxo-2H,3H,4H,6H-pyrimido[2,1-b][1,3]thiazine-7-carbonitrile | C19H21FN4O2S | 388.1369 | **** | NT |
| 126 | 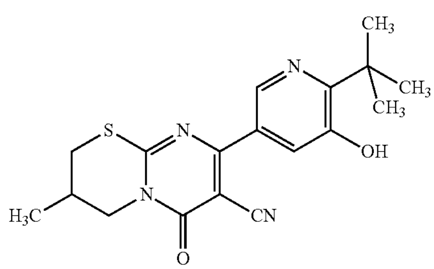 [SMILES: CC1CSc2nc(-c3cnc(C(C)(C)C)c(O)c3)c(C#N)c(=O)n2C1] | 8-(6-tert-butyl-5-hydroxypyridin-3-yl)-3-methyl-6-oxo-2H,3H,4H,6H-pyrimido[2,1-b][1,3]thiazine-7-carbonitrile | C18H20N4O2S | 356.1307 | **** | NT |
| 127 | 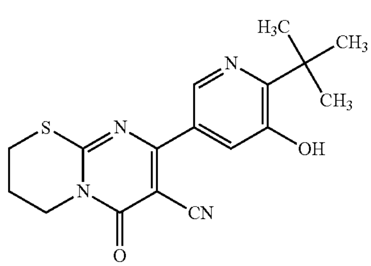 [SMILES: CC(C)(C)c1ncc(-c2nc3n(c(=O)c2C#N)CCCS3)cc1O] | 8-(6-tert-butyl-5-hydroxypyridin-3-yl)-6-oxo-2H,3H,4H,6H-pyrimido[2,1-b][1,3]thiazine-7-carbonitrile | C17H18N4O2S | 342.115 | **** | NT |
| 128 | 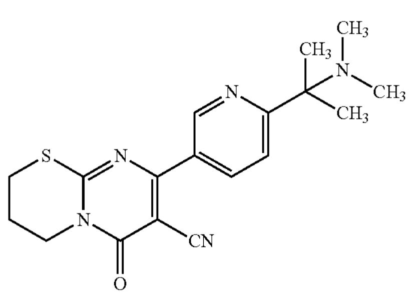 [SMILES: CN(C)C(C)(C)c1ccc(-c2nc3n(c(=O)c2C#N)CCCS3)cn1] | 8-(6-[2-(dimethylamino)propan-2-yl]pyridin-3-yl)-6-oxo-2H,3H,4H,6H-pyrimido[2,1-b][1,3]thiazine-7-carbonitrile | C18H21N5OS | 355.1467 | NA | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 129 | 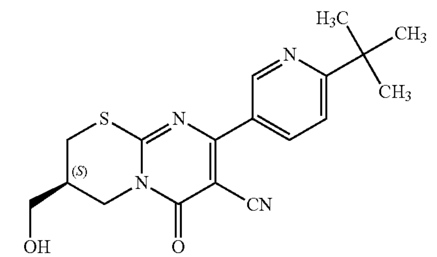 | (3S)-8-(6-tert-butylpyridin-3-yl)-3-(hydroxymethyl)-6-oxo-2H,3H,4H,6H-pyrimido[2,1-b][1,3]thiazine-7-carbonitrile | C18H20N4O2S | 356.1307 | **** | NT |
| 130 | 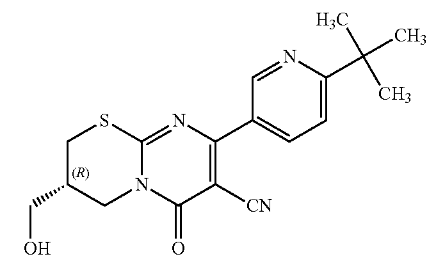 | (3R)-8-(6-tert-butylpyridin-3-yl)-3-(hydroxymethyl)-6-oxo-2H,3H,4H,6H-pyrimido[2,1-b][1,3]thiazine-7-carbonitrile | C18H20N4O2S | 356.1307 | ** | NT |
| 131 | 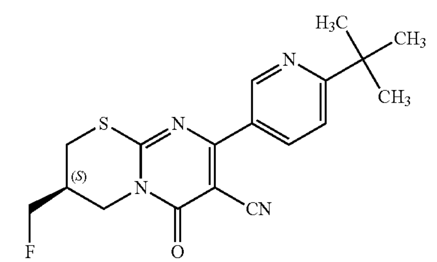 | (3S)-8-(6-tert-butylpyridin-3-yl)-3-(fluoromethyl)-6-oxo-2H,3H,4H,6H-pyrimido[2,1-b][1,3]thiazine-7-carbonitrile | C18H19FN4OS | 358.1264 | **** | NT |
| 132 | 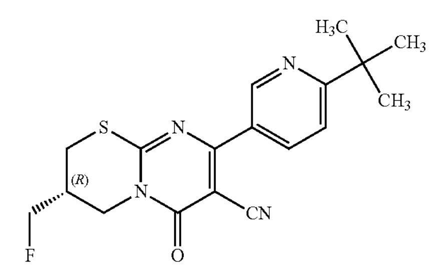 | (3R)-8-(6-tert-butylpyridin-3-yl)-3-(fluoromethyl)-6-oxo-2H,3H,4H,6H-pyrimido[2,1-b][1,3]thiazine-7-carbonitrile | C18H19FN4OS | 358.1264 | ** | NT |
| 133 | 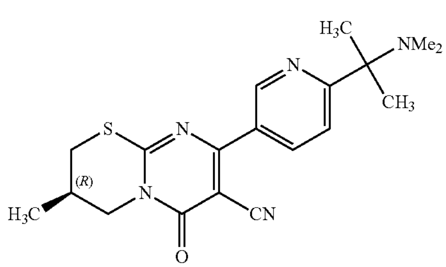 | (3R)-8-{6-[2-(dimethylamino)propan-2-yl]pyridin-3-yl}-3-methyl-6-oxo-2H,3H,4H,6H-pyrimido[2,1-b][1,3]thiazine-7-carbonitrile | C19H23N5OS | 369.1623 | Inhibitor | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 134 | 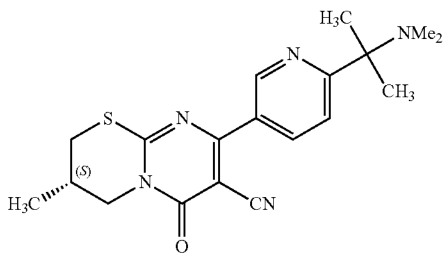 | (3S)-8-{6-[2-(dimethylamino)propan-2-yl]pyridin-3-yl}-3-methyl-6-oxo-2H,3H,4H,6H-pyrimido[2,1-b][1,3]thiazine-7-carbonitrile | C19H23N5OS | 369.1623 | NA | NT |
| 135 | 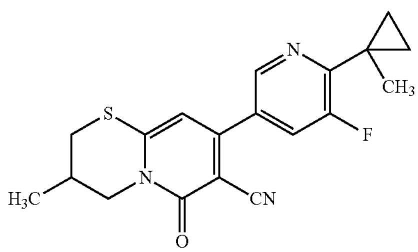 [SMILES: CC1CSc2cc(-c3cnc(C4(C)CC4)c(F)c3)c(C#N)c(=O)n2C1] | 8-[5-fluoro-6-(1-methyl-cyclopropyl)pyridin-3-yl]-3-methyl-6-oxo-2H,3H,4H,6H-pyrido[2,1-b][1,3]thiazine-7-carbonitrile | C19H18FN3OS | 355.1155 | **** | NT |
| 136 | 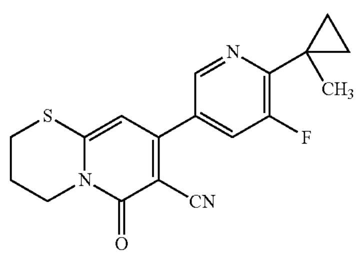 [SMILES: CC1(c2ncc(-c3cc4n(c(=O)c3C#N)CCCS4)cc2F)CC1] | 8-[5-fluoro-6-(1-methyl-cyclopropyl)pyridin-3-yl]-6-oxo-2H,3H,4H,6H-pyrido[2,1-b][1,3]thiazine-7-carbonitrile | C18H16FN3OS | 341.0998 | **** | NT |
| 137 | 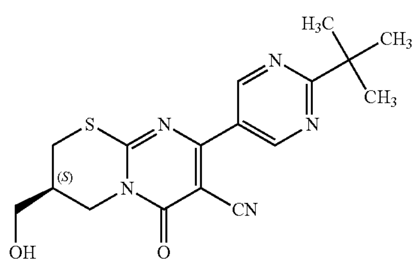 | (3S)-8-(2-tert-butylpyrimidin-5-yl)-3-(hydroxymethyl)-6-oxo-2H,3H,4H,6H-pyrimido[2,1-b][1,3]thiazine-7-carbonitrile | C17H19N5O2S | 357.1259 | ** | NT |
| 138 | 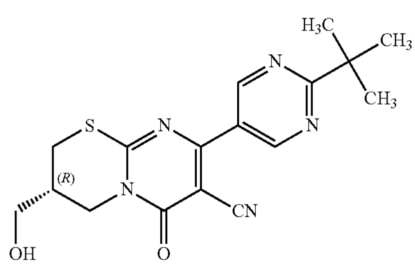 | (3R)-8-(2-tert-butylpyrimidin-5-yl)-3-(hydroxymethyl)-6-oxo-2H,3H,4H,6H-pyrimido[2,1-b][1,3]thiazine-7-carbonitrile | C17H19N5O2S | 357.1259 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 139 | 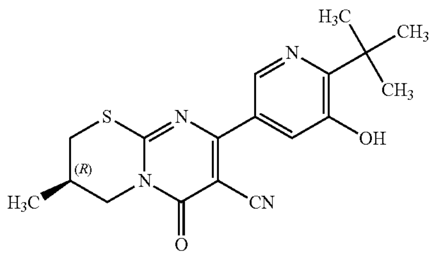 | (3R)-8-(6-tert-butyl-5-hydroxypyridin-3-yl)-3-methyl-6-oxo-2H,3H,4H,6H-pyrimido[2,1-b][1,3]thiazine-7-carbonitrile | C18H20N4O2S | 356.1307 | **** | NT |
| 140 | 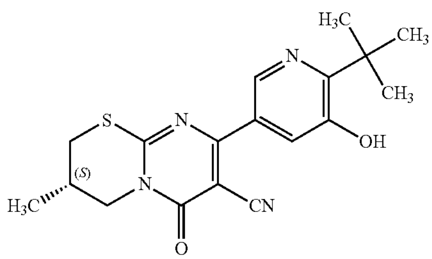 | (3S)-8-(6-tert-butyl-5-hydroxypyridin-3-yl)-3-methyl-6-oxo-2H,3H,4H,6H-pyrimido[2,1-b][1,3]thiazine-7-carbonitrile | C18H20N4O2S | 356.1307 | *** | NT |
| 141 | 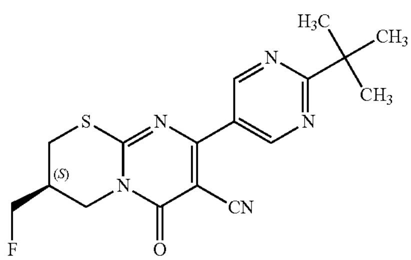 | (3S)-8-(2-tert-butylpyrimidin-5-yl)-3-(fluoromethyl)-6-oxo-2H,3H,4H,6H-pyrimido[2,1-b][1,3]thiazine-7-carbonitrile | C17H18FN5OS | 359.1216 | *** | NT |
| 142 | 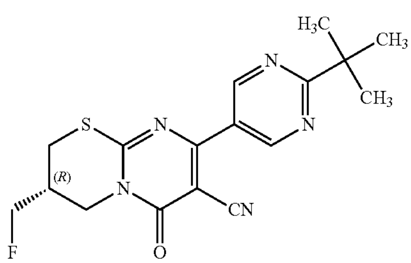 | (3R)-8-(2-tert-butylpyrimidin-5-yl)-3-(fluoromethyl)-6-oxo-2H,3H,4H,6H-pyrimido[2,1-b][1,3]thiazine-7-carbonitrile | C17H18FN5OS | 359.1216 | *** | NT |
| 143 | 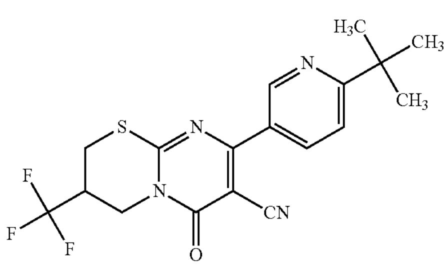 [SMILES: CC(C)(C)c1ccc(-c2nc3n(c(=O)c2C#N)CC(C(F)(F)F)CS3)cn1] | 8-(6-tert-butylpyridin-3-yl)-6-oxo-3-(trifluoromethyl)-2H,3H,4H,6H-pyrimido[2,1-b][1,3]thiazine-7-carbonitrile | C18H17F3N4OS | 394.1075 | ** | NT |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 144 | 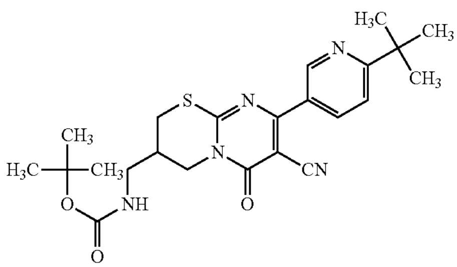 [SMILES: CC(C)(C)OC(=O)NCC1CSc2nc(-c3ccc(C(C)(C)C)nc3)c(C#N)c(=O)n2C1] | tert-butyl N-{[8-(6-tert-butylpyridin-3-yl)-7-cyano-6-oxo-2H,3H,4H,6H-pyrimido[2,1-b][1,3]thiazin-3-yl]methyl} carbamate | C23H29N5O3S | 455.1991 | **** | NT |
| 145 | 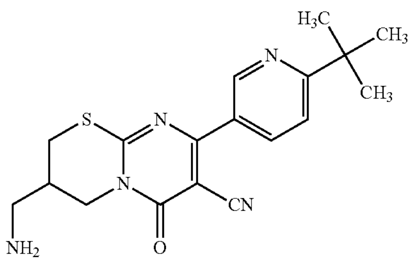 [SMILES: CC(C)(C)c1ccc(-c2nc3n(c(=O)c2C#N)CC(CN)CS3)cn1] | 3-(aminomethyl)-8-(6-tert-butylpyridin-3-yl)-6-oxo-2H,3H,4H,6H-pyrimido[2,1-b][1,3]thiazine-7-carbonitrile | C18H21N5OS | 355.1467 | * | NT |
| 146 | 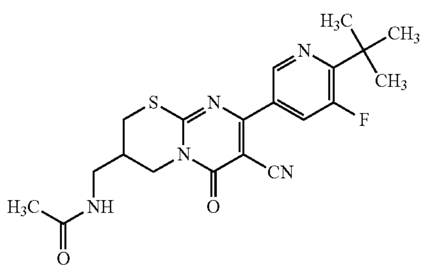 [SMILES: CC(=O)NCC1CSc2nc(-c3cnc(C(C)(C)C)c(F)c3)c(C#N)c(=O)n2C1] | N-{[8-(6-tert-butyl-5-fluoropyridin-3-yl)-7-cyano-6-oxo-2H,3H,4H,6H-pyrimido[2,1-b][1,3]thiazin-3-yl]methyl} acetamide | C20H22FN5O2S | 415.1478 | **** | NT |
| 147 | 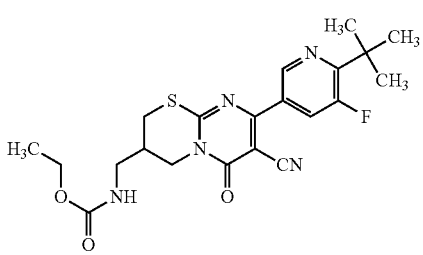 [SMILES: CCOC(=O)NCC1CSc2nc(-c3cnc(C(C)(C)C)c(F)c3)c(C#N)c(=O)n2C1] | ethyl N-{[8-(6-(tert-butyl-5-fluoropyridin-3-yl)-7-cyano-6-oxo-2H,3H,4H,6H-pyrimido[2,1-b][1,3]thiazin-3-yl]methyl} carbamate | C21H24FN5O3S | 445.1584 | **** | NT |
| 148 | 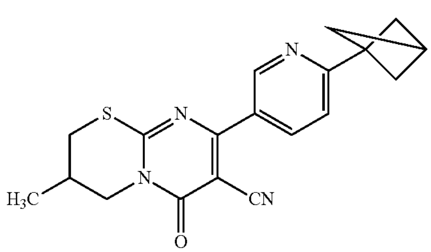 [SMILES: CC1CSc2nc(-c3ccc(C45CC(C4)C5)nc3)c(C#N)c(=O)n2C1] | 8-(6-{bicyclo[1.1.1]pentan-1-yl}pyridin-3-yl)-3-methyl-6-oxo-2H,3H,4H,6H-pyrimido[2,1-b][1,3]thiazine-7-carbonitrile | C19H18N4OS | 350.1201 | ** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 149 | 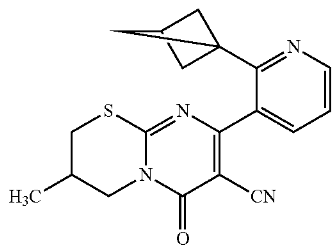 [SMILES: CC1CSc2nc(-c3cccnc3C34CC(C3)C4)c(C#N)c(=O)n2C1] | 8-(2-{bicyclo[1.1.1]pentan-1-yl}pyridin-3-yl)-3-methyl-6-oxo-2H,3H,4H,6H-pyrimido[2,1-b][1,3]thiazine-7-carbonitrile | C19H18N4OS | 350.1201 | NA | NT |
| 150 | 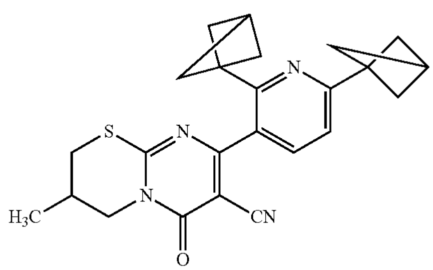 [SMILES: CC1CSc2nc(-c3ccc(C45CC(C4)C5)nc3C34CC(C3)C4)c(C#N)c(=O)n2C1] | 8-[2,6-bis({bicyclo[1.1.1]pentan-1-yl})pyridin-3-yl]-3-methyl-6-oxo-2H,3H,4H,6H-pyrimido[2,1-b][1,3]thiazine-7-carbonitrile | C24H24N4OS | 416.1671 | Inhibitor | NT |
| 151 | 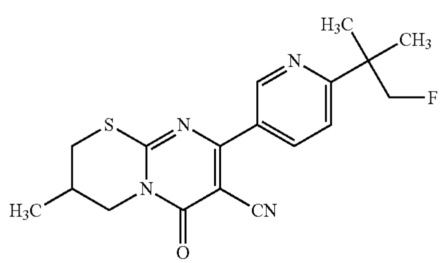 [SMILES: CC1CSc2nc(-c3ccc(C(C)(C)CF)nc3)c(C#N)c(=O)n2C1] | 8-(6-(1-fluoro-2-methylpropan-2-yl)pyridin-3-yl]-3-methyl-6-oxo-2H,3H,4H,6H-pyrimido[2,1-b][1,3]thiazine-7-carbonitrile | C18H19FN4OS | 358.1264 | *** | NT |
| 152 | 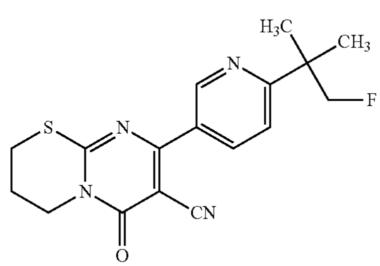 [SMILES: CC(C)(CF)c1ccc(-c2nc3n(c(=O)c2C#N)CCCS3)cn1] | 8-[6-(1-fluoro-2-methylpropan-2-yl)pyridin-3-yl]-6-oxo2H,3H,4H,6H-pyrimido[2,1-b][1,3]thiazine-7-carbonitrile | C17H17FN4OS | 344.1107 | ** | NT |
| 153 | 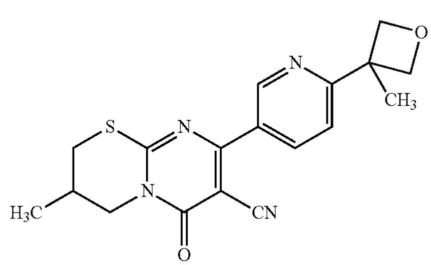 [SMILES: CC1CSc2nc(-c3ccc(C4(C)COC4)nc3)c(C#N)c(=O)n2C1] | 3-methyl-8-[6-(3-methyloxetan-3-yl)pyridin-3-yl]-6-oxo-2H,3H,4H,6H-pyrimido[2,1-b][1,3]thiazine-7-carbonitrile | C18H18N4O2S | 354.115 | ** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 154 | 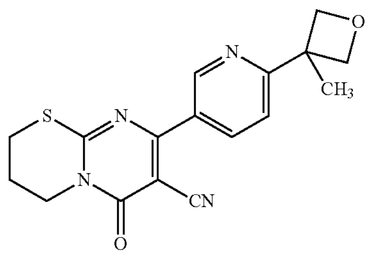 [SMILES: CC1(c2ccc(-c3nc4n(c(=O)c3C#N)CCCS4)cn2)COC1] | 8-[6-(3-methyloxetan-3-yl)pyridin-3-yl]-6-oxo-2H,3H,4H,6H-pyrimido[2,1-b][1,3]thiazine-7-carbonitrile | C17H16N4O2S | 340.0994 | * | NT |
| 155 | 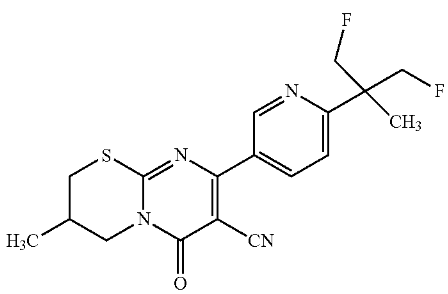 [SMILES: CC1CSc2nc(-c3ccc(C(C)(CF)CF)nc3)c(C#N)c(=O)n2C1] | 8-[6-(1,3-difluoro-2-methylpropan-2-yl)pyridin-3-yl]-3-methyl-6-oxo-2H,3H,4H,6H-pyrimido[2,1-b][1,3]thiazine-7-carbonitrile | C18H18F2N4OS | 376.1169 | ** | NT |
| 156 | 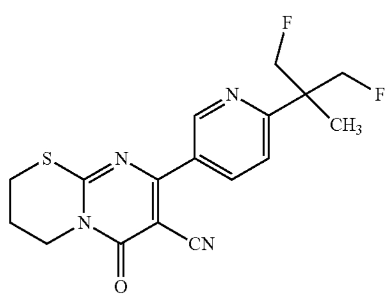 [SMILES: CC(CF)(CF)c1ccc(-c2nc3n(c(=O)c2C#N)CCCS3)cn1] | 8-[6-(1,3-difluoro-2-methylpropan-2yl)pyridin-3-yl]-6-oxo-2H,3H,4H,6H-pyrimido[2,1-b][1,3]thiazine-7-carbonitrile | C17H16F2N4OS | 362.1013 | ** | NT |
| 157 | 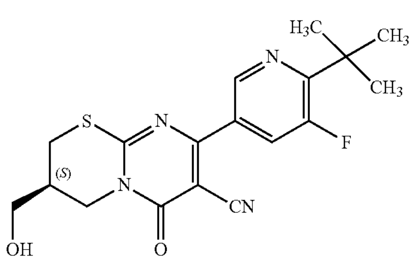 | (3S)-8-(6-tert-butyl-5-fluoropyridin-3-yl)-3-(hydroxymethyl)-6-oxo-2H,3H,4H,6H-pyrimido[2,1-b][1,3]thiazine-7-carbonitrile | C18H19FN4O2S | 374.1213 | **** | NT |
| 158 | 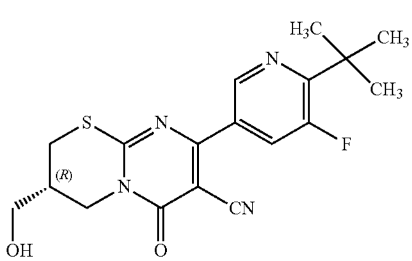 | (3R)-8-(6-tert-butyl-5-fluoropyridin-3-yl)-3-(hydroxymethyl)-6-oxo-2H,3H,4H,6H-pyrimido[2,1-b][1,3]thiazine-7-carbonitrile | C18H19FN4O2S | 374.1213 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 159 | 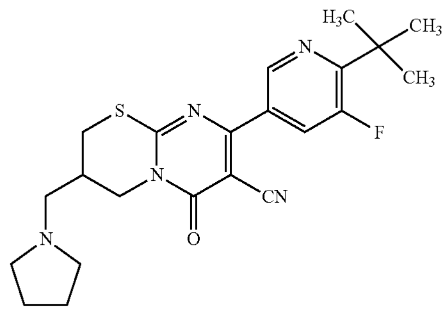 [SMILES: CC(C)(C)c1ncc(-c2nc3n(c(=O)c2C#N)CC(CN2CCCC2)CS3)cc1F] | 8-(6-tert-butyl-5-fluoropyridin-3-yl)-6-oxo-3-[(pyrrolidin-1-yl)methyl]-2H,3H,4H,6H-pyrimido[2,1-b][1,3]thiazine-7-carbonitrile | C22H26FN5OS | 427.1842 | * | NT |
| 160 | 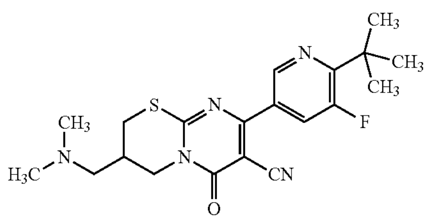 [SMILES: CN(C)CC1CSc2nc(-c3cnc(C(C)(C)C)c(F)c3)c(C#N)c(=O)n2C1] | 8-(6-tert-butyl-5-fluoropyridin-3-yl)-3-[(dimethylamino)methyl]-6-oxo-2H,3H,4H,6H-pyrimido[2,1-b][1,3]thiazine-7-carbonitrile | C20H24FN5OS | 401.1686 | * | NT |
| 161 | 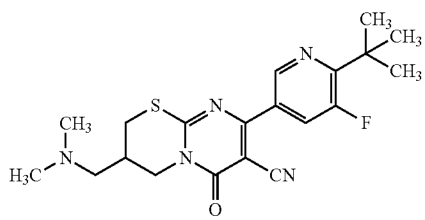 [SMILES: CN(C)CC1CSc2nc(-c3cnc(C(C)(C)C)c(F)c3)c(C#N)c(=O)n2C1] | 8-(6-tert-butyl-5-fluoropyridin-3-yl)-7-cyano-N,N-dimethyl-6-oxo-2H,3H,4H,6H-pyrimido[2,1-b][1,3]thiazine-3-carboxamide | C20H22FN5O2S | 415.1478 | ** | NT |
| 162 | 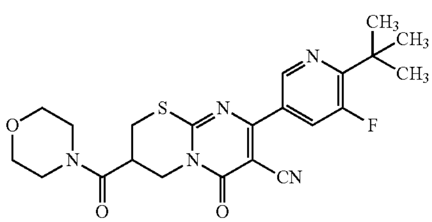 [SMILES: CC(C)(C)c1ncc(-c2nc3n(c(=O)c2C#N)CC(C(=O)N2CCOCC2)CS3)cc1F] | 8-(6-tert-butyl-5-fluoropyridin-3-yl)-3-(morpholine-4-carbonyl)-6-oxo-2H,3H,4H,6H-pyrimido[2,1-b][1,3]thiazine-7-carbonitrile | C22H24FN5O3S | 457.1584 | ** | NT |
| 163 | 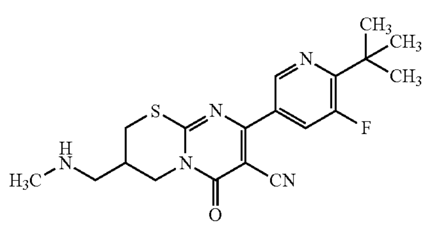 [SMILES: CNCC1CSc2nc(-c3cnc(C(C)(C)C)c(F)c3)c(C#N)c(=O)n2C1] | 8-(6-tert-butyl-5-fluoropyridin-3-yl)-7-cyano-N-methyl-6-oxo-2H,3H,4H,6H-pyrimido[2,1-b][1,3]thiazine-3-carboxamide | C19H20FN5O2S | 401.1322 | **** | NT |
| 164 | 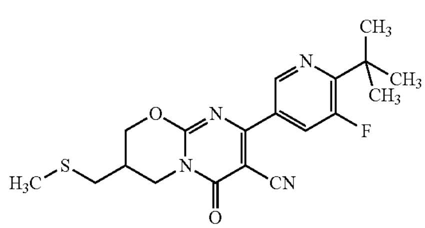 [SMILES: CSCC1COc2nc(-c3cnc(C(C)(C)C)c(F)c3)c(C#N)c(=O)n2C1] | 8-(6-tert-butyl-5-fluoropyridin-3-yl)-3-[(methylsulfanyl)methyl]-6-oxo-2H,3H,4H,6H-pyrimido[2,1-b][1,3]oxazine-7-carbonitrile | C19H21FN4O2S | 388.1369 | * | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 165 | 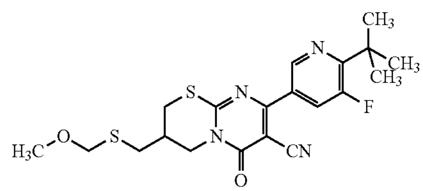 [SMILES: COCSCC1CSc2nc(-c3cnc(C(C)(C)C)c(F)c3)c(C#N)c(=O)n2C1] | 8-(6-tert-butyl-5-fluoropyridin-3-yl)-3-{[(methoxymethyl)sulfanyl]methyl}-6-oxo-2H,3H,4H,6H-pyrimido[2,1-b][1,3]oxazine-7-carbonitrile | C20H23FN4O3S | 418.1475 | **** | NT |
| 166 | 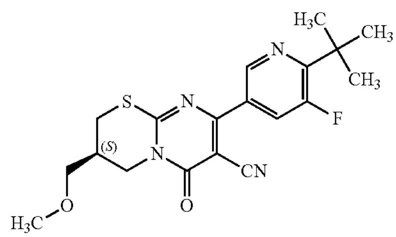 | (3S) 8 (6 tert-butyl-5-fluoropyridin-3-yl)-3-(methoxymethyl)-6-oxo-2H,3H,4H,6H-pyrimido[2,1-b][1,3]thiazine-7-carbonitrile | C19H21FN4O2S | 388.1369 | **** | NT |
| 167 | 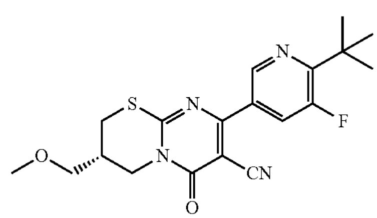 [SMILES: COC[C@@H]1CSc2nc(-c3cnc(C(C)(C)C)c(F)c3)c(C#N)c(=O)n2C1] | (3R)-8-(6-tert-butyl-5-fluoropyridin-3-yl)-3-(methoxymethyl)-6-oxo-2H,3H,4H,6H-pyrimido[2,1-b][1,3]thiazine-7-carbonitrile | C19H21FN4O2S | 388.1369 | **** | NT |
| 168 | 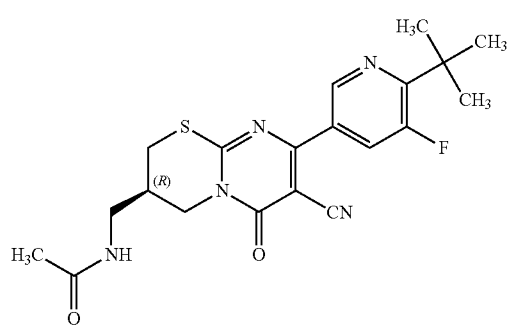 | N-{[(3R)-8-(6-tert-butyl-5-fluoropyridin-3-yl)-7-cyano-6-oxo-2H,3H,4H,6H-pyrimido[2,1-b][1,3]thiazin-3-yl]methyl}acetamide | C20H22FN5O2S | 415.1478 | *** | NT |
| 169 | 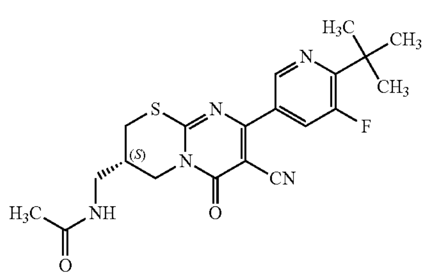 | N-{[(3S)-8-(6-tert-butyl-5-fluoropyridin-3-yl)-7-cyano-6-oxo-2H,3H,4H,6H-pyrimido[2,1-b][1,3]thiazin-3-yl]methyl]acetamide | C20H22FN5O2S | 415.1478 | **** | NT |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 170 | 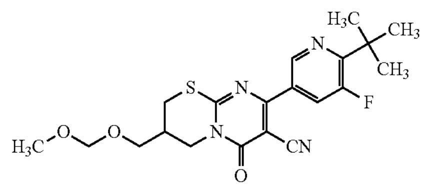 [SMILES: COCOCC1CSc2nc(-c3cnc(C(C)(C)C)c(F)c3)c(C#N)c(=O)n2C1] | 8-(6-tert-butyl-5-fluoropyridin-3-yl)-3-[(methoxymethoxy)methyl]-6-oxo-2H,3H,4H,6H-pyrimido[2,1-b][1,3]thiazine-7-carbonitrile | C20H23FN4O3S | 418.1475 | **** | NT |
| 171 | 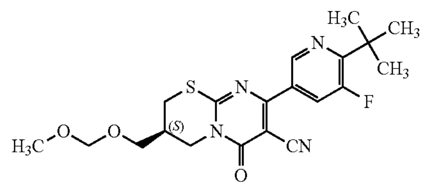 | (3S)-8-(6-tert-butyl-5-fluoropyridin-3-yl)-3-[(methoxymethoxy)methyl]-6-oxo-2H,3H,4H,6H-pyrimido[2,1-b][1,3]thiazine-7-carbonitrile | C20H23FN4O3S | 418.1475 | **** | NT |
| 172 | 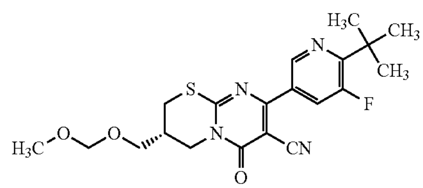 [SMILES: COCOC[C@@H]1CSc2nc(-c3cnc(C(C)(C)C)c(F)c3)c(C#N)c(=O)n2C1] | (3R)-8-(6-tert-butyl-5-fluoropyridin-3-yl)-3-[(methoxymethoxy)methyl]-6-oxo-2H,3H,4H,6H-pyrimido[2,1-b][1,3]thiazine-7-carbonitrile | C20H23FN4O3S | 418.1475 | **** | NT |
| 173 | 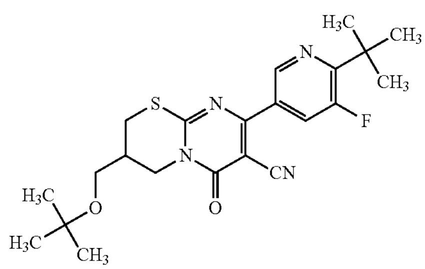 [SMILES: CC(C)(C)OCC1CSc2nc(-c3cnc(C(C)(C)C)c(F)c3)c(C#N)c(=O)n2C1] | 3-[(tert-butoxy)methyl]-8-(6-tert-butyl-5-fluoropyridin-3-yl)-6-oxo-2H,3H,4H,6H-pyrimido[2,1-b][1,3]thiazine-7-carbonitrile | C22H27FN4O2S | 430.1839 | * | NT |
| 174 | 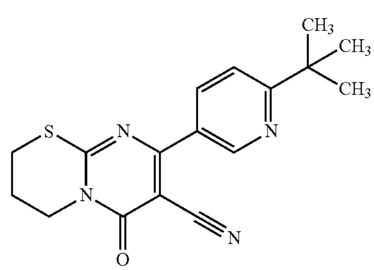 [SMILES: CC(C)(C)c1ccc(-c2nc3n(c(=O)c2C#N)CCCS3)cn1] | 8-(6-tert-butylpyridin-3-yl)-6-oxo-2H,3H,4H,6H-pyrimido[2,1-b][1,3]thiazine-7-carbonitrile | C17H18N4OS | 326.1201 | * | * |
| 175 | 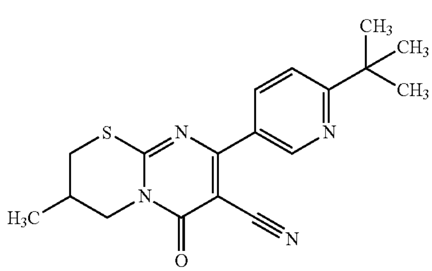 [SMILES: CC1CSc2nc(-c3ccc(C(C)(C)C)nc3)c(C#N)c(=O)n2C1] | 8-(6-tert-butylpyridin-3-yl)-3-methyl-6-oxo-2H,3H,4H,6H-pyrimido[2,1-b][1,3]thiazine-7-carbonitrile | C18H20N4OS | 340.1358 | ** | * |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 176 | 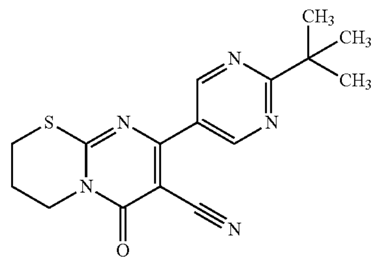 [SMILES: CC(C)(C)c1ncc(-c2nc3n(c(=O)c2C#N)CCCS3)cn1] | 8-(2-tert-butylpyrimidin-5-yl)-6-oxo-2H,3H,4H,6H-pyrimido[2,1-b][1,3]thiazine-7-carbonitrile | C16H17N5OS | 327.1154 | * | * |
| 177 | 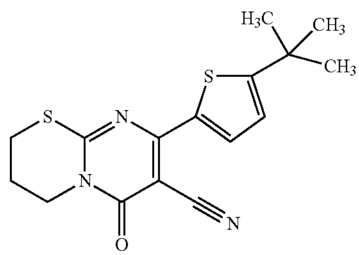 [SMILES: CC(C)(C)c1ccc(-c2nc3n(c(=O)c2C#N)CCCS3)s1] | 8-(5-tert-butylthiophen-2-yl)-6-oxo-2H,3H,4H,6H-pyrimido[2,1-b][1,3]thiazine-7-carbonitrile | C16H17N3OS2 | 331.0813 | NT | *** |
| 178 | 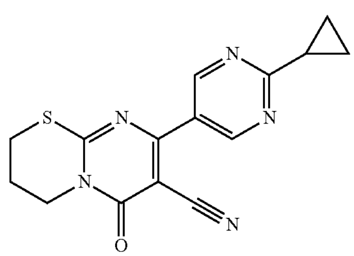 [SMILES: N#Cc1c(-c2cnc(C3CC3)nc2)nc2n(c1=O)CCCS2] | 8-(2-cyclopropyl-pyrimidin-5-yl)-6-oxo-2H,3H,4H,6H-pyrimido[2,1-b][1,3]thiazine-7-carbonitrile | C15H13N5OS | 311.0841 | * | *** |
| 179 | 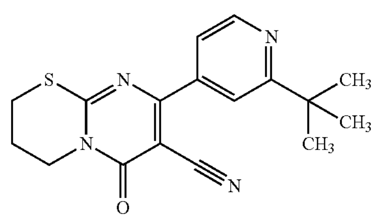 [SMILES: CC(C)(C)c1cc(-c2nc3n(c(=O)c2C#N)CCCS3)ccn1] | 8-(2-tert-butylpyridin-4-yl)-6-oxo-2H,3H,4H,6H-pyrimido[2,1-b][1,3]thiazine-7-carbonitrile | C17H18N4OS | 326.1201 | * | *** |
| 180 | 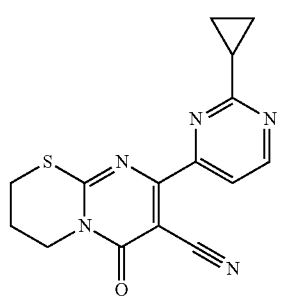 [SMILES: N#Cc1c(-c2ccnc(C3CC3)n2)nc2n(c1=O)CCCS2] | 8-(2-cyclopropyl-pyrimidin-4-yl)-6-oxo-2H,3H,4H,6H-pyrimido[2,1-b][1,3]thiazine-7-carbonitrile | C15H13N5OS | 311.0841 | NA | NA |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 181 | 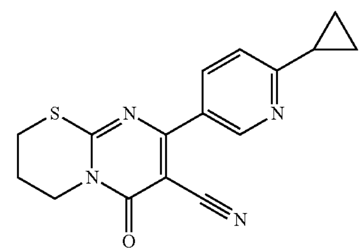 [SMILES: N#Cc1c(-c2ccc(C3CC3)nc2)nc2n(c1=O)CCCS2] | 8-(6-cyclopropyl-pyridin-3-yl)-6-oxo-2H,3H,4H,6H-pyrimido[2,1-b][1,3]thiazine-7-carbonitrile | C16H14N4OS | 310.0888 | * | *** |
| 182 | 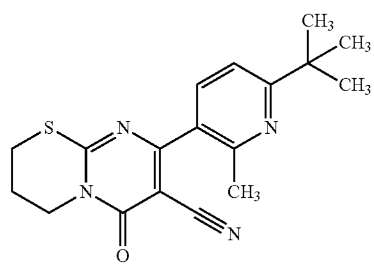 [SMILES: Cc1nc(C(C)(C)C)ccc1-c1nc2n(c(=O)c1C#N)CCCS2] | 8-(6-tert-butyl-2-methylpyridin-3-yl)-6-oxo-2H,3H,4H,6H-pyrimido[2,1-b][1,3]thiazine-7-carbonitrile | C18H20N4OS | 340.1358 | * | *** |
| 183 | 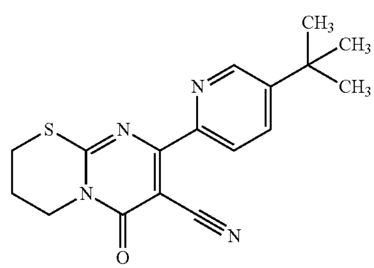 [SMILES: CC(C)(C)c1ccc(-c2nc3n(c(=O)c2C#N)CCCS3)nc1] | 8-(5-tert-butylpyridin-2-yl)-6-oxo-2H,3H,4H,6H-pyrimido[2,1-b][1,3]thiazine-7-carbonitrile | C17H18N4OS | 326.1201 | * | *** |
| 184 | 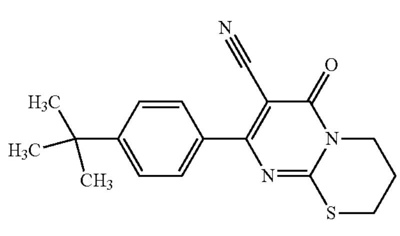 [SMILES: CC(C)(C)c1ccc(-c2nc3n(c(=O)c2C#N)CCCS3)cc1] | 8-(4-tert-butylphenyl)-6-oxo-2H,3H,4H,6H-pyrimido[2,1-b][1,3]thiazine-7-carbonitrile | C18H19N3OS | 325.1249 | ** | * |
| 185 | 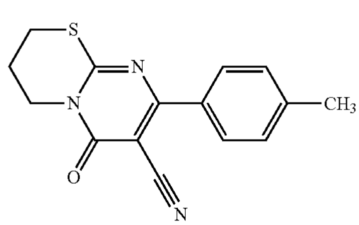 [SMILES: Cc1ccc(-c2nc3n(c(=O)c2C#N)CCCS3)cc1] | 8-(4-methylphenyl)-6-oxo-2H,3H,4H,6H-pyrimido[2,1-b][1,3]thiazine-7-carbonitrile | C15H13N3OS | 283.0779 | NT | ** |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 186 | 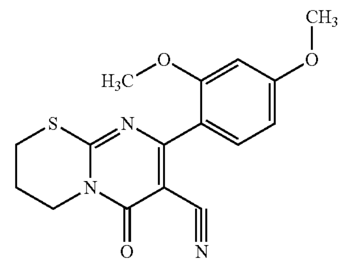 [SMILES: COc1ccc(-c2nc3n(c(=O)c2C#N)CCCS3)c(OC)c1] | 8-(2,4-dimethoxyphenyl)-6-oxo-2H,3H,4H,6H-pyrimido[2,1-b][1,3]thiazine-7-carbonitrile | C16H15N3O3S | 329.0834 | NT | * |
| 187 | 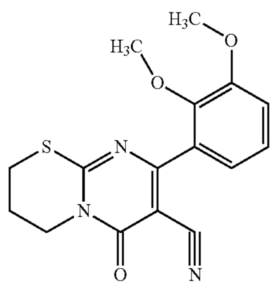 [SMILES: COc1cccc(-c2nc3n(c(=O)c2C#N)CCCS3)c1OC] | 8-(2,3-dimethoxyphenyl)-6-oxo-2H,3H,4H,6H-pyrimido[2,1-b][1,3]thiazine-7-carbonitrile | C16H15N3O3S | 329.0834 | NT | NA |
| 188 | 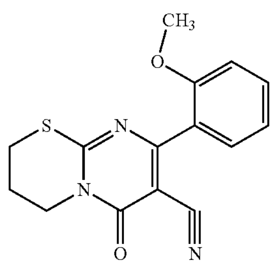 [SMILES: COc1ccccc1-c1nc2n(c(=O)c1C#N)CCCS2] | 8-(2-methoxyphenyl)-6-oxo-2H,3H,4H,6H-pyrimido[2,1-b][1,3]thiazine-7-carbonitrile | C15H13N3O2S | 299.0728 | NT | * |
| 189 | 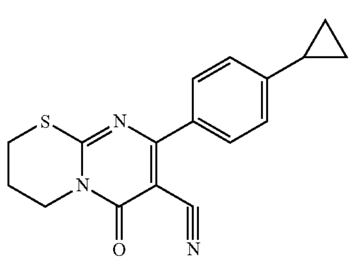 [SMILES: N#Cc1c(-c2ccc(C3CC3)cc2)nc2n(c1=O)CCCS2] | 8-(4-cyclopropylphenyl)-6-oxo-2H,3H,4H,6H-pyrimido[2,1-b][1,3]thiazine-7-carbonitrile | C17H15N3OS | 309.0936 | * | * |
| 190 | 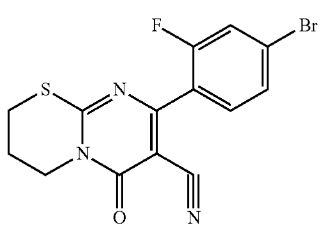 [SMILES: N#Cc1c(-c2ccc(Br)cc2F)nc2n(c1=O)CCCS2] | 8-(4-bromo-2-fluorophenyl)-6-oxo-2H,3H,4H,6H-pyrimido[2,1-b][1,3]thiazine-7-carbonitrile | C14H9BrFN3OS | 364.9634 | NT | NA |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 191 | 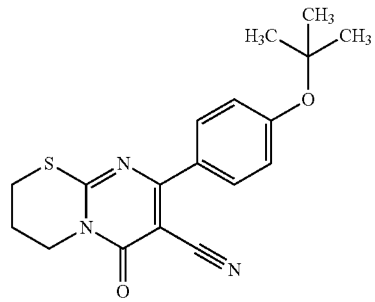 [SMILES: CC(C)(C)Oc1ccc(-c2nc3n(c(=O)c2C#N)CCCS3)cc1] | 8-[4-(tert-butoxy) phenyl]-6-oxo-2H,3H,4H,6H-pyrimido[2,1-b][1,3]thiazine-7-carbonitrile | C18H19N3O2S | 341.1198 | NT | NA |
| 192 | 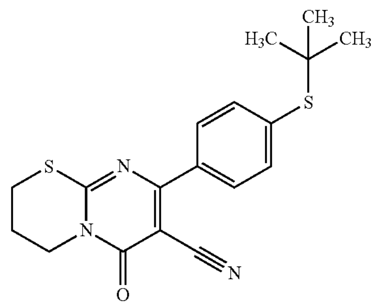 [SMILES: CC(C)(C)Sc1ccc(-c2nc3n(c(=O)c2C#N)CCCS3)cc1] | 8-[4-(tert-butylsulfanyl) phenyl]-6-oxo-2H,3H,4H,6H-pyrimido[2,1-b][1,3]thiazine-7-carbonitrile | C18H19N3OS2 | 357.097 | NT | NA |
| 193 | 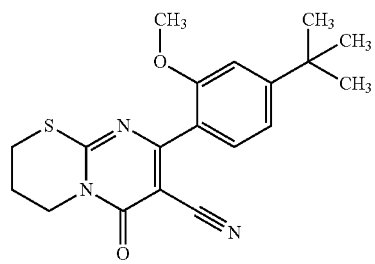 [SMILES: COc1cc(C(C)(C)C)ccc1-c1nc2n(c(=O)c1C#N)CCCS2] | 8-(4-tert-butyl-2-methoxyphenyl)-6-oxo-2H,3H,4H,6H-pyrimido[2,1-b][1,3]thiazine-7-carbonitrile | C19H21N3O2S | 355.1354 | ** | NT |
| 194 | 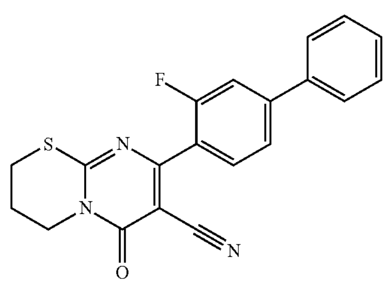 [SMILES: N#Cc1c(-c2ccc(-c3ccccc3)cc2F)nc2n(c1=O)CCCS2] | 8-{3-fluoro-[1,1'-biphenyl]-4-yl}-6-oxo-2H,3H,4H,6H-pyrimido[2,1-b][1,3]thiazine-7-carbonitrile | C20H14FN3OS | 363.0842 | NT | * |
| 195 | 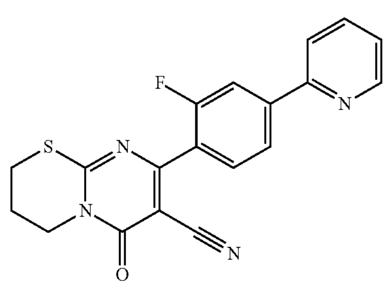 [SMILES: N#Cc1c(-c2ccc(-c3ccccn3)cc2F)nc2n(c1=O)CCCS2] | 8-[2-fluoro-4-(pyridin-2-yl)phenyl]-6-oxo-2H,3H,4H,6H-pyrimido[2,1-b][1,3]thiazine-7-carbonitrile | C19H13FN4OS | 364.0794 | NT | NA |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 196 | 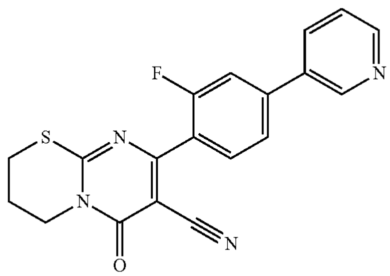 [SMILES: N#Cc1c(-c2ccc(-c3cccnc3)cc2F)nc2n(c1=O)CCCS2] | 8-[2-fluoro-4-(pyridin-3-yl)phenyl]-6-oxo-2H,3H,4H,6H-pyrimido[2,1-b][1,3]thiazine-7-carbonitrile | C19H13FN4OS | 364.0794 | NT | NA |
| 197 | 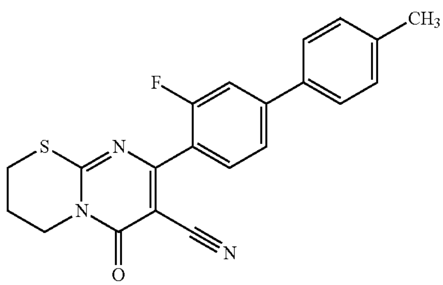 [SMILES: Cc1ccc(-c2ccc(-c3nc4n(c(=O)c3C#N)CCCS4)c(F)c2)cc1] | 8-{3-fluoro-4'-methyl-[1,1'-biphenyl]-4-yl}-6-oxo-2H,3H,4H,6H-pyrimido[2,1-b][1,3]thiazine-7-carbonitrile | C21H16FN3OS | 377.0998 | * | * |
| 198 | 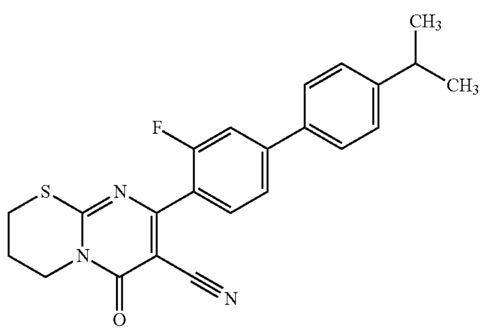 [SMILES: CC(C)c1ccc(-c2ccc(-c3nc4n(c(=O)c3C#N)CCCS4)c(F)c2)cc1] | 8-[3-fluoro-4'-(propan-2-yl)-[1,1'-biphenyl]-4-yl]-6-oxo-2H,3H,4H,6H-pyrimido[2,1-b][1,3]thiazine-7-carbonitrile | C23H20FN3OS | 405.1311 | * | * |
| 199 | 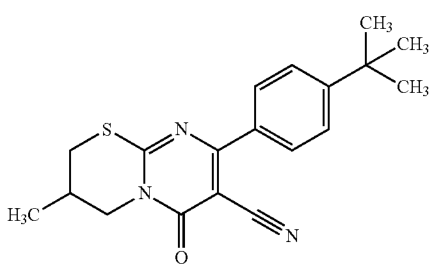 [SMILES: CC1CSc2nc(-c3ccc(C(C)(C)C)cc3)c(C#N)c(=O)n2C1] | 8-(4-tert-butylphenyl)-3-methyl-6-oxo-2H,3H,4H,6H-pyrimido[2,1-b][1,3]thiazine-7-carbonitrile | C19H21N3OS | 339.1405 | ** | * |
| 200 | 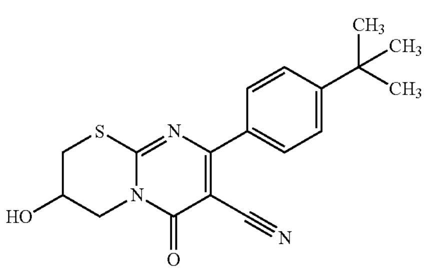 [SMILES: CC(C)(C)c1ccc(-c2nc3n(c(=O)c2C#N)CC(O)CS3)cc1] | 8-(4-tert-butylphenyl)-3-hydroxy-6-oxo-2H,3H,4H,6H-pyrimido[2,1-b][1,3]thiazine-7-carbonitrile | C18H19N3O2S | 341.1198 | NA | ** |

-continued

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 201 | 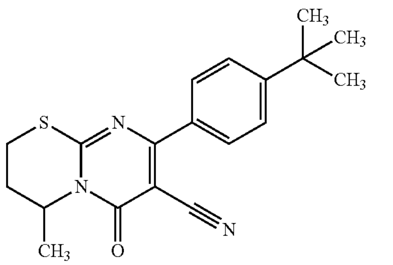 [SMILES: CC1CCSc2nc(-c3ccc(C(C)(C)C)cc3)c(C#N)c(=O)n21] | 8-(4-tert-butylphenyl)-4-methyl-6-oxo-2H,3H,4H,6H-pyrimido[2,1-b][1,3]thiazine-7-carbonitrile | C19H21N3OS | 339.1405 | * | *** |
| 202 | 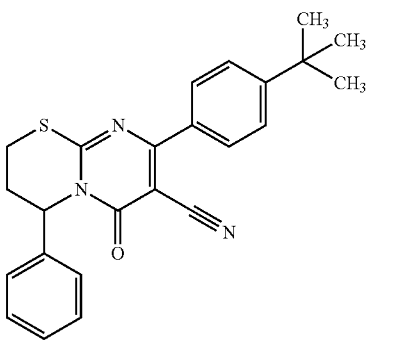 [SMILES: CC(C)(C)c1ccc(-c2nc3n(c(=O)c2C#N)C(c2ccccc2)CCS3)cc1] | 8-(4-tert-butylphenyl)-6-oxo-4-phenyl-2H,3H,4H,6H-pyrimido[2,1-b][1,3]thiazine-7-carbonitrile | C24H23N3OS | 401.1562 | Inhibitor | * |
| 203 | 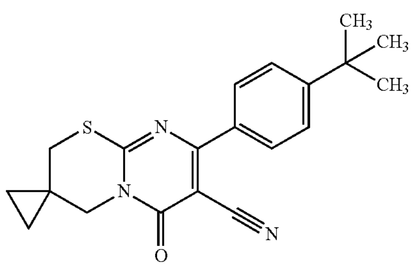 [SMILES: CC(C)(C)c1ccc(-c2nc3n(c(=O)c2C#N)CC2(CC2)CS3)cc1] | 8'-(4-tert-butylphenyl)-6'-oxo-4',6'-dihydro-2'H-spiro[cyclopropane-1,3'-pyrimido[2,1-b][1,3]thiazine]-7'-carbonitrile | C20H21N3OS | 351.1405 | NT | *** |
| 204 | 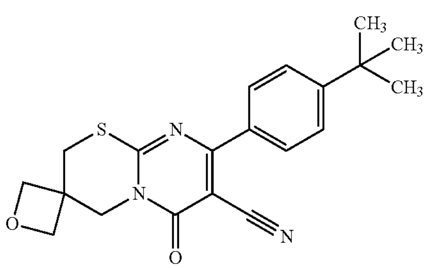 [SMILES: CC(C)(C)c1ccc(-c2nc3n(c(=O)c2C#N)CC2(COC2)CS3)cc1] | 8'-(4-tert-butylphenyl)-6'-oxo-4',6'-dihydro-2'H-spiro[oxetane-3,3'-pyrimido[2,1-b][1,3]thiazine]-7'-carbonitrile | C20H21N3O2S | 367.1354 | * | * |
| 205 | 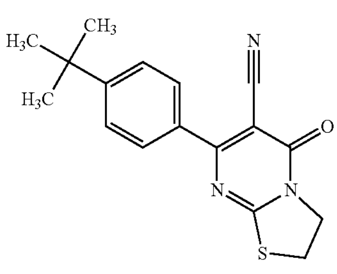 [SMILES: CC(C)(C)c1ccc(-c2nc3n(c(=O)c2C#N)CCS3)cc1] | 7-(4-tert-butylphenyl)-5-oxo-2H,3H,5H-[1,3]thiazolo[3,2-a]pyrimidine-6-carbonitrile | C17H17N3OS | 311.1092 |  | * |

ACTIVITY TABLE

| Example # | Structure | IUPAC | Chemical formula | Exact mass (g/mol) | NR2D Oocyte % Potentiation @ 10 uM | NR2D Percent CIQ Avg Max Measured Effect |
|---|---|---|---|---|---|---|
| 206 | 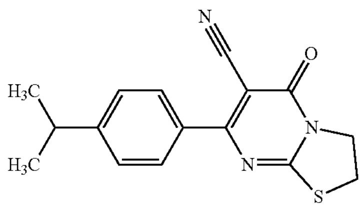 [SMILES: CC(C)c1ccc(-c2nc3n(c(=O)c2C#N)CCS3)cc1] | 5-oxo-7-[4-(propan-2-yl)phenyl]-2H,3H,5H-[1,3]thiazolo[3,2-a]pyrimidine-6-carbonitrile | C16H15N3OS | 297.0936 | * | ** |
| 207 | 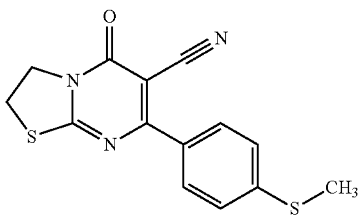 [SMILES: CSc1ccc(-c2nc3n(c(=O)c2C#N)CCS3)cc1] | 7-[4-(methylsulfanyl)phenyl]-5-oxo-2H,3H,5H-[1,3]thiazolo[3,2-a]pyrimidine-6-carbonitrile | C14H11N3OS2 | 301.0344 | NT | *** |
| 208 | 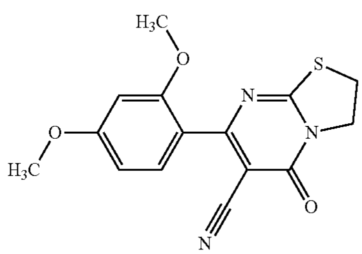 [SMILES: COc1ccc(-c2nc3n(c(=O)c2C#N)CCS3)c(OC)c1] | 7-(2,4-dimethoxyphenyl)-5-oxo-2H,3H,5H-[1,3]thiazolo[3,2-a]pyrimidine-6-carbonitrile | C15H13N3O3S | 315.0678 | Inhibitor | ** |
| 209 | 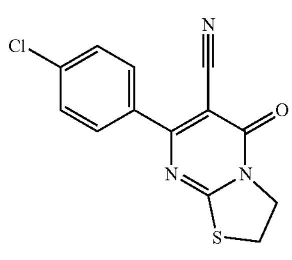 [SMILES: N#Cc1c(-c2ccc(Cl)cc2)nc2n(c1=O)CCS2] | 7-(4-chlorophenyl)-5-oxo-2H,3H,5H-[1,3]thiazolo[3,2-a]pyrimidine-6-carbonitrile | C13H8ClN3OS | 289.0077 | Inhibitor | * |
| 210 | 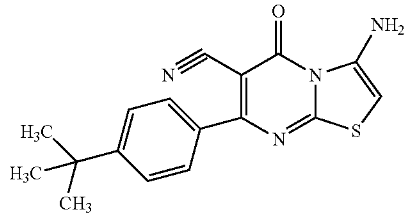 [SMILES: CC(C)(C)c1ccc(-c2nc3scc(N)n3c(=O)c2C#N)cc1] | 3-amino-7-(4-tert-butylphenyl)-5-oxo-5H-[1,3]thiazolo[3,2-a]pyrimidine-6-carbonitrile | C17H16N4OS | 324.1045 | NT | * |

| Activity Table Key | | | |
|---|---|---|---|
| % Potentiation (NR2D oocytes) | | % CIQ Max (NR2D) | |
| >1000 | **** | >200 | **** |
| 500-1000 | *** | 100-200 | *** |
| 100-500 | ** | 50-100 | ** |
| 10-100 | * | 10-50 | * |
| <10 inhibitor | NA inhibitor | Not active Not Tested | NA NT |
| Not tested | NT | | |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The invention claimed is:

1. A compound of the Formula Ic:

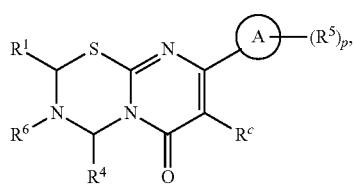

or a pharmaceutically acceptable salt thereof, wherein
$R^1$ is selected from the group consisting of hydrogen, halogen, $C_{1-6}$alkyl, $C_{2-6}$alkenyl, $C_{2-6}$alkynyl, $C_{1-6}$alkoxy, $C_{3-6}$cycloalkyl, —C(O)OH, —C(O)OC$_{1-6}$alkyl, $(C_{3-6})$ cycloalkyl and phenyl (optionally substituted by one, two or three substituents each selected from halogen, $C_{1-6}$alkyl, $C_{1-6}$alkoxy, —C(O)OH, —C(O)OC$_{1-6}$alkyl and NR$^a$R$^b$);
$R^4$ is selected from the group consisting of hydrogen, $C_{1-6}$alkyl, $C_{2-6}$alkenyl, $C_{2-6}$alkynyl, —CO$_2$H, —CO$_2$C$_{1-6}$alkyl, —CO$_2$ NR$^a$R$^b$, NR$^a$R$^b$, $C_{3-6}$cycloalkyl and phenyl (optionally substituted by one or two substituents each selected from halogen or methyl);
$R^5$ independently for each occurrence is selected from the group consisting of hydrogen, $C_{1-6}$alkyl, $C_{1-6}$alkoxy, halogen, cyano, OH, $C_{2-6}$alkenyl, $C_{2-6}$alkynyl, $C_{3-6}$cycloalkyl, heteroaryl, phenyl, —NR$^a$R$^b$, —C(O)OH, $C_{1-6}$alkylcarbonyl, $C_{1-6}$alkoxycarbonyl, (NR$^a$R$^b$) carbonyl-, $C_{1-6}$alkyl-S(O)$_w$— (where w is 0, 1 or 2), and R$^a$R$^b$N—SO$_w$— (where w is 0, 1 or 2); wherein heteroaryl and phenyl may optionally be substituted by one, two or three substituents each selected from the group consisting of halogen, cyano, $C_{1-6}$alkyl, $C_{1-6}$alkoxy, and —NR$^a$R$^b$; wherein one or more carbon atoms of said $C_{3-6}$cycloalkyl may be optionally replaced by N or O; or two $R^5$, together with two adjacent carbons on ring A to which they are attached, form a 5-7 membered unsaturated, partially unsaturated or saturated carbocyclic or heterocyclic ring;
$R^6$ for each occurrence is independently selected from the group consisting of hydrogen, $C_{1-6}$alkyl, $C_{3-6}$cycloalkyl, —C(O)—C$_{1-6}$alkyl, and phenyl (optionally substituted by one or two substituents each selected from halogen or methyl);
Ring A is pyridinyl, pyrimidinyl or pyridazinyl;
$R^C$ is selected from the group consisting of cyano, hydrogen, halogen, S(C$_{1-6}$) alkyl, S(O)(C$_{1-6}$) alkyl, SO$_2$ (C$_{1-6}$)alkyl, C(O)NR$^a$R$^b$, —C(O)OH, —C(O)O(C$_{1-6}$) alkyl, (C$_{1-6}$)alkyl, (C$_{2-6}$) alkenyl, (C$_{2-6}$) alkynyl and heteroaryl (optionally substituted by $C_{1-4}$alkyl or halogen);
$R^a$ and $R^b$ are independently selected, for each occurrence, from the group consisting of: hydrogen, $C_{1-4}$alkylcarbonyl, $C_{1-6}$alkoxycarbonyl, cyclopropyl, and $C_{1-3}$alkyl; wherein $C_{1-3}$alkyl may optionally be substituted on a carbon not bound to the nitrogen by one or more substituents each selected from the group consisting of fluorine, cyano, oxo and hydroxyl; or $R^a$ and $R^b$, together with the nitrogen to which they are attached, form a 4-6 membered heterocyclic ring which may have an additional heteroatom selected from O, S, or N (optionally substituted by one or two methyl groups); and wherein the 4-6 membered heterocyclic ring may optionally be substituted on a carbon not bound to the nitrogen by one or more substituents; and
p is 0, 1, 2 or 3.

2. The compound of claim 1, wherein $R^5$ is independently for each occurrence selected from the group consisting of hydrogen, halogen, methoxy, methyl, ethyl, propyl, isopropyl, cyclopropyl, t-butyl, t-butyloxy, t-butylthio, pyridinyl (optionally substituted by halogen), and phenyl (optionally substituted by halogen).

3. The compound of claim 1, wherein $R^5$ is t-butyl.

4. The compound of claim 1, wherein Re is-CN.

5. The compound of claim 1, wherein p is 1.

6. The compound of claim 1, wherein p is 2.

7. The compound of claim 1, wherein $R^4$ is selected from the group consisting of hydrogen, $C_{1-4}$alkyl, and phenyl.

8. The compound of claim 1, wherein $R^4$ is hydrogen.

9. The compound of claim 1, wherein $R^1$ is selected from the group consisting of hydrogen, $(C_{1-6})$ alkyl, $(C_{2-6})$ alkenyl, $(C_{2-6})$ alkynyl, $(C_{3-6})$ cycloalkyl and phenyl (optionally substituted by one or two substituents each selected from halogen or methyl), t is 0, 1 or 2.

10. The compound of claim 1, wherein $R^1$ is hydrogen.

11. A pharmaceutically acceptable composition comprising a compound according to claim 1, and a pharmaceutically acceptable excipient.

12. A method of treating a patient suffering from a neuropsychiatric disorder comprising administering a compound according to claim 1, to the patient.

13. The method according to claim 12, wherein the neuropsychiatric disorder is selected from schizophrenia, depression, an autism spectrum disorder, and Rett syndrome.

14. A compound, wherein the compound is selected from:

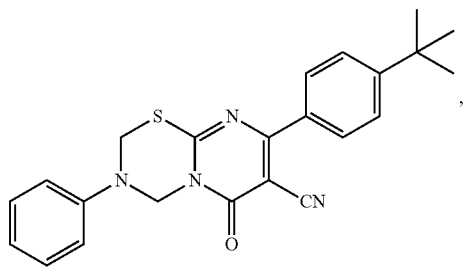

,

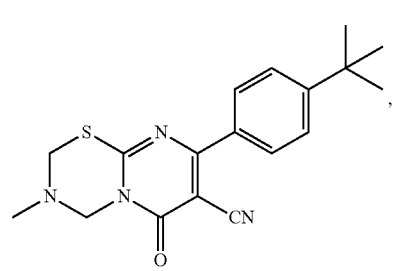

,

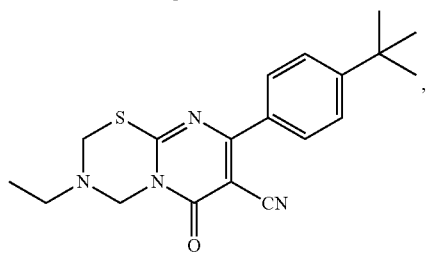

,

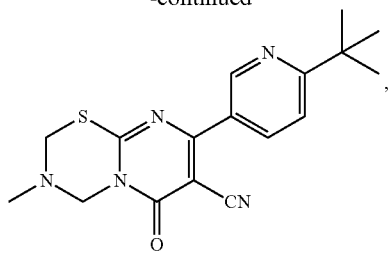

,

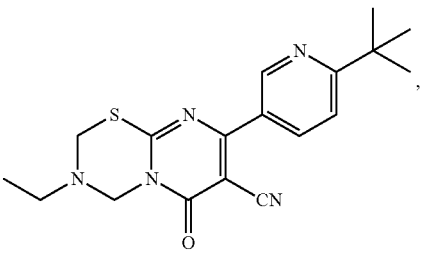

,

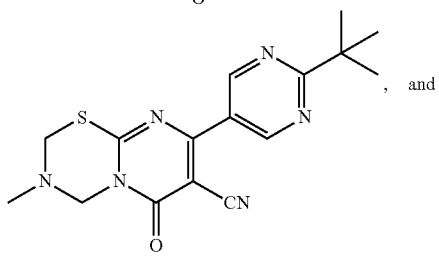

, and

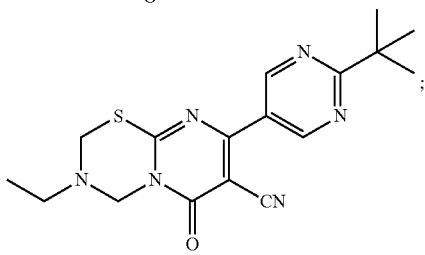

;

or a pharmaceutically acceptable salt of any of the foregoing.

* * * * *

UNITED STATES PATENT AND TRADEMARK OFFICE
CERTIFICATE OF CORRECTION

PATENT NO.           : 12,358,929 B2                                    Page 1 of 1
APPLICATION NO.      : 18/368244
DATED                : July 15, 2025
INVENTOR(S)          : David R. Anderson et al.

It is certified that error appears in the above-identified patent and that said Letters Patent is hereby corrected as shown below:

In the Claims

At Column 338, Claim number 4, Line number 53, please replace "Re" with --$R^c$--.

Signed and Sealed this
Twenty-sixth Day of August, 2025

Coke Morgan Stewart
*Acting Director of the United States Patent and Trademark Office*